United States Patent
Zhu et al.

(10) Patent No.: US 7,312,235 B2
(45) Date of Patent: Dec. 25, 2007

(54) BENZAMIDE INHIBITORS OF FACTOR XA

(75) Inventors: Bing-Yan Zhu, Belmont, CA (US);
Penglie Zhang, Foster City, CA (US);
Erick A. Goldman, Berkeley, CA (US);
Zhaozhong Jon Jia, San Mateo, CA
(US); Shawn Bauer, San Bruno, CA
(US); Wenrong Huang, Cupertino, CA
(US); John Woolfrey, Burlingame, CA
(US); Robert M. Scarborough, Half
Moon Bay, CA (US)

(73) Assignee: Millennium Pharmaceuticals, Inc.,
Cambridge, MA (US)

( * ) Notice: Subject to any disclaimer, the term of this patent is extended or adjusted under 35 U.S.C. 154(b) by 780 days.

(21) Appl. No.: 10/115,135

(22) Filed: Apr. 1, 2002

(65) Prior Publication Data

US 2003/0069250 A1 Apr. 10, 2003

Related U.S. Application Data

(60) Provisional application No. 60/279,696, filed on Mar. 30, 2001.

(51) Int. Cl.
*A61K 31/497* (2006.01)
*A61K 31/445* (2006.01)
*A61K 31/44* (2006.01)
*A61K 31/00* (2006.01)

(52) U.S. Cl. ............. 514/352; 514/210.2; 514/253.01;
514/318; 514/332; 514/336; 514/341; 514/343;
544/360; 546/194; 546/256; 546/309

(58) Field of Classification Search ................ 544/360;
514/352, 210.2, 253.01, 318, 332, 336, 341,
514/343; 546/309, 194, 256
See application file for complete search history.

(56) References Cited

U.S. PATENT DOCUMENTS

| | | | |
|---|---|---|---|
| 4,588,587 A | | 5/1986 | Gasic |
| 6,376,515 B2 * | | 4/2002 | Zhu et al. .................... 514/318 |
| 6,720,317 B1 * | | 4/2004 | Zhu et al. .............. 514/217.09 |
| 6,835,739 B2 * | | 12/2004 | Zhu et al. .................... 514/318 |
| 6,844,367 B1 * | | 1/2005 | Zhu et al. .................... 514/620 |

FOREIGN PATENT DOCUMENTS

| | | |
|---|---|---|
| CA | 2 301 559 A1 | 3/1999 |
| EP | 798295 A1 | 10/1997 |
| WO | WO 94/13693 A1 | 6/1994 |
| WO | WO 97/21437 A1 | 6/1997 |
| WO | WO 97/30971 A1 | 8/1997 |
| WO | WO 98/28269 A1 | 7/1998 |
| WO | WO 99/00121 A1 | 1/1999 |
| WO | WO 99/00127 A1 | 1/1999 |
| WO | WO 99/42439 A1 | 8/1999 |
| WO | WO 01/19788 A2 | 3/2001 |
| WO | WO 01/19788 A3 | 3/2001 |
| WO | WO 02/079145 A1 | 10/2002 |

OTHER PUBLICATIONS

Herron et al., 2000, "1,2-dibenzamidobenzene inhibitors of human factor Xa," *J. Med. Chem.* 43:859-872.

Wiley et al., 2000, "Structure-based design of potent, amidine-derived inhibitors of factor Xa: Evaluation of selectivity, anticoagulant activity, and antithrombotic activity," *J. Med. Chem.* 43:883-899.

Claeson, G., "Synthetic Peptides and Peptidomimetics as Substrates and Inhibitors of Thrombin and Other Proteases in the Blood Coagulation System", *Blood Coag. Fibrinol.*, 1994. 5:411-436 (1994).

Elodi et al., "Optimization of conditions for the catalytic effect of the factor IXa-factor VIII complex: probable role of the complex in the amplification of blood coagulation", Thromb. Res. 1979. 15:617-629.

Hauptmann, J. et al., "Comparison of the Anticoagulant and Antithrombotic Effects of Synthetic Thrombin and Factor Xa Inhibitors", Thromb. Haemost., 1990. 63:220-223.

Hitomi, Y. et al., "Inhibitory Effect of New Synthetic Protease Inhibitor (FUT-175) on the Coagulation System", *Haemostasis*, 1985. 15:164-168.

Kam, C.M. et al., "Mechanism Based Isocoumarin Inhibitors for Trypsin and Blood Coagulation Serine Proteases: New Anticoagulants", Biochemistry, 1988. 27:2547-2557.

Nutt, E. et al., "The Amino Acid Sequence of Antistasin, a Potent Inhibitor of Factor Xa Reveals a Repeated Internal Structure", J. Biol. Chem., 1988. 263:10162-10167.

Sturzebecher, J. et al., "Synthetic Inhibitors of Bovine Factor Xa and Thrombin. Comparison of Their Anticoagulant Efficiency", Thromb. Res., 54:245-252 (1989).

Tidwell, R.R. et al., "Strategies for Anticoagulation With Synthetic Protease Inhibitors. Xa Inhibitors Versus Thrombin Inhibitors", Thromb. Res., 1980. 19:339-349.

Turner, A.D. et al., "p-Amidino Esters as Irreversible Inhibitors of Factor IXa and Xa and Thrombin", Biochemistry, 1986. 25:4929-4935.

Waxman, L., et al., "Tick Anticoagulant Peptide (TAP) is a Novel Inhibitor of Blood Coagulation Factor Xa", Science, 248:593-596 (1990).

\* cited by examiner

*Primary Examiner*—Peter O'Sullivan
(74) *Attorney, Agent, or Firm*—Foley & Lardner LLP

(57) ABSTRACT

Novel benzamide compounds, their salts and compositions related thereto having activity against mammalian Factor Xa are disclosed. The compounds are useful in vitro or in vivo for preventing or treating coagulation disorders.

20 Claims, No Drawings

BENZAMIDE INHIBITORS OF FACTOR XA

RELATED APPLICATIONS

This application claims the benefit of priority under 35 U.S.C.119(e) to U.S. Provisional Application No. 60/279,696 filed on Mar. 30, 2001 which is herein incorporated in its entirety by reference.

FIELD OF INVENTION

This invention relates to novel compounds which are potent and highly selective inhibitors of isolated factor Xa or when assembled in the prothrombinase complex. These compounds show selectivity for factor Xa versus other proteases of the coagulation (e.g. thrombin, fVIIa, fIXa) or the fibrinolytic cascades (e.g. plasminogen activators, plasmin). In another aspect, the present invention relates to novel monoamidino-containing compounds, their pharmaceutically acceptable salts, and pharmaceutically acceptable compositions thereof which are useful as potent and specific inhibitors of blood coagulation in mammals. In yet another aspect, the invention relates to methods for using these inhibitors as therapeutic agents for disease states in mammals characterized by coagulation disorders.

BACKGROUND OF THE INVENTION

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", Blood Coag. Fibrinol. 5, 411-436 (1994). Several classes of anticoagulants currently used in the clinic directly or indirectly affect thrombin (i.e. heparins, low-molecular weight heparins, heparin-like compounds and coumarins).

A prothrombinase complex, including Factor Xa (a serine protease, the activated form of its Factor X precursor and a member of the calcium ion binding, gamma carboxyglutamyl (Gla)-containing, vitamin K dependent, blood coagulation glycoprotein family), converts the zymogen prothrombin into the active procoagulant thrombin. Unlike thrombin, which acts on a variety of protein substrates as well as at a specific receptor, factor Xa appears to have a single physiologic substrate, namely prothrombin. Since one molecule of factor Xa may be able to generate up to 138 molecules of thrombin (Elodi et al., Thromb. Res. 15, 617-619 (1979)), direct inhibition of factor Xa as a way of indirectly inhibiting the formation of thrombin may be an efficient anticoagulant strategy. Therefore, it has been suggested that compounds which selectively inhibit factor Xa may be useful as in vitro diagnostic agents, or for therapeutic administration in certain thrombotic disorders, see e.g., WO 94/13693.

Polypeptides derived from hematophagous organisms have been reported which are highly potent and specific inhibitors of factor Xa. U.S. Pat. No. 4,588,587 describes anticoagulant activity in the saliva of the Mexican leech, *Haementeria officinalis*. A principal component of this saliva was shown to be the polypeptide factor Xa inhibitor, antistasin (ATS), by Nutt, E. et al., "The Amino Acid Sequence of Antistasin, a Potent Inhibitor of Factor Xa Reveals a Repeated Internal Structure", *J. Biol. Chem.*, 263, 10162-10167 (1988). Another potent and highly specific inhibitor of Factor Xa, called tick anticoagulant peptide (TAP), has been isolated from the whole body extract of the soft tick *Ornithidoros moubata*, as reported by Waxman, L., et al., "Tick Anticoagulant Peptide (TAP) is a Novel Inhibitor of Blood Coagulation Factor Xa" *Science*, 248, 593-596 (1990).

Factor Xa inhibitory compounds which are not large polypeptide-type inhibitors have also been reported including: Tidwell, R. R. et al., "Strategies for Anticoagulation With Synthetic Protease Inhibitors. Xa Inhibitors Versus Thrombin Inhibitors", Thromb. Res., 19 339-349 (1980); Turner, A. D. et al., "p-Amidino Esters as Irreversible Inhibitors of Factor IXa and Xa and Thrombin", Biochemistry, 25, 4929-4935 (1986); Hitomi, Y. et al., "Inhibitory Effect of New Synthetic Protease Inhibitor (FUT-175) on the Coagulation System", Haemostasis, 15, 164-168 (1985); Sturzebecher, J. et al., "Synthetic Inhibitors of Bovine Factor Xa and Thrombin. Comparison of Their Anticoagulant Efficiency", Thromb. Res., 54, 245-252 (1989); Kam, C. M. et al., "Mechanism Based Isocoumarin Inhibitors for Trypsin and Blood Coagulation Serine Proteases: New Anticoagulants", Biochemistry, 27, 2547-2557 (1988); Hauptmann, J. et al., "Comparison of the Anticoagulant and Antithrombotic Effects of Synthetic Thrombin and Factor Xa Inhibitors", Thromb. Haemost., 63, 220-223 (1990); and the like.

Others have reported Factor Xa inhibitors which are small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal C($=$NH)—NH$_2$ group; WO 97/21437 describes benzimidazole compounds substituted by a basic radical which are connected to a naphthyl group via a straight or branched chain alkylene, —C($=$O) or —S($=$O)$_2$ bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group.

There exists a need for effective therapeutic agents for the regulation of hemostasis, and for the prevention and treatment of thrombus formation and other pathological processes in the vasculature induced by thrombin such as restenosis and inflammation. In particular, there continues to be a need for compounds which selectively inhibit factor Xa or its precursors. Compounds that have different combinations of bridging groups and functional groups than compounds previously discovered are needed, particularly compounds which selectively or preferentially bind to Factor Xa. Compounds with a higher degree of binding to Factor Xa than to thrombin are desired, especially those compounds having good bioavailability and/or solubility.

SUMMARY OF THE INVENTION

The present invention relates to novel compounds which inhibit factor Xa, their pharmaceutically acceptable isomers, salts, hydrates, solvates and prodrug derivatives, and pharmaceutically acceptable compositions thereof which have particular biological properties and are useful as potent and specific inhibitors of blood coagulation in mammals.

One aspect of the invention relates to compounds having formula I which are inhibitors of factor Xa for the treatment of cardiovascular diseases:

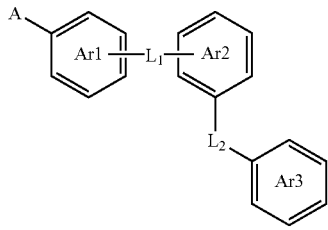

I wherein:
Ar1, Ar2 and Ar3 are each independently selected from the group consisting of:

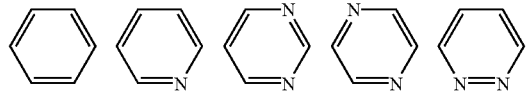
and

Ar1 may be optionally substituted with 0-2 R;
  each R is independently selected from the group consisting of halo, haloalkyl, alkyl, alkoxy, thioalkoxy, haloalkoxy, alkoxyalkoxy, dialkylaminoalkoxy, $(alkyl)_{1-2}$amino, 1-pyrrolidinyl, 1-piperidinyl, hydroxy, cyano, $(alkyl)_{0-2}$ aminocarbonyl, $(alkyl)_{0-2}$aminoalkyl, $(alkyl)_{0-2}$aminosulfonyl, alkylsulfonyl, alkynyl and C≡CH;
Ar3 may be optionally substituted with 0-2 $R^1$;
  each $R^1$ is independently selected from the group consisting of halo, haloalkyl, alkenyl, alkoxy, haloalkoxy, alkenyl, alkenyl alkyl or C≡CH;
L1 is independently a direct link, $(alkyl)_{0-2}$aminocarbonyl, $(alkyl)_{1-2}$amino or $(alkyl)_{0-2}$aminocarbonyl;
L2 is independently $(alkyl)_{0-2}$aminocarbonyl, $(alkyl)_{1-2}$amino, or $(alkyl)_{0-2}$aminocarbonyl;
Ar2 may be optionally substituted with 0-3 $R^{1d}$ groups,
  each $R^{1d}$ is independently selected from the group consisting of:
    hydrogen, alkyl, halo, haloalkyl, aryl, heteroaryl, nitro, cyano, carboxyl alkyl carboxylamino alkyl, carboxylamino $(alkyl)_{0-2}$, alkyl hydroxy, alkyl amino alkylamino $(alkyl)_{0-2}$, carbonyl alkyl, —C(=NO-alkyl) alkyl, cyano, alkenylcarboxyl alkyl, formyl, alkenyl, alkynyl, and alkenyl carboxyl alkyl;

a radical having the formula:
—C(=NH)—X where X is independently an amino, amino alkyl, amino dialkyl, pyrrolidinyl or piperidinyl;
a radical having the formula:
Q-imidazolinyl; wherein Q is a direct bond, amino, alkylamino;
wherein the imidazolinyl may be substituted on N with alkyl;
a radical having the formula:

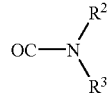

wherein each $R^2$ and $R^3$ is independently selected from the group consisting of hydrogen, alkoxyalkyl, alkylsulfonyl(alkyl), alkylamino $(alkyl)_{0-3}$, alkyl; or $R^2$ and $R^3$ taken together to form a 6-membered saturated ring containing optionally O, N, or S where the N maybe substituted wherein alkyl and the S may be substituted with 1-2 oxygen;
hydroxy, alkoxy, halo alkoxy, alkoxycarboxy alkyl, alkoxy carbonyl amino $(alkyl)_{0-2}$, alkoxy alkoxy, alkoxy hydroxy, alkoxysulfonyl alkyl, alkoxy alkoxy alkoxy, alkoxy-S-alkyl, alkoxy sulfonyl alkyl, alkoxy amino $(alkyl)_{0-2}$, alkoxyamino (alkyl alkoxy)$_{1-2}$, alkoxy oxy acyl, alkoxy hydroxy, alkoxy amino alkyl alkyl hydroxy;
a radical of the formula:
—O-alkyl-O— alkyl-$R^4$ wherein $R^4$ is independently alkoxy, amino $(alkyl)_{0-2}$, or a 5-6 membered ring containing 1 or 2 N.
a radical of the formula:
alkoxy-$R^5$, wherein $R^5$ is independently amino $(alkyl)_{0-2}$, a 5 or 6 membered ring containing 1 to 4 N or 1N and 1O, the ring optionally substituted with alkyl;
a radical of the formula:

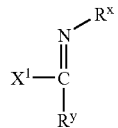

wherein $R^x$ is independently hydrogen, cyano or nitro;
$R^y$ is independently amino (alkyl), cycloalkyl, or phenyl;
X1 is a direct bond or amino $(alkyl)_{0-1}$; or $R^x$ and $R^y$ taken together form an imidazolyl substituted on N with alkyl;
—S—, alkyl alkoxy, —S— alkyl, sulfonyl-alkyl alkoxy, S—Ph, SO$_2$Ph, sulfonylamino $(alkyl)_{0-2}$, sulfonyl alkyl amino $(alkyl)_{0-2}$, amino $(alkyl)_{0-2}$, aminosulfonyl alkyl, aminocarbonyl alkyl amino alkyl amino $(alkyl)_{0-2}$; amino (alkyl hydroxy)$_{1-2}$, amino (alkyl alkoxy)$_{1-2}$, amino alkyl carboxyl $(alkyl)_{0-1}$, amino alkyl carbonylamino $(alkyl)_{0-2}$, amino (alkyl) (alkylcarboxyl $(alkyl)_{0-1}$), amino (alkyl) (alkyl carbonyl amino $(alkyl)_{0-2}$), amino (alkyl) (alkylamino $(alkyl)_{0-2}$), amino (alkyl) (alkyl alkoxy), amino (alkyl) (alkyl hydroxy); or
a 5 or 6 membered saturated heterocyclic ring containing one or more N, O, S atoms; the heterocyclic ring optionally substituted by alkyl or N-protective group;

N is optionally substituted by alkyl, carbonyl alkyl, sulfonyl alkyl or a N-protective group; or carbon substituted with a hydroxy, carboxy, carboxy alkyl, carbonylamino or amino; or S is optionally substituted with one or two O;

a radical of the formula:

amino (alkyl) (alkyl)—R$^6$ where R$^6$ is pyrrolidinyl, piperidinyl, morpholinyl, thiomorpholinyl wherein R$^6$ is optionally substituted by dioxy;

an imidazolinyl optionally substituted with alkyl on N, amino (alkyl) imidazolinyl optionally substituted with alkyl on N;

a radical of the formula:

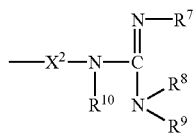

wherein X$^2$ is a direct link or amino (alkyl)$_{0-1}$-alkyl-;

R$^7$ is hydrogen, or cyano;

R$^{10}$ is independently hydrogen or alkyl;

Each R$^8$ and R$^9$ is independently hydrogen or alkyl;

an amino-alkyl-amino (alkyl)(imidazolyl optionally substituted with alkyl on N;

A is independently

I. phenyl, pyridinyl or imidazolyl optionally substituted with one or more R$^{11}$ groups; each R$^{11}$ independently halo, cyano, carbonylamino (alkyl)$_{0-2}$, alkyl amino, alkylamino (alkyl)$_{0-2}$, sulfonylamino, sulfonyl alkyl; alkyl which may be optionally substituted with 3-6 membered nitrogen containing ring; the 3-6 membered ring maybe substituted by alkyl hydroxy;

II. a radical of formula:

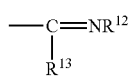

wherein R$^{12}$ is independently hydrogen, alkyl or 3-4 membered N containing ring;

R$^{13}$ is amino (alkyl)$_{0-2}$, or a 3-6 membered nitrogen containing ring;

III. a 5-7 membered ring containing 1 to 4 N optionally substituted with alkyl, alkylamino (alkyl)$_{0-2}$), amino (alkyl)$_{0-2}$), oxy, carbonyl alkylamino (alkyl)$_{0-2}$, thio (alkyl), imino; or IV. a radical of the formula:

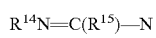

R$^{14}$N=C(R$^{15}$)—N wherein each R$^{14}$ and R$^{15}$ can be hydrogen, or alkyl;

V. a radical of the formula:

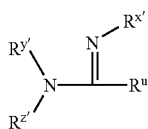

wherein R$^{x'}$ is independently hydrogen, cyano, nitro, alkyl, a 4-membered N containing ring, acyl, sulfonyl alkyl;

R$^u$ is a direct bond, alkylamino (alkyl)$_{0-1}$;

each R$^{y'}$ and R$^{z'}$ is independently hydrogen, hydroxy, alkyl, alkoxy, alkoxyphenyl, halophenyl, alkyl piperidinyl, amino (alkyl)$_{0-2}$, phenyl, halo (alkyl), aminosulfonyl alkyl, pyrrolidinyl, pyrimidinyl, pyrridinyl, alkylphenyl, alkylhalophenyl, alkylcyano, alkoxy alkyl, alkyl hydroxy, alkylsulfonyl alkyl, alkylamino acetyl, alkylamino sulfonyl alkyl, alkenyl, alkynyl, alkylcycloalkyl, cycloalkyl, or 5-6 membered N containing ring optionally substituted with alkyl, alkylcarboxyl, alkylcarboxyl (alkyl), alkylamino (alkyl)$_{0-2}$, alkylpyrrolidinyl, alkylpiperazinyl, alkylamino alkyl alkoxy, alkyl thiomorpholinyl optionally substituted with oxy or dioxy;

R$^{y'}$ and R$^{z'}$ taken together to form a 3-7 membered ring containing one or more N, O, S atoms; said ring may be optionally substituted by alkyl, halo, hydroxy, alkylhydroxy, oxy, carboxyl, carboxyalkyl, carboxyalkyl, carboxylamino, alkylcarboxylamino, alkylamine, aminoacetyl, pyridinyl, pyrimidinyl, alkoxyphenyl, alkylpiperidyl,

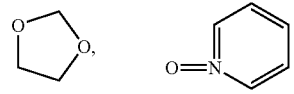

VI. a radical of the formula:

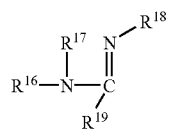

wherein each R$^{16}$ or R$^{17}$ is independently hydrogen or alkyl;

R$^{19}$ is independently alkyl; haloalkyl, phenyl, pyrimidyl, cycloalkyl, thiophenyl or alkylcyano;

R$^{15}$ is alkyl;

VII. a radical of the formula:

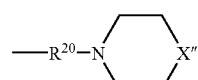

wherein R$^{20}$ is alkyl;

X" is independently C, O, or N; X is optionally substituted with alkyl; dioxy, amino (alkyl)$_{0-2}$, hydroxy, alkylcarboxy, alkylcarboxy alkyl, alkyl alkoxy, alkylmino (alkyl)$_{0-2}$, alkylpyrrolidinyl, alkylphenyl, alkylpyridinyl acetyl, carboxylalkyl, carbonylamino (alkyl)$_{0-2}$, sulfonylalkyl, carboxyl, pyridinyl, pyridinyl substituted with oxy, phenyl, halophenyl,

VIII.

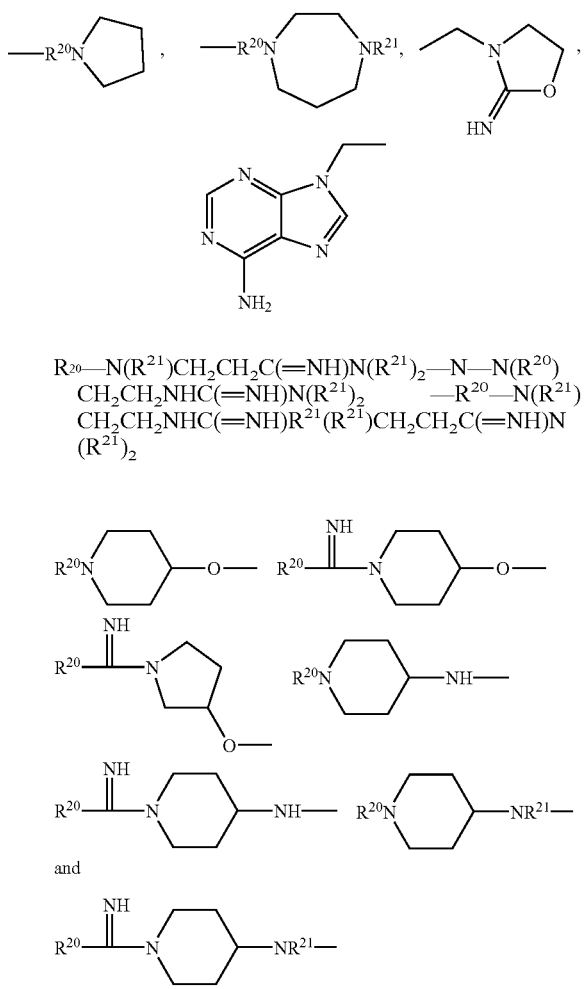

$R^{20}$—N($R^{21}$)CH$_2$CH$_2$C(=NH)N($R^{21}$)$_2$—N—N($R^{20}$)
CH$_2$CH$_2$NHC(=NH)N($R^{21}$)$_2$   —$R^{20}$—N($R^{21}$)
CH$_2$CH$_2$NHC(=NH)$R^{21}$($R^{21}$)CH$_2$CH$_2$C(=NH)N
($R^{21}$)$_2$ and wherein each $R^{20}$ and $R^{21}$ is independently alkyl;
IX. a radical of the formula:

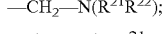—CH$_2$—N($R^{21}R^{22}$);

wherein each $R^{21}$ or R is independently:
alkyl, halo alkyl, alkylphenyl, alkylhydroxy, alkyl alkoxyy, alkylsulfonyl alkyl, alkylcyano, alkylcarboxy, alkylcarbonylamino (alkyl)$_{0-2}$, alkylcarboxyl alkyl, alkylamino which may be optionally substituted with alkyl alkoxy, alkylpiperidinyl, alkylmorpholinyl, alkylpyrrolidinyl, piperazinyl substituted with C$_{0-3}$ alkyl or alkyl;
X. a cycloalkyl, cycloheteroalkyl containing one or more S, N, or O atoms which may be substituted with oxy, alkyl, acetyl, alkylalkylcarboxyl, alkylhydroxy, alkylcarboxy alkyl, alkylamino, alkyl alkoxy, carboxy, amino, phenyl, pyrridinyl or pyrimidinyl; said pyrimidinyl maybe substituted with amino group;
Each $R^{21}$ or $R^{22}$ maybe independently a 5-6 membered ring containing 1 to 4 N,
O, or S atoms which maybe optionally substituted with amino;
and all pharmaceutically acceptable isomers, salts, hydrates, solvates and prodrug derivatives thereof.

In another aspect, the invention relates to methods of using these inhibitors as diagnostic reagents or as therapeutic agents for disease states in mammals characterized by undesired thrombosis or which have coagulation disorders, such as in the treatment or prevention of any thrombotically mediated acute coronary or cerebrovascular syndrome, any thrombotic syndrome occurring in the venous system, any coagulopathy, and any thrombotic complications associated with extracorporeal circulation or instrumentation, and for the inhibition of coagulation in biological samples.

In another aspect, the invention relates to novel compounds which are potent and highly selective inhibitors of isolated factor Xa when assembled in the prothrombinase complex. These compounds show selectivity for factor Xa versus other proteases of the coagulation cascade (e.g. thrombin, etc.) or the fibrinolytic cascade, and are useful as diagnostic reagents as well as antithrombotic agents.

In certain aspects of this invention, compounds are provided which are useful as diagnostic reagents. In another aspect, the present invention includes pharmaceutical compositions comprising a pharmaceutically effective amount of the compounds of this invention and a pharmaceutically acceptable carrier. In yet another aspect, the present invention includes methods comprising using the above compounds and pharmaceutical compositions for preventing or treating disease states characterized by undesired thrombosis or disorders of the blood coagulation process in mammals, or for preventing coagulation in stored blood products and samples. Optionally, the methods of this invention comprise administering the pharmaceutical composition in combination with an additional therapeutic agent such as an antithrombotic and/or a thrombolytic agent and/or an anticoagulant.

Other aspects, objects, features and advantages of the present invention would be apparent to one of ordinary skill in the art from the following detailed description illustrating the preferred embodiments of the invention.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified alkenyl and alkinyl each refer to radicals having from 1-12 carbon atoms, more preferably, 1-8 carbon atoms, most preferably, 1-3 carbon atoms.

The term "alkyl" refers to saturated aliphatic groups including straight-chain, branched-chain and cyclic groups having the number of carbon atoms specified, or if no number is specified, having up to 12 carbon atoms, preferably 1-9 carbon atoms, more preferably, 1-6 carbon atoms, most preferably 1-3 carbon atoms. The term "cycloalkyl" as used herein refers to a mono-, bi-, or tricyclic aliphatic ring having 3 to 14 carbon atoms and preferably 3 to 7 carbon atoms.

As used herein, the terms "carbocyclic ring structure" and "C$_{3-16}$ carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2]bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from loweralkoxy, loweralkyl, loweralkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthyhnethyl, phenethyl, benzyhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5-7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement(s) would result in a stable compound. Nitrogen atoms in a ring structure may be quatemized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocylic and bicyclic heterocylic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cirnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzoffuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocylic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to —$CH_2$—.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, flmaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

In one embodiment, the present invention provides a compound according to the formula I:

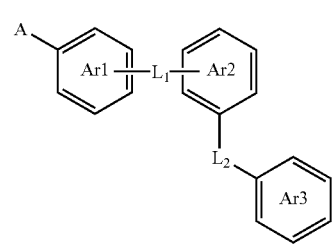

I wherein:

Ar1, Ar2 and Ar3 are each independently selected from the group consisting of:

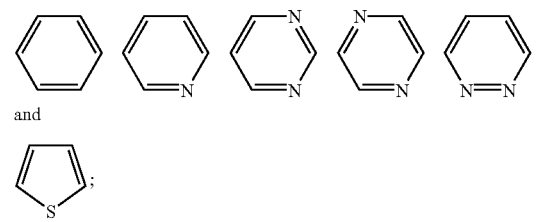

Ar1 may be optionally substituted with 0-2 R; each R is independently selected from the group consisting of halogen, haloalkyl, OMe, Me, CF3, SMe, OCF3, OCH2CH2OMe, OCH2CH2NMe2, NMe2, NHMe, 1-pyrrolidine, 1-piperidine, OH, CN, CONH2, CH2NH2, $SO_2NH2$, $SO_2Me$, C≡CH and C≡CH;

Ar3 may be optionally substituted with 0-2 $R^1$; each $R^1$ is independently selected from the group consisting of halogen, haloalkyl, OMe, Me, CF3, OCF3, C≡CH, C≡CH, —CH=CH2 and CH=CHMe;

L1 is a direct link, —CONH—, —CON(Me)—, —CH2NH2, —NHCO—, or —N(Me)CO—;

L2 is —CONH, —NHCO, or —N(Me)CO—;

Ar2 is independently selected from the group consisting of:

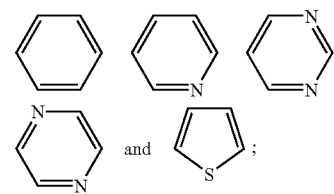

and Ar2 may be optionally substituted with 0-3 $R^{1d}$ groups; each $R^{1d}$ is independently selected from the group consisting of:

H, —Me, halogen, haloalkyl, aryl, heteroaryl, —$CH_3$, —Et, -isopropyl, —$CF_3$, —$NO_2$, —CN, —$CO_2H$, —$CO_2Me$, —$CO_2Et$, —$CONH_2$, —CONHMe, —CONMe₂, —CH₂OH, —CH₂NH₂, —CH₂NHMe, —CH₂NMe₂, —COMe, —C(=NOMe)Me, —C(=NOH)Me, —CH2COOH, —CH2COOEt, —CH2CH2COOEt, —CH2CH2COOH, —CH=CHCN, —CH=CHCOOEt, —CH=CHCOOH, —CH(OH)Me, —CHO, —CH=CH2,

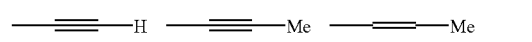
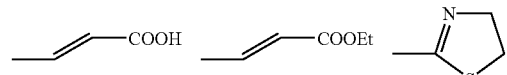
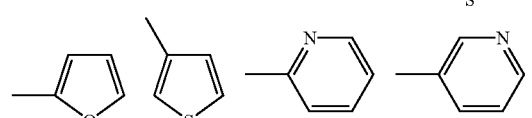
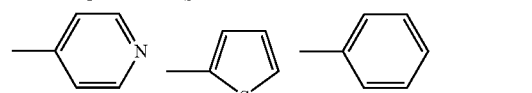
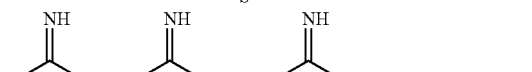
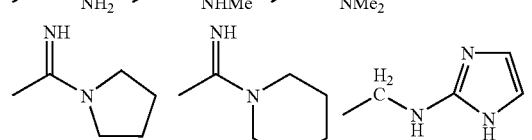
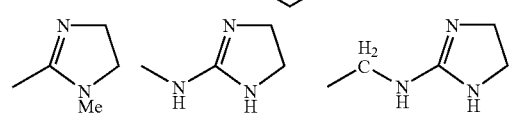
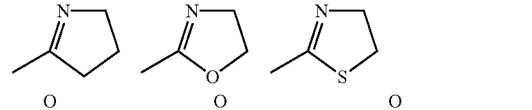
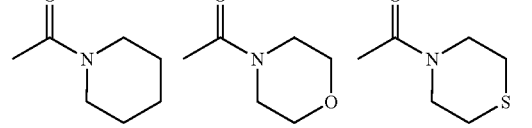
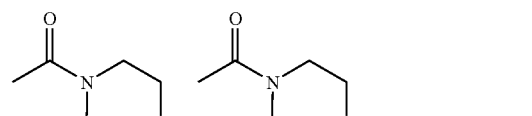
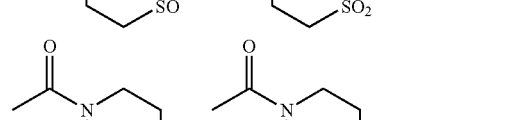
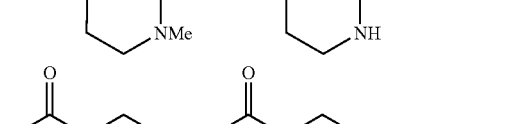
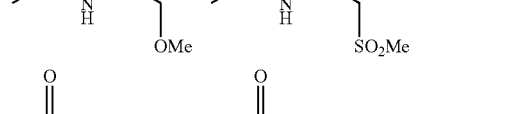
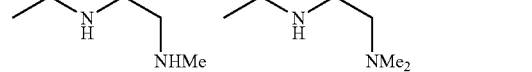

-continued

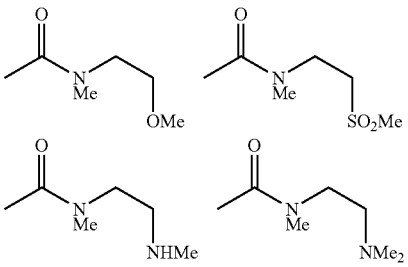

—OH, —OCH₃, —OCF₃, —OCH₂F, —OCHF₂, —OCH₂CF₃, —OCF₂CF₃, —OCH₂CO₂H, —OCH₂CO₂Me, —OCH₂CO₂Et, —OCH₂CONH₂, —OCH₂CONMe₂, —OCH₂CONHMe, —OCH₂CH₂OMe, —OCH2CH₂OH, —OCH₂CH₂OEt, —OCH₂CH₂SO₂Me, —OCH2CH2OCH2CH₂OMe, —OCH2CH2SMe, —OCH2CH2SO2Me, —OCH₂CH₂NH₂, —OCH₂CH₂NHMe, —OCH₂CH₂NMe₂, —OCH2CH2N(CH₂CH₂OMe)₂, —OCH2CH₂OAc, —OCH₂CH₂OH, —OCH2CH₂OCH2CH₂OMe, —OCH2CH2NH2, —OCH2CH2CH2N(Me)CH2CH₂OH,

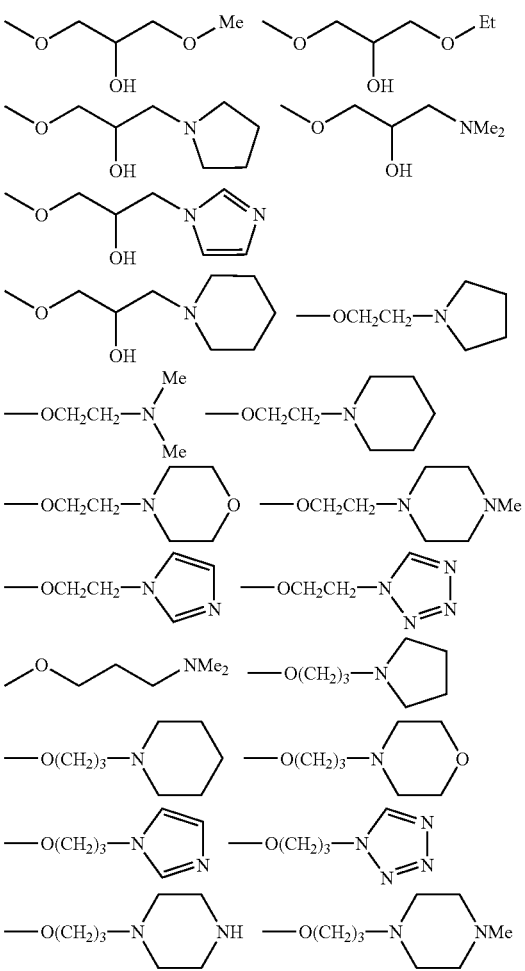

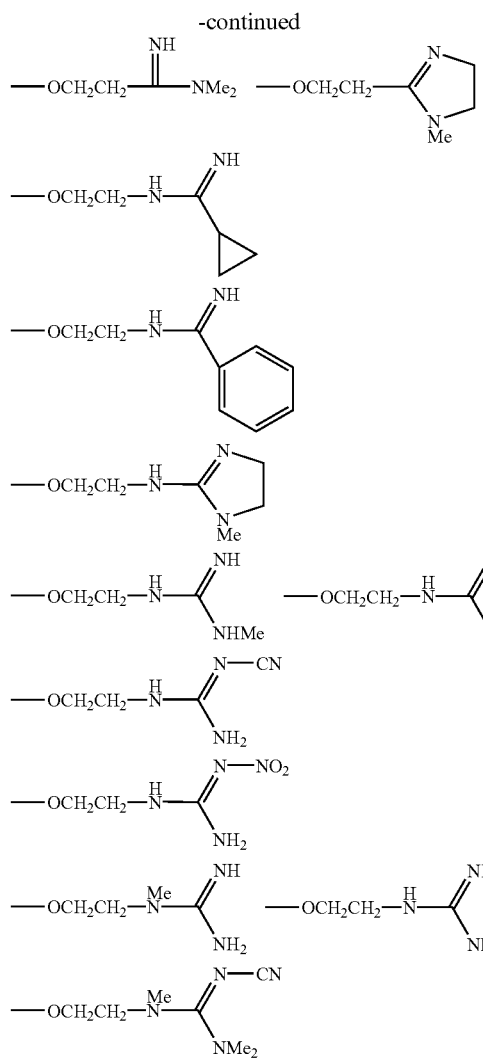

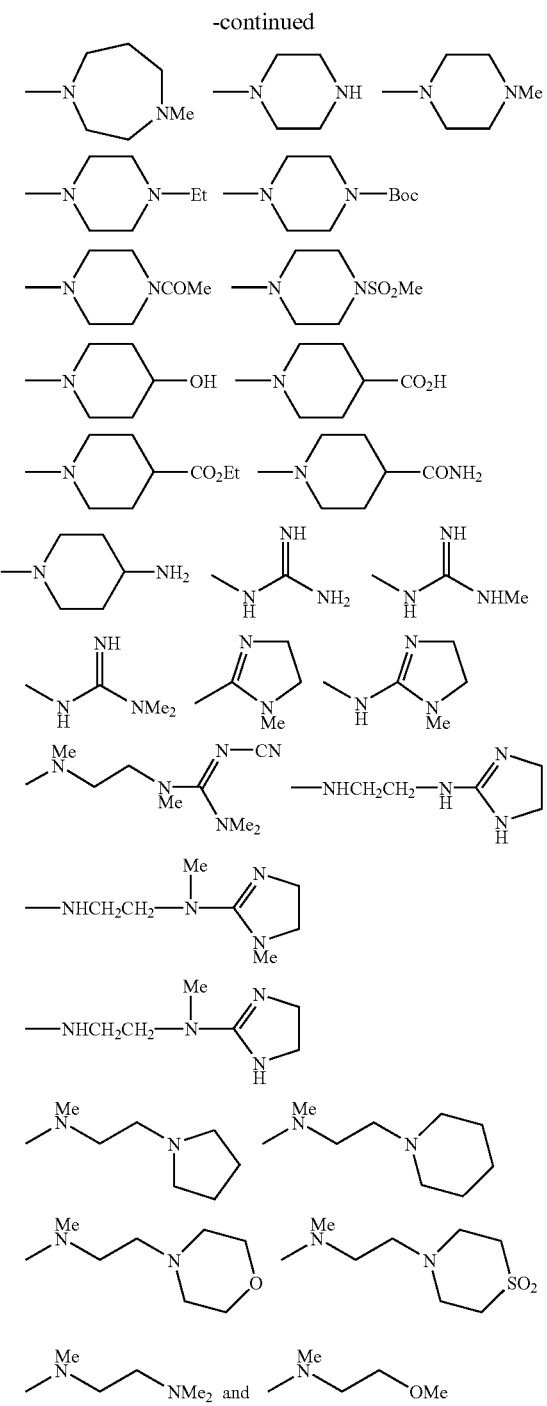

—SCH$_2$CH$_2$OMe, —SO$_2$CH$_2$CH$_2$OMe, —SCH$_3$, —SEt, —SPh, —SO2Ph, —SO$_2$NH$_2$, —SO$_2$CH$_3$, —SO$_2$NMe$_2$, —SO2CH2CH2NMe2, —NH$_2$, —NMe$_2$, —NHMe, —NHSO$_2$Me, —NHCOMe, —NHCH$_2$CH$_2$NHMe, —NHCH$_2$CH$_2$NMe$_2$, —N(CH$_2$CH$_2$OH)$_2$, —N(CH$_2$CH$_2$OMe)$_2$, —NHCH$_2$CO$_2$H, —NHCH$_2$CO$_2$Et, —NHCH$_2$CO$_2$Et, —NHCH$_2$CONH$_2$, —NHCH$_2$CONMe$_2$, —NHCH$_2$CONHMe, —N(CH$_3$)CH$_2$CO$_2$H, —N(CH$_3$)CH$_2$CO$_2$Et, —(NMe)CH2COOH, —N(Me)CH2CONH2, —N(Me)CH2CH2NMe2, —N(Me)CH2CH$_2$OMe, —N(Me)CH2CH$_2$OH, —NHCH2CH$_2$OMe, —NHCH$_2$CH$_2$OMe,

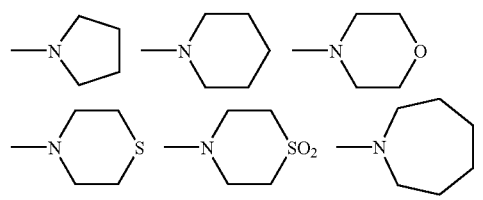

A is independently selected from the group consisting of:

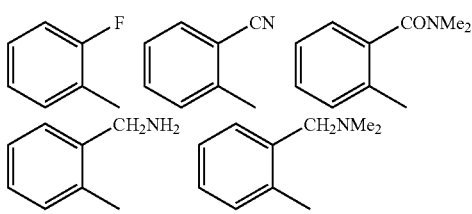

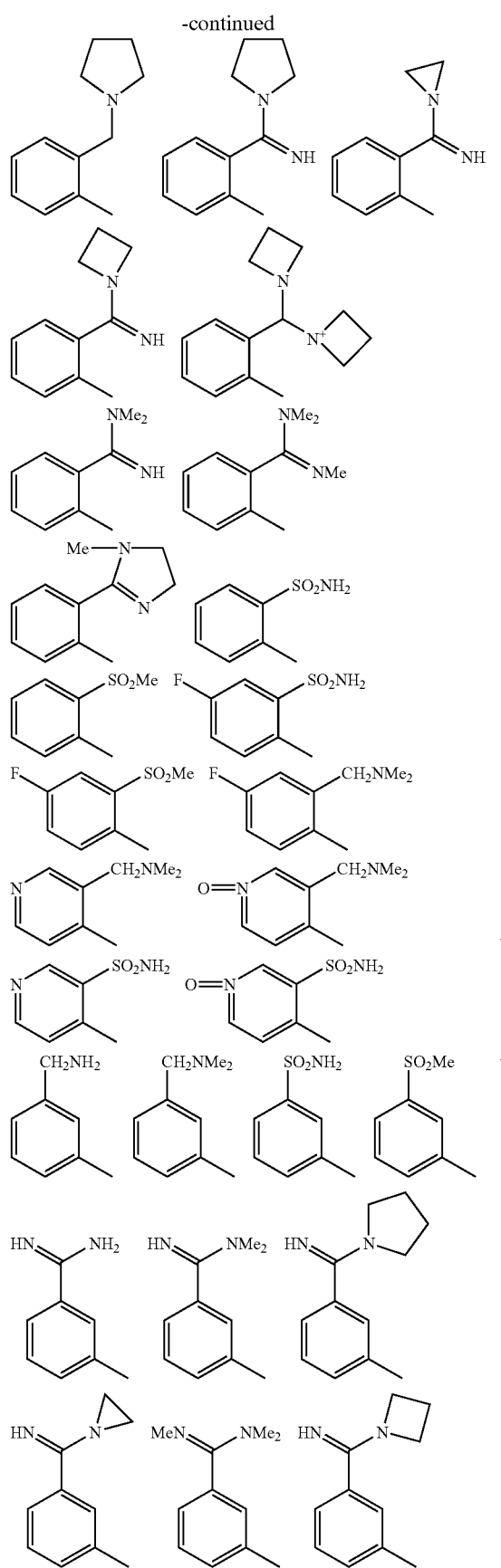
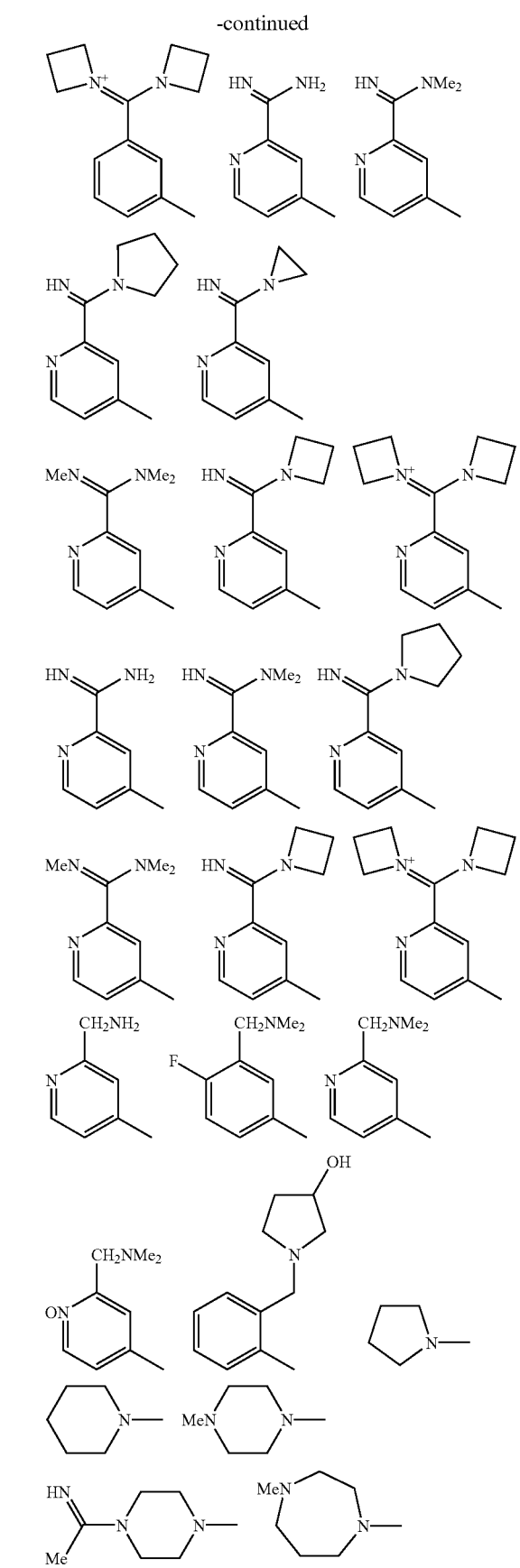

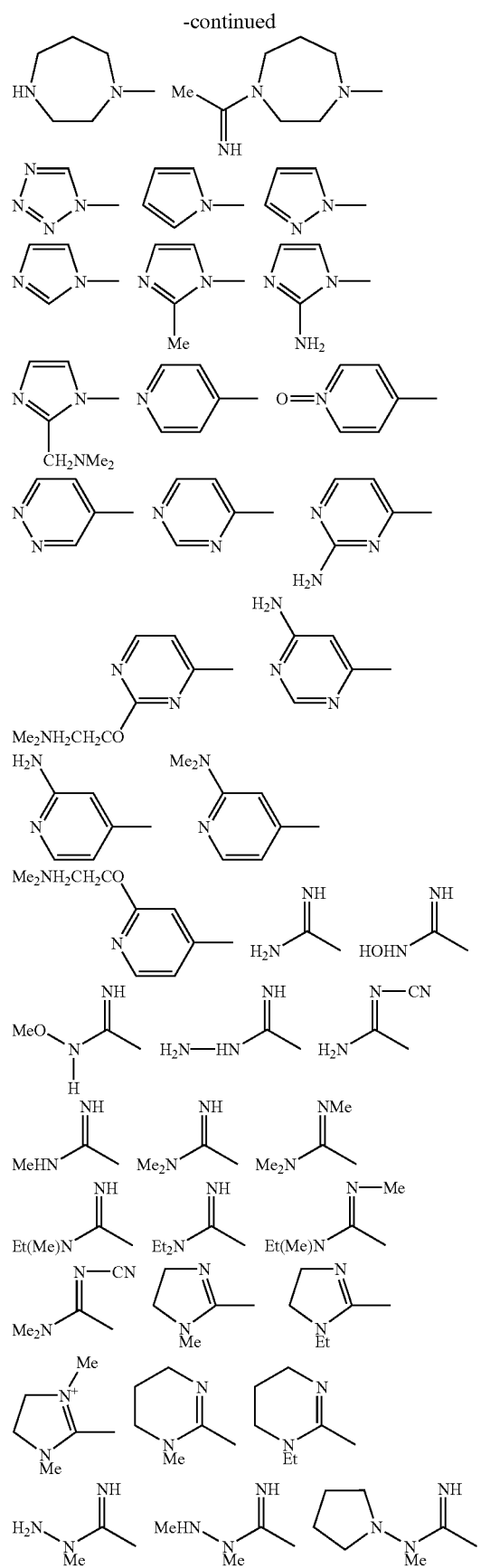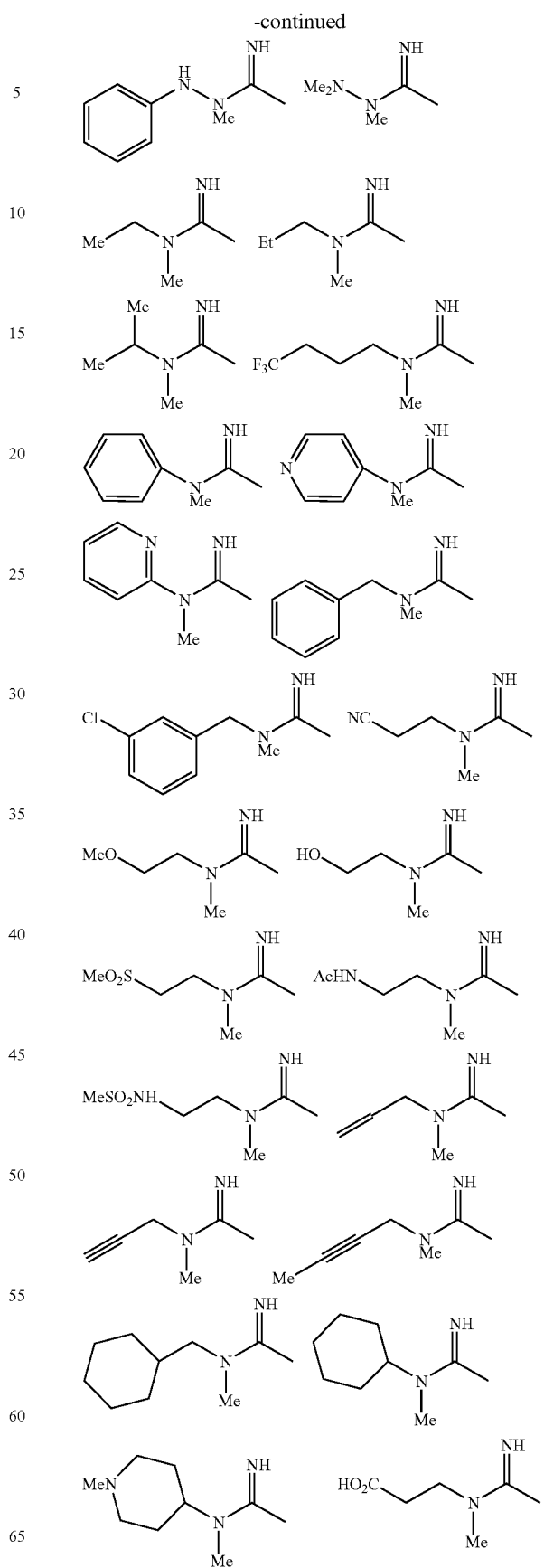

-continued
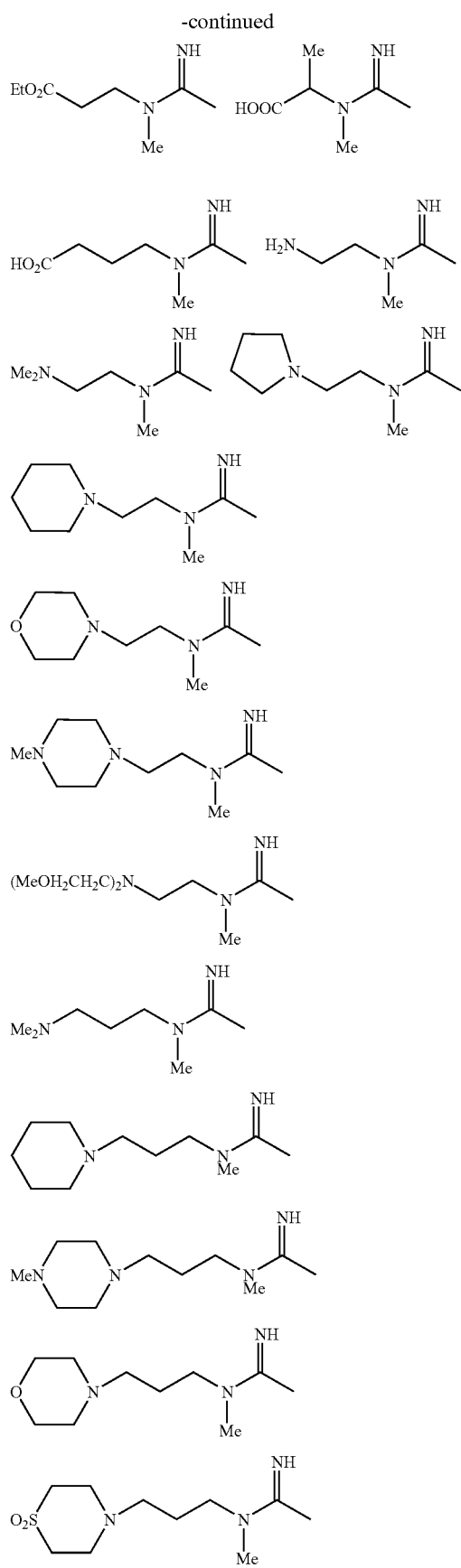
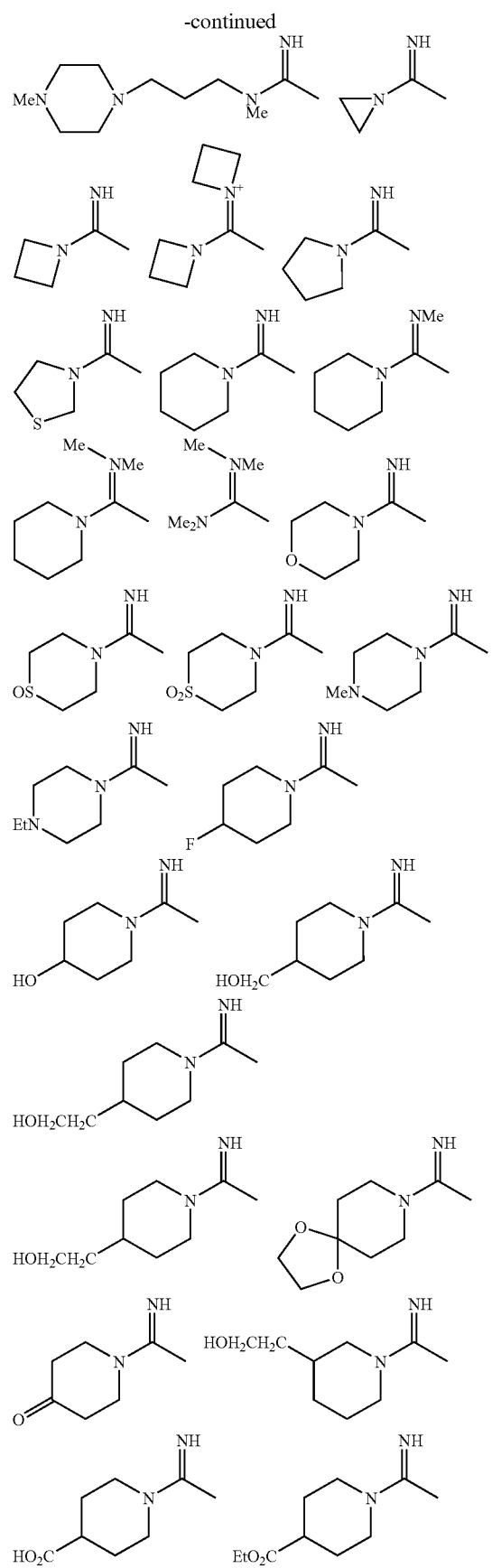

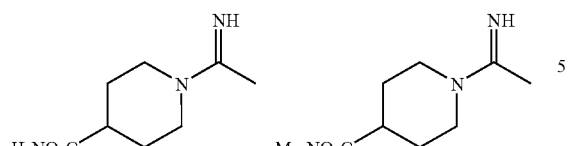
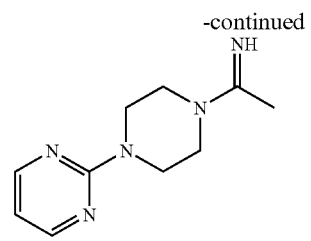
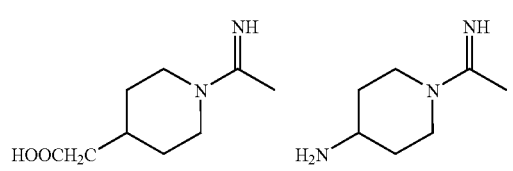
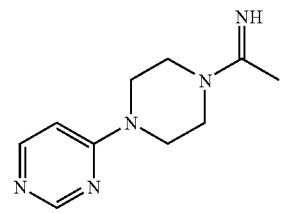
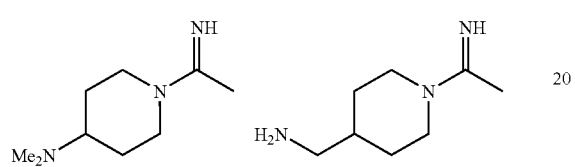
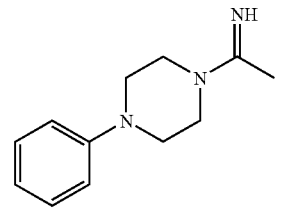
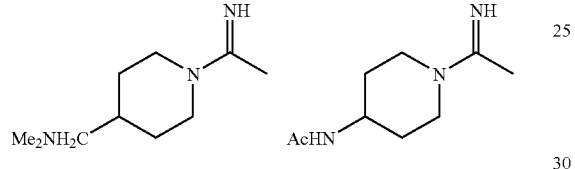
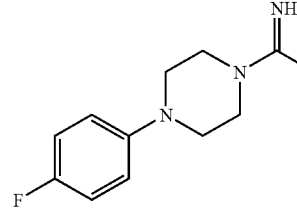
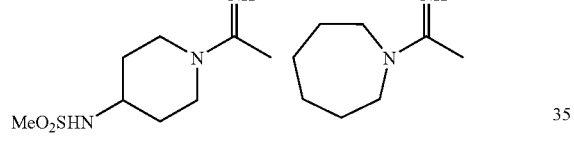
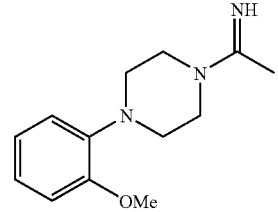
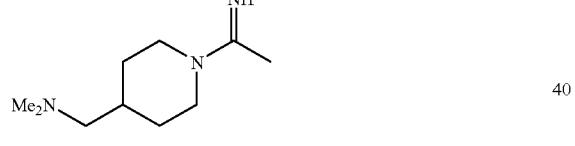
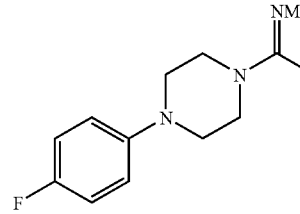
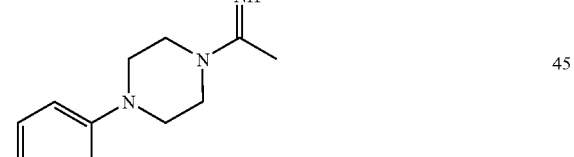
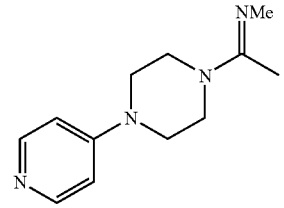
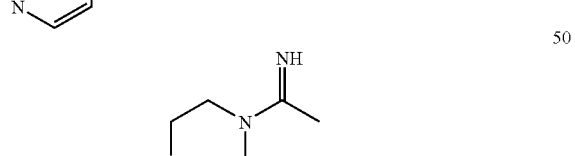
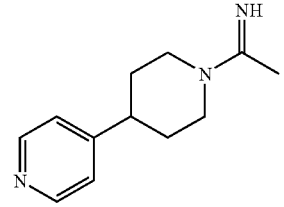
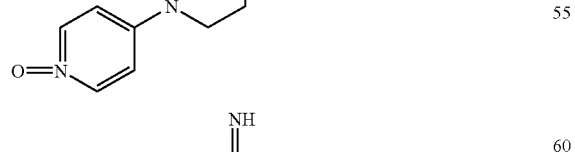
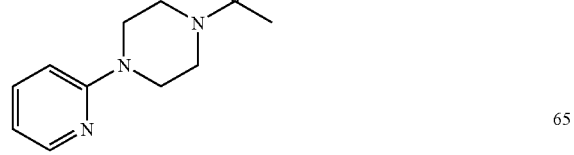

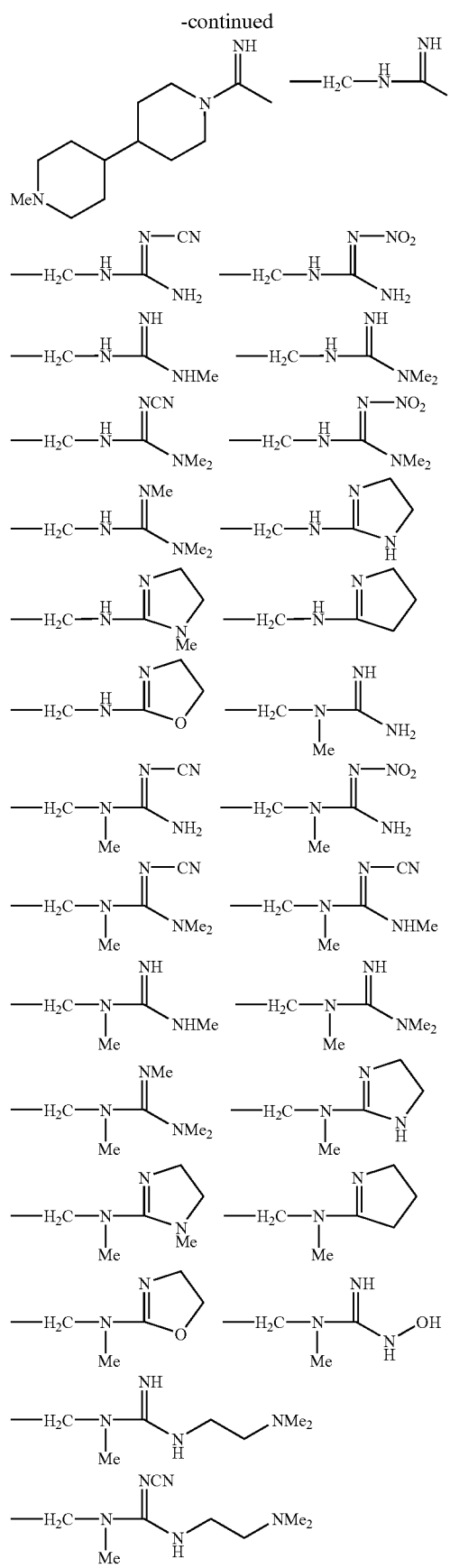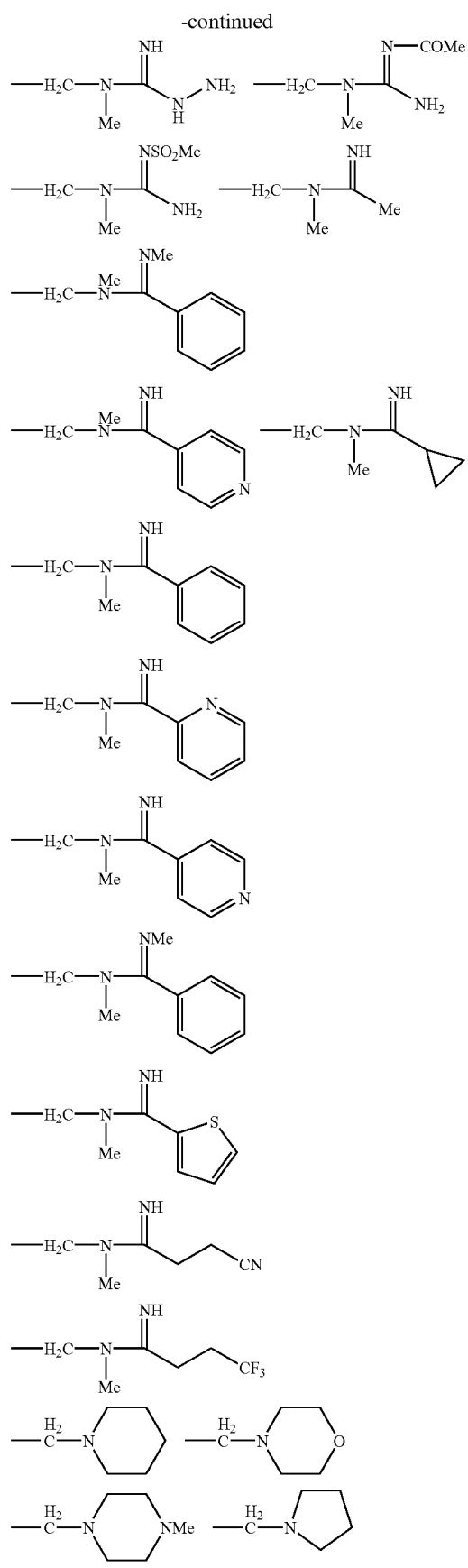

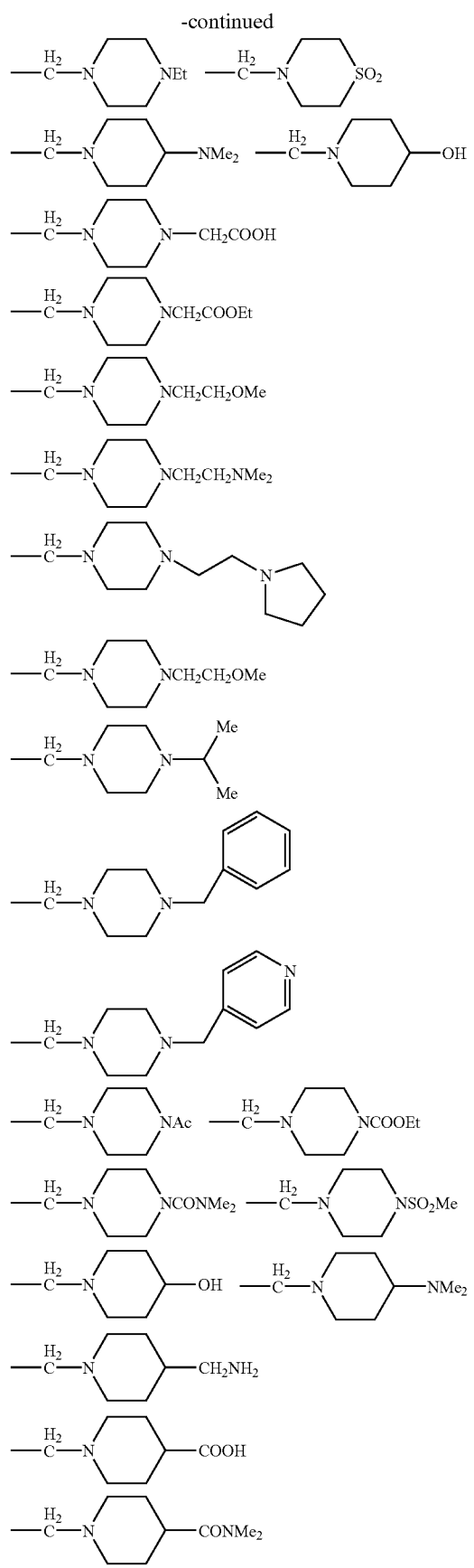
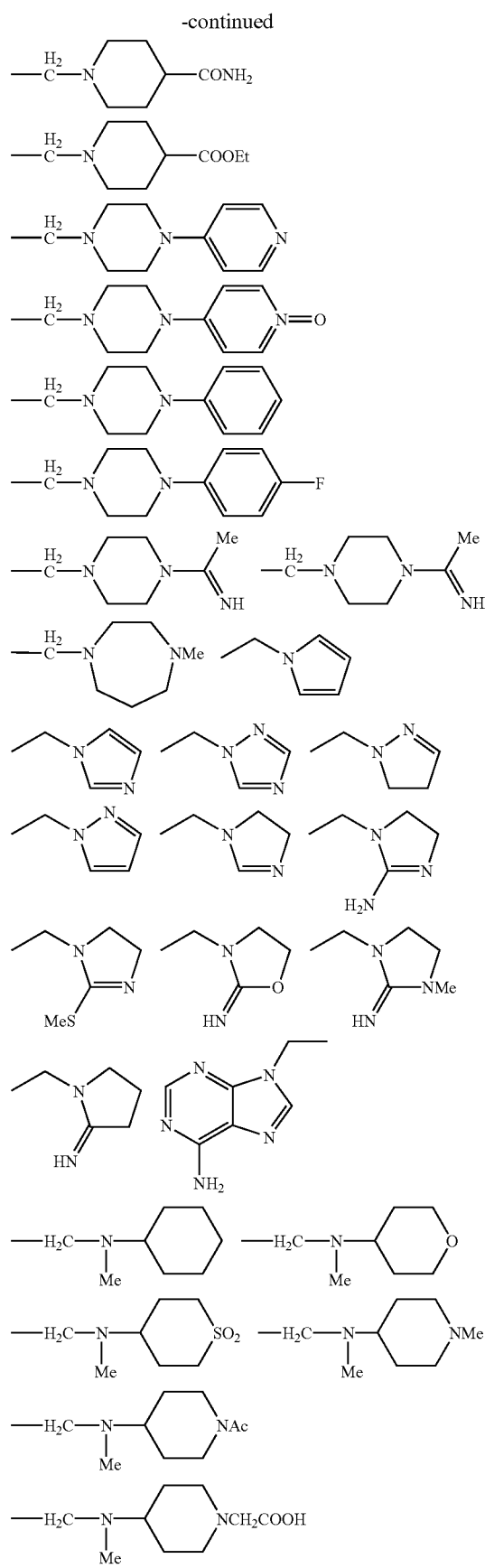

-continued
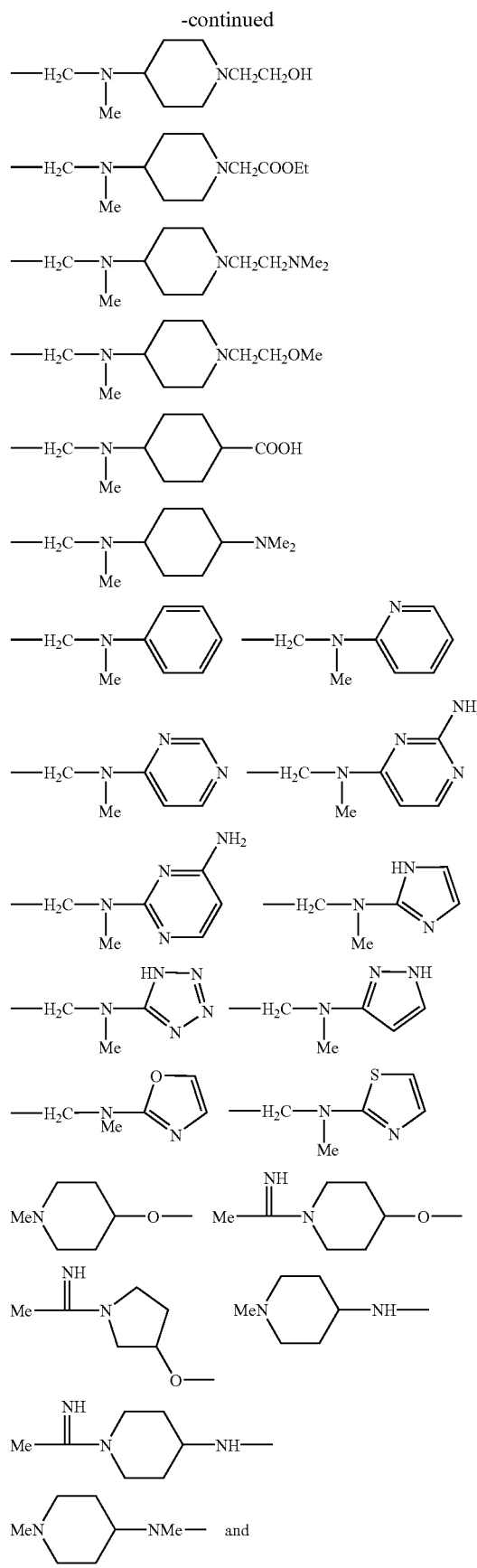
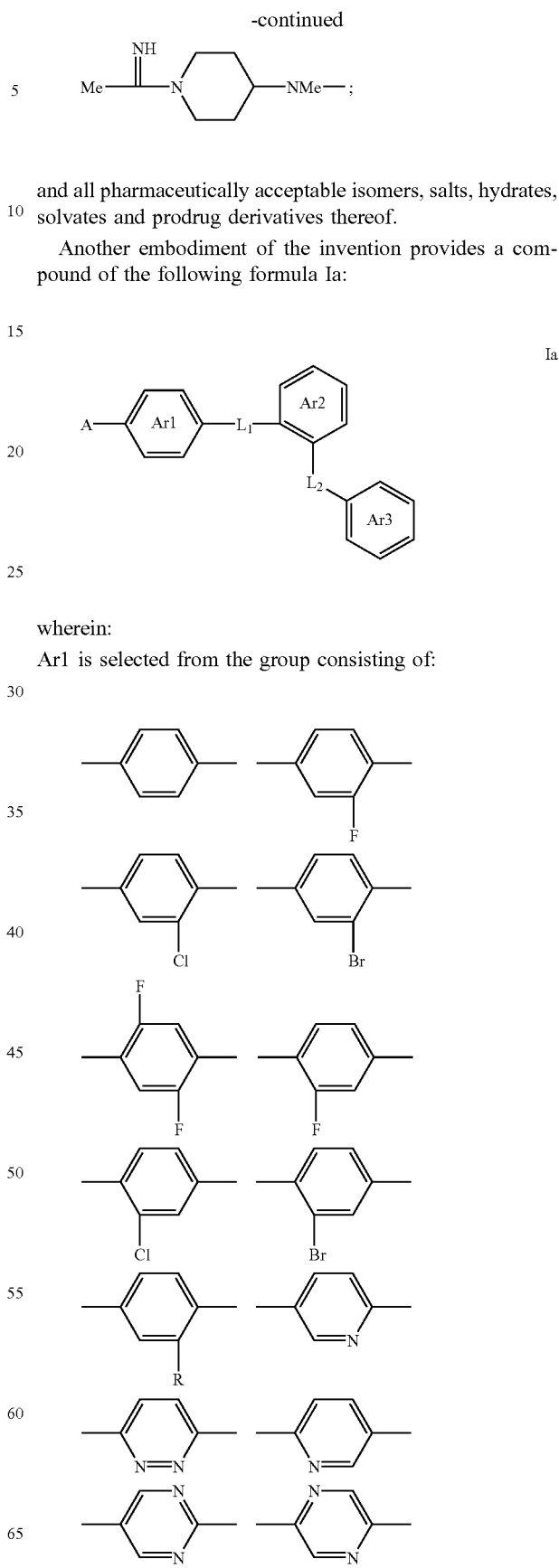
and all pharmaceutically acceptable isomers, salts, hydrates, solvates and prodrug derivatives thereof.
Another embodiment of the invention provides a compound of the following formula Ia:
wherein:
Ar1 is selected from the group consisting of:

-continued

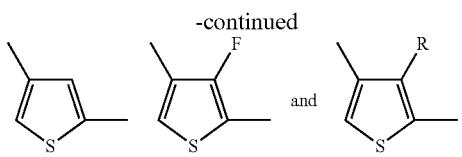 and 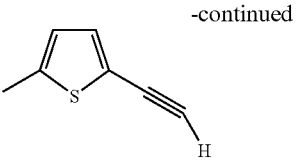

each R is independently Cl, OMe, NMe2, OCH2CH2OMe, —OCH2CH2NMe2,

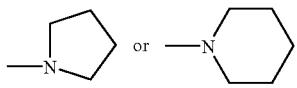

L1 is a direct link, —CONH, —CH2NH—, or —NHCO—;
L2 is —CONH, or —NHCO;
Ar3 is independently selected from the group consisting of:

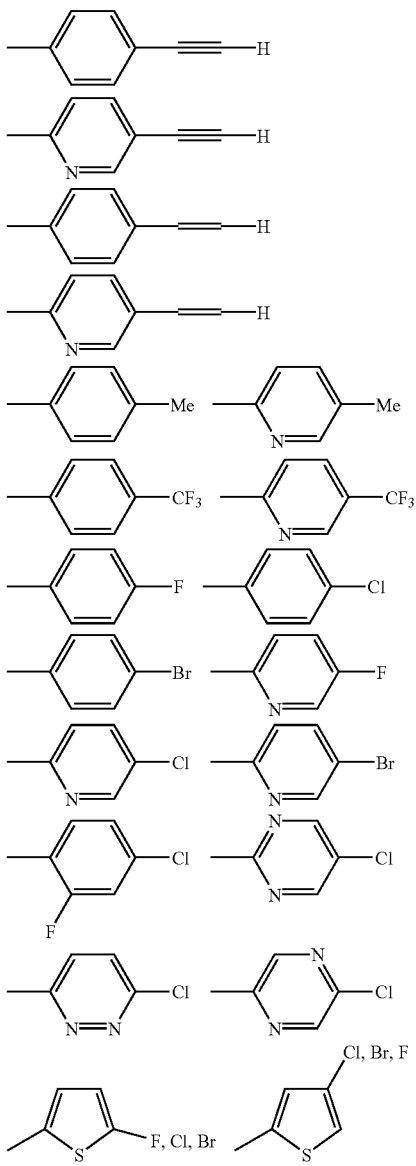

-continued

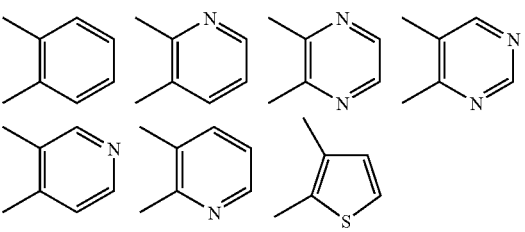

Ar2 is independently selected from the group consisting of:

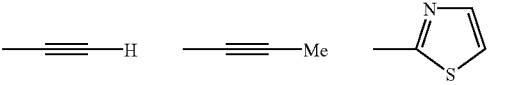

And Ar2 may be optionally substituted with 0-3 $R^{1d}$ group; each $R^{1d}$ is independently selected from the group consisting of:

H, —Me, —F, —Cl, —Br, I, —$CH_3$, —$CF_3$, —CN, —$CO_2H$, —$CO_2Me$, —$CO_2Et$, —$CONH_2$, —CONHMe, —$CONMe_2$, —$CH_2NHMe$, —$CH_2NMe_2$, —COMe, —CH2COOH,

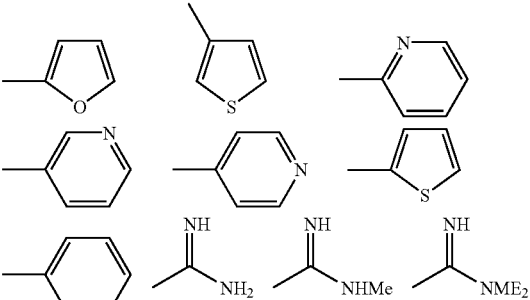

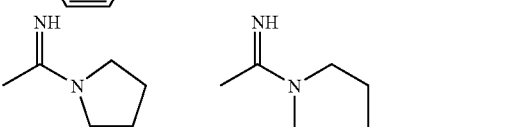

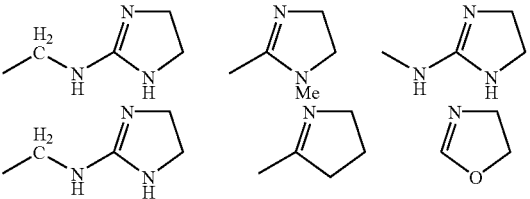

—$OCH_3$, —$OCF_3$, —$OCH_2F$, —$OCHF_2$, —$OCH_2CF_3$, —$OCF_2CF_3$, —$OCH_2CO_2H$, —$OCH_2CO_2Me$, —$OCH_2CO_2Et$, —$OCH_2CONH_2$, —$OCH_2CONMe_2$, —$OCH_2CONHMe$, —$OCH_2CH_2OMe$, —$OCH_2CH_2NHMe$, —$OCH_2CH_2NMe_2$,

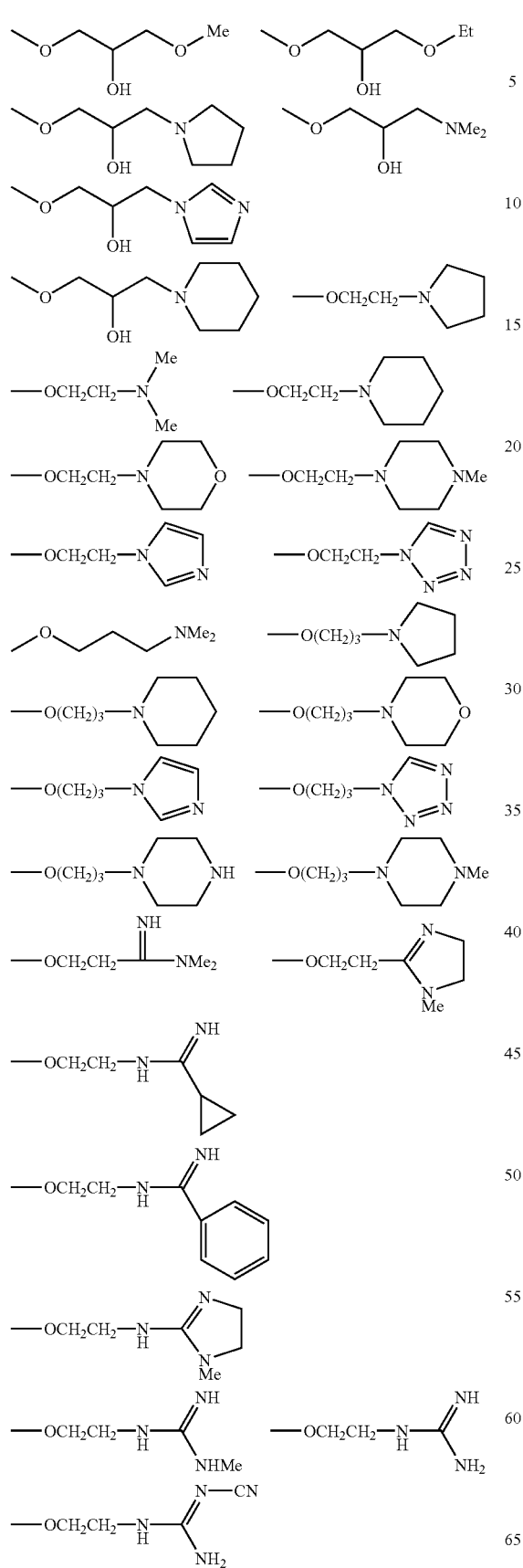
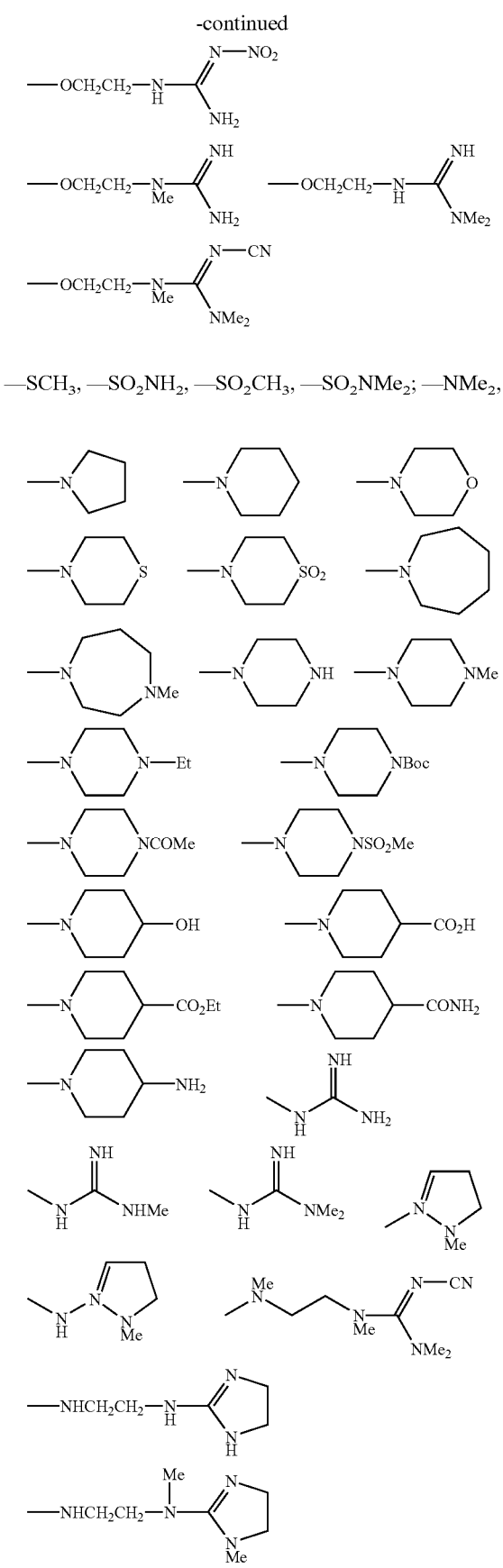

-continued
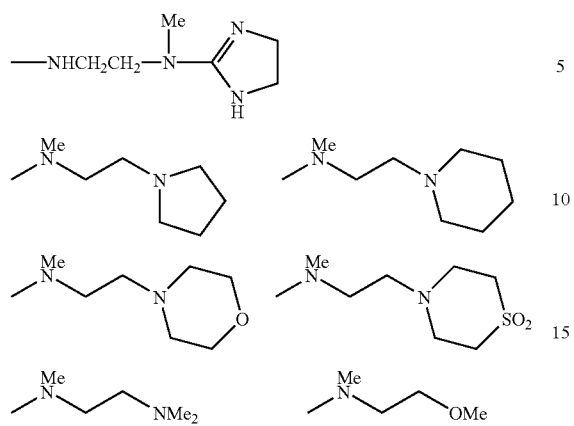
A is independently selected from the group consisting of:
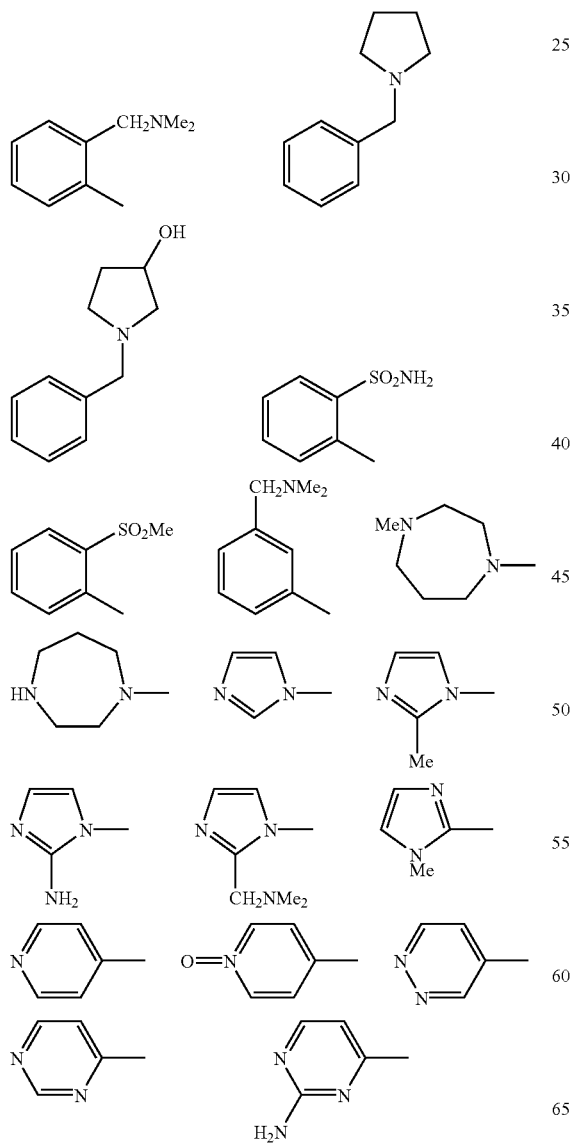
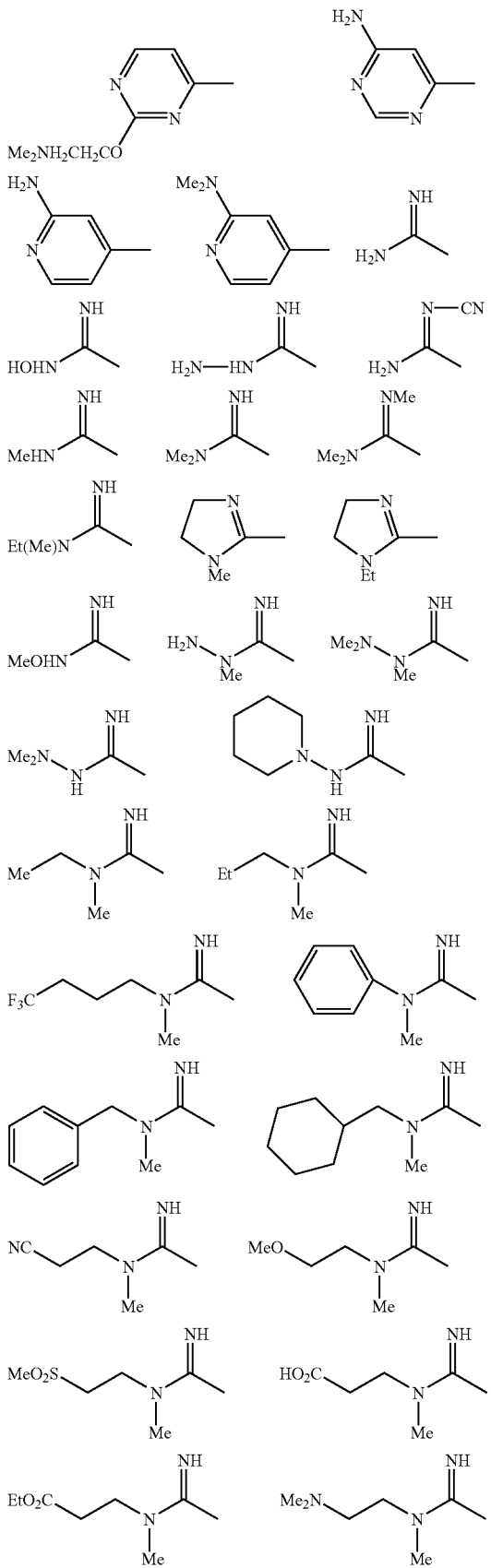

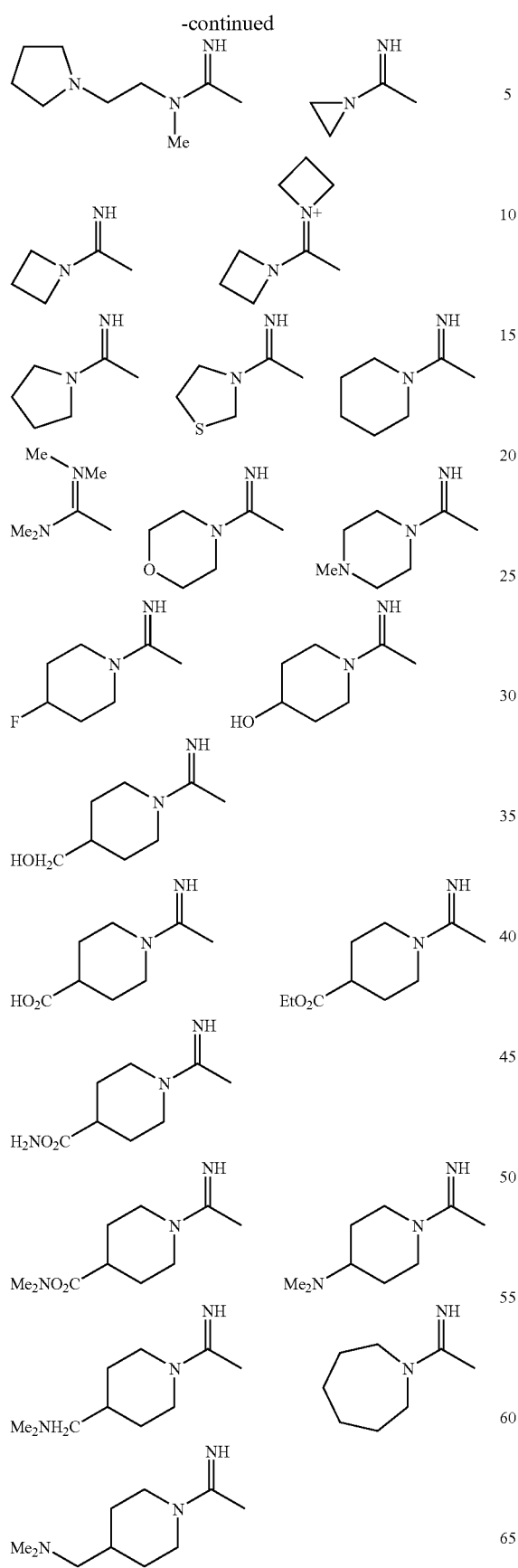
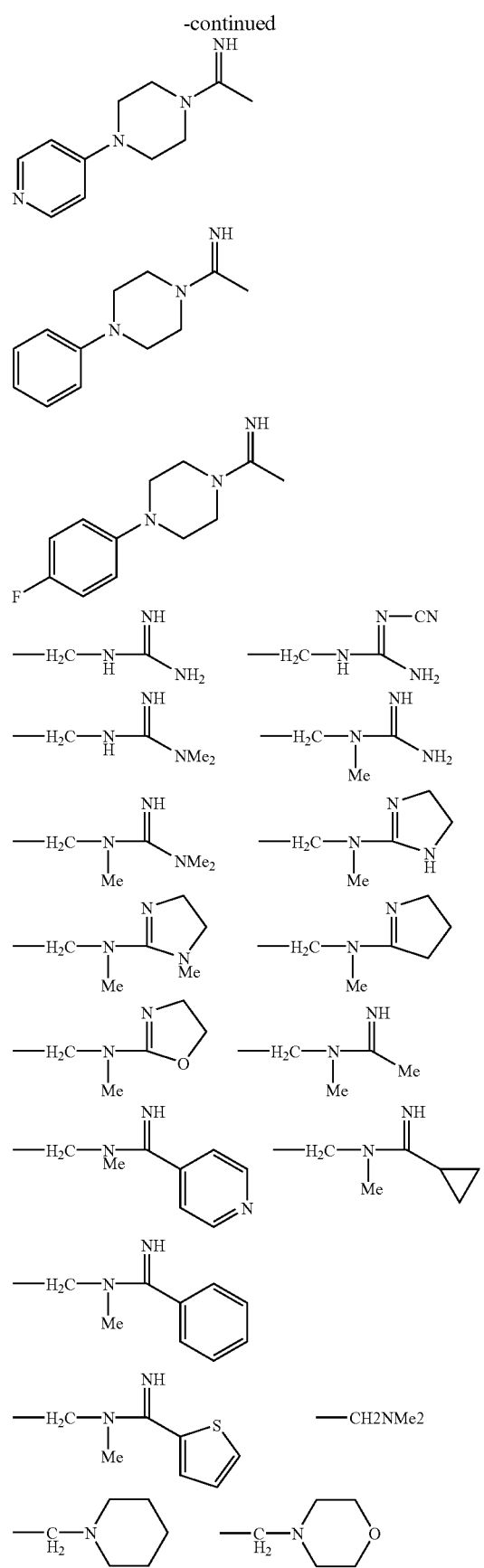

-continued and all pharmaceutically acceptable isomers, salts, hydrates, solvates and prodrug derivatives thereof.

Another embodiment of the invention provides a compound of the following formula:

wherein:
Ar1 is independently selected from:

each R is independently Cl, OMe, NHMe, NMe2, OCH2CH$_2$OMe, or —OCH2CH2NMe2;

Ar3 is independently selected from group consisting of:

-continued

Ar2 is independently selected from the group consisting of:

and ;

Ar2 may be optionally substituted with 0-3 $R^{1d}$ groups; each $R^{1d}$ is independently the group consisting of:

H, —Me, —Cl, Br, C≡CH, C≡CH,

—OCH$_3$, —OCF$_3$, —OCH$_2$F, —OCHF$_2$, —OCH$_2$CF$_3$, —OCF$_2$CF$_3$, —OCH$_2$CO$_2$H, —OCH$_2$CO$_2$Me, —OCH$_2$CO$_2$Et, —OCH$_2$CONH$_2$, —OCH$_2$CONMe$_2$, —OCH$_2$CONHMe, —OCH$_2$CH$_2$OMe, —OCH$_2$CH$_2$NMe$_2$,

-continued

—NMe$_2$, —NHCH$_2$CH$_2$NMe$_2$, —N(CH$_2$CH$_2$OMe)$_2$, —NHCH$_2$CO$_2$H, —NHCH$_2$CO$_2$Et, —NHCH$_2$CO$_2$Et, —NHCH$_2$CONH$_2$, —NHCH$_2$CONMe$_2$, —N(Me)CH2CH2NMe2, —N(Me)CH2CH$_2$OMe, —NHCH2CH$_2$OMe, —NHCH$_2$CH$_2$OMe,

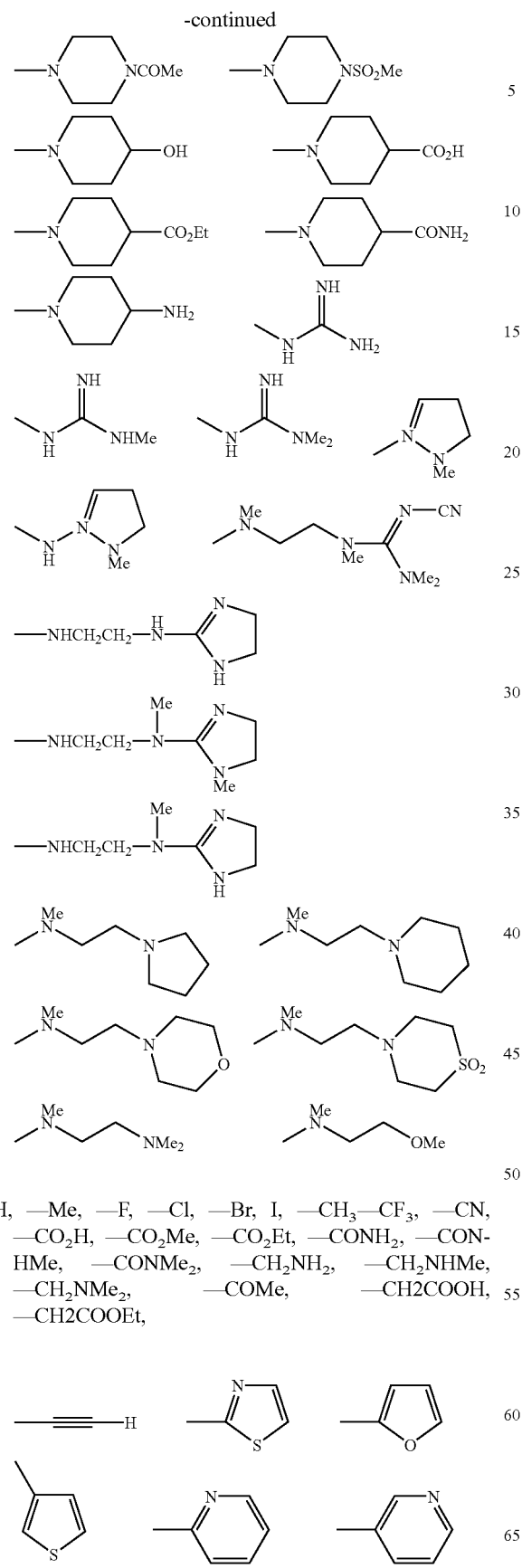
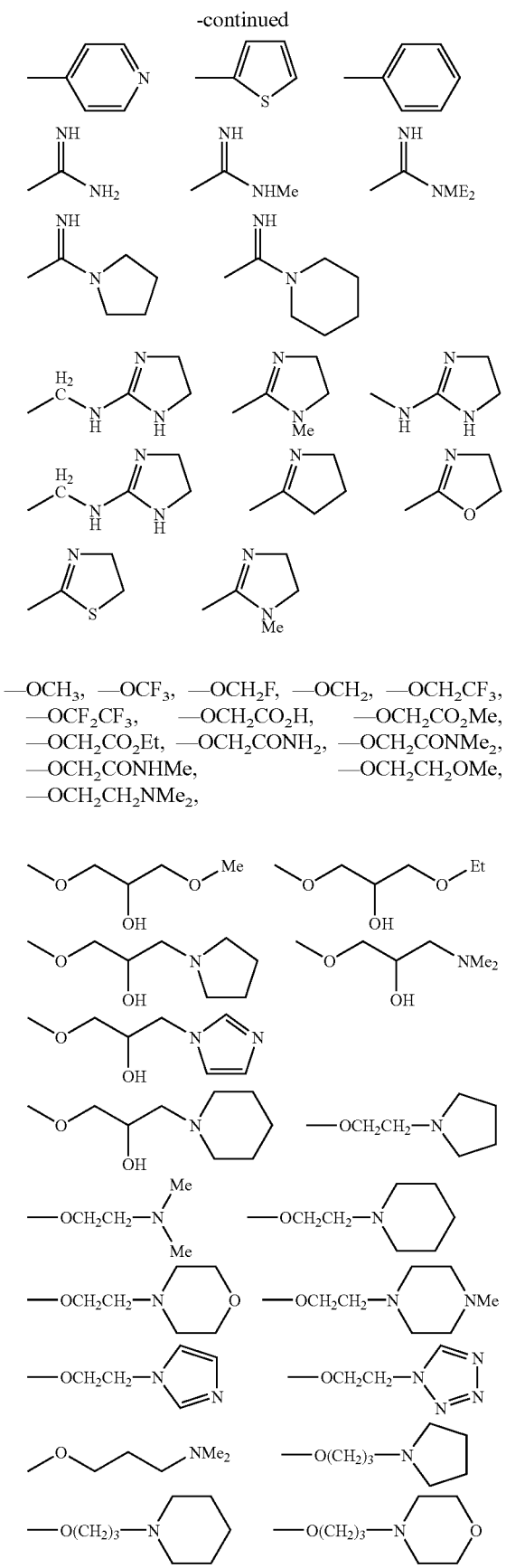

-continued
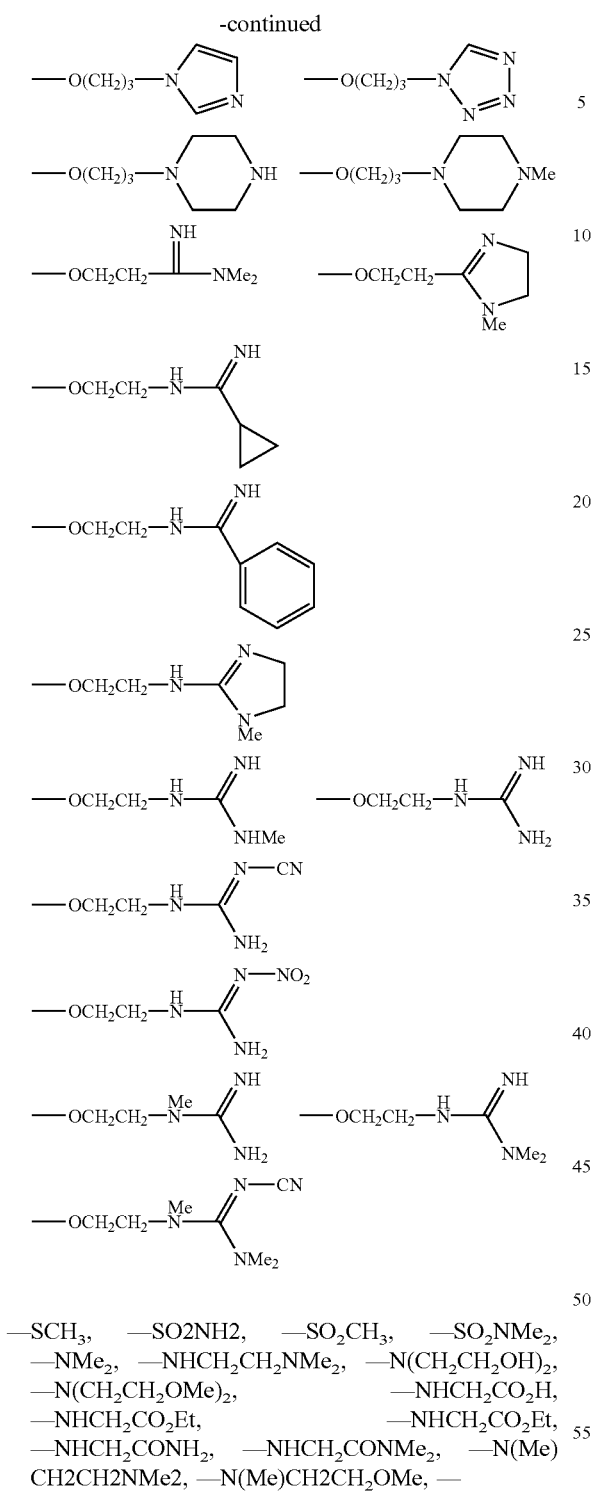
—SCH₃, —SO2NH2, —SO₂CH₃, —SO₂NMe₂, —NMe₂, —NHCH₂CH₂NMe₂, —N(CH₂CH₂OH)₂, —N(CH₂CH₂OMe)₂, —NHCH₂CO₂H, —NHCH₂CO₂Et, —NHCH₂CO₂Et, —NHCH₂CONH₂, —NHCH₂CONMe₂, —N(Me)CH2CH2NMe2, —N(Me)CH₂CH₂OMe, —
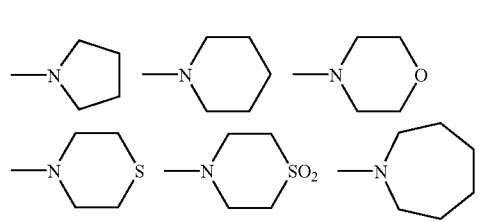
-continued
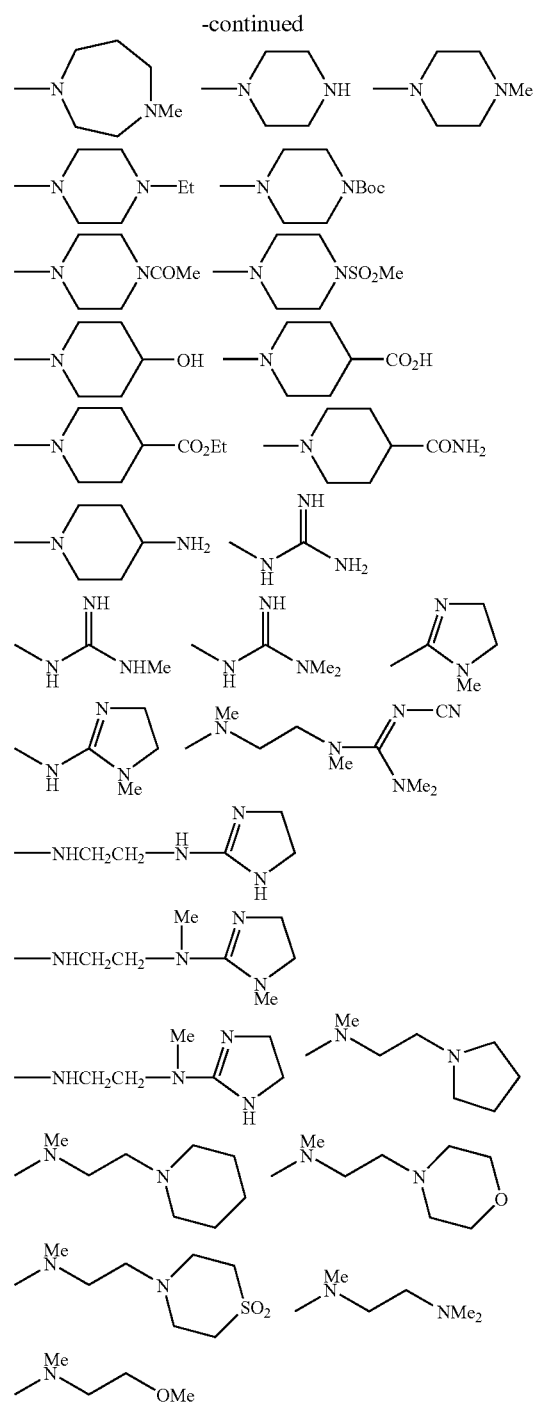
A is independently selected from the group consisting of:
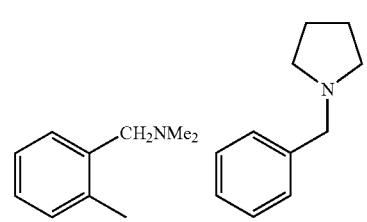

-continued
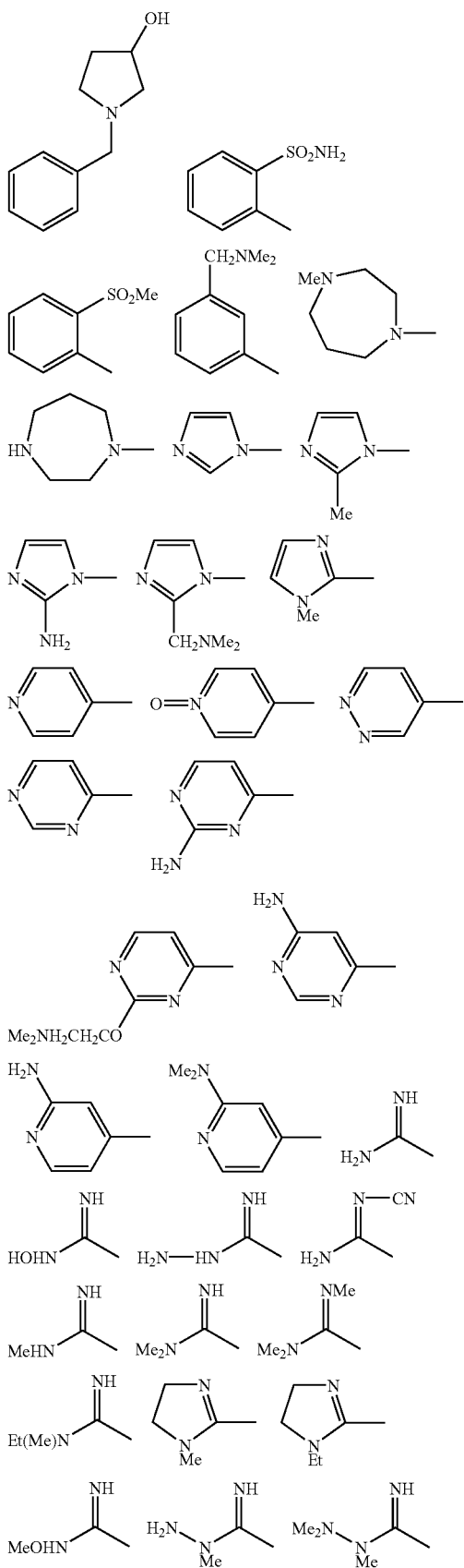
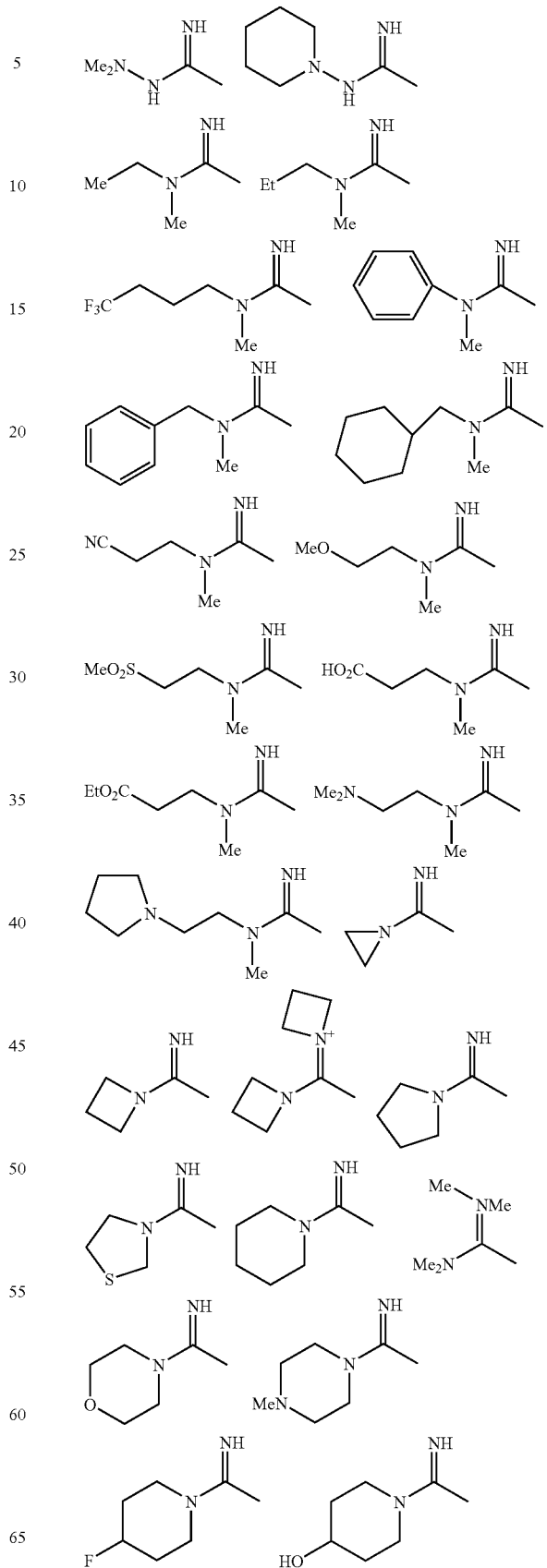

-continued
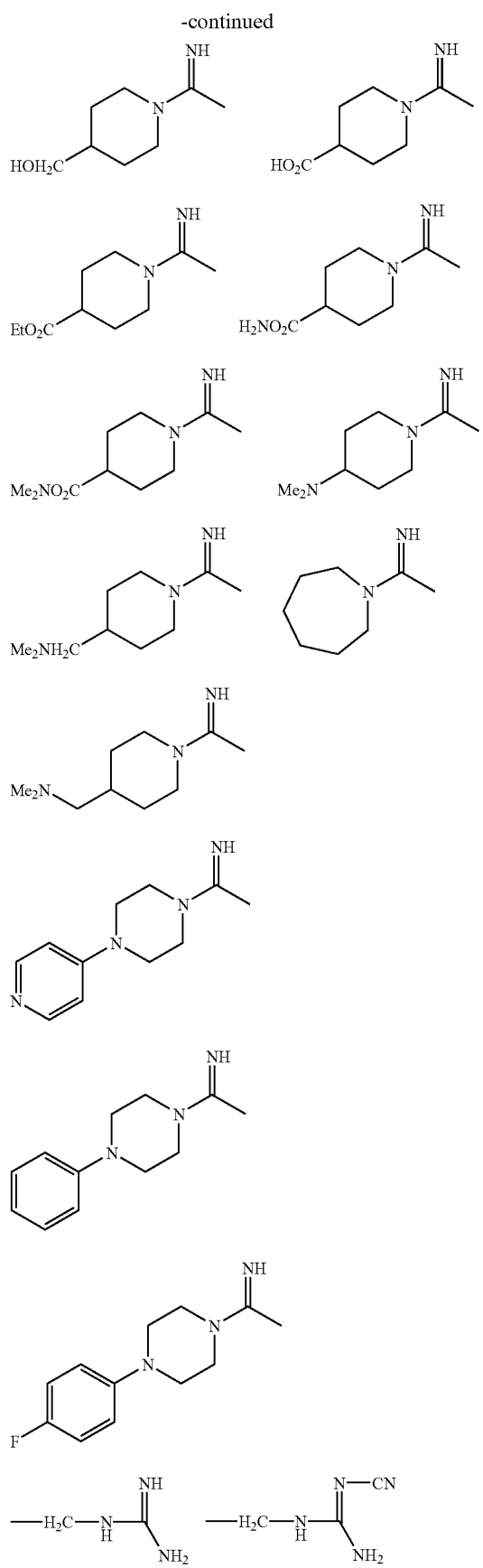
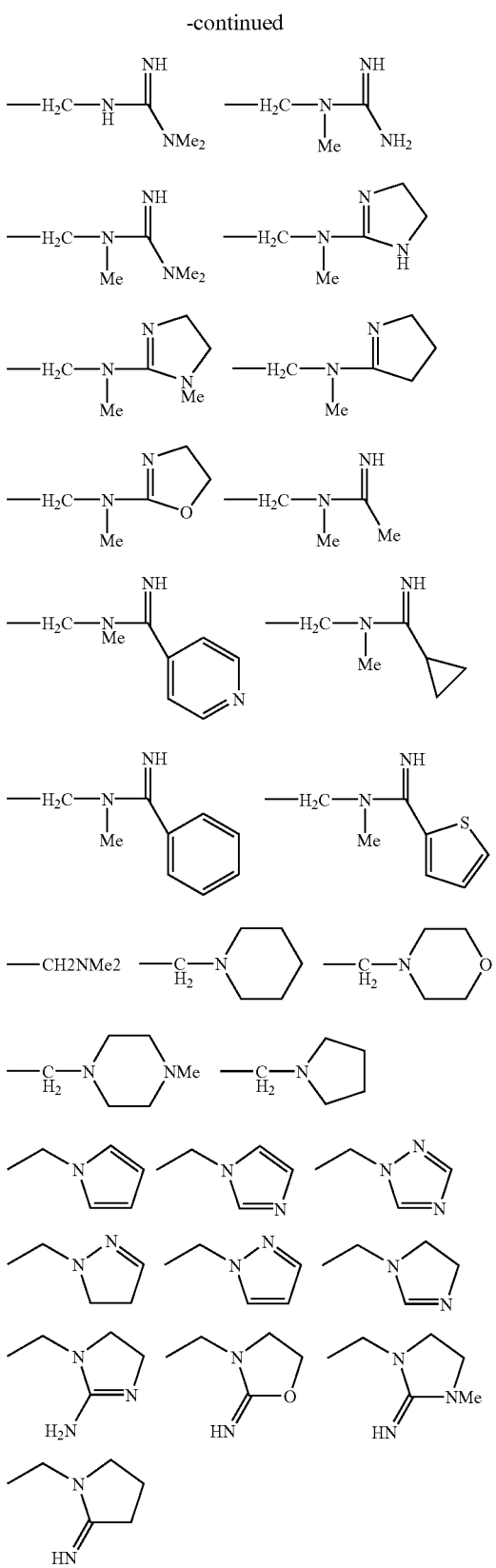
and all pharmaceutically acceptable isomers, salts, hydrates, solvates and prodrug derivatives thereof.

Still, a further embodiment of the invention provides a compound of the following formula:

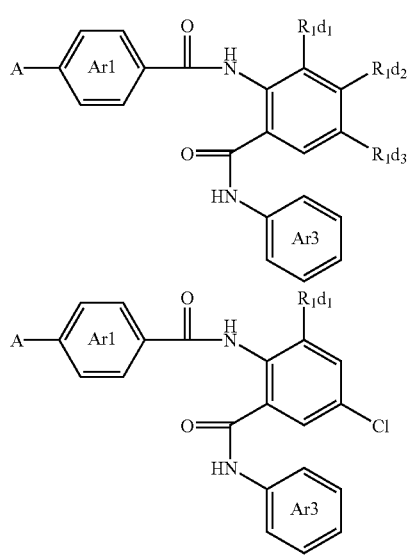

wherein:
Ar1 is independently selected from the group consisting of:

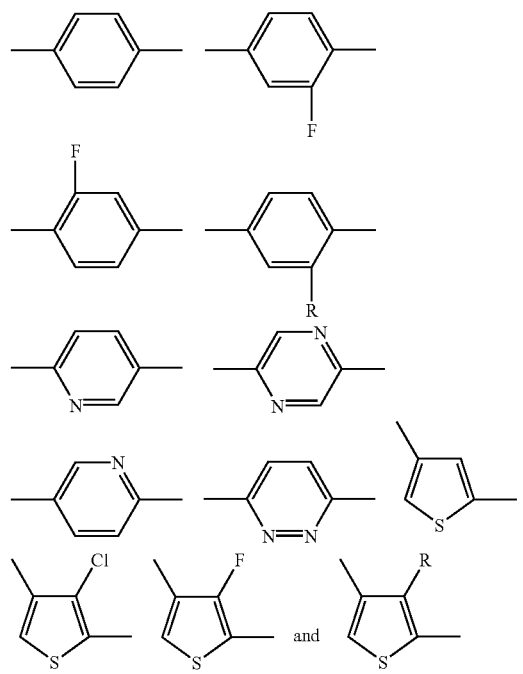

each R is independently Me, OMe, NH2, NHe, NMe2, —SMe, —SO2Me, OCH2CH2OMe, —OCH2CH2NMe2, Ar3 is independently selected from the group consisting of:

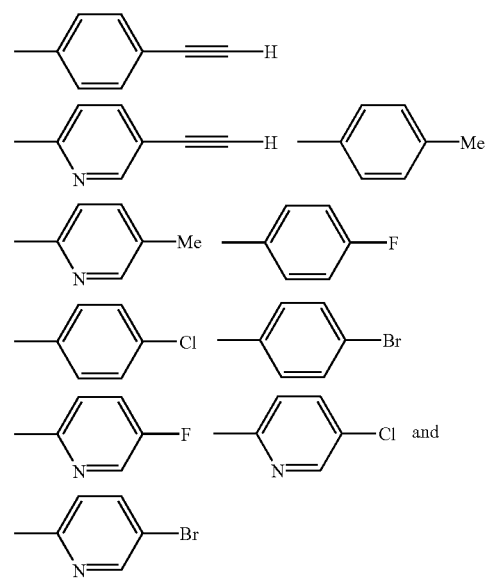

each $R^{1d1}$ is independently selected from the group consisting of:

H, —Me, —Cl, —OCH$_3$, —OCF$_3$, —OCH$_2$F, —OCHF$_2$, —OCH$_2$CF$_3$, —OCF$_2$CF$_3$, —OCH$_2$CO$_2$H, —OCH$_2$CO$_2$Me, —OCH$_2$CO$_2$Et, —OCH$_2$CONH$_2$, —OCH$_2$CONMe$_2$, —OCH$_2$CONHMe, —OCH$_2$CH$_2$OMe, —OCH$_2$CH$_2$NMe$_2$,

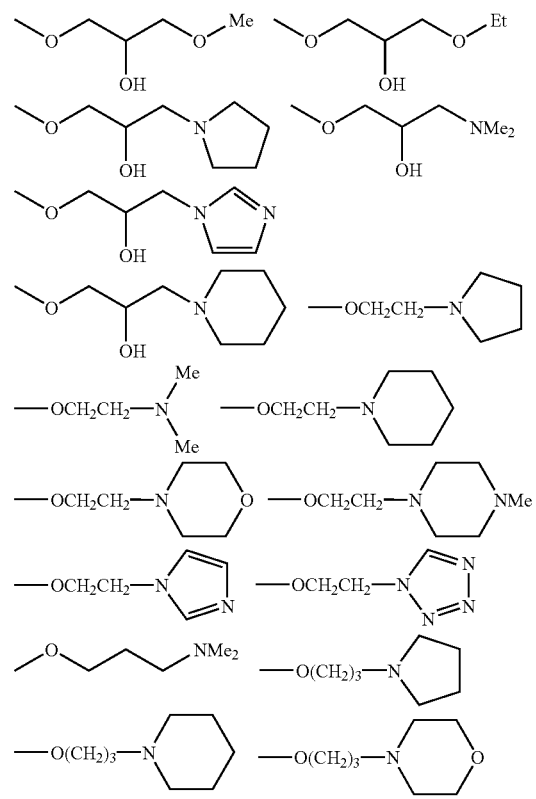

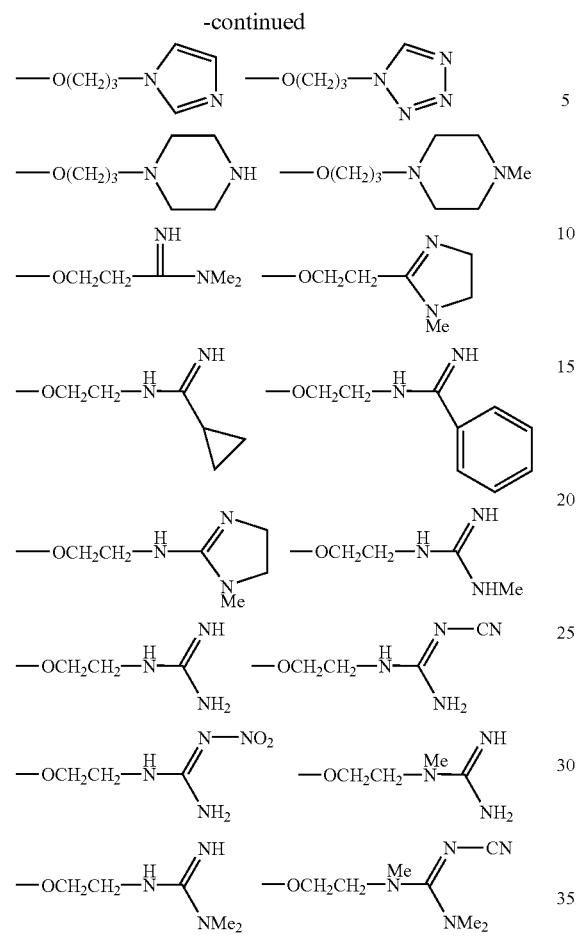
—NMe2, —NHCH₂CH₂NMe₂, —N(CH₂CH₂OMe)₂, —NHCH₂CO₂H, —NHCH₂CO₂Et, —NHCH₂CO₂Et, —NHCH₂CONH₂, —NHCH₂CONMe₂, —N(Me)CH2CH2NMe2, —N(Me)CH2CH₂OMe, —NHCH2CH₂OMe, —NHCH₂CH₂OMe,
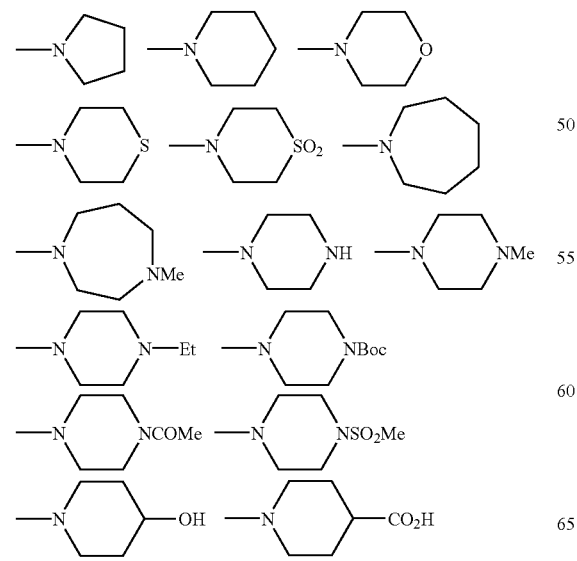
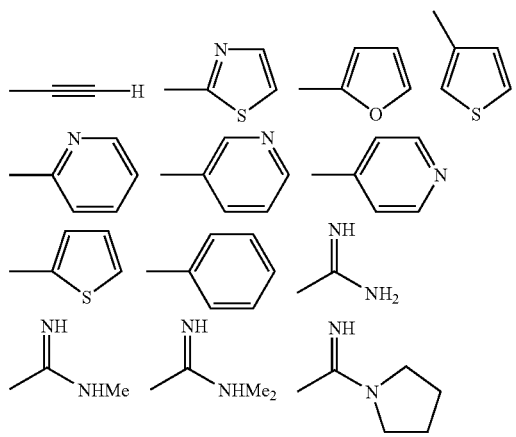
each $R^{1d2}$ and $R^{1d3}$ is independently selected from the group consisting of:
H, —Me, —F, —Cl, —Br, I, —CH₃—CF₃, —CN, —CO₂H, —CO₂Me, —CO₂Et, —CONH₂, —CONHMe, —CONMe₂, —CH₂NH₂, —CH₂NHMe, —CH₂NMe₂, —COMe, —CH2COOH, —CH2COOEt,

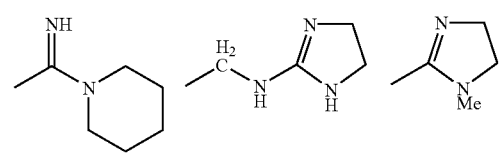
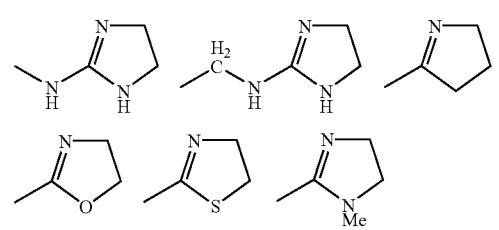
—OCH₃, —OCF₃, —OCH₂F, —OCHF₂, —OCH₂CF₃, —OCF₂CF₃, —OCH₂CO₂H, —OCH₂CO₂Me, —OCH₂CO₂Et, —OCH₂CONH₂, —OCH₂CONMe₂, —OCH₂CONHMe, —OCH₂CH₂OMe, —OCH₂CH₂NMe₂,
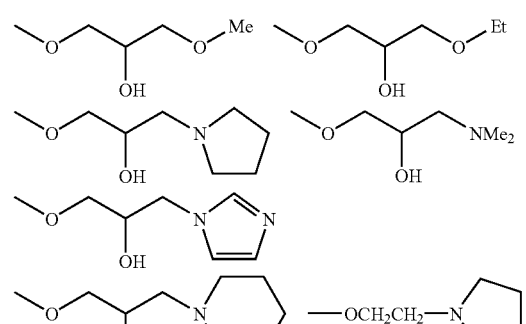
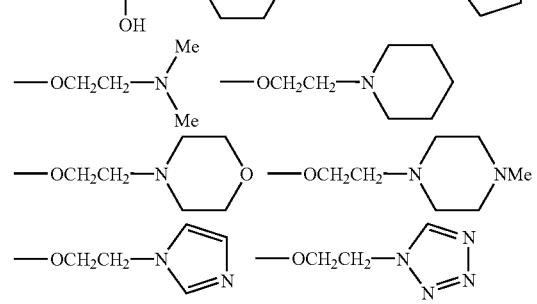
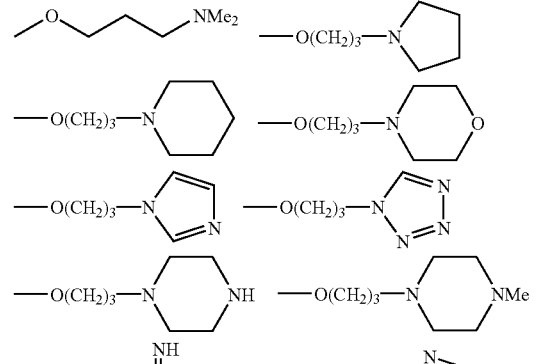
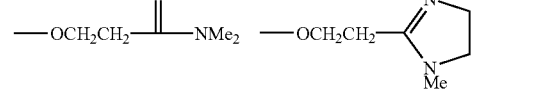
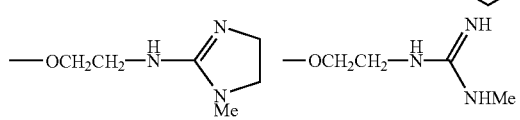
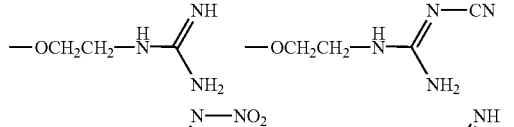
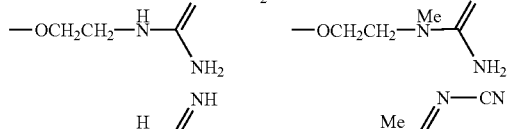
—SCH₃, —SO₂NH₂, —SO₂CH₃, —SO₂NMe₂, —NMe₂, —NHCH₂CH₂NMe₂, —N(CH₂CH₂OH)₂, —N(CH₂CH₂OMe)₂, —NHCH₂CO₂H, —NHCH₂CO₂Et, —NHCH₂CO₂Et, —NHCH₂CONH₂, —NHCH₂CONMe₂, —N(Me)CH2CH2NMe2, —N(Me)CH2CH₂OMe, —
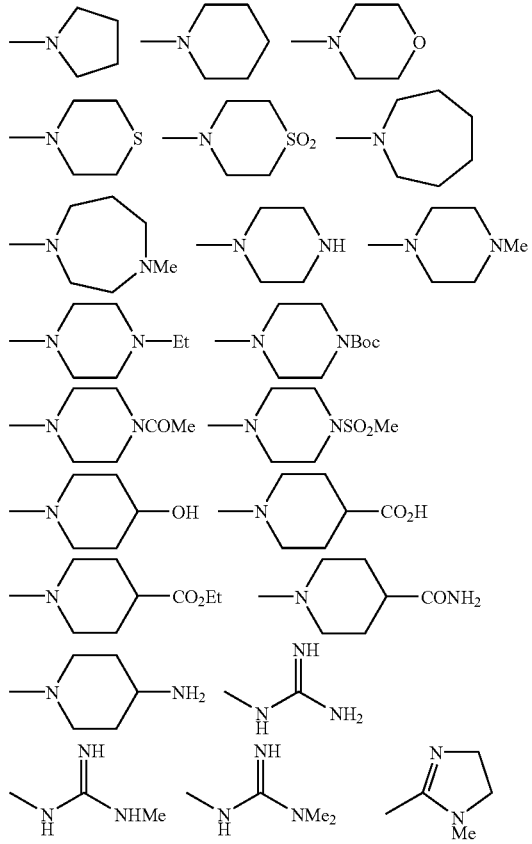

-continued and A is independently selected from group consisting of:

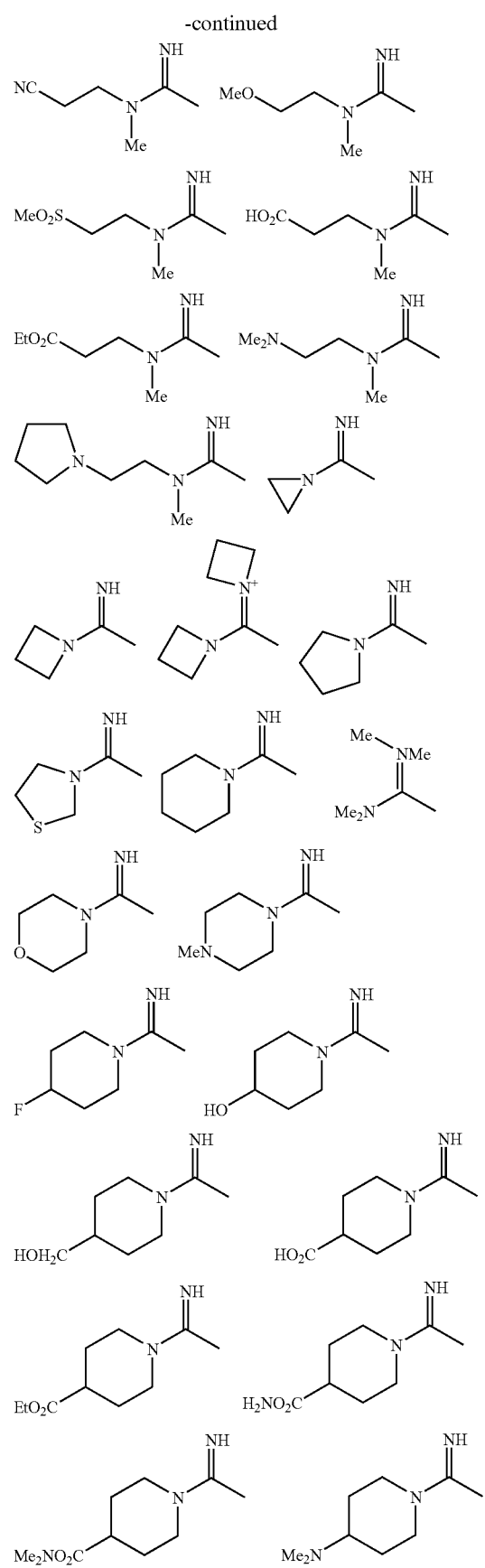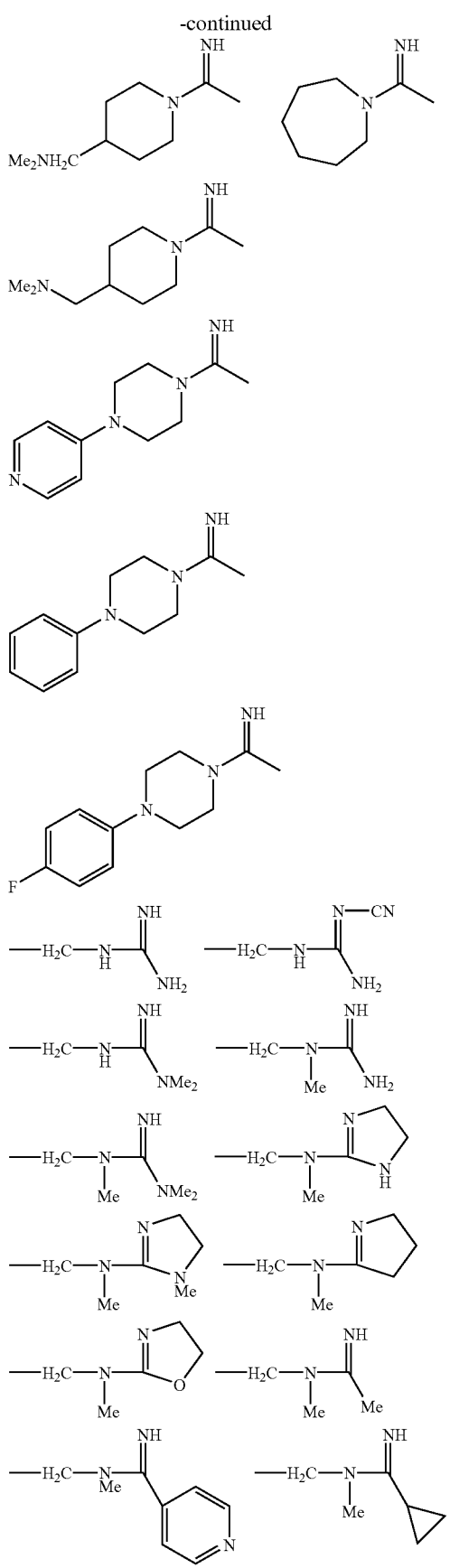

and all pharmaceutically acceptable isomers, salts, hydrates, solvates and prodrug derivatives thereof.

Another embodiment of the invention provides the compounds of the following formula:

wherein:
Ar1 is independently selected from the group consisting of:

each R is independently Cl, OMe, NMe2, OCH2CH$_2$OMe, —OCH2CH2NMe2,

Ar3 is independently selected from the group consisting of:

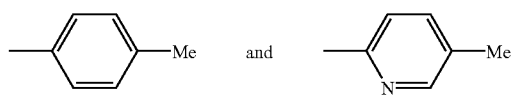

each $R^{1d1}$ is independently H, —Me, —Cl,
—OCH$_3$, —OCH$_2$CH$_2$OMe, —OCH$_2$CH$_2$NMe$_2$,
—NMe$_2$, —N(Me)CH2CH2NMe2, —N(Me)CH2CH2OMe,

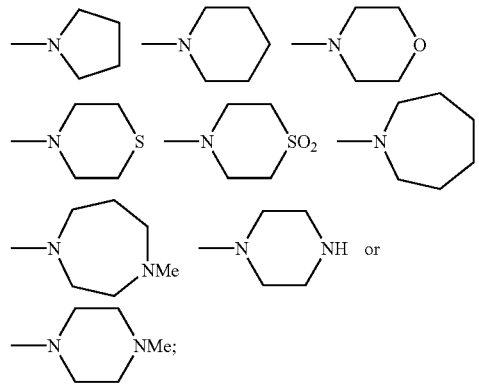

each R1d2 and R1d3 is independently selected from the group consisting of:

H, C≡CH, C≡CH, —Me, —F, —Cl, —Br, —CF$_3$, —CN, —CO$_2$H, —CO$_2$Me, —CO$_2$Et, —CONH$_2$, —CH$_2$NMe$_2$, —COMe, —NMe2, —SMe, —SCH$_2$CH$_2$OMe, —SO$_2$CH$_2$CH$_2$OMe, —SCH$_3$, —SO2NH2, —SO$_2$CH$_3$, —SO$_2$NMe$_2$, and —SO2CH2CH2NMe2;

and A is independently selected from group consisting of:

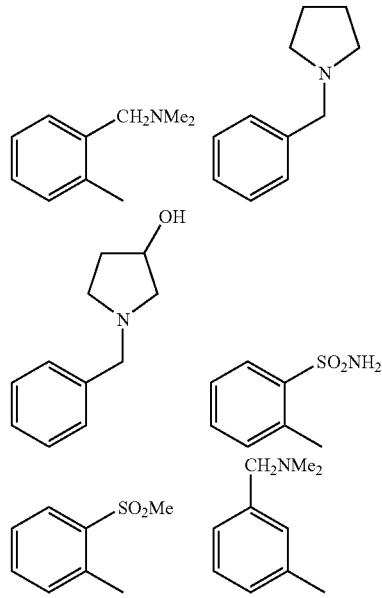

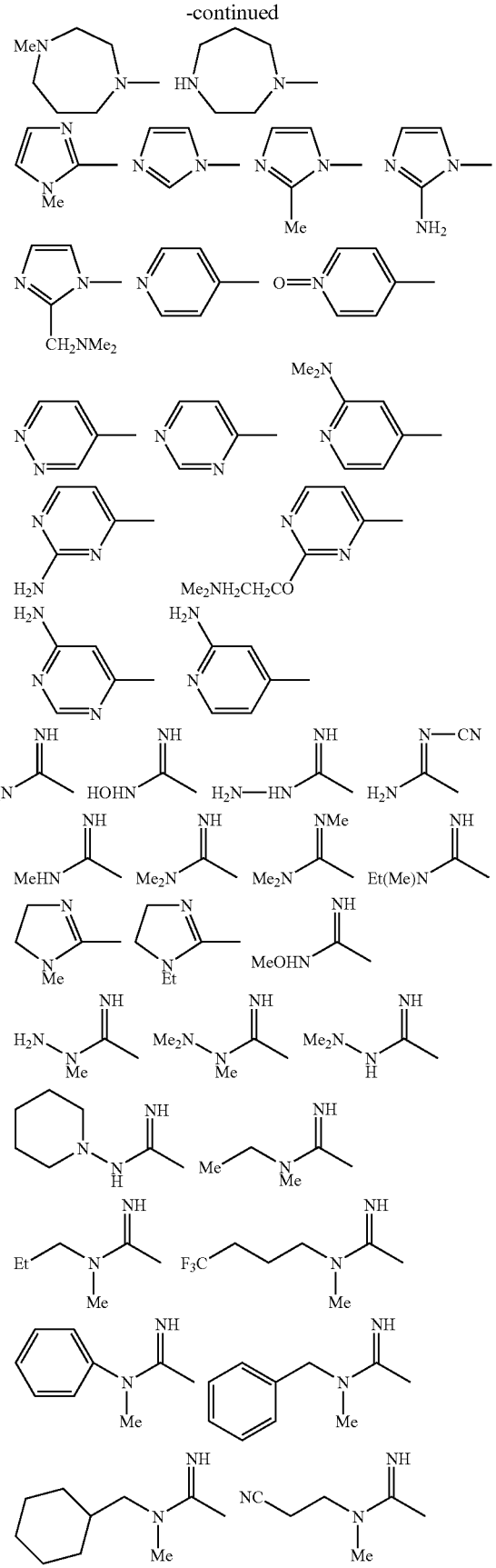

-continued
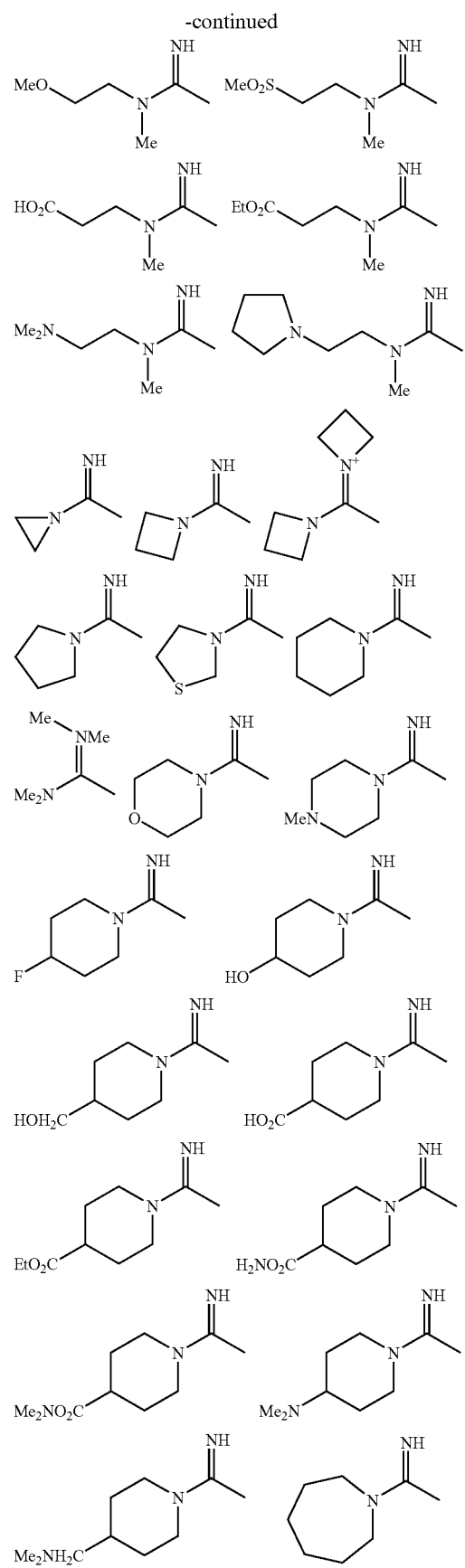
-continued
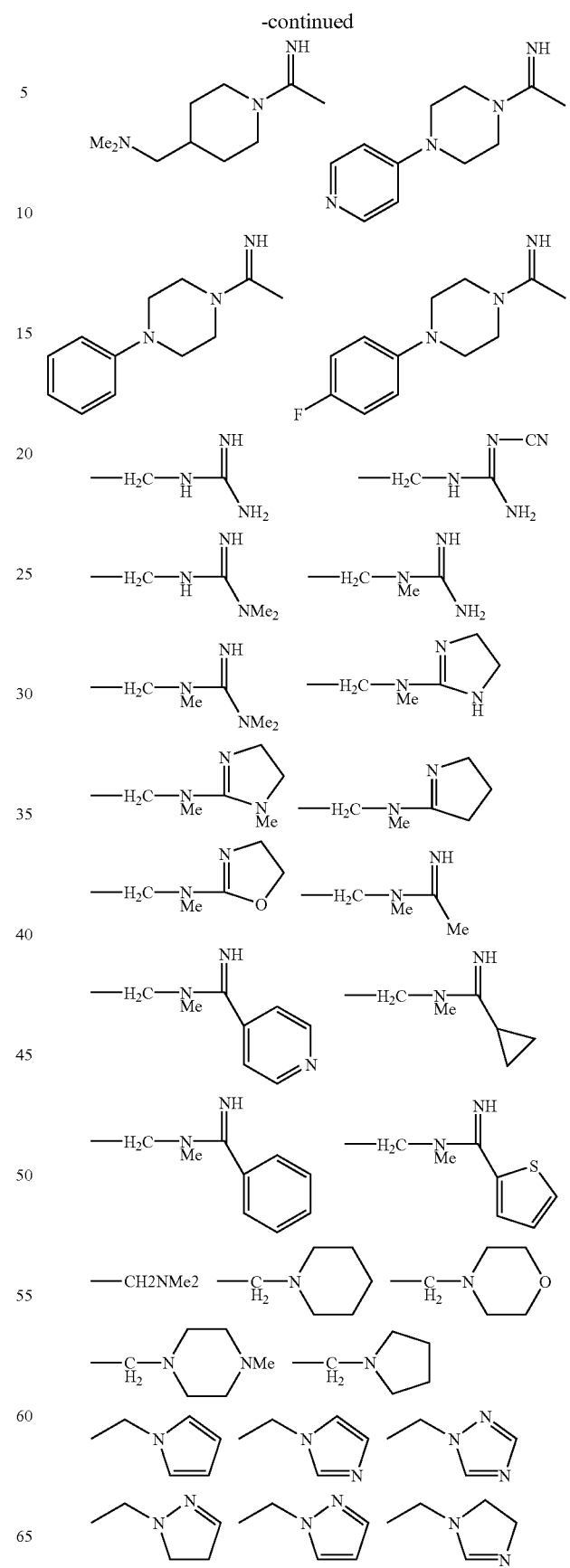

-continued

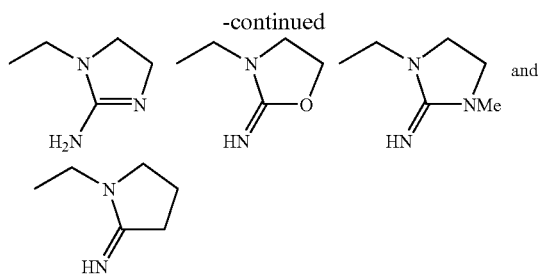

and and all pharmaceutically acceptable isomers, salts, hydrates, solvates and prodrug derivatives thereof.

Still another embodiment of the invention provides the compounds of the following formula:

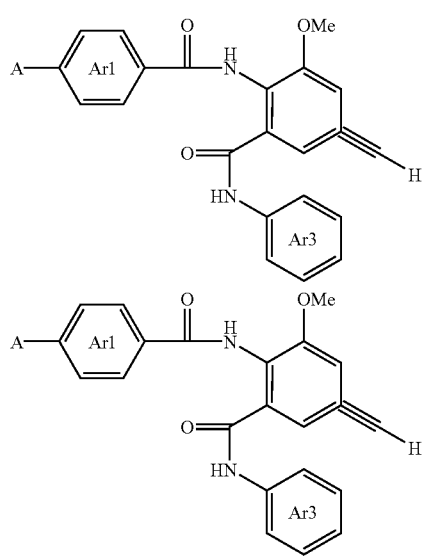

wherein:
Ar1 is independently selected from the group consisting of:

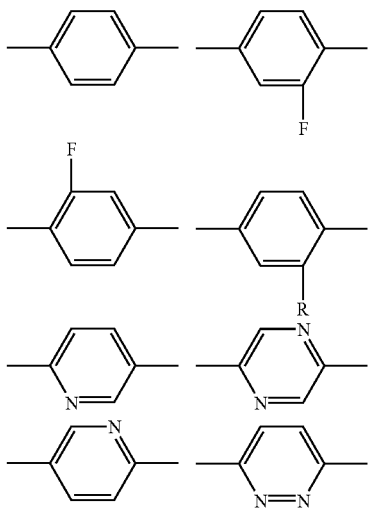

-continued

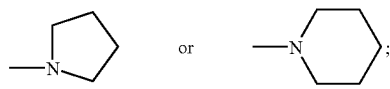

and each R is independently Cl, OMe, NMe2, OCH2CH2OMe, —OCH2CH2NMe2,

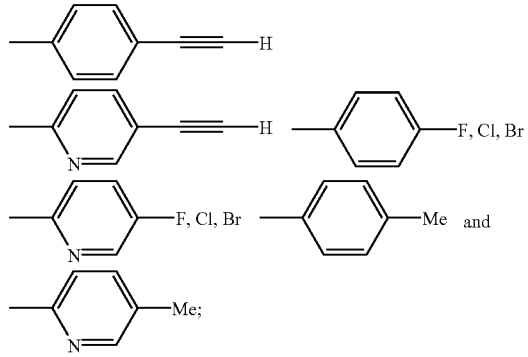

Ar3 is independently selected from the group consisting of:

and A is independently selected from group consisting of:

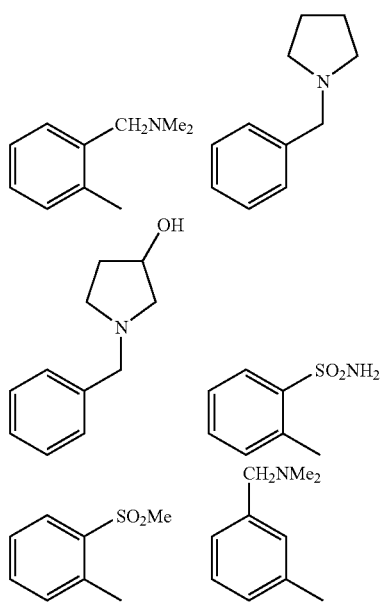

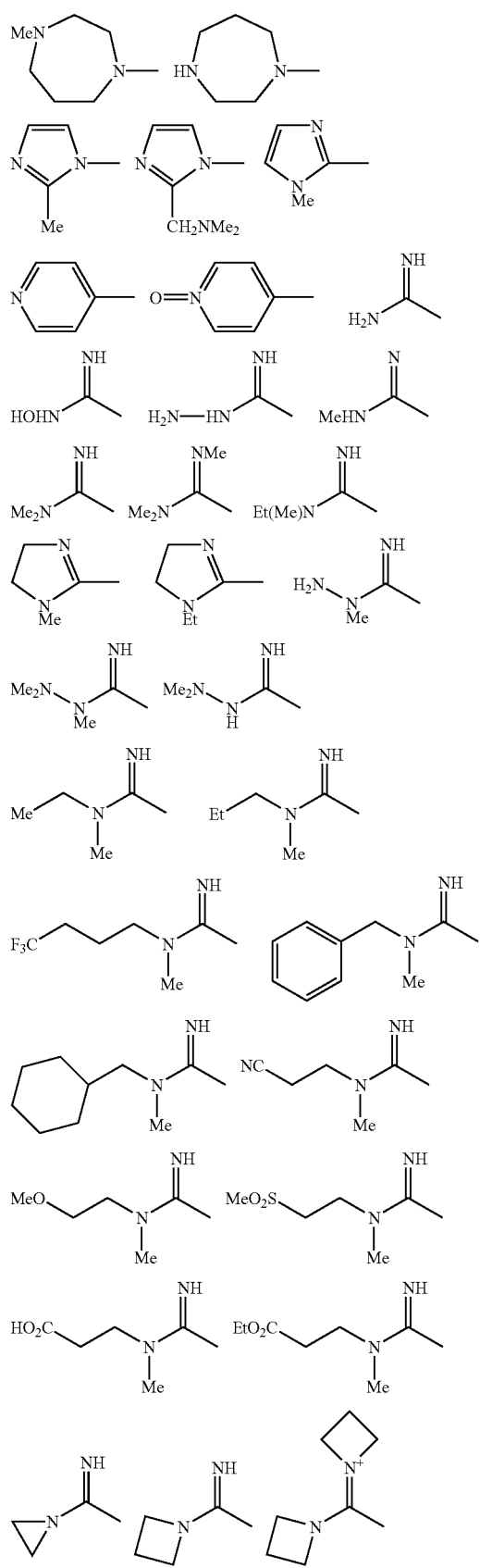
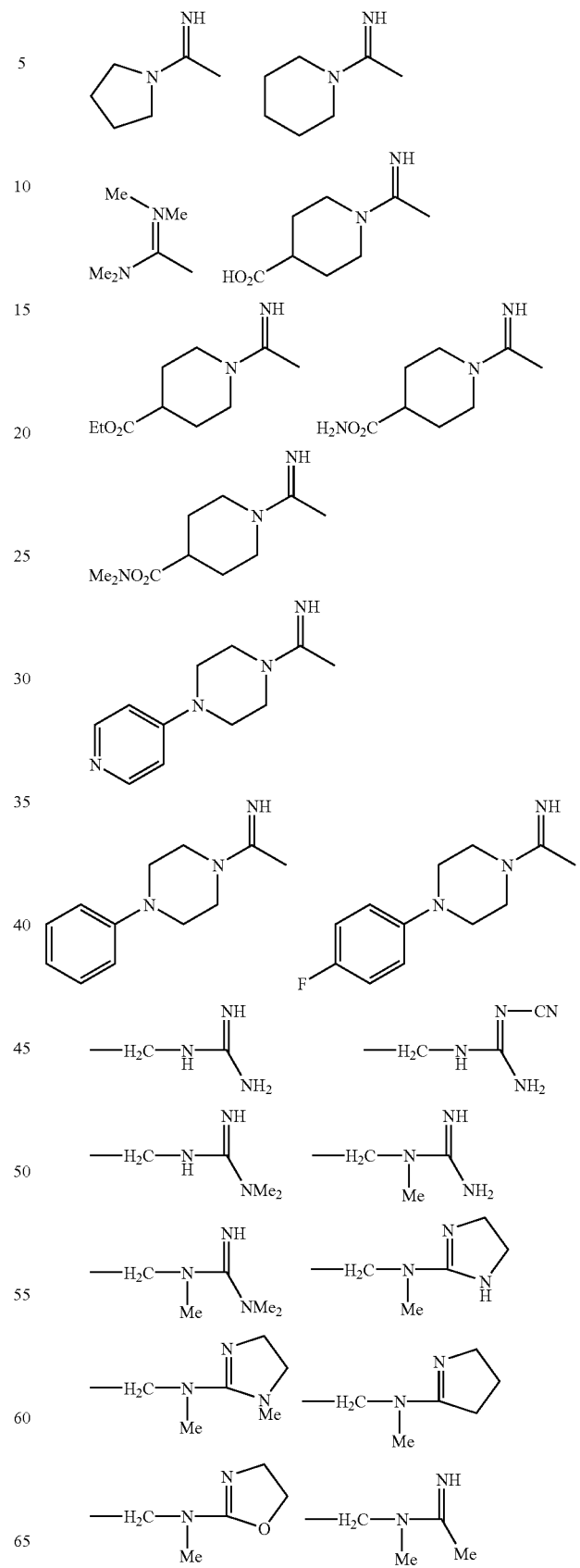

-continued
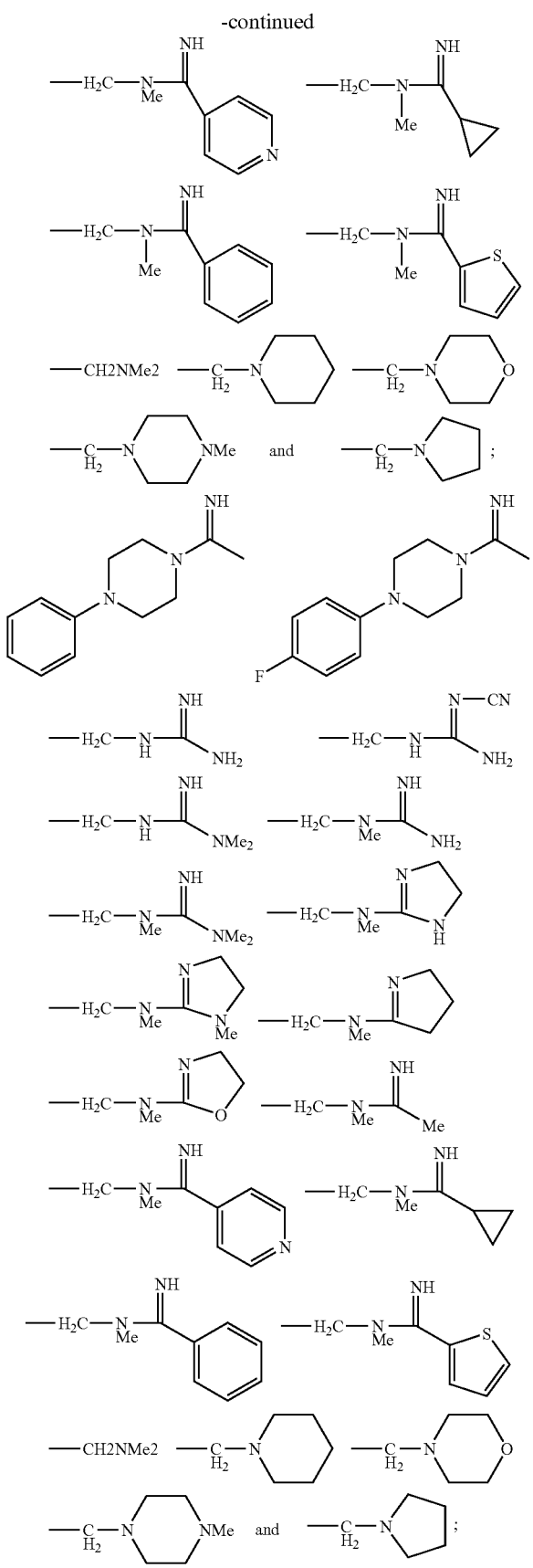
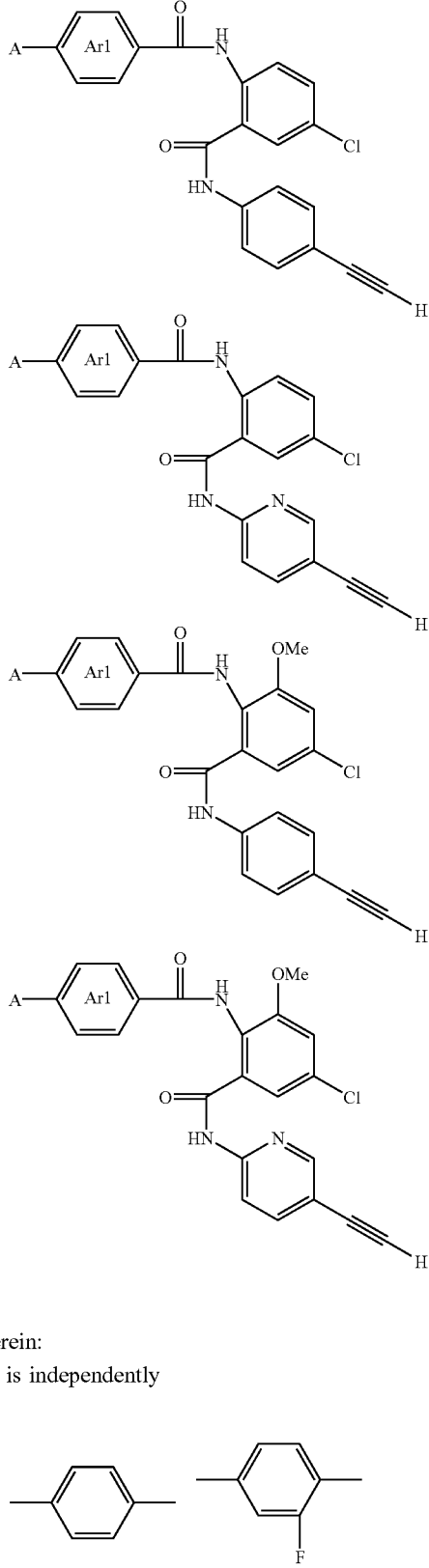
and all pharmaceutically acceptable isomers, salts, hydrates, solvates and prodrug derivatives thereof.
Another embodiment of the present invention provides the compounds of the following formula:
wherein:
Ar1 is independently
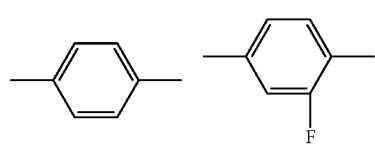

-continued
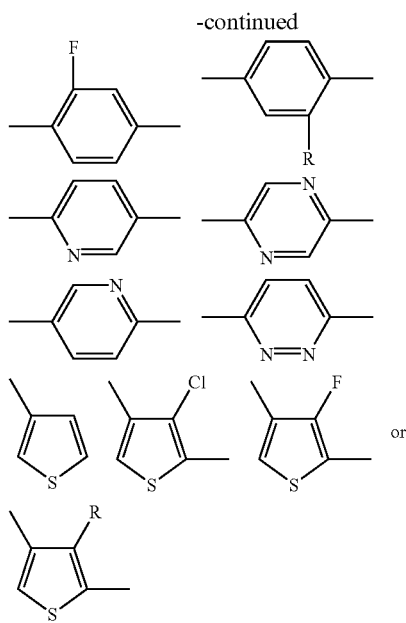
each R is independently —Cl, —OMe, —NMe2, —OCH2CH2OMe, —OCH2CH2NMe2,
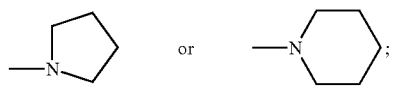
and A is independently selected from group consisting of:
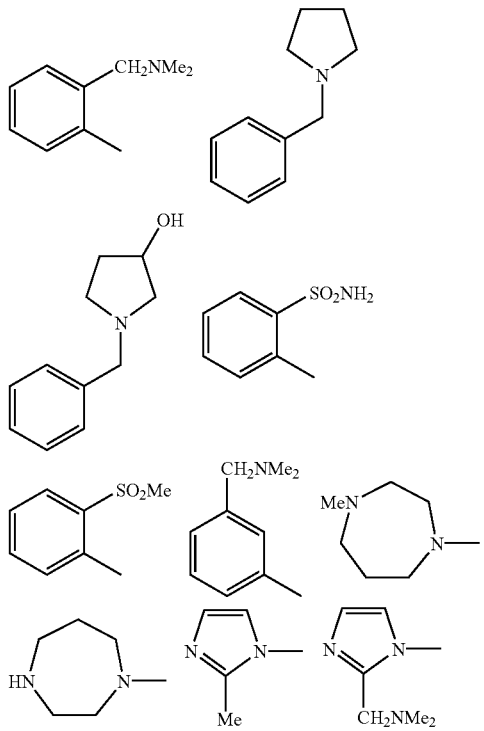
-continued
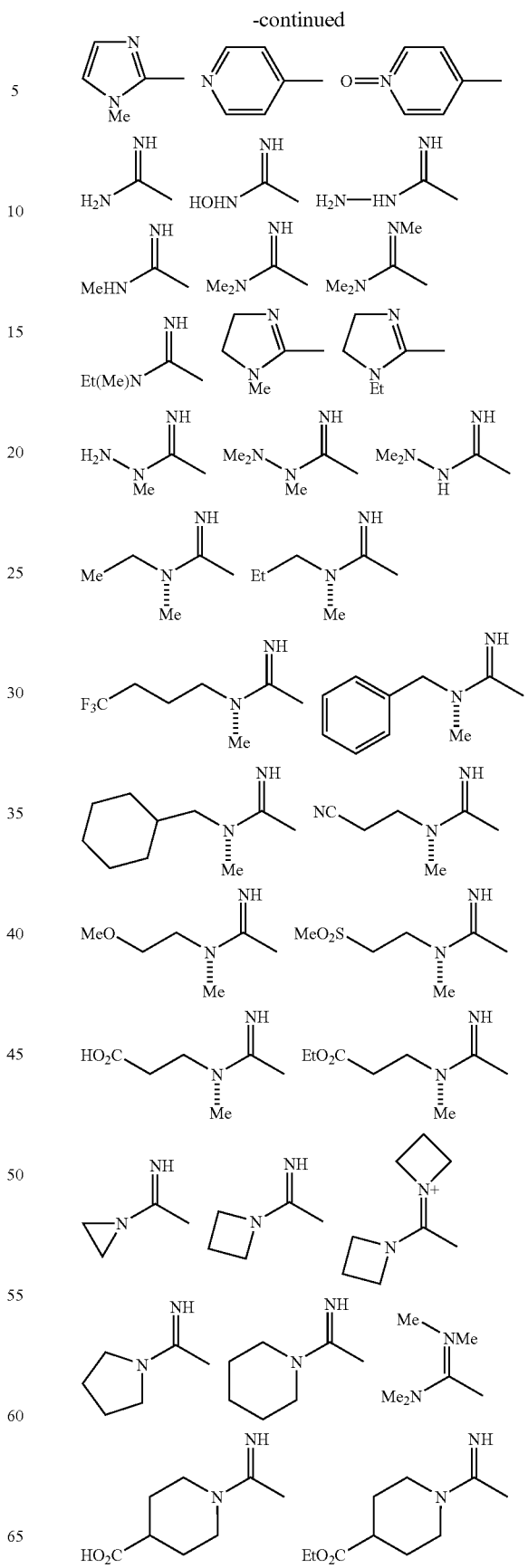

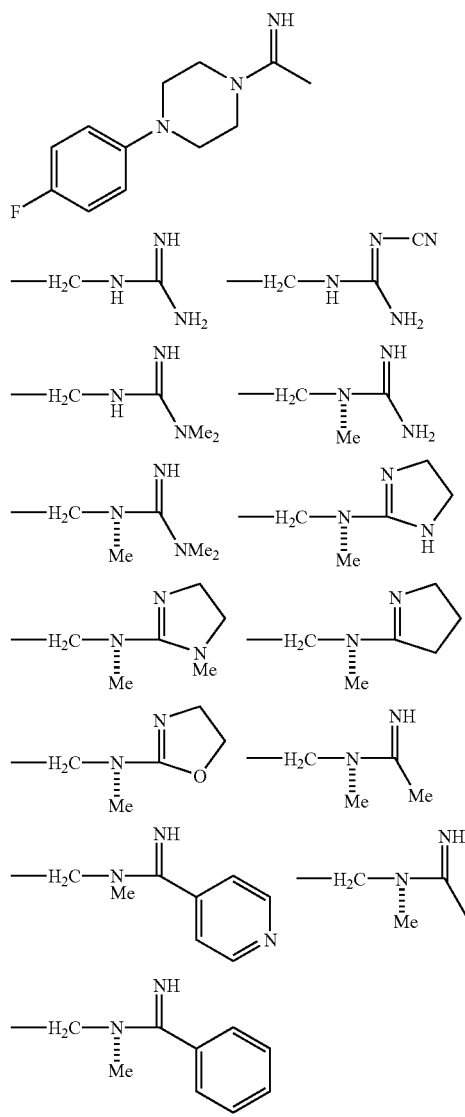
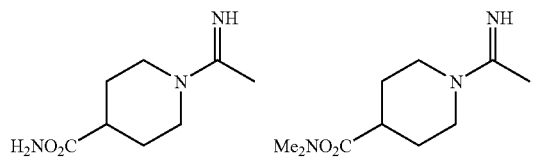
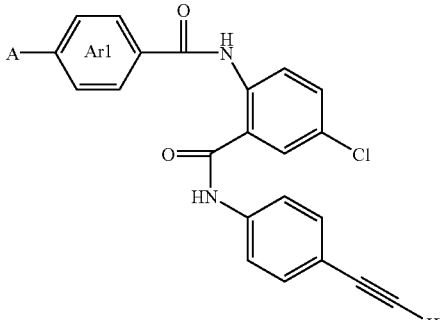
and all pharmaceutically acceptable isomers, salts, hydrates, solvates and prodrug derivatives thereof.
Another embodiment of the invention provides the compounds of the following formula:
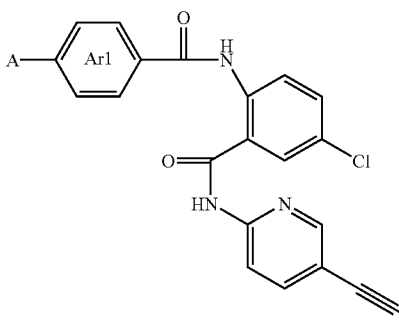
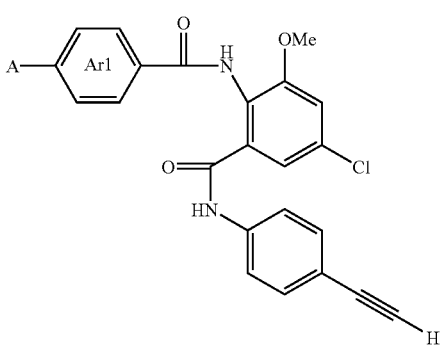

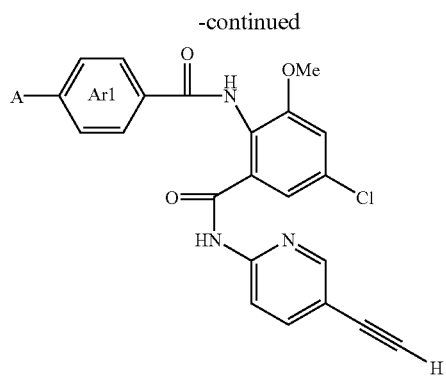
wherein:
Ar1 is independently
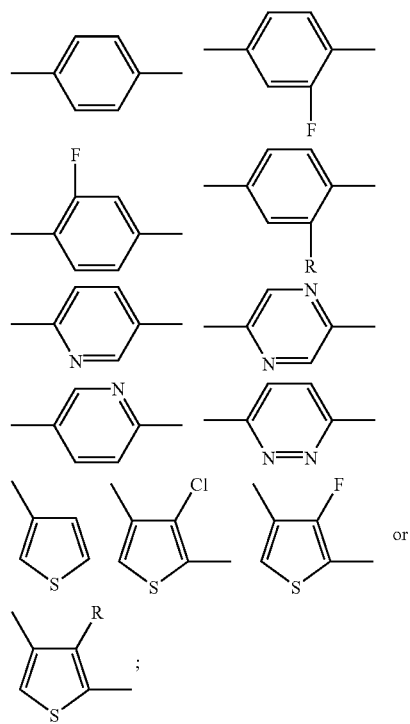
each R is independently —Cl, —OMe, —NMe2, —OCH2CH2OMe, —OCH2CH2NMe2,
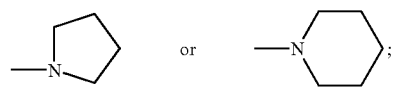
and A is independently selected from group consisting of:
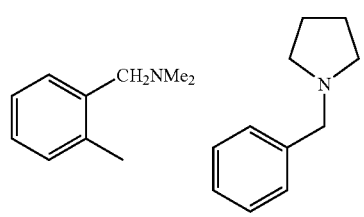
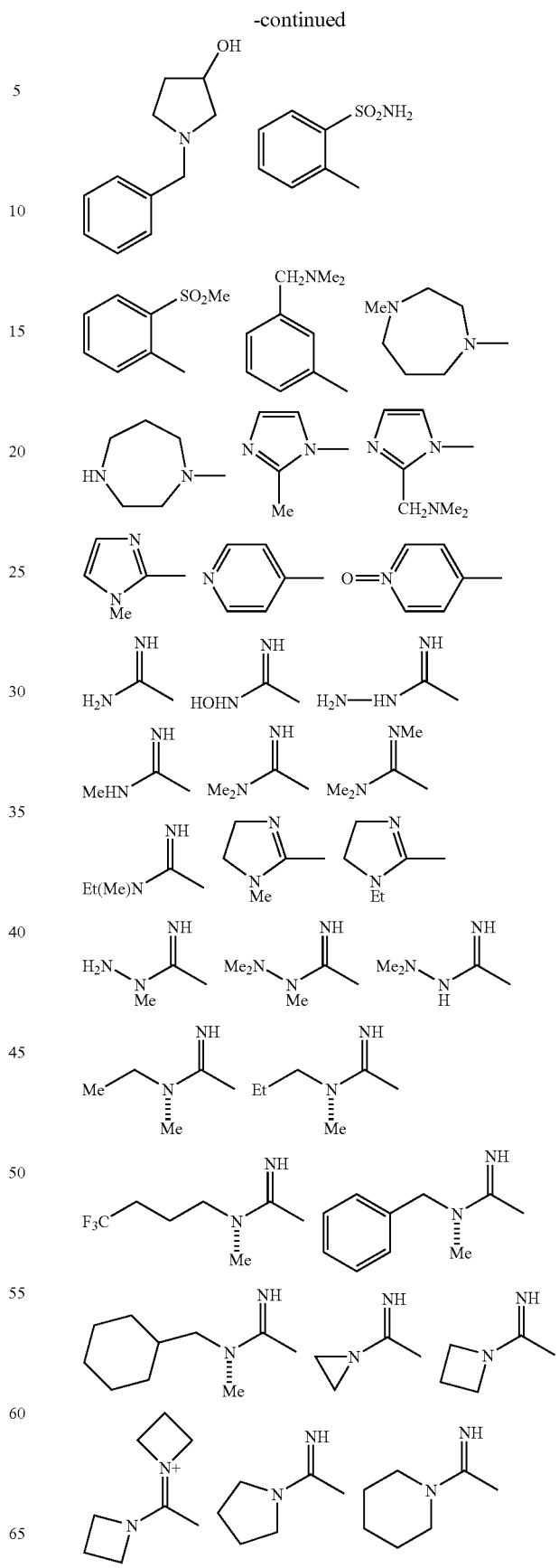

-continued
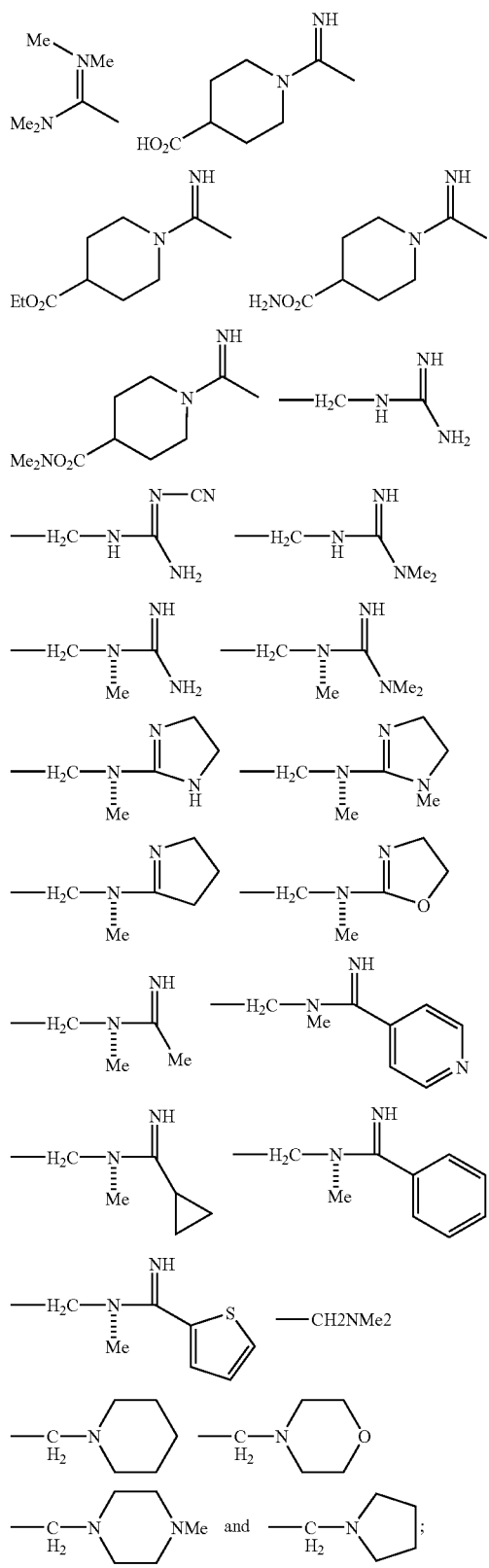
and all pharmaceutically acceptable isomers, salts, hydrates, solvates and prodrug derivatives thereof.
Another embodiment of the invention provides compounds of the following formula:
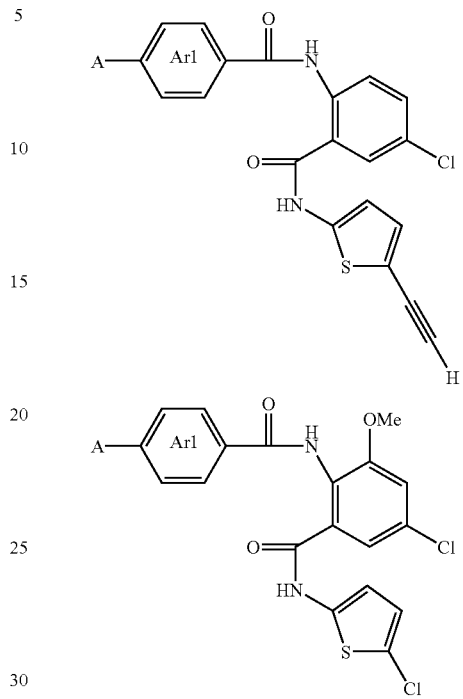
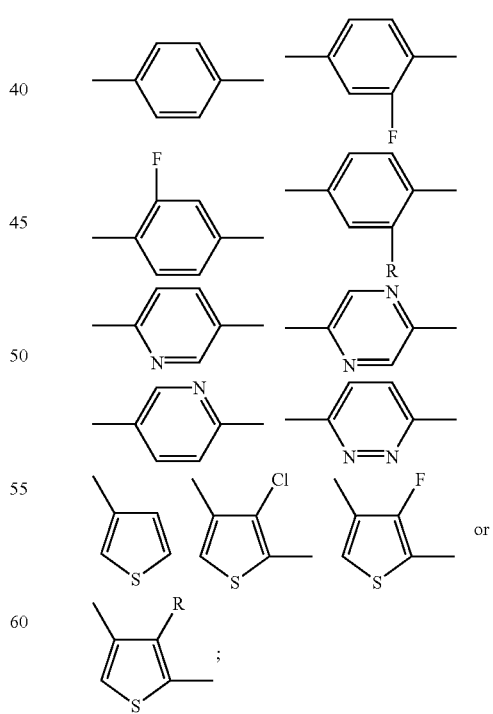
wherein:
Ar1 is independently
;
each R is independently —Cl, —OMe, —NMe2, —OCH2CH2OMe, —OCH2CH2NMe2,

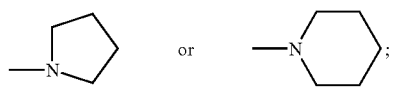
and A is independently selected from group consisting of:
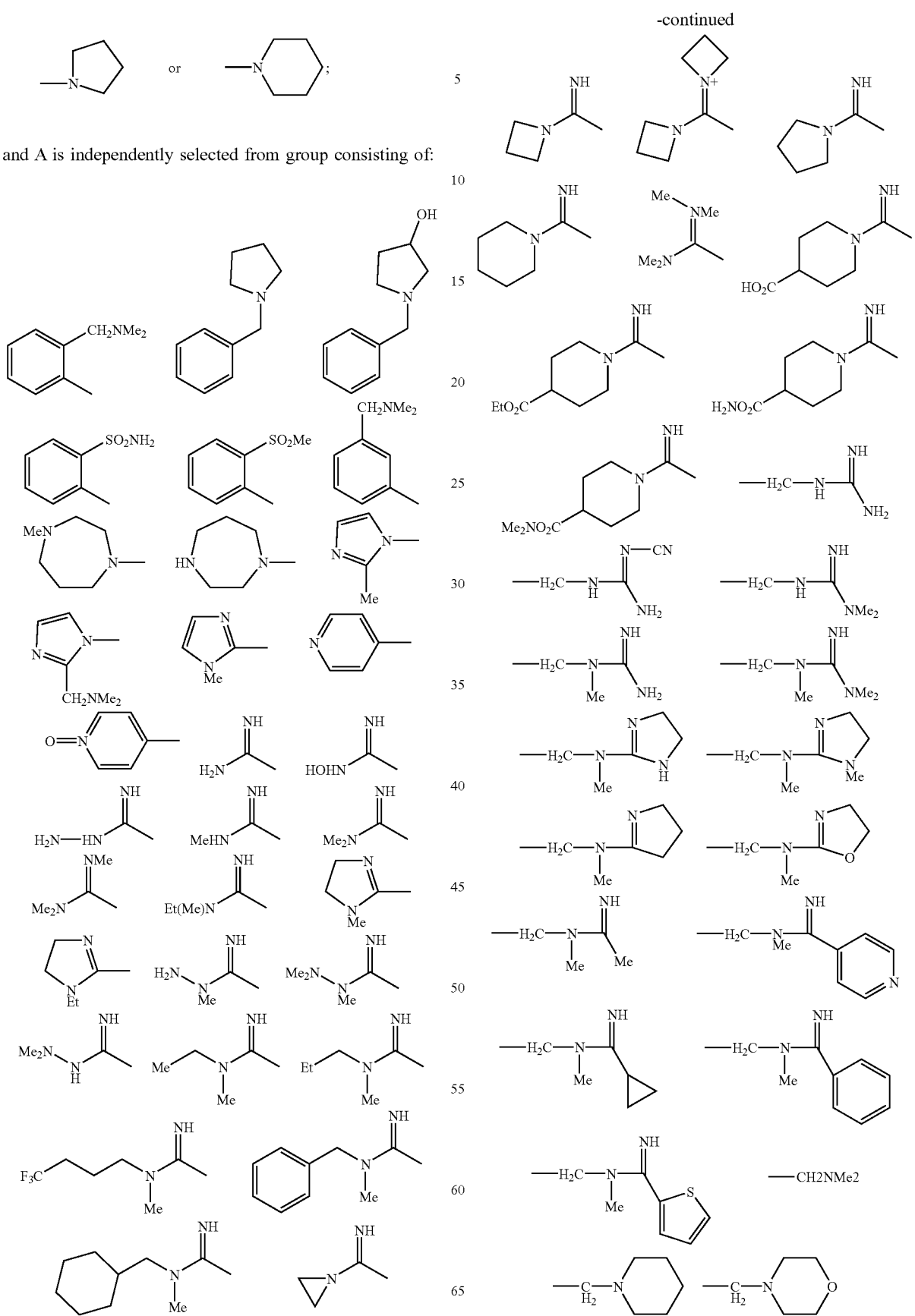

-continued

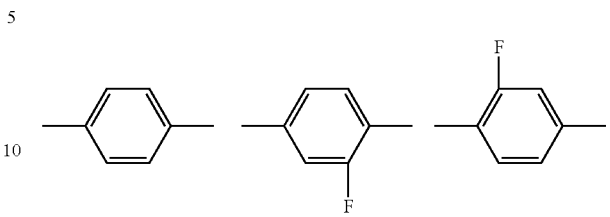

and all pharmaceutically acceptable isomers, salts, hydrates, solvates and prodrug derivatives thereof.

Another embodiment of the invention provides the compounds of the following formula:

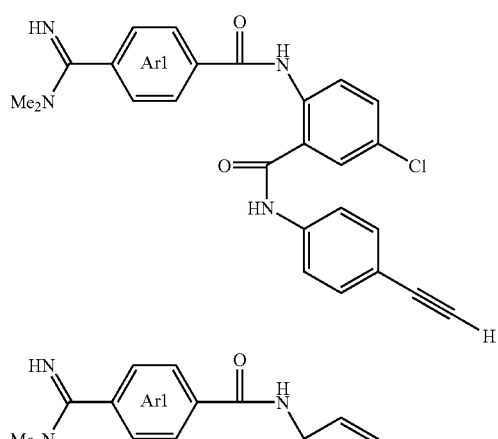

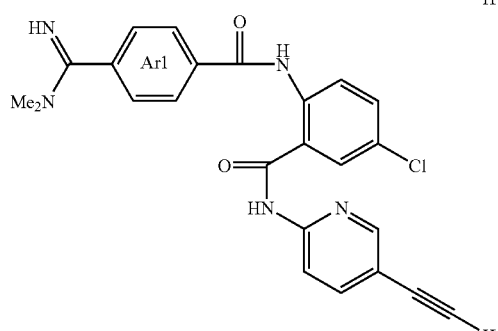

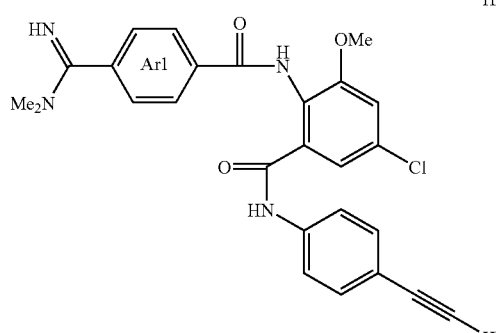

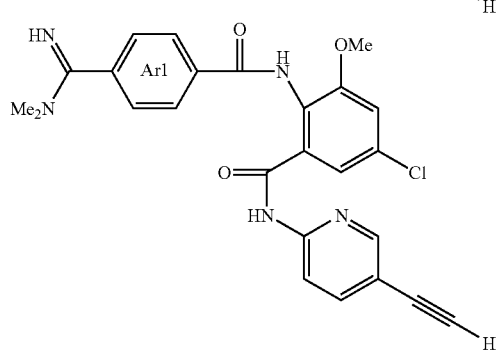

wherein:
Ar1 is independently

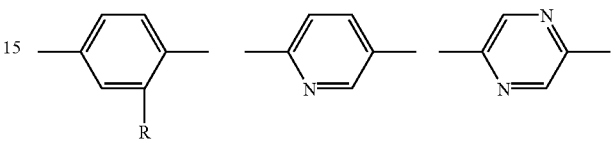

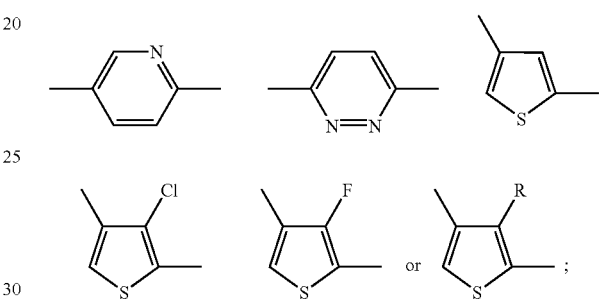

each R is independently —Cl, —OMe, —NMe2, —OCH2CH2OMe, —OCH2CH2NMe2

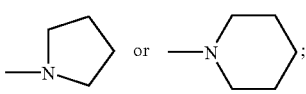

and all pharmaceutically acceptable isomers, salts, hydrates, solvates and prodrug derivatives thereof.

A further embodiment of the invention provides the compounds of the following formula:

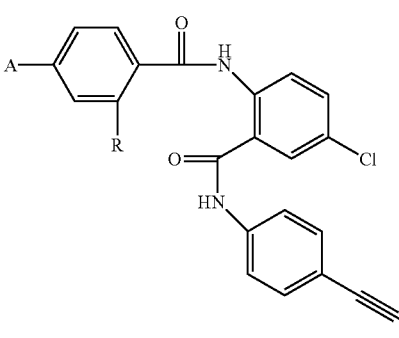

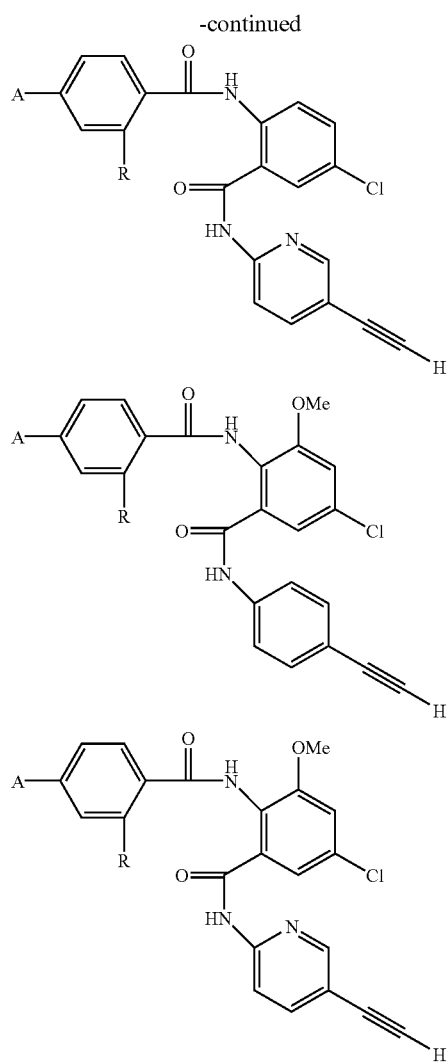
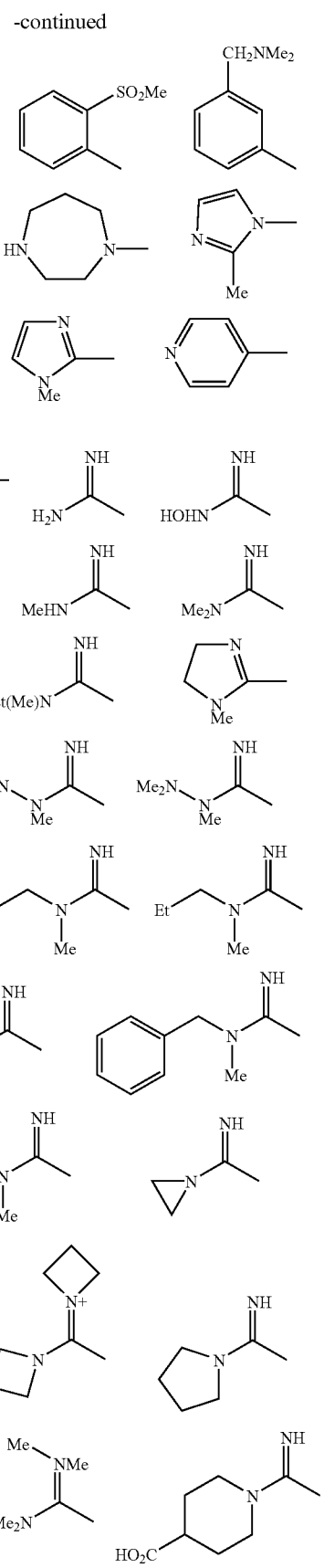
wherein:
each R is independently —H, —F, —Cl, —OMe, —NMe2, —OCH2CH2OMe, —OCH2CH2NMe2,
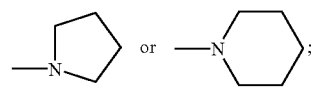
A is independently selected from the group consisting of:
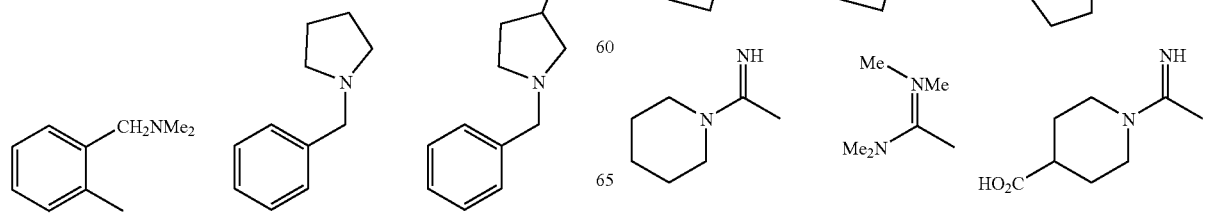

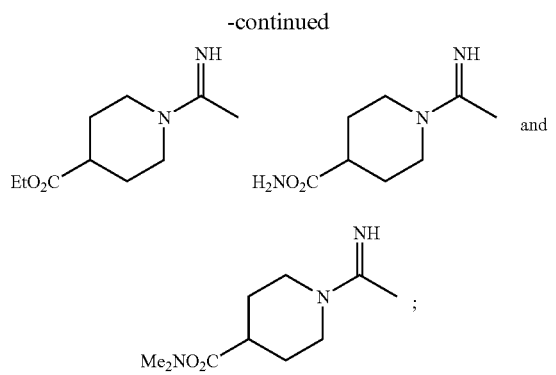
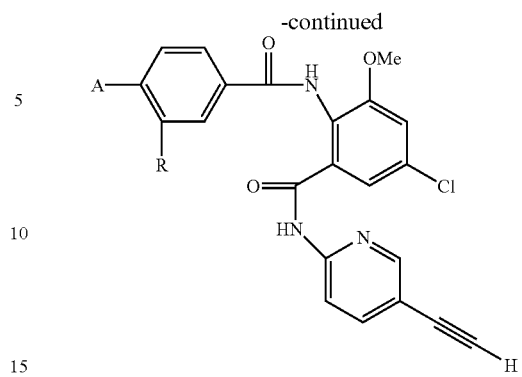
and all pharmaceutically acceptable isomers, salts, hydrates, solvates and prodrug derivatives thereof.
Another embodiment of the invention provides the compounds of the following formula:
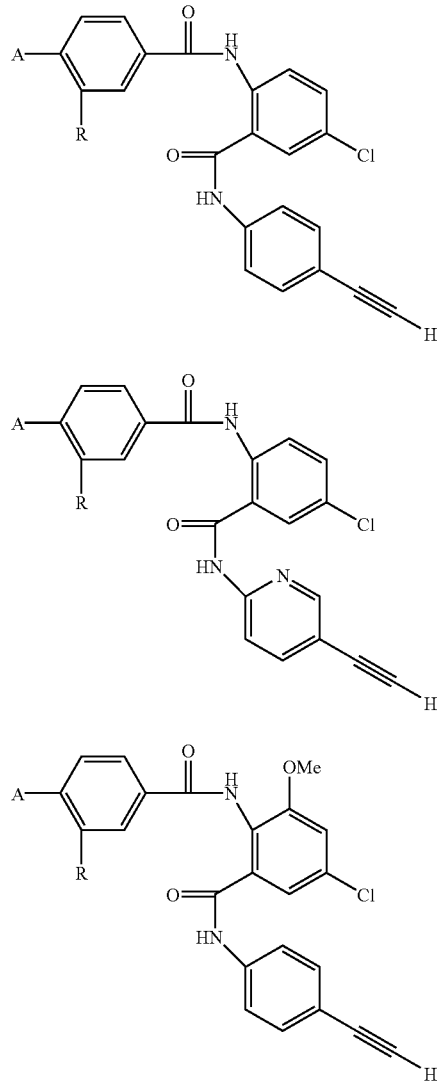
wherein
each R is independently —H, —F, —Cl, —OMe, —NMe2, —OCH2CH2OMe, —OCH2CH2NMe2,
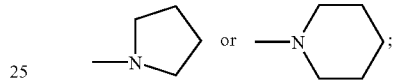
A is independently selected from the group consisting of:
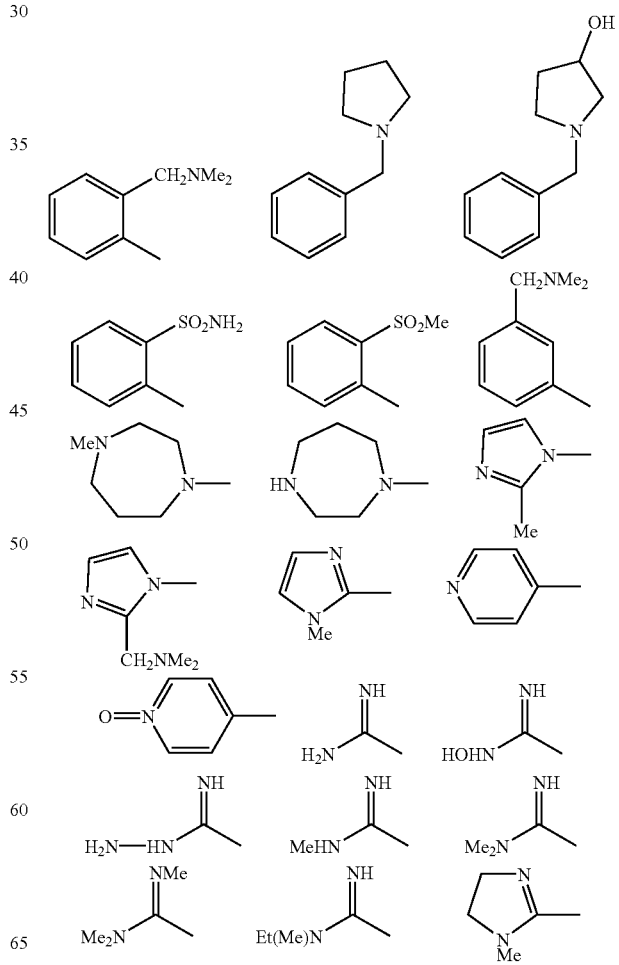

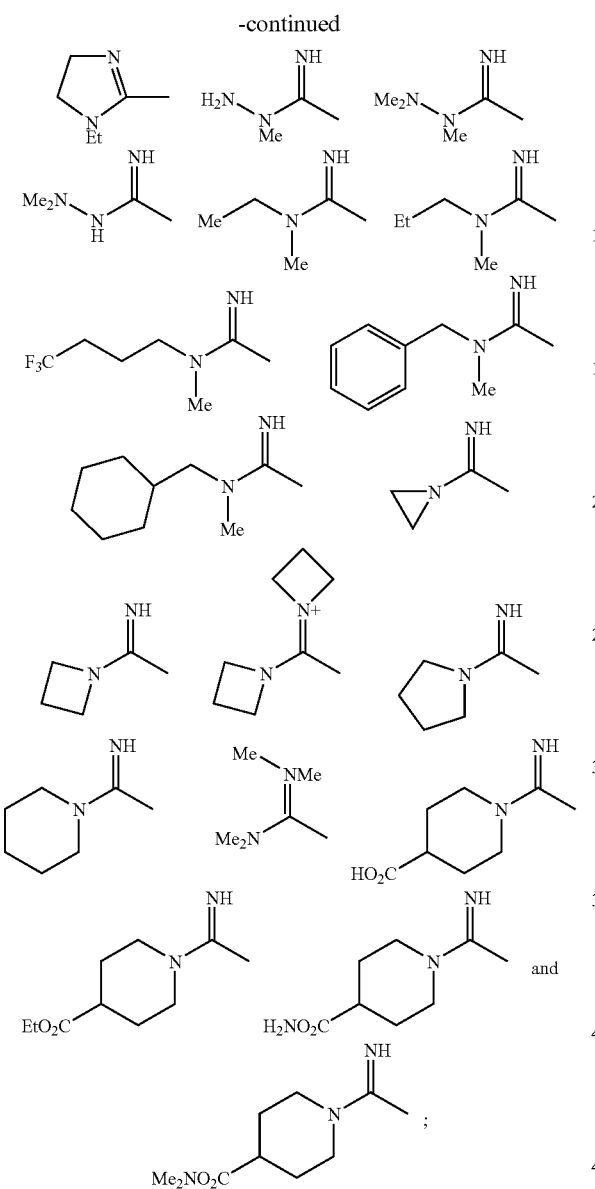
and all pharmaceutically acceptable isomers, salts, hydrates, solvates and prodrug derivatives thereof.
Another embodiment of the present invention of the following formula:
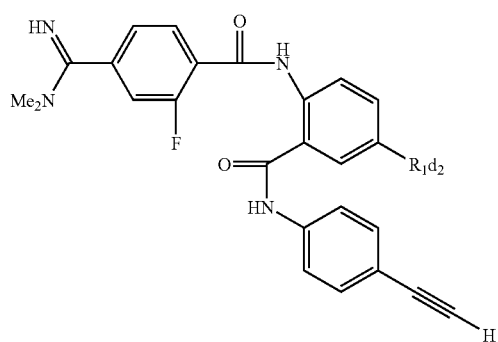
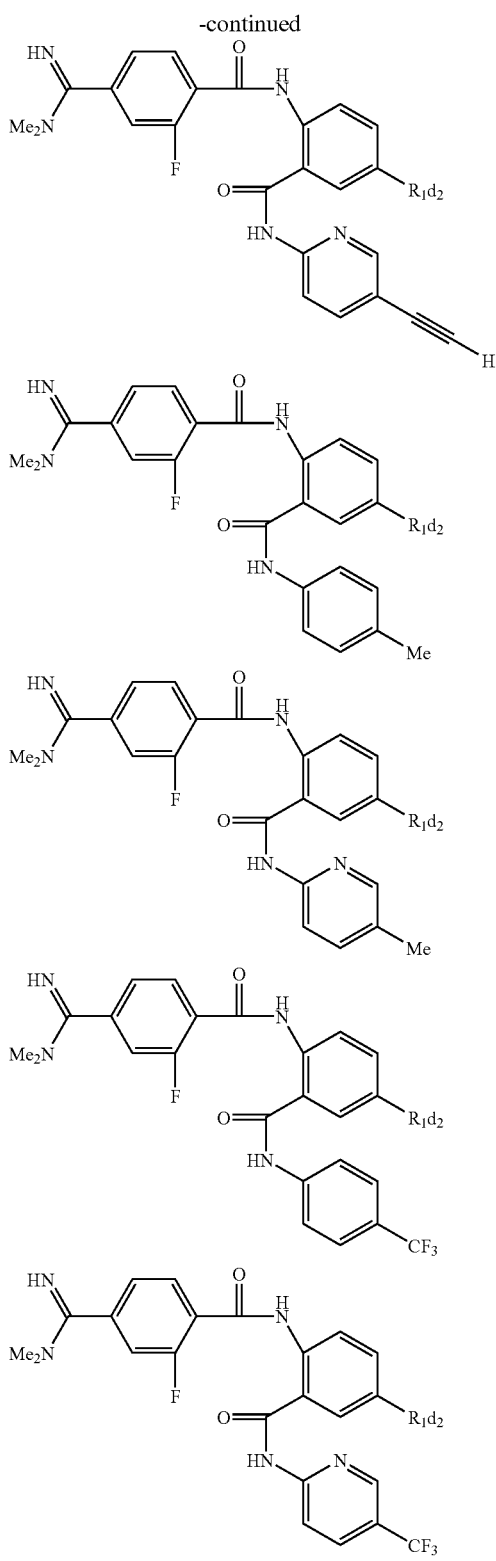
wherein:
each R1d2 is independently H, F, Cl, Br, OMe or SMe;
and all pharmaceutically acceptable isomers, salts, hydrates, solvates and prodrug derivatives thereof.

Another embodiment of the invention provides the compounds of the following formula:

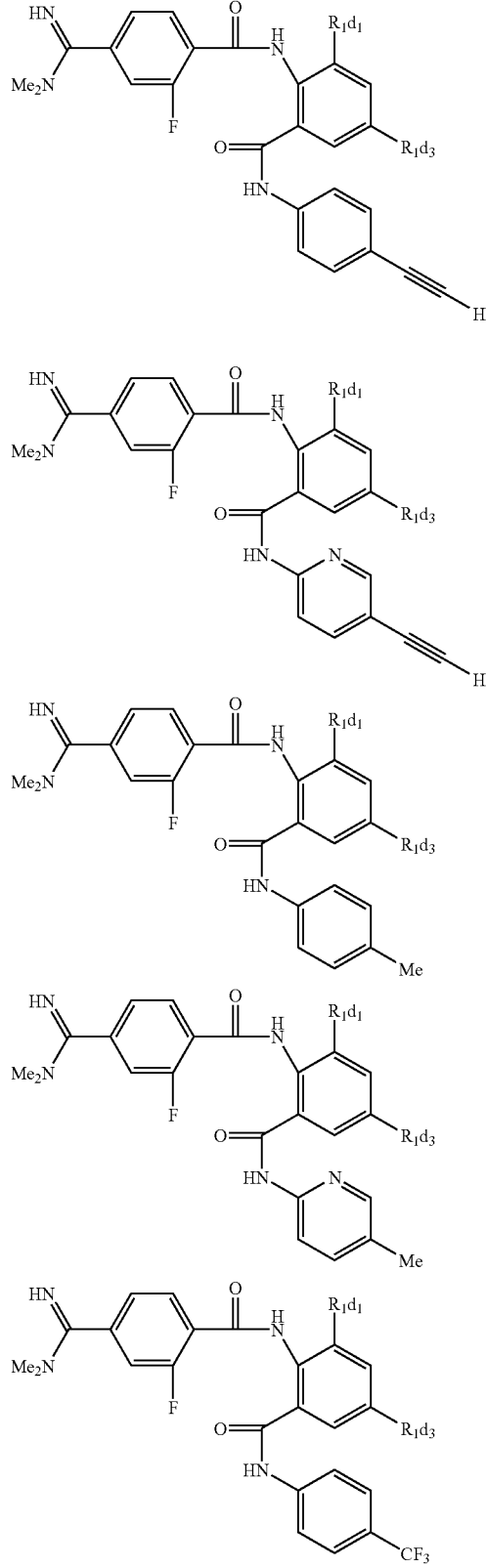

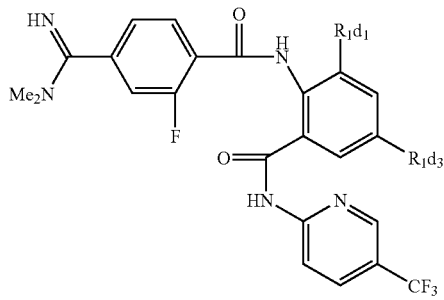

wherein:
each $R^{1d1}$ is independently H, OMe, or NMe2;
each $R^{1d3}$ is independently Cl or Br, C≡CH or C≡CH;
and all pharmaceutically acceptable isomers, salts, hydrates, solvates and prodrug derivatives thereof.

Another embodiment of the invention provides the compounds of the following formula:

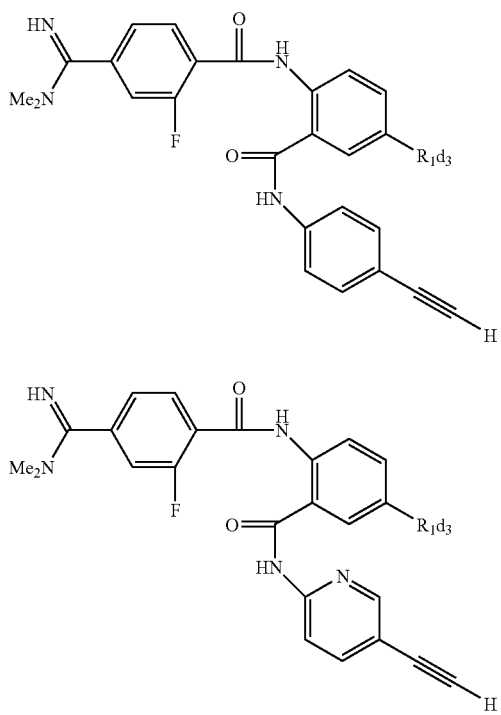

wherein:
each $R^{1d3}$ is independently H, Cl, Br, SMe, C≡CH or C≡CH;

and all pharmaceutically acceptable isomers, salts, hydrates, solvates and prodrug derivatives thereof.

A further embodiment of the present invention provides the compounds of the following formula:

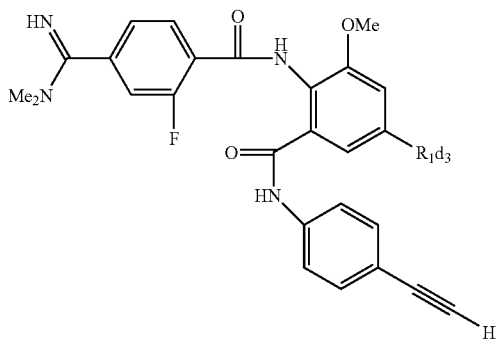

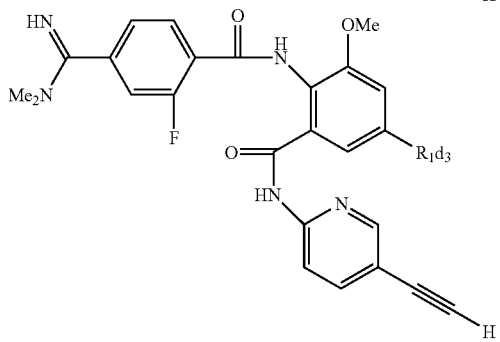

wherein:
each $R^{1d3}$ is independently Cl, Br, C≡CH or C≡CH;
and all pharmaceutically acceptable isomers, salts, hydrates, solvates and prodrug derivatives thereof.

Another embodiment of the present invention provides the compounds of the following formula:

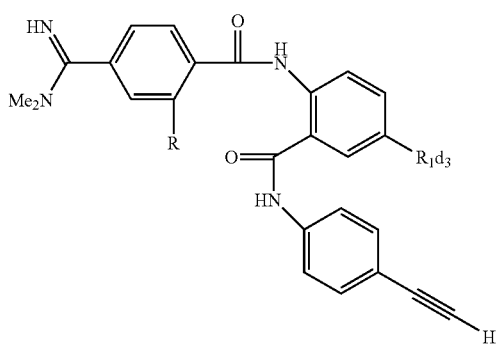

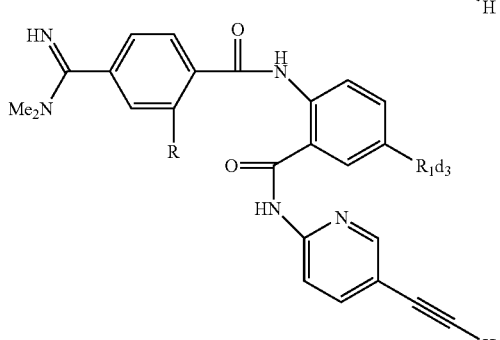

wherein:
each R is independently —H, —F, —Cl, —OMe, —NMe2, —OCH2CH2OMe, —OCH2CH2NMe2,

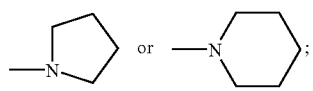

each R1d3 is independently Cl, Br, SMe, C≡CH or C≡CH;
and all pharmaceutically acceptable isomers, salts, hydrates, solvates and prodrug derivatives thereof.

A further embodiment of the present invention provides the compounds of the following formula:

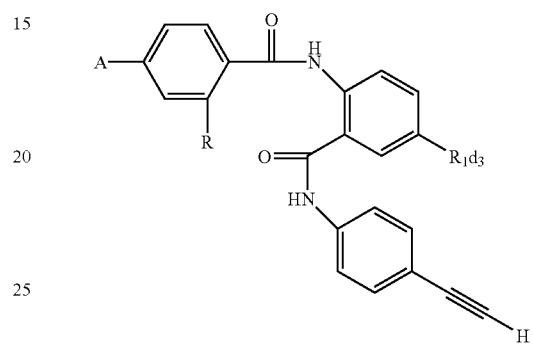

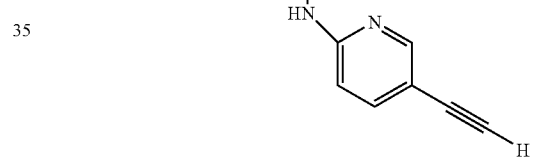

wherein:
each R is independently —H, —F, —Cl, —OMe, —NMe2, —OCH2CH2OMe, —OCH2CH2NMe2,

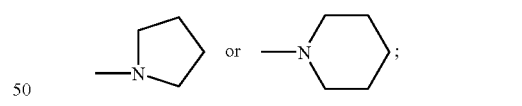

each R1d3 is independently —Cl, —Br, SMe, C≡CH or C≡CH;
A is independently selected from the group consisting of:

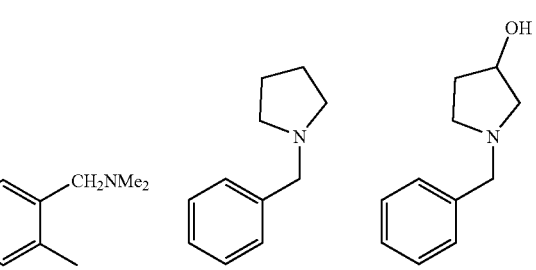

-continued

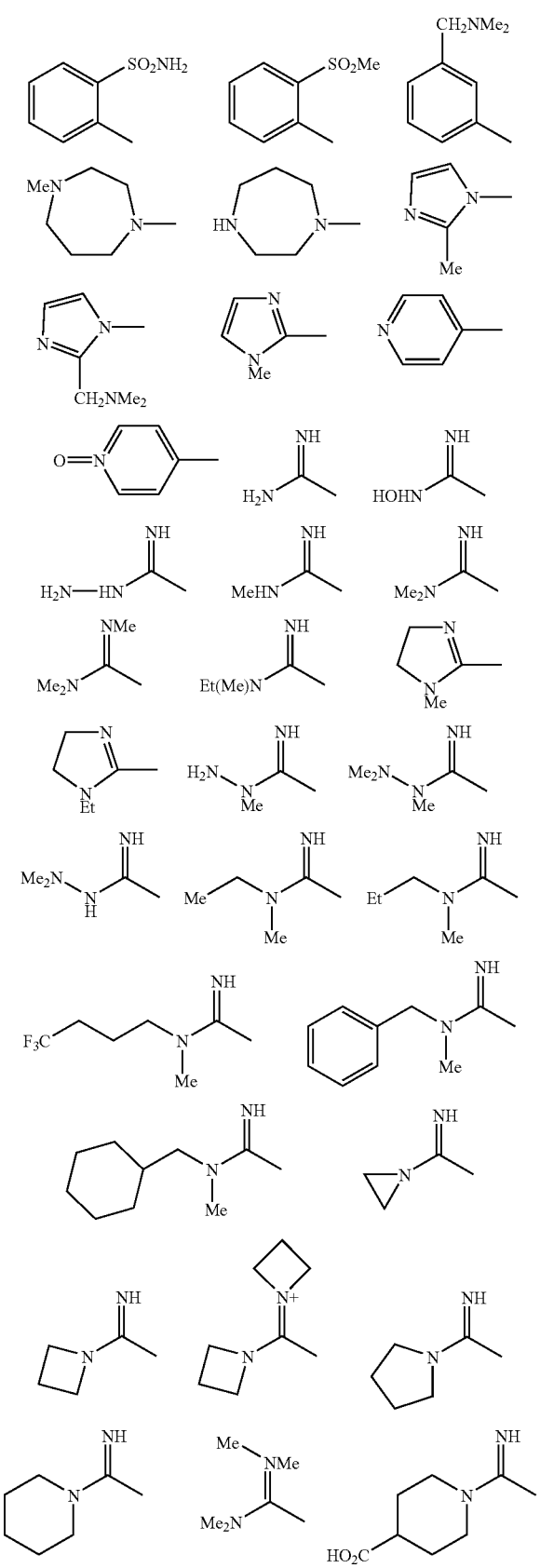

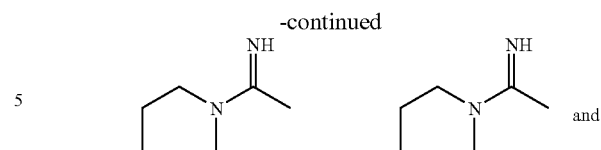

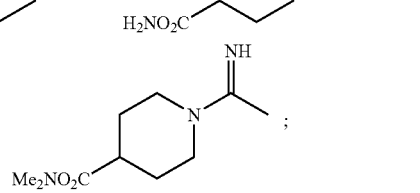

and all pharmaceutically acceptable isomers, salts, hydrates, solvates and prodrug derivatives thereof.

Another embodiment of the invention provides the compounds of the following formula:

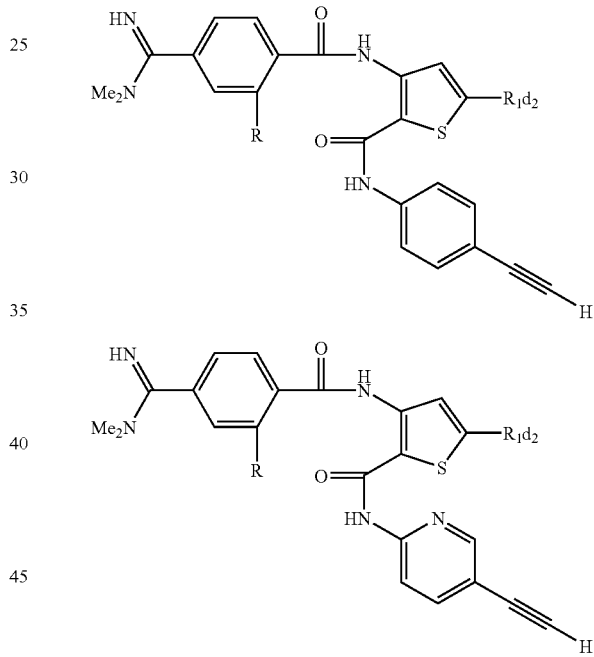

wherein:

each R is independently —H, —F, —Cl, —OMe, —NMe2, —OCH2CH2OMe, —OCH2CH2NMe2,

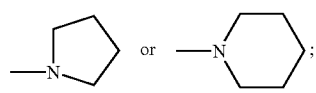

each R1d2 is independently H, Cl, Br, SMe, C≡CH or C≡CH;

and all pharmaceutically acceptable isomers, salts, hydrates, solvates and prodrug derivatives thereof.

Another embodiment of the present invention provides the following formula:
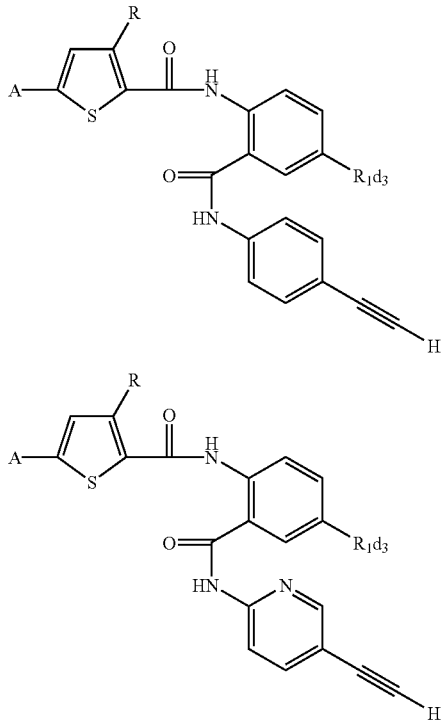
wherein:
each R is independently —H, —F, —Cl, —OMe, —SMe, —NMe2, —OCH2CH₂OMe, —OCH2CH2NMe2,
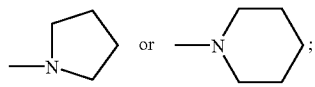;
each R¹d3 is independently Cl, Br, SMe, C≡CH or C≡CH;
A is independently selected from the group consisting of:
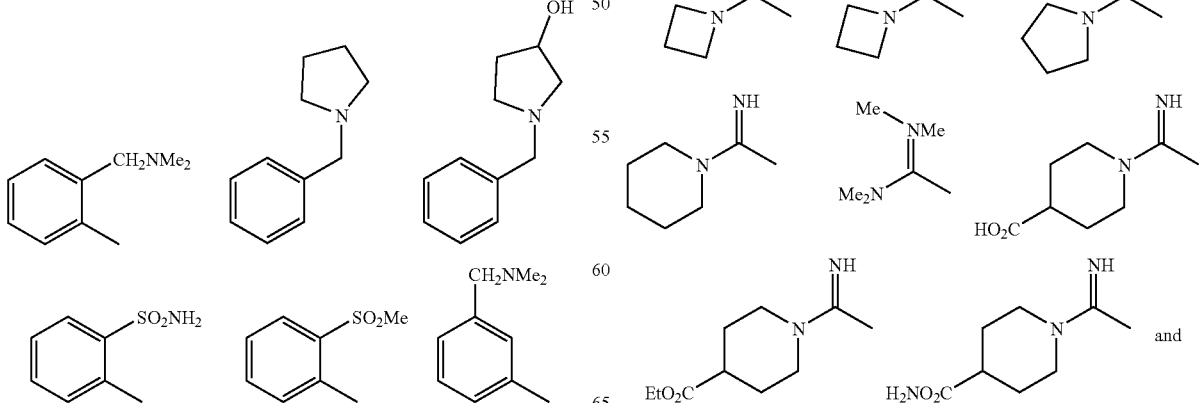
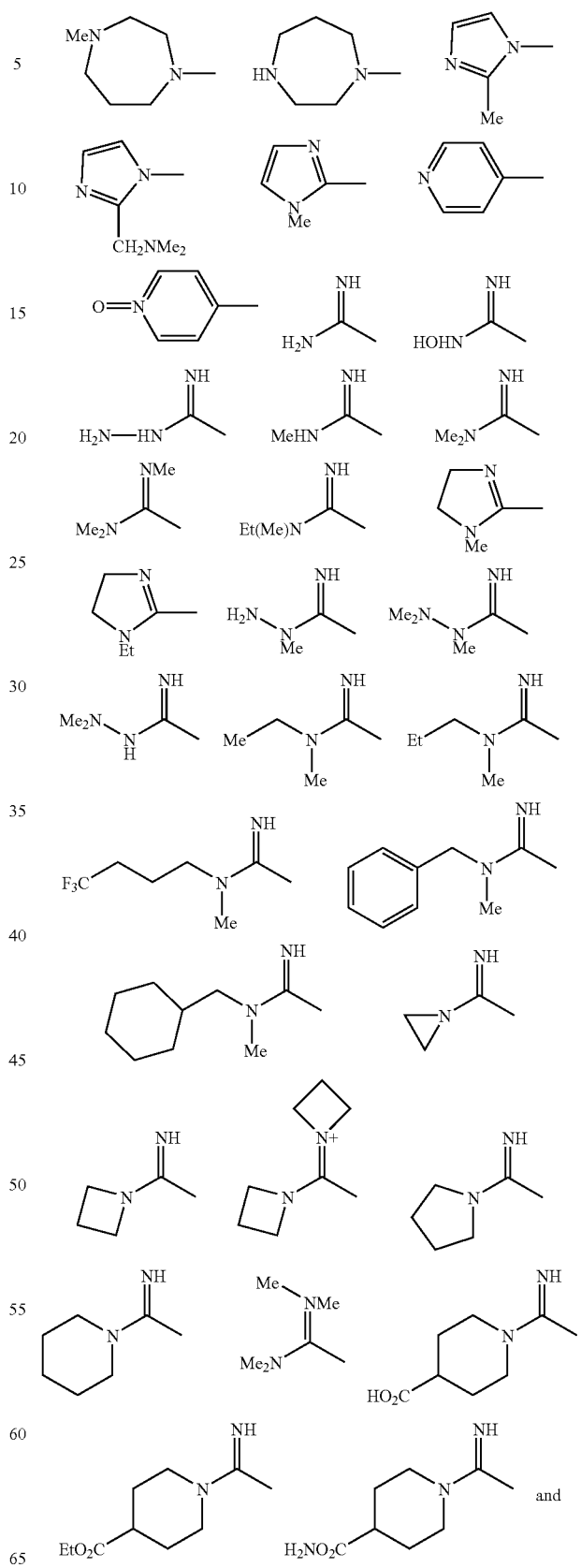

-continued

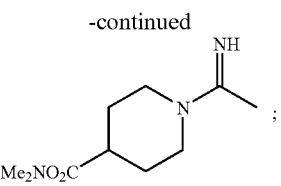

and all pharmaceutically acceptable isomers, salts, hydrates, solvates and prodrug derivatives thereof.

Another embodiment of the invention provides the compounds of the following formula:

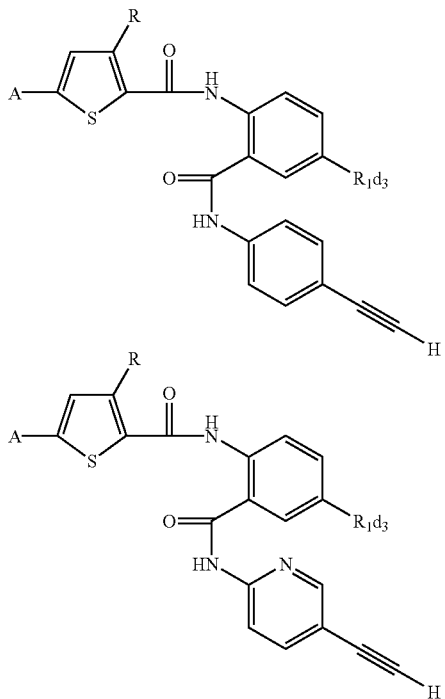

wherein:
each R is independently —H, —F, —Cl, —OMe, —NMe2, —OCH2CH2OMe, —OCH2CH2NMe2,

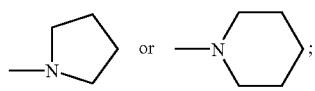

each R1d3 is independently Cl, Br, SMe, C≡CH or C≡CH;
A is independently selected from the group consisting of:

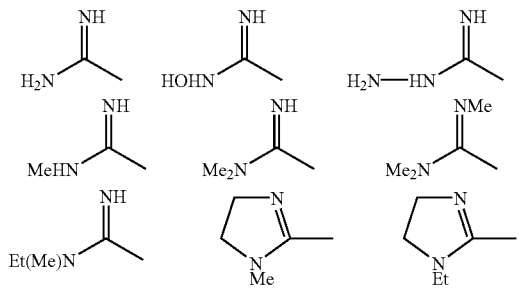

-continued

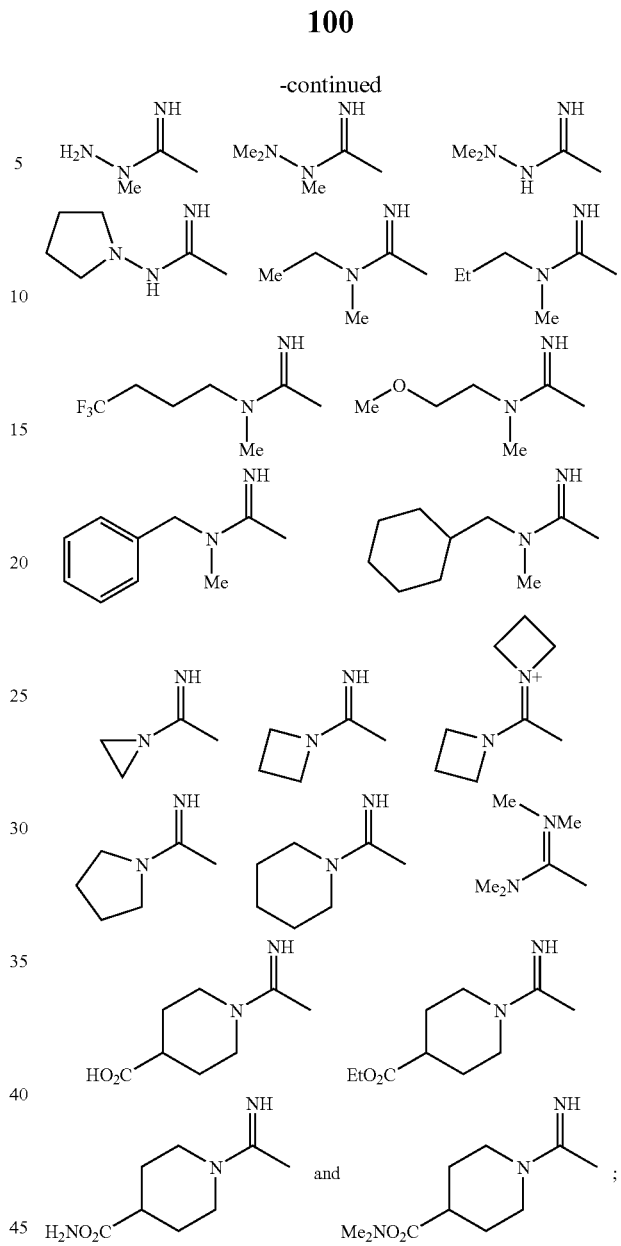

and all pharmaceutically acceptable isomers, salts, hydrates, solvates and prodrug derivatives thereof.

Another embodiment of the present invention provides the compounds of the following formula:

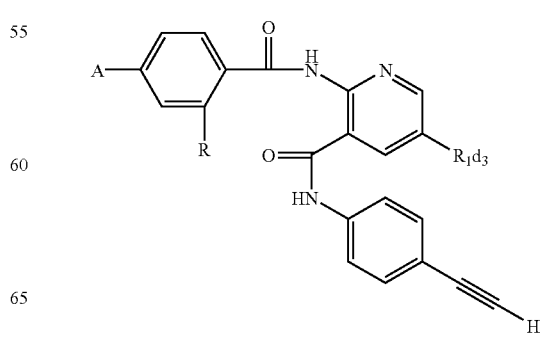

-continued

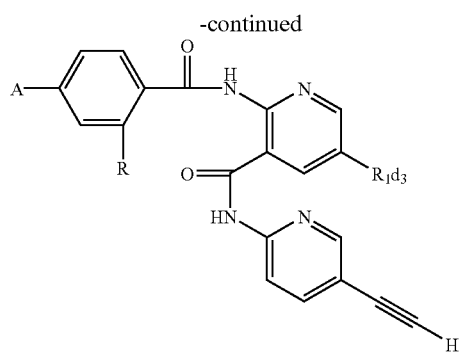

wherein:
each R is independently —H, —F, —Cl, —OMe, —NMe2, —OCH2CH2OMe, —OCH2CH2NMe2,

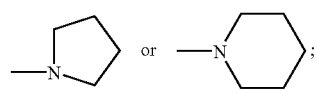

each R1d3 is independently Cl, Br, SMe, C≡CH or C≡CH;
A is independently selected from the group consisting of:

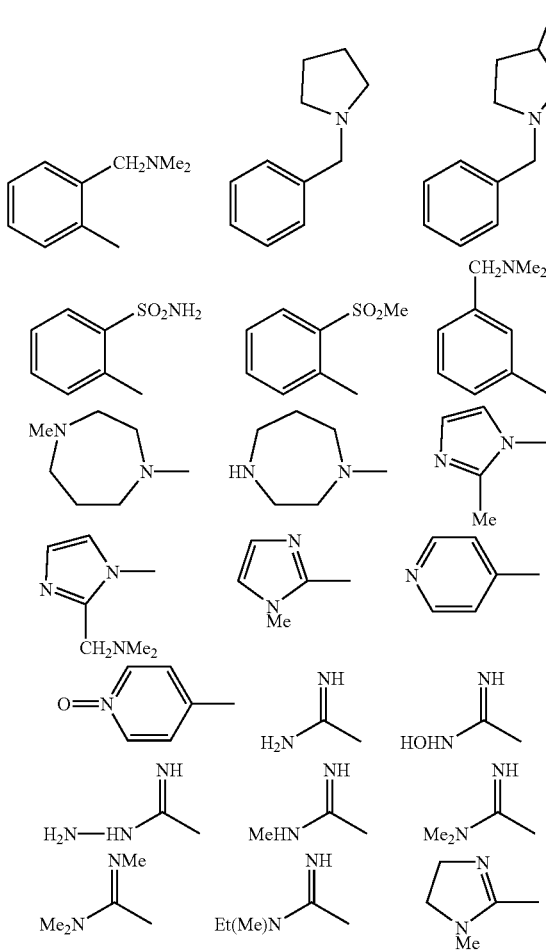

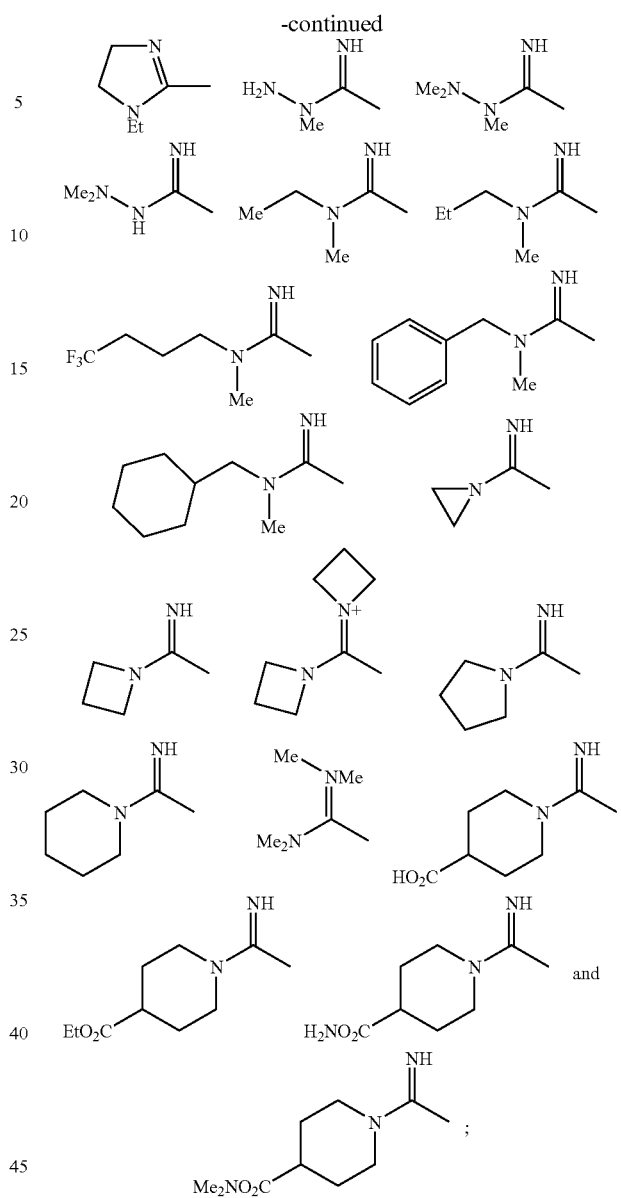

and all pharmaceutically acceptable isomers, salts, hydrates, solvates and prodrug derivatives thereof.

Another embodiment of the invention provides compounds of the following formula:

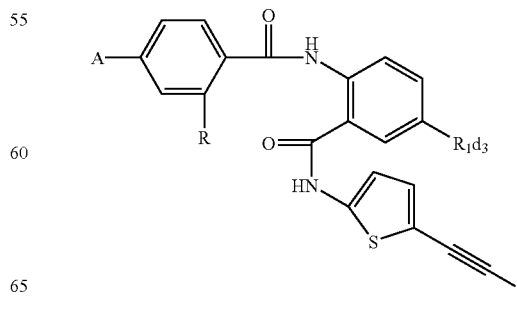

wherein:
each R is independently —H, —F, —Cl, —OMe, —NMe2, —OCH2CH2OMe, —OCH2CH2NMe2,

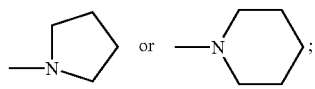

each R1d3 is independently Cl, Br, SMe, C≡CH or C≡CH;
A is independently selected from the group consisting of:

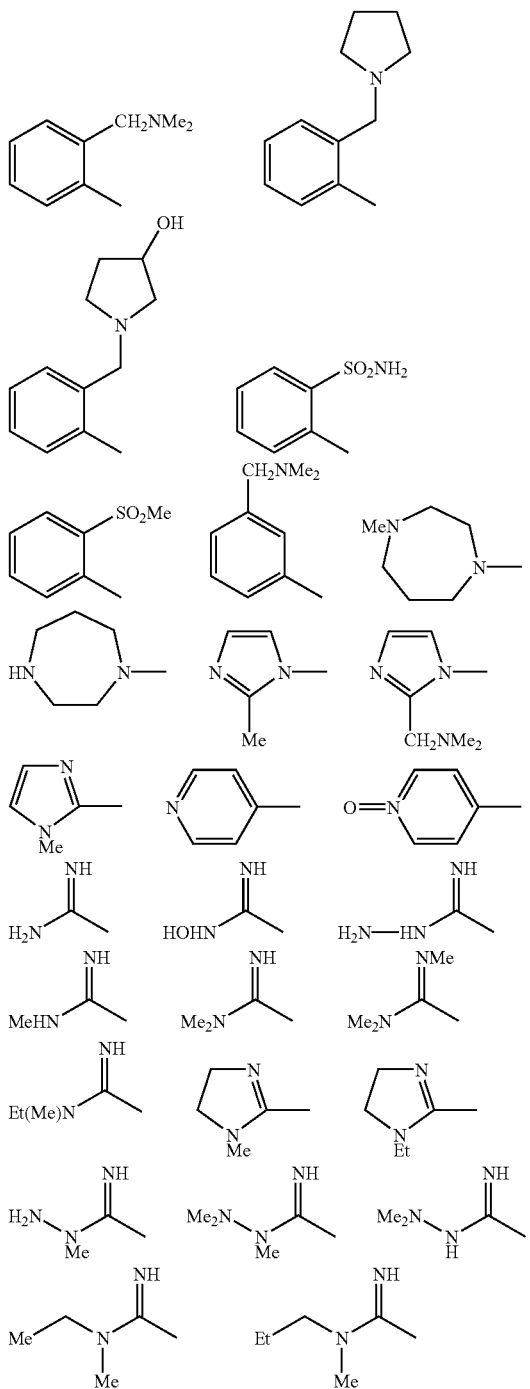

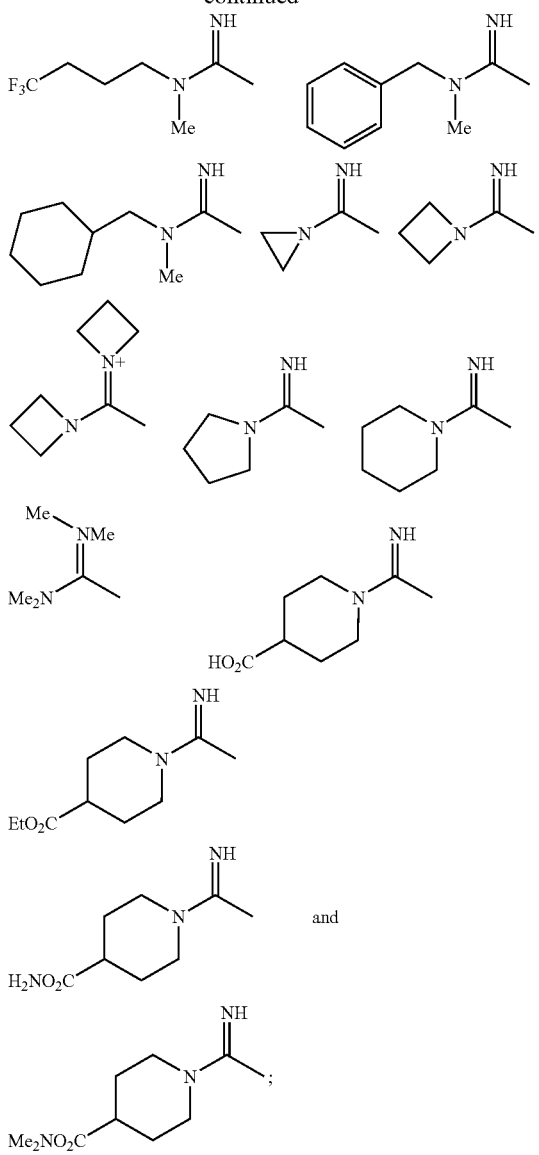

and all pharmaceutically acceptable isomers, salts, hydrates, solvates and prodrug derivatives thereof.

Another embodiment of the present invention provides the compounds of the following formula:

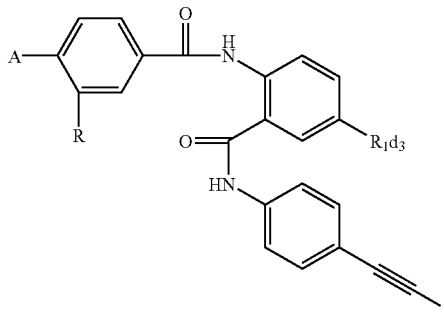

-continued
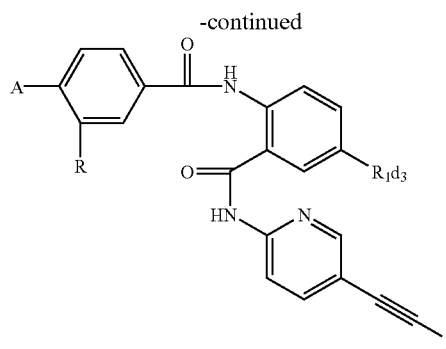
wherein:
each R is independently —H, —F, —Cl, —OMe, —NMe2, —OCH2CH2OMe, —OCH2CH2NMe2,
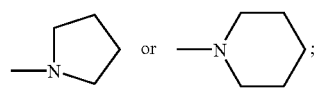
each R1d3 is independently Cl, Br, SMe, C≡CH or C≡CH;
A is independently selected from the group consisting of:
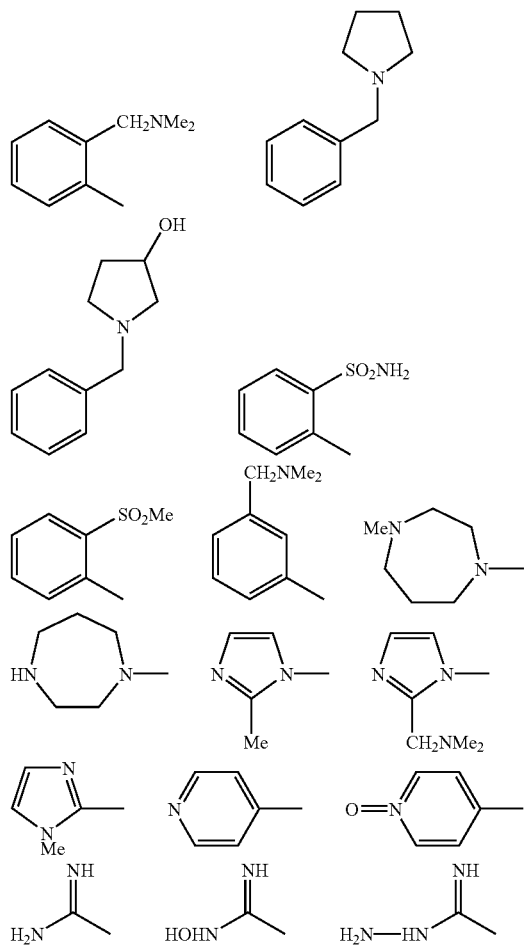
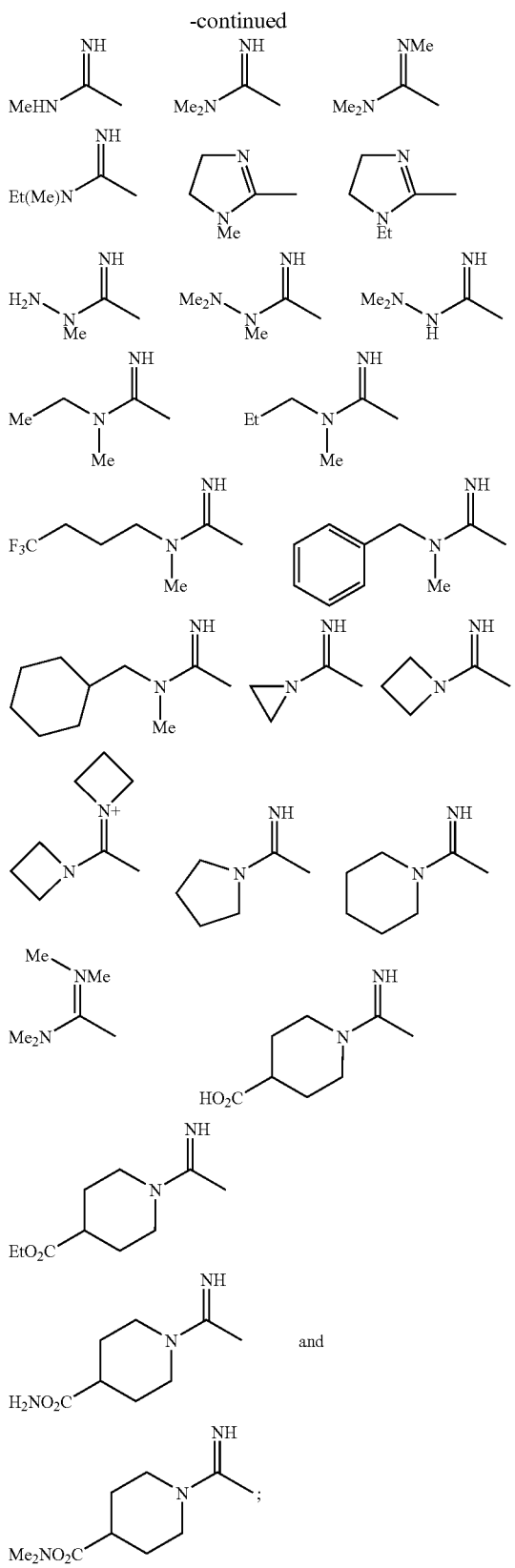
and all pharmaceutically acceptable isomers, salts, hydrates, solvates and prodrug derivatives thereof.

Another embodiment of the present invention provides the compounds of the following formula:

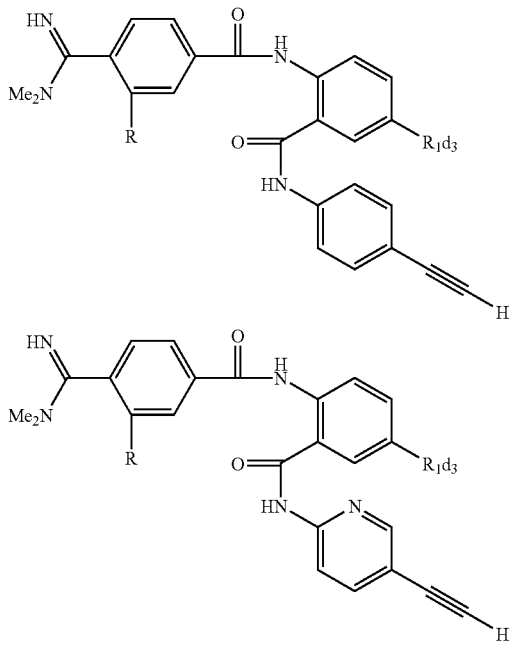

wherein:

each R is independently —H, —F, —Cl, —OMe, —NMe2, —OCH2CH2OMe, —OCH2CH2NMe2,

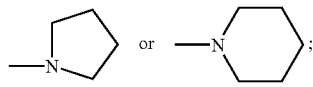

each R1d3 is independently Cl, Br, SMe, C≡CH or C≡CH;

and all pharmaceutically acceptable isomers, salts, hydrates, solvates and prodrug derivatives thereof.

The invention also encompasses all pharmaceutically acceptable salts, hydrates, solvates, and prodrug derivatives of the above compounds. In addition, the above compounds can exist in various isomeric and tautomeric forms, and all such forms are meant to be included in the invention, along with pharmaceutically acceptable salts, hydrates, solvates, and prodrug derivatives of such isomers and tautomers.

The compounds of the invention may be isolated as the free acid or base or converted to salts of various inorganic and organic acids and bases. Such salts are within the scope of the invention. Non-toxic and physiologically compatible salts are particularly useful, but less desirable salts may have use in the processes of isolation and purification.

A number of methods are useful for the preparation of the salts described above and are known to those skilled in the art. For example, the free acid or free base form of a compound of one of the formulas above can be reacted with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Prodrug Derivatives of Compounds

The invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of the invention which have groups cleavable under metabolic conditions. Prodrugs become the compounds of the invention which are pharmaceutically active in vivo, when they undergo solvolysis under physiological conditions or undergo enzymatic degradation. Prodrug compounds of the invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7-9, 21-24, Elsevier, Amsterdam 1985 and Silverman, The Organic Chemistry of Drug Design and Drug Action, pp. 352-401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of the invention may be combined with other features herein taught to enhance bioavailability.

The compounds of the present invention may also be used alone or in combination or in combination with other therapeutic or diagnostic agents. In certain preferred embodiments, the compounds of the invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successful thrombolytic therapy and/or reduce the time to reperfusion. These compounds may also allow for reduced doses of the thrombolytic agents to be used and therefore minimize potential hemorrhagic side-effects. The compounds of the invention can be utilized in vivo, ordinarily in mammals such as primates, (e.g. humans), sheep, horses, cattle, pigs, dogs, cats, rats and mice, or in vitro.

The biological properties of the compounds of the present invention can be readily characterized by methods that are well known in the art such as, for example, by the in vitro protease activity assays and in vivo studies to evaluate antithrombotic efficacy, and effects on hemostasis and hematological parameters, such as are illustrated in the examples.

Diagnostic applications of the compounds of the invention will typically utilize formulations in the form of solutions or suspensions. In the management of thrombotic disorders, the compounds of the invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of the invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

As mentioned above, the compounds of this invention find utility as therapeutic agents for disease states in mammals which have disorders of coagulation such as in the treatment or prevention of unstable angina, refractory angina, myocardial infarction, transient ischemic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries. Further, these compounds are useful for the treatment or prophylaxis of those diseases which involve the production and/or action of factor Xa/prothrombinase complex. This includes a number of thrombotic and prothrombotic states in which the coagulation cascade is activated which include but are not limited to, deep venous thrombosis, pulmonary embolism, myocardial infarction, stroke, thromboembolic complications of surgery and peripheral arterial occlusion.

Accordingly, a method for preventing or treating a condition in a mammal characterized by undesired thrombosis comprises administering to the mammal a therapeutically effective amount of a compound of this invention. In addition to the disease states noted above, other diseases treatable or preventable by the administration of compounds of this invention include, without limitation, occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

The compounds of the invention also find utility in a method for inhibiting the coagulation biological samples, which comprises the administration of a compound of the invention.

The compounds of the present invention may also be used in combination with other therapeutic or diagnostic agents. In certain preferred embodiments, the compounds of this invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successful thrombolytic therapy and/or reduce the time to reperfusion. These compounds may also allow for reduced doses of the thrombolytic agents to be used and therefore minimize potential hemorrhagic side-effects. The compounds of this invention can be utilized in vivo, ordinarily in mammals such as primates, (e.g. humans), sheep, horses, cattle, pigs, dogs, cats, rats and mice, or in vitro.

The biological properties of the compounds of the present invention can be readily characterized by methods that are well known in the art, for example by the in vitro protease activity assays and in vivo studies to evaluate antithrombotic efficacy, and effects on hemostasis and hematological parameters, such as are illustrated in the examples.

Diagnostic applications of the compounds of this invention will typically utilize formulations in the form of solutions or suspensions. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be 3-11, more preferably 5-9 and most preferably 7-8. It will be understood that use of certain of the foregoing excipients, carriers, or stabilizers will result in the formation of cyclic polypeptide salts. While the preferred route of administration is by injection, other methods of administration are also anticipated such as orally, intravenously (bolus and/or infusion), subcutaneously, intramuscularly, colonically, rectally, nasally, transdermally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyinylpyrrolidinone, pyran copolymer, polyhydroxy-propyl-methacrylamide-phenol, polyhydroxyethyl-aspartamide-phenol, or polyethyleneoxide-polylysine substituted with palmitoyl residues. Furthermore, compounds of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The "therapeutically effective amount" of a compound of the present invention will depend on the route of administration, the type of warm-blooded animal being treated, and the physical characteristics of the specific animal under consideration. These factors and their relationship to determining this amount are well known to skilled practitioners in the medical arts. This amount and the method of administration can be tailored to achieve optimal efficacy but will depend on such factors as weight, diet, concurrent medication and other factors which as noted hose skilled in the medical arts will recognize.

The "therapeutically effective amount" of the compound of the present invention can range broadly depending upon the desired affects and the therapeutic indication. Typically, dosages will be between about 0.01 mg/kg and 100 mg/kg body weight, preferably between about 0.01 and 10 mg/kg, body weight.

"Pharmaceutically acceptable carriers" for therapeutic use are well known in the pharmaceutical art, and are described, for example, in Remingtons Pharmaceutical Sciences, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used.

The compounds of the invention can be administered orally or parenterally in an effective amount within the dosage range of about 0.1 to 100 mg/kg, preferably about 0.5 to 50 mg/kg and more preferably about 1 to 20 mg/kg on a regimen in a single or 2 to 4 divided daily doses and/or continuous infusion.

Typically, about 5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Preparation of Compounds

The compounds of the present invention may be synthesized by either solid or liquid phase methods described and referenced in standard textbooks, or by a combination of both methods. These methods are well known in the art. See, Bodanszky, "The Principles of Peptide Synthesis", Hafner, et al., Eds., Springer-Verlag, Berlin, 1984.

Starting materials used in any of these methods are commercially available from chemical vendors such as Aldrich, Sigma, Nova Biochemicals, Bachem Biosciences, and the like, or may be readily synthesized by known procedures.

Reactions are carried out in standard laboratory glassware and reaction vessels under reaction conditions of standard temperature and pressure, except where otherwise indicated.

During the synthesis of these compounds, the functional groups of the amino acid derivatives used in these methods are protected by blocking groups to prevent cross reaction during the coupling procedure. Examples of suitable blocking groups and their use are described in "The Peptides: Analysis, Synthesis, Biology", Academic Press, Vol. 3 (Gross, et al., Eds., 1981) and Vol. 9 (1987), the disclosures of which are incorporated herein by reference.

Compounds according to the invention can be synthesized utilizing procedures well known in the art. The reaction products are isolated and purified by conventional methods, typically by solvent extraction into a compatible solvent. The products may be further purified by column chromatography or other appropriate methods.

Compositions and Formulations

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of the structures recited above with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Diagnostic applications of the compounds of this invention will typically utilize formulations such as solution or suspension. In the management of thrombotic disorders the compounds of this invention maybe utilized in compositions such as tablets, capsules or elixirs for oral administration, suppositories, sterile solutions or suspensions or injectable administration, and the like, or incorporated into shaped articles. Subjects in need of treatment (typically manimalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in *Remington 's Pharmaceutical Sciences*, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyinalpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of this invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyinylpyrrolidone, pyran copolymer, polyhydroxy-propyl-methacrylamide-phenol, polyhydroxyethyl-aspartamide-phenol, or polyethyleneoxide-polylysine substituted with palmitoyl residues. Furthermore, the factor Xa inhibitors of this invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For injection by hypodermic needle, it may be assumed the dosage is delivered into the body's fluids. For other routes of administration, the absorption efficiency must be individually determined for each inhibitor by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about i0.10 mg/kg to about 20 mg/kg. Advantageously, the compounds of this invention may be administered several times daily, and other dosage regimens may also be useful.

Typically, about 0.5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

In practicing the methods of this invention, the compounds of this invention may be used alone or in combination, or in combination with other therapeutic or diagnostic agents. In certain preferred embodiments, the compounds of this inventions may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals such as primates, such as humans, sheep, horses, cattle, pigs, dogs, cats, rats and mice, or in vitro.

The preferred compounds of the present invention are characterized by their ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The compounds of this present invention, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Anticoagulant therapy is also useful to prevent coagulation of stored whole blood and to prevent coagulation in other biological samples for testing or storage. Thus the compounds of this invention can be added to or contacted with any medium containing or suspected to contain factor Xa and in which it is desired that blood coagulation be inhibited, e.g., when contacting the mammal's blood with material such as vascular grafts, stents, orthopedic prostheses, cardiac stents, valves and prostheses, extra corporeal circulation systems and the like.

The following examples are provided to illustrate the invention. The examples are not intended to limit the scope of the present invention and they should not be so interpreted. Amounts are in weight parts or weight percentages unless otherwise indicated. Without further description, it is believed that one of ordinary skill in the art can, using the preceding description and the following illustrative examples, make and utilize the compounds of the present invention and practice the claimed methods.

EXAMPLES
Examples of Chemical Production Process General Reaction Schemes
Scheme 1
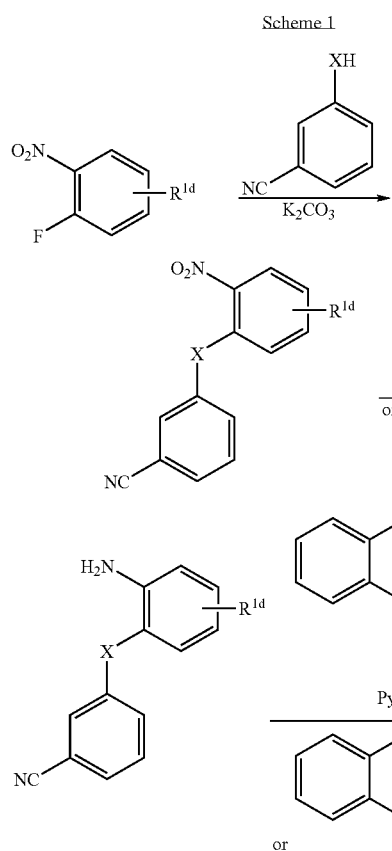
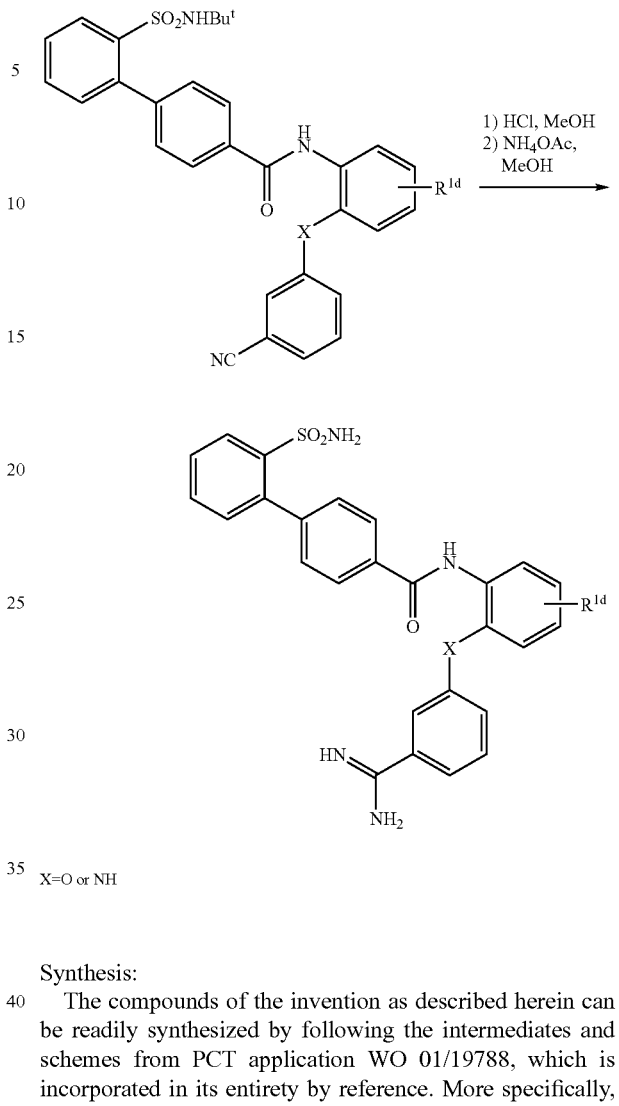
X=O or NH
Synthesis:
The compounds of the invention as described herein can be readily synthesized by following the intermediates and schemes from PCT application WO 01/19788, which is incorporated in its entirety by reference. More specifically,
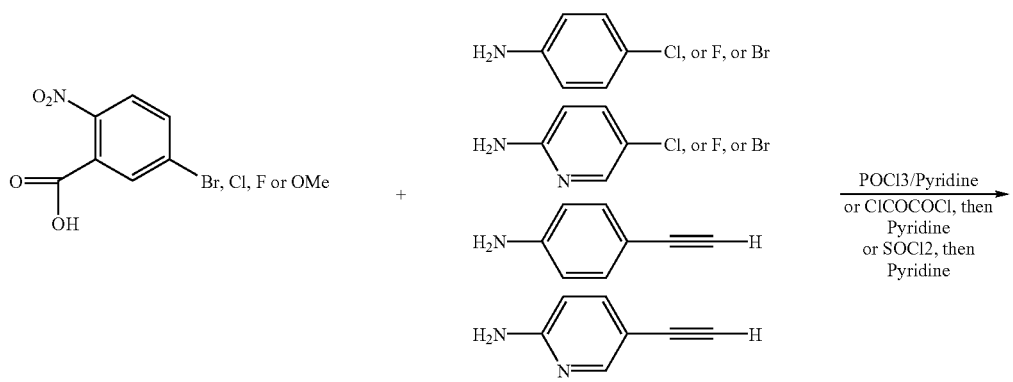

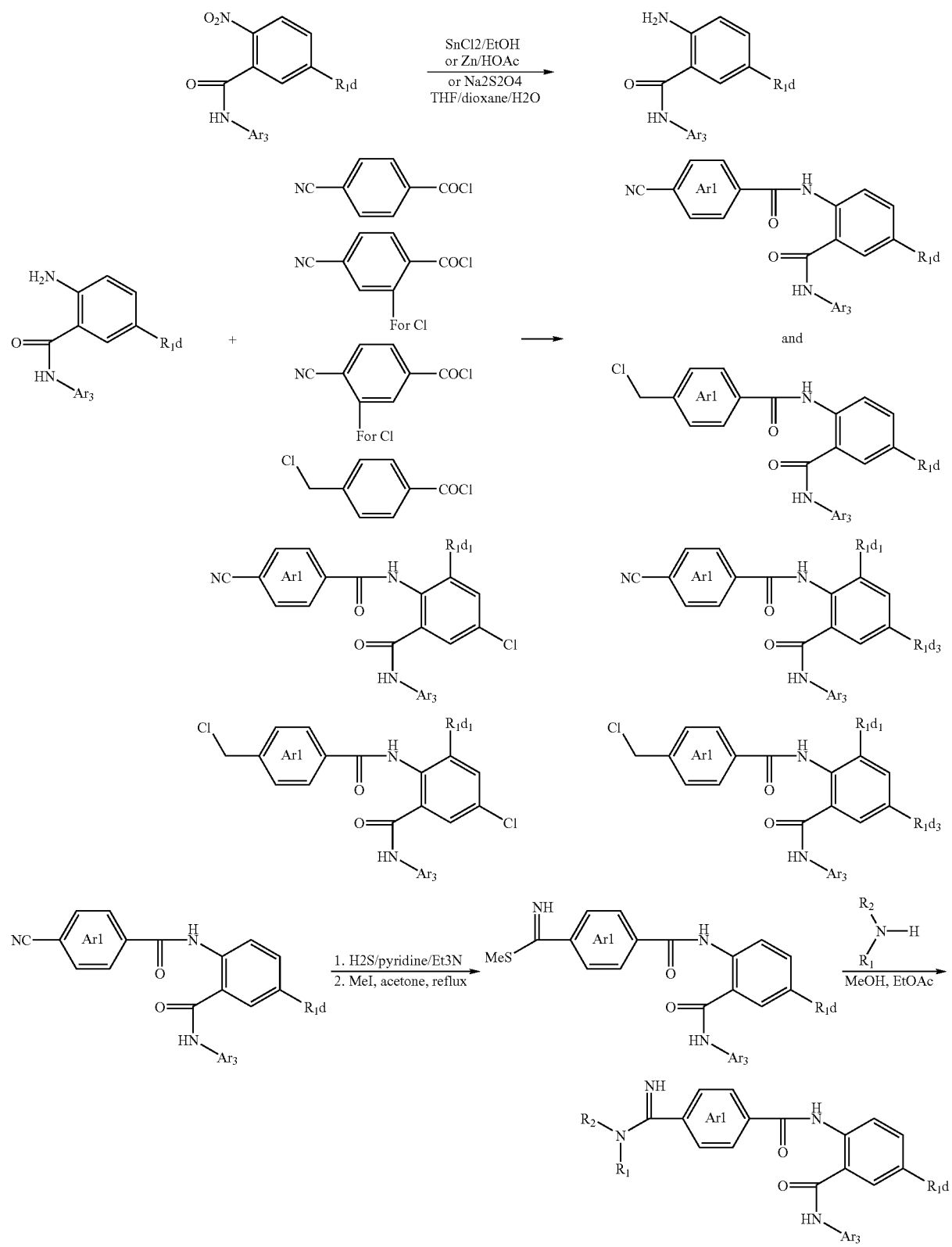

-continued
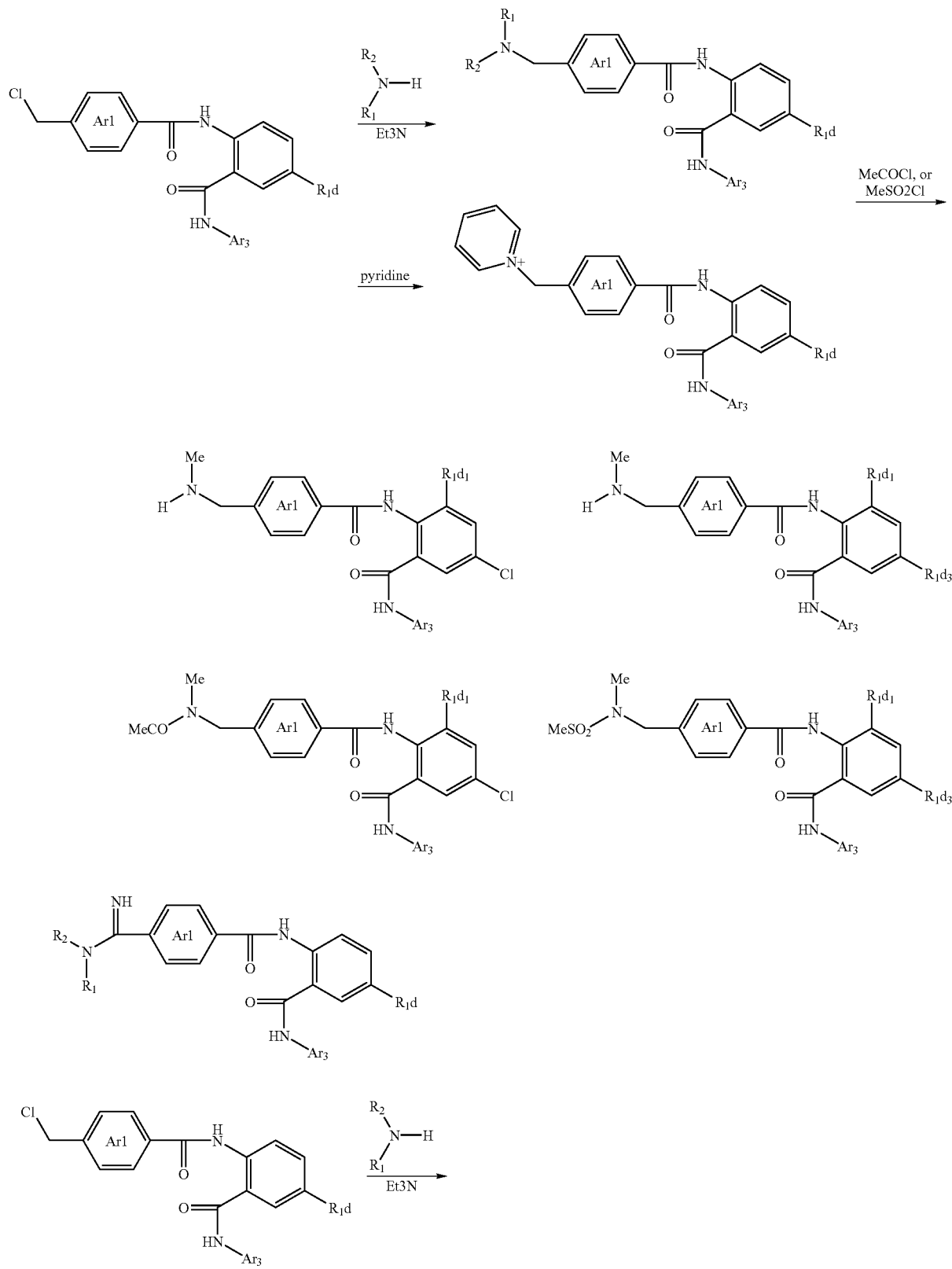

-continued
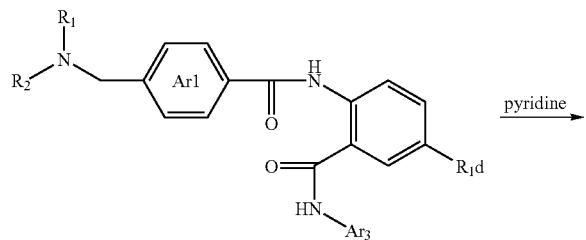
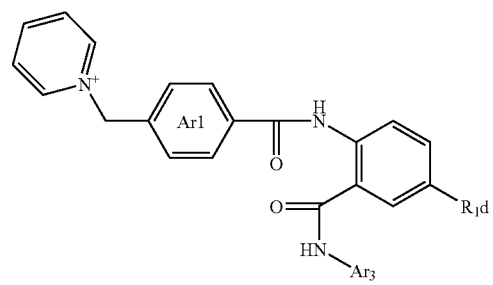
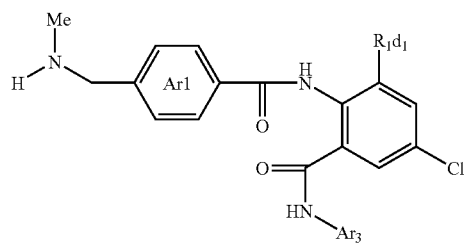
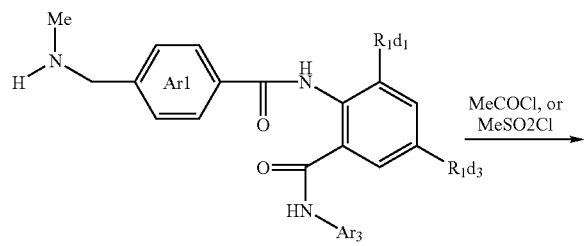
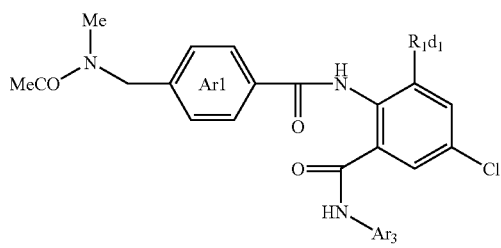
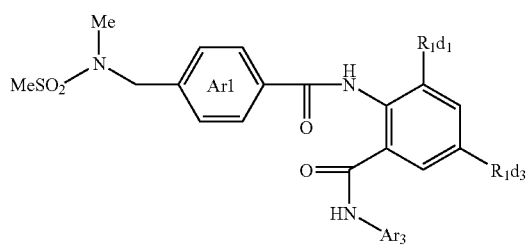

EXAMPLES AND PROCEDURES

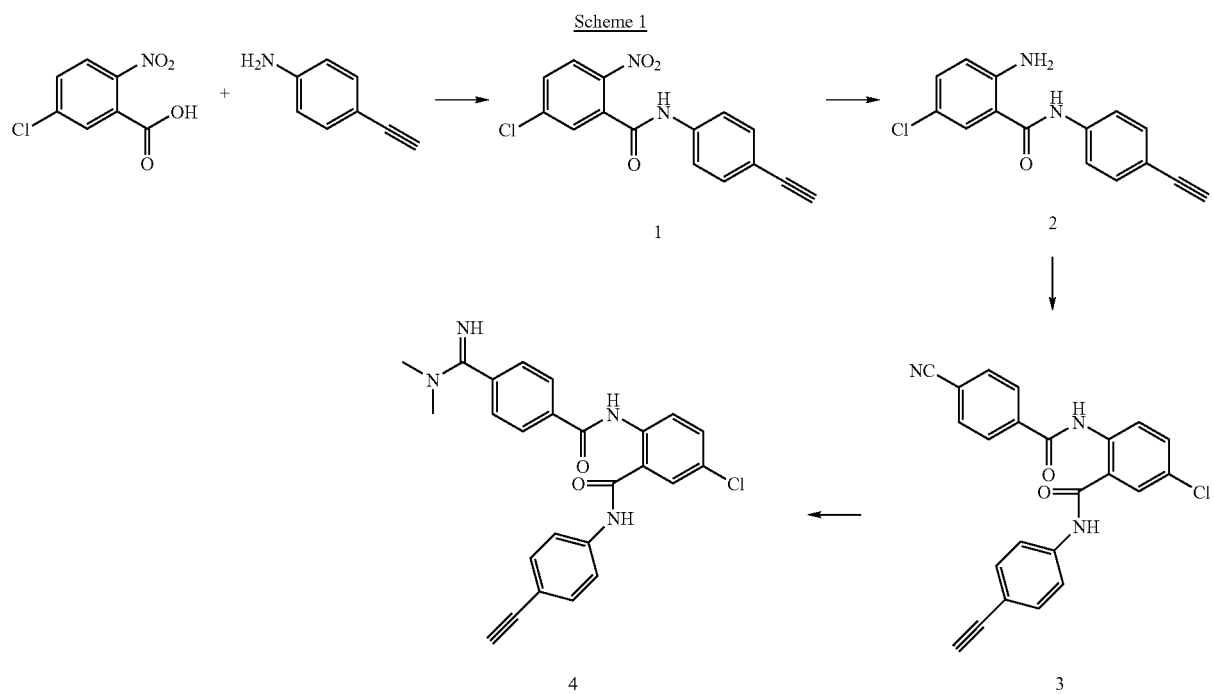

Scheme 1

Example 1

{4-[(dimethylamino)iminomethyl]phenyl}-N-{4-chloro-2-[N-(4-ethynylphenyl)carbamoyl]phenyl}-carboxamide (4)

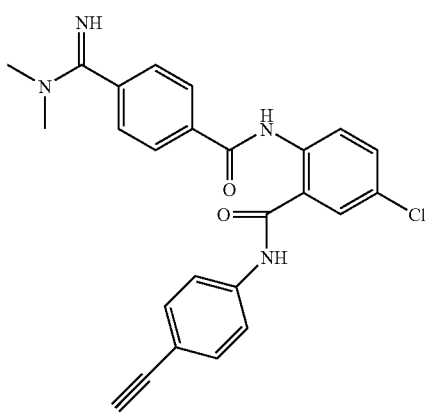

Step 1:

To a stirring solution of 4-ethynylaniline (4.9 g, 42 mmol) and 5-chloro-2-nitrobenzoic acid (8.1 g, 40 mmol) in anhydrous pyridine (40 mL) at −0° C. was added $POCl_3$ (12.0 g, 80 mmol) dropwise. Upon completion of addition, The reaction was quenched with ice water. The mixture was concentrated and diluted with EtOAc (150 mL). The organic solution was washed with 1N HCl (2×) and brine, dried and evaporated to give compound 1 (9.6 g, 80%) as a brownish solid. MS found for $C_{14}H_8ClN_3O_3$ as $(M+Na)^+$: 323.0.

Step 2:

To a solution of compound 1 (9.6 g, 32 mmol) in THF (80 mL) and 1,4-dioxane (80 mL) was added an aqueous solution of $Na_2S_2O_4$ (27.8 g, 160 mmol in 160 mL water). The mixture was stirred at rt for 1 h. The organic solvent was removed by rotavap. The aqueous solution was basified by $NaHCO_3$ to pH=9 and extracted with EtOAc (150 mL). The organic layer was washed with brine, dried and evaporated to give compound 1 (8.2 g, 95%) as a yellow solid. MS found for $C_{14}H_{10}ClN_3O$ as $(M+H)^+$: 271.1.

Step 3:

To a solution of compound 2 (1.0 g, 3.7 mmol) in $CH_2Cl_2$ (20 mL) and pyridine (2 mL) was added 4-cyano-benzoyl-chloride (800 mg, 5.4 mmol). After stirring at ambient temperatures overnight, the mixture was concentrated. The product was precipitated out from a mixture of THF, MeOH and water. Upon filtration, 1.2 g of compound 3 was obtained (81% yield) as an offwhite solid. MS found for $C_{23}H_{14}ClN_3O_2$ as $(M+Na)^+$: 422.0.

Step 4:

To a solution of compound 3 (150 mg) in 10% $Et_3N$/pyridine (5 mL) at 0° C. was bubbled dry $H_2S$ gas to saturation. The mixture was stirred at ambient temperatures overnight. The volatile was removed to dryness. The residue was suspended in anhydrous acetone (10 mL), followed by addition of MeI (0.2 mL). The reaction mixture was refluxed for 3 hour. The solvent was removed by rotary evaporation. The residue was dissolved in anhydrous MeOH (5 mL). A mixture of dimethylamine (0.32 mL, 2N in THF) and AcOH (37 μL) was added to the solution. The resulting mixture was refluxed for 1 hour, concentrated and subjected to RP-HPLC purification to give the title compound 4. MS found for $C_{25}H_{21}ClN_4O_2$ $(M+H)^+$: 445.1.

Example 2

N-{4-chloro-2-[N-(4-ethynylphenyl)carbamoyl]phenyl}[4-(1-methyl(2-imidazolin-2-yl))phenyl]-carboxamide

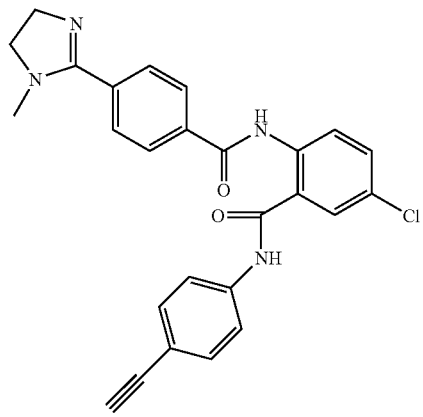

The titled compound was made by the procedure similar to that described in example 1.
MS found for $C_{26}H_{21}ClN_4O_2$ (M+H)$^+$: 457.1.

Example 3

Ethyl 1-{[4-(N-{4-chloro-2-[N-(4-ethynylphenyl)carbamoyl]phenyl}carbamoyl)phenyl]iminomethyl}-piperidine-4-carboxylate

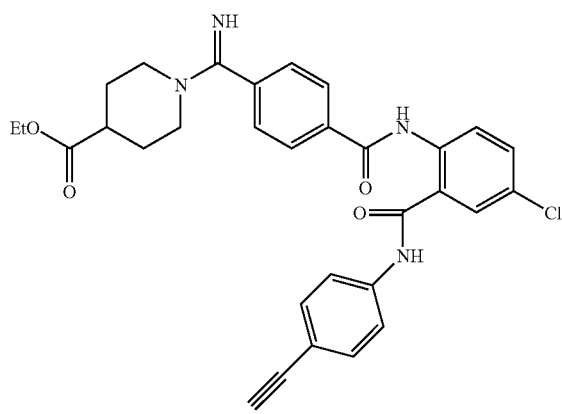

The titled compound was made by the procedure similar to that described in example 1.
MS found for $C_{31}H_{29}ClN_4O_4$ as (M+H)$^+$: 557.2.

Example 4

1-{[4-(N-{4-chloro-2-[N-(4-ethynylphenyl)carbamoyl]phenyl}carbamoyl)phenyl]iminomethyl}-piperidine-4-carboxylic Acid

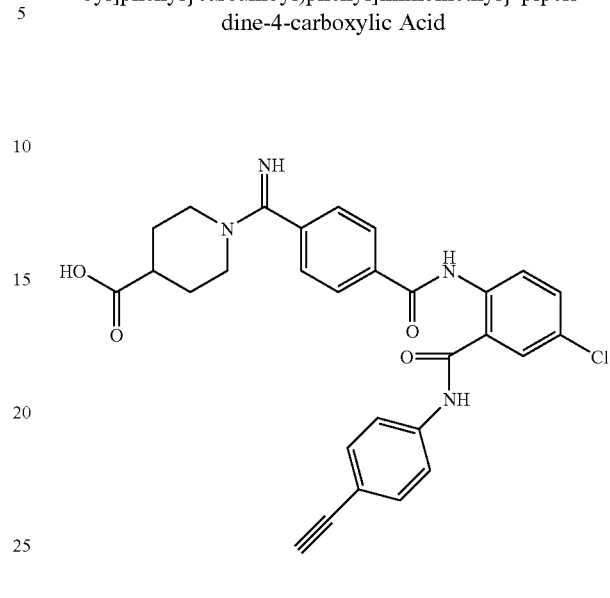

To a solution of ethyl 1-{[4-(N-{4-chloro-2-[N-(4-ethynylphenyl)carbamoyl]phenyl}carbamoyl)-phenyl]iminomethyl}piperidine-4-carboxylate in EtOH was added 1N aq. LiOH (1 mL). The mixture was stirred for 3 hours, concentrated and purified by RP-HPLC to give the titled compound. MS found for $C_{29}H_{25}ClN_4O_4$ (M+1)$^+$: 529.1.

Example 5

1-{[4-(N-{4-chloro-2-[N-(4-ethynylphenyl)carbamoyl]phenyl}carbamoyl)phenyl]iminomethyl}-piperidine-4-carboxamide

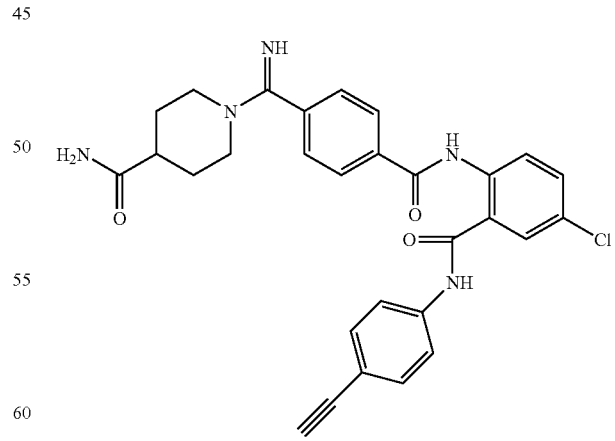

The titled compound was made by the procedure similar to that described in example 1.
MS found for $C_{29}H_{26}ClN_5O_3$ as (M+H)$^+$: 528.1.

Example 6

N-{4-chloro-2-[N-(4-ethynylphenyl)carbamoyl]phenyl}(4-{[4-(hydroxymethyl)piperidyl]iminomethyl}phenyl)carboxamide

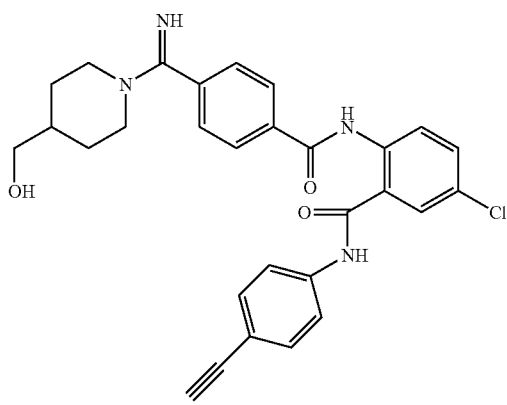

The titled compound was made by the procedure similar to that described in example 1.
MS found for $C_{29}H_{27}ClN_4O_3$ as $(M+H)^+$: 515.2.

Example 7

[4-({[2-(dimethylamino)ethyl]methylamino}iminomethyl)phenyl]-N-{4-chloro-2-[N-(4-ethynylphenyl)carbamoyl]phenyl}carboxamide

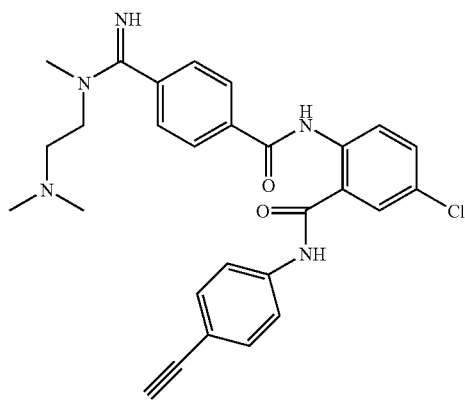

The titled compound was made by the procedure similar to that described in example 1.
MS found for $C_{28}H_{28}ClN_5O_2$ as $(M+H)^+$: 502.2.

Example 8

{4-[(dimethylamino)iminomethyl]-2-fluorophenyl}-N-{4-chloro-2-[N-(4-ethynylphenyl)carbamoyl]phenyl}carboxamide

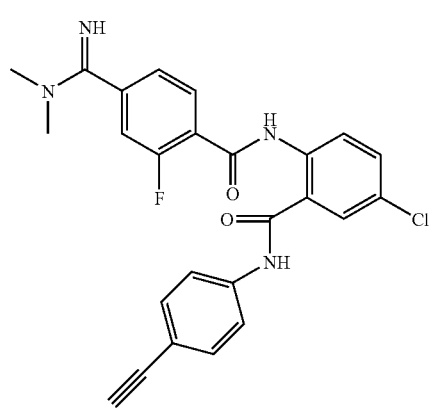

The titled compound was made by the procedure similar to that described in example 1.
MS found for $C_{25}H_{20}ClFN_4O_2$ as $(M+H)^+$: 463.1.

Example 9

N-{4-chloro-2-[N-(4-ethynylphenyl)carbamoyl]phenyl}[2-fluoro-4-(1-methyl(2-imidazolin-2-yl))phenyl]carboxamide

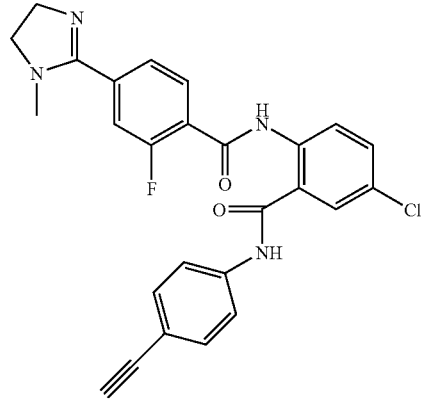

The titled compound was made by the procedure similar to that described in example 1.
MS found for $C_{26}H_{20}ClFN_4O_2$ as $(M+H)^+$: 475.1.

Example 10

Ethyl 1-{[4-(N-{4-chloro-2-[N-(4-ethynylphenyl)carbamoyl]phenyl}carbamoyl)-3-fluorophenyl]iminomethyl}piperidine-4-carboxylate

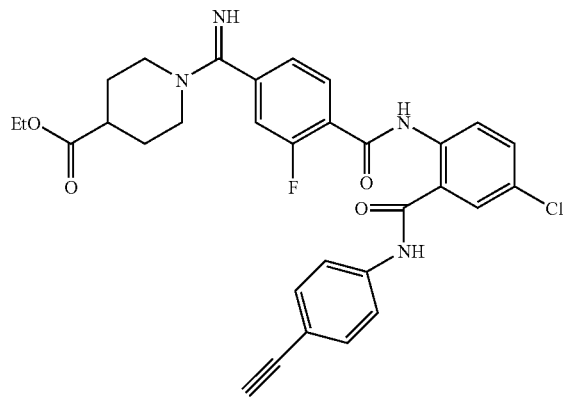

The titled compound was made by the procedure similar to that described in example 1.
MS found for $C_{31}H_{28}ClFN_4O_4$ as $(M+H)^+$: 575.2.

Example 11

1-{[4-(N-{4-chloro-2-[N-(4-ethynylphenyl)carbamoyl]phenyl}carbamoyl)-3-fluorophenyl]iminomethyl}piperidine-4-carboxylic Acid

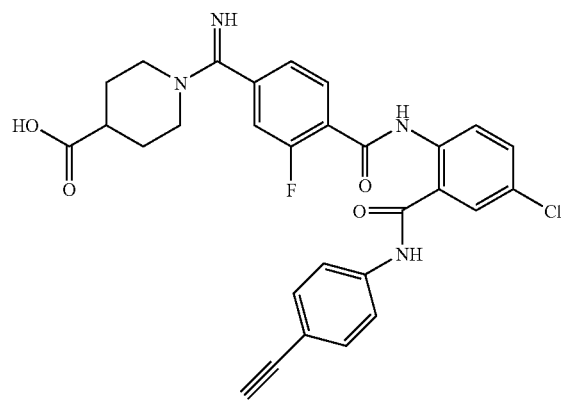

The titled compound was made by the procedure similar to that described in example 4.
MS found for $C_{29}H_{24}ClFN_4O_4$ as $(M+H)^+$: 547.1.

Example 12

1-{[4-(N-{4-chloro-2-[N-(4-ethynylphenyl)carbamoyl]phenyl}carbamoyl)-3-fluorophenyl]iminomethyl}piperidine-4-carboxamide

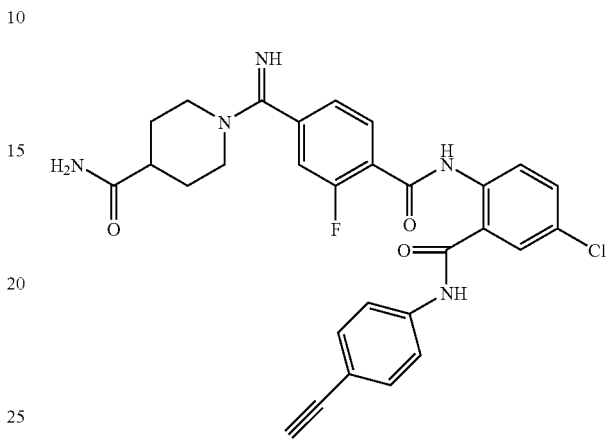

The titled compound was made by the procedure similar to that described in example 1.
MS found for $C_{29}H_{25}ClFN_5O_3$ as $(M+H)^+$: 546.1.

Example 13

N-{4-chloro-2-[N-(4-ethynylphenyl)carbamoyl]phenyl}(2-fluoro-4-{[4-(hydroxymethyl)piperidyl]iminomethyl}phenyl)carboxamide

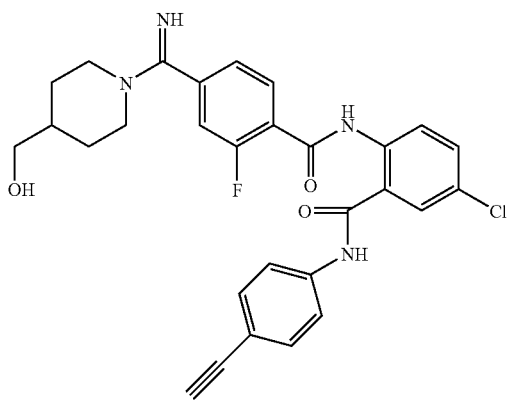

The titled compound was made by the procedure similar to that described in example 1.
MS found for $C_{29}H_{26}ClFN_4O_3$ as $(M+H)^+$: 533.2.

Example 14

[4-({[2-(dimethylamino)ethyl]methylamino}iminomethyl)-2-fluorophenyl]-N-{4-chloro-2-[N-(4-ethynylphenyl)carbamoyl]phenyl}carboxamide

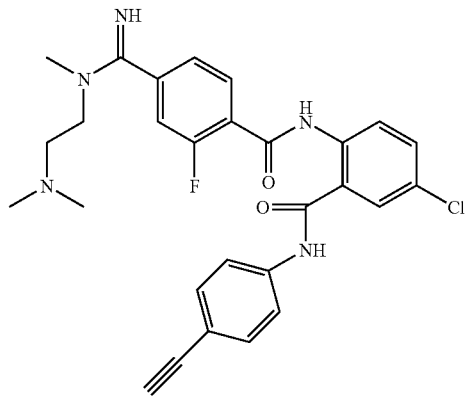

The titled compound was made by the procedure similar to that described in example 1.
MS found for $C_{28}H_{27}ClFN_5O_2$ as $(M+H)^+$: 520.2.

Example 15

N-{4-chloro-2-[N-(4-ethynylphenyl)carbamoyl]phenyl}{4-[(ethylmethylamino)iminomethyl]-2-fluorophenyl}carboxamide

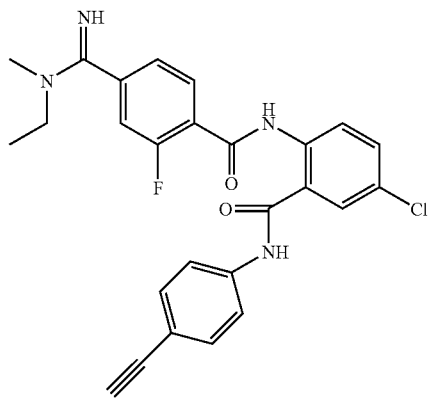

The titled compound was made by the procedure similar to that described in example 1.
MS found for $C_{26}H_{22}ClFN_4O_2$ as $(M+H)^+$: 477.1.

Example 16

[4-({[3-(dimethylamino)propyl]methylamino}iminomethyl)-2-fluorophenyl]-N-{4-chloro-2-[N-(4-ethynylphenyl)carbamoyl]phenyl}carboxamide

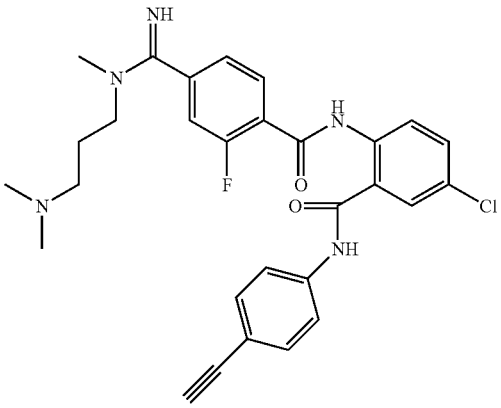

The titled compound was made by the procedure similar to that described in example 1.
MS found for $C_{29}H_{29}ClFN_5O_2$ as $(M+H)^+$: 534.2.

Example 17

{4-[(dimethylamino)iminomethyl]phenyl}-N-{2-[N-(4-ethynylphenyl)carbamoyl]-4-methoxyphenyl}carboxamide

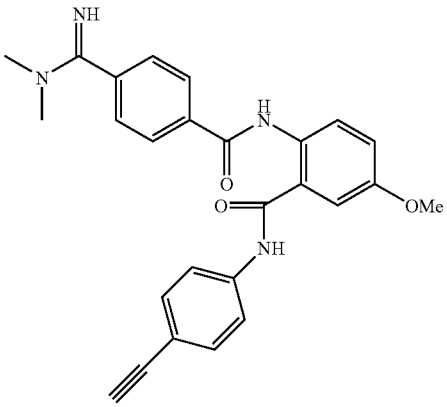

The titled compound was made by the procedure similar to that described in example 1.
MS found for $C_{26}H_{24}N_4O_3$ as $(M+H)^+$: 441.2.

Example 18

N-{2-[N-(4-ethynylphenyl)carbamoyl]-4-methoxyphenyl}[4-(1-methyl(2-imidazolin-2-yl))phenyl]carboxamide

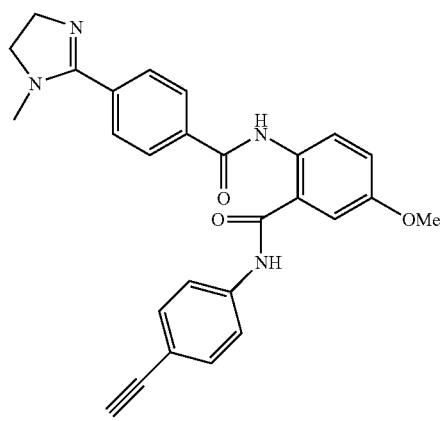

The titled compound was made by the procedure similar to that described in example 1.
MS found for $C_{27}H_{24}N_4O_3$ as $(M+H)^+$: 453.2.

Example 19

Ethyl 1-{[4-(N-{2-[N-(4-ethynylphenyl)carbamoyl]-4-methoxyphenyl}carbamoyl)phenyl]iminomethyl}piperidine-4-carboxylate

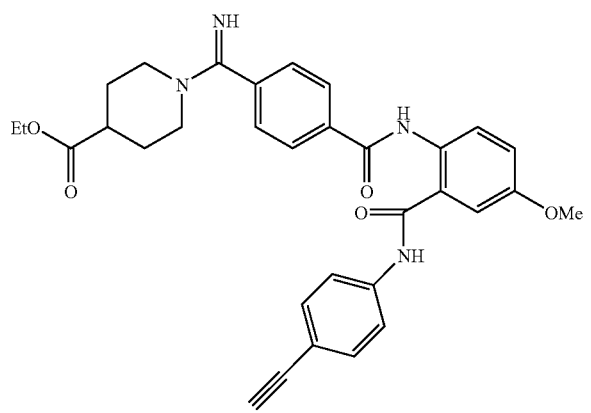

The titled compound was made by the procedure similar to that described in example 1.
MS found for $C_{32}H_{32}N_4O_5$ as $(M+H)^+$: 553.3.

Example 20

Methyl 1-{[4-(N-{2-[N-(4-ethynylphenyl)carbamoyl]-4-methoxyphenyl}carbamoyl)phenyl]iminomethyl}piperidine-4-carboxylate

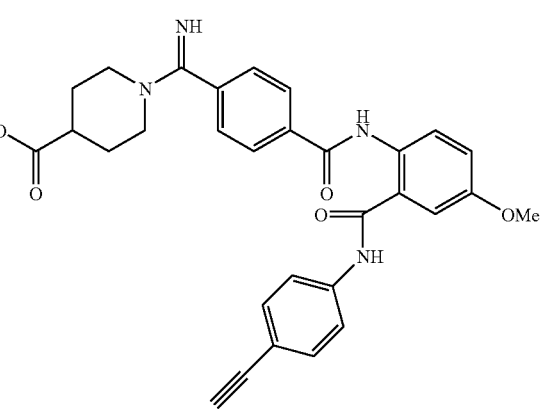

The titled compound was made by the procedure similar to that described in example 1.
MS found for $C_{31}H_{30}N_4O_5$ as $(M+H)^+$: 539.2.

Example 21

1-{[4-(N-{2-[N-(4-ethynylphenyl)carbamoyl]-4-methoxyphenyl}carbamoyl)phenyl]iminomethyl}piperidine-4-carboxylic Acid

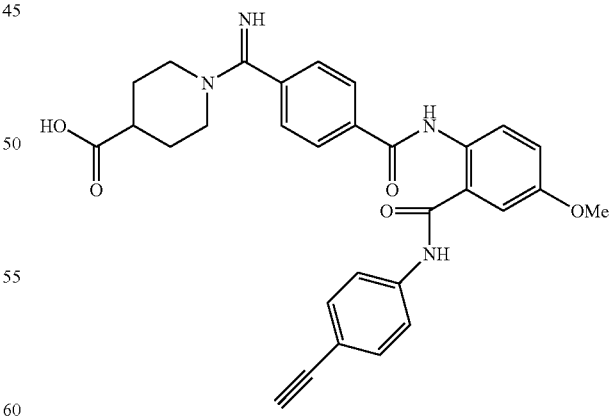

The titled compound was made by the procedure similar to that described in example 1.
MS found for $C_{30}H_{28}N_4O_5$ as $(M+H)^+$: 525.2.

Example 22

1-{[4-(N-{2-[N-(4-ethynylphenyl)carbamoyl]-4-methoxyphenyl}carbamoyl)phenyl]iminomethyl}piperidine-4-carboxamide

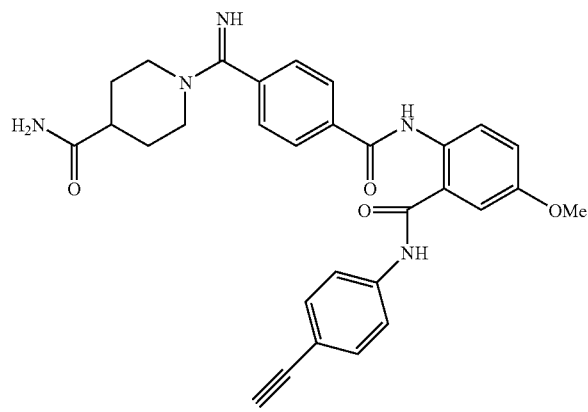

The titled compound was made by the procedure similar to that described in example 1.
MS found for $C_{30}H_{29}N_5O_4$ as $(M+H)^+$: 524.2.

Example 23

[4-({[2-(dimethylamino)ethyl]methylamino}iminomethyl)phenyl]-N-{2-[N-(4-ethynylphenyl)carbamoyl]-4-methoxyphenyl}carboxamide

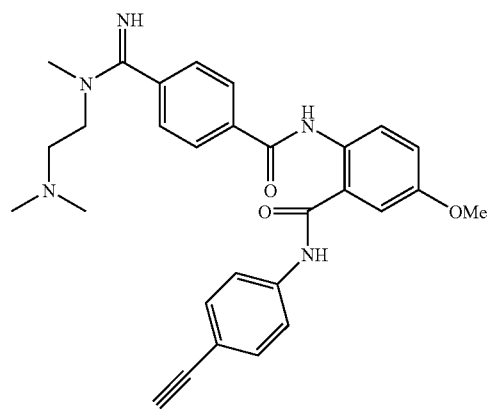

The titled compound was made by the procedure similar to that described in example 1.
MS found for $C_{29}H_{31}N_5O_3$ as $(M+H)^+$: 498.2.

Example 24

{4-[(dimethylamino)iminomethyl]-2-fluorophenyl}-N-{2-[N-(4-ethynylphenyl)carbamoyl]-4-methoxyphenyl}carboxamide

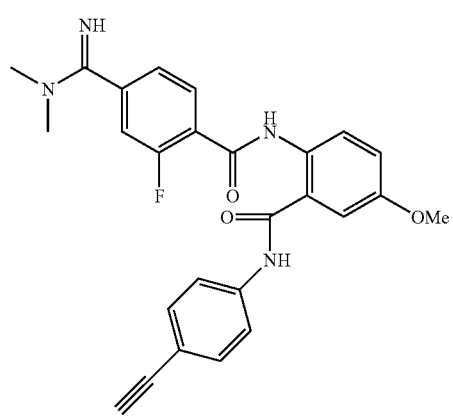

The titled compound was made by the procedure similar to that described in example 1.
MS found for $C_{26}H_{23}FN_4O_3$ as $(M+H)^+$: 459.1.

Example 25

N-{2-[N-(4-ethynylphenyl)carbamoyl]-4-methoxyphenyl}[2-fluoro-4-(1-methyl(2-imidazolin-2-yl))phenyl]carboxamide

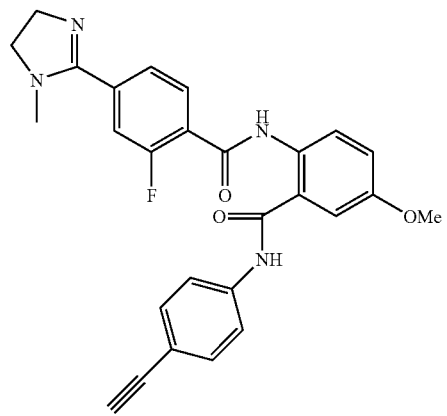

The titled compound was made by the procedure similar to that described in example 1.
MS found for $C_{27}H_{23}FN_4O_3$ as $(M+H)^+$: 471.1.

Example 26

Ethyl 1-{[4-(N-{2-[N-(4-ethynylphenyl)carbamoyl]-4-methoxyphenyl}carbamoyl)-3-fluorophenyl]iminomethyl}piperidine-4-carboxylate

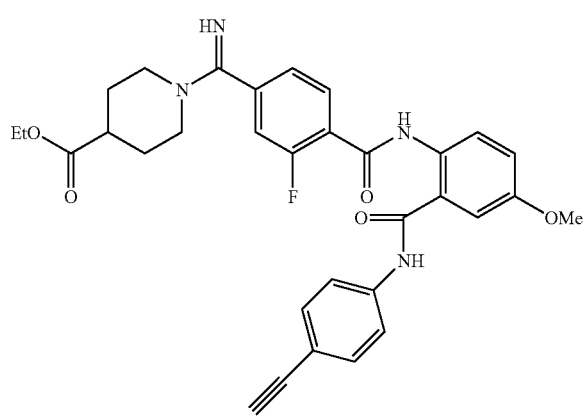

The titled compound was made by the procedure similar to that described in example 1.

MS found for $C_{32}H_{31}FN_4O_5$ as $(M+H)^+$: 571.2.

Example 27

Methyl 1-{[4-(N-{2-[N-(4-ethynylphenyl)carbamoyl]-4-methoxyphenyl}carbamoyl)-3-fluorophenyl]iminomethyl}piperidine-4-carboxylate

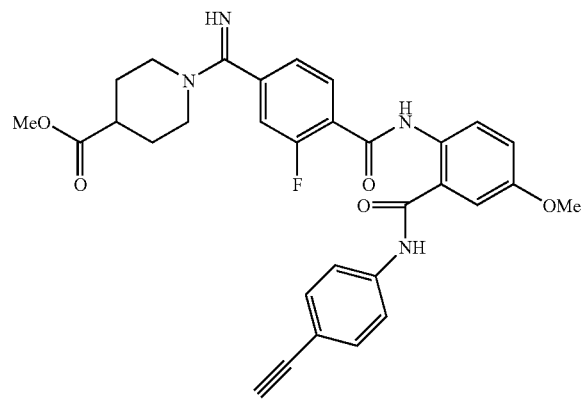

The titled compound was made by the procedure similar to that described in example 1.

MS found for $C_{31}H_{29}FN_4O_5$ as $(M+H)^+$: 557.2.

Example 28

1-{[4-(N-{2-[N-(4-ethynylphenyl)carbamoyl]-4-methoxyphenyl}carbamoyl)-3-fluorophenyl]iminomethyl}piperidine-4-carboxylic Acid

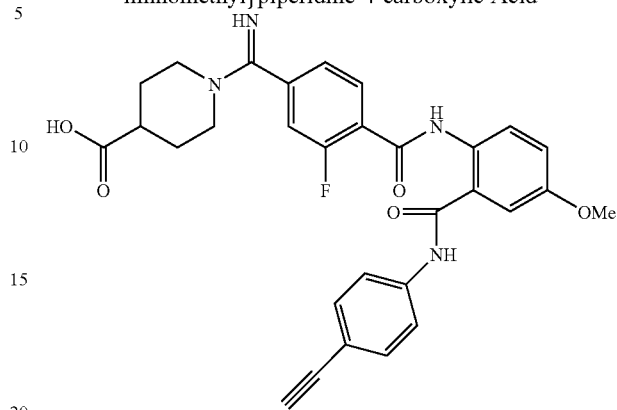

The titled compound was made by the procedure similar to that described in example 4.

MS found for $C_{30}H_{27}FN_4O_5$ as $(M+H)^+$: 543.2.

Example 29

1-{[4-(N-{2-[N-(4-ethynylphenyl)carbamoyl]-4-methoxyphenyl}carbamoyl)-3-fluorophenyl]iminomethyl}piperidine-4-carboxamide

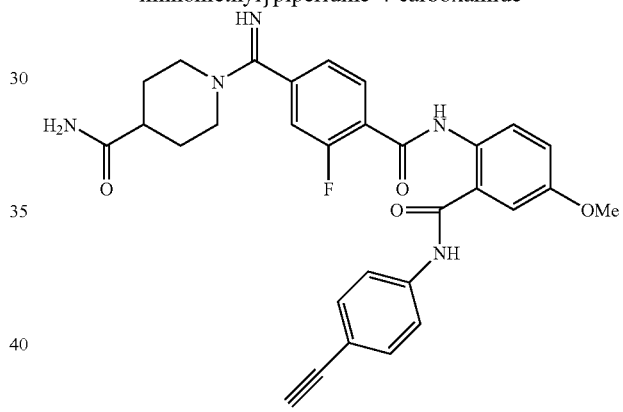

The titled compound was made by the procedure similar to that described in example 1.

MS found for $C_{30}H_{28}FN_5O_4$ as $(M+H)^+$: 542.2.

Example 30

[4-({[3-(dimethylamino)propyl]methylamino}iminomethyl)-2-fluorophenyl]-N-{2-[N-(4-ethynylphenyl)carbamoyl]-4-methoxyphenyl}carboxamide

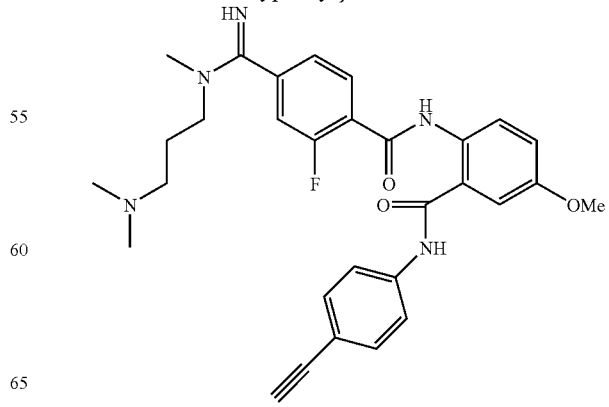

The titled compound was made by the procedure similar to that described in example 1.
MS found for $C_{30}H_{32}FN_5O_3$ as $(M+H)^+$: 530.2.

Example 31

N-{2-[N-(4-ethynylphenyl)carbamoyl]-4-methoxyphenyl}[2-fluoro-4-(iminopiperidylmethyl)phenyl]carboxamide

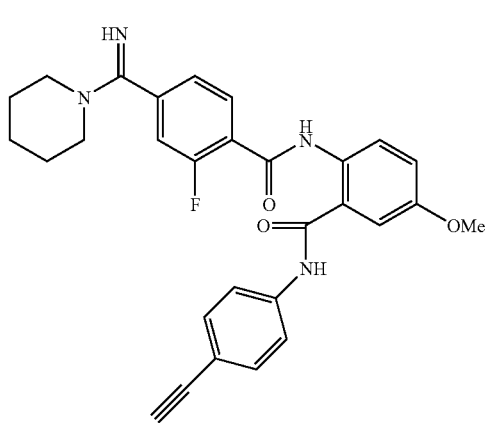

The titled compound was made by the procedure similar to that described in example 1.
MS found for $C_{29}H_{27}FN_4O_3$ as $(M+H)^+$: 499.2.

Example 32

4-(N-{2-[N-(4-ethynylphenyl)carbamoyl]-4-methoxyphenyl}carbamoyl)-3-fluorobenzenecarboxamidine

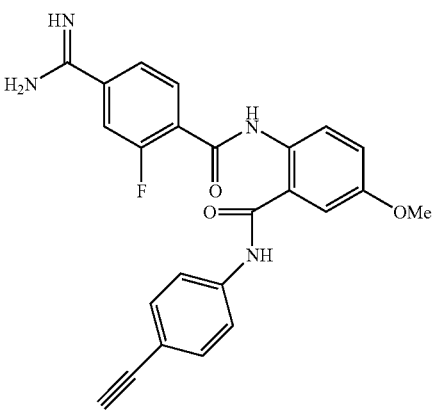

The titled compound was made by the procedure similar to that described in example 1.
MS found for $C_{24}H_{19}FN_4O_3$ as $(M+H)^+$: 431.2.

Scheme 2

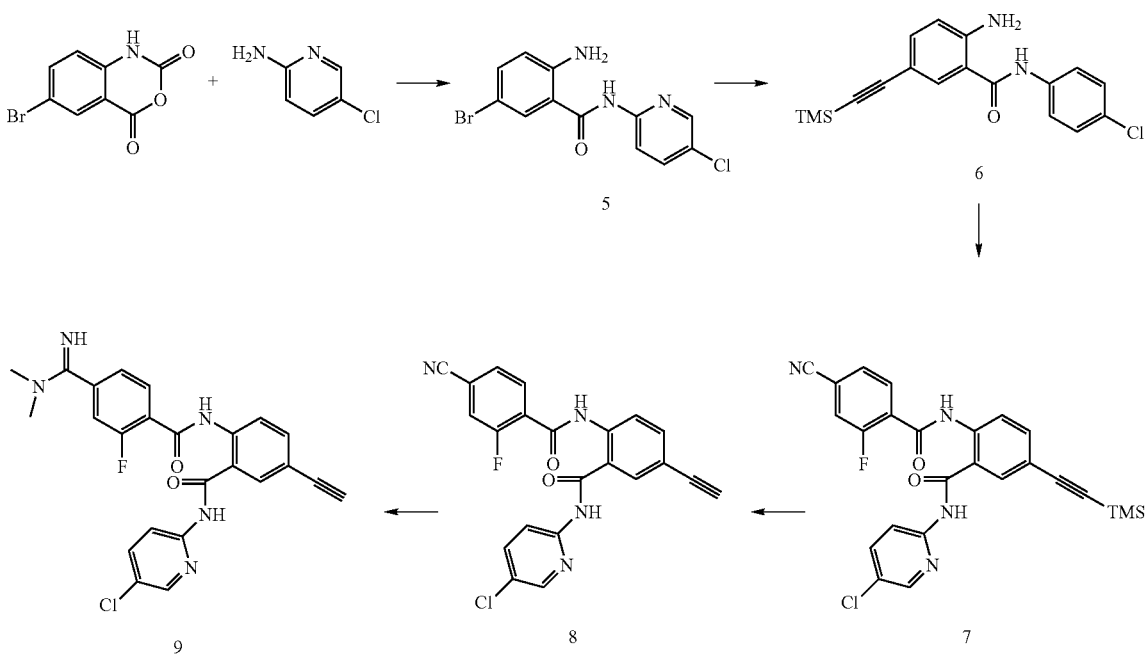

Example 33

{4-[(dimethylamino)iminomethyl]-2-fluorophenyl}-
N-{2-[N-(5-chloro(2-pyridyl))carbamoyl]-4-
ethynylphenyl}carboxamide (9)

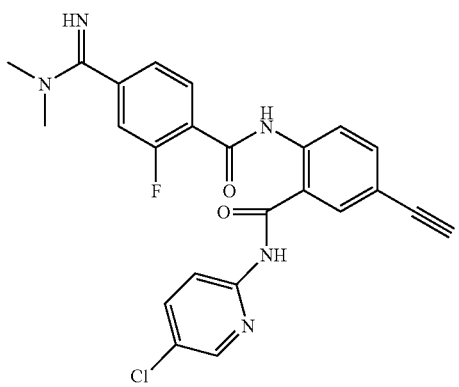

Step 1:

To a solution of 2-amino-5-chloropyridine (6.4 g, 50 mmol) in anhydrous THF (60 mL) at −78° C. was added Lithium bis(trimethylsilyl)amide (1N solution in THF, 100 mL) via a double ended needle. The mixture was stirred at −78° C. for 30 min. To this solution, a suspension of 5-bromoisatoic anhydride (12.1 g, 50 mmol) in anhydrous THF (60 mL) was added via a double ended needle. The mixture was stirred at −78° C. for 20 min and then warmed up to rt and stirred for 3 h. The reaction was quenched with sat. NH$_4$Cl (100 mL). The organic layer was diluted with EtOAc, washed with sat. NaHCO$_3$, sat. NaCl, 1N HCl, sat NaCl, dried and evaporated to give compound 5 as an offwhite solid (12 g, 73.6%). $^1$H NMR (DMSO-d$_6$, 400 MHz): δ 10.77 (s, 1H), 8.39 (d, 1H), 8.07 (d, 1H), 7.9 (dd, 1H), 7.84 (d, 1H), 7.3 (dd, 1H), 6.7 (dd, 1H), 6.5 (s, 2H).

Step 2:

To a solution of compound 5 (5.0 g, 15 mmol) in BuNH$_2$ (20 mL) was added tetrakis(triphenylphosphine)Pd(0) (520 mg, 0.45 mmol), CuI (57 mg, 0.45 mmol) and (trimethylsilyl)acetylene (2.94 g, 30 mmol). The mixture was stirred under reflux for 2 h, then cooled down to rt. To the mixture was added water and EtOAc. The organic layer was washed with 1 N HCl, sat. NaCl, sat NaHCO$_3$, and sat. NaCl again, dried and evaporated. The crude product was passed through a short plug of silica gel to give compound 6 (4.8 g, 91%). MS found for $C_{17}H_{18}ClN_3OSi$ as (M+H)$^+$: 344.1.

Step 3:

To a suspension of 4-cyano-2-fluoro benzoic acid (650 mg, 3.9 mmol) in CH$_2$Cl$_2$ (20 mL) were added 2 drops of DMF and oxalyl chloride (0.7 mL, 7.8 mmol). The mixture was stirred at rt overnight and became a clear solution. The volatile was evaporated to dryness to give 4-cyano-2-fluoro-bezoyl chloride. To a solution of compound 6 (900 mg, 2.62 mmol) in THF (10 mL) was added a THF solution of 4-cyano-2-fluoro-bezoyl chloride. The mixture was stirred for 1 h, and concentrated. The residue was dissolved in EtOAc, washed with sat NaHCO$_3$ and water. The organic layer was dried and evaporated to give compound 7 (1.2 g, 94% yield). MS found for $C_{25}H_{20}ClFN_4O_2Si$ as (M+H)$^+$: 491.1.

Step 4:

To a solution of compound 7 (1.2 g, 2.4 mmol) in THF (10 mL) was added tetrabutylammonium fluoride (1N solution in THF, 2.6 mL). The mixture was stirred for 1 h and concentrated. The residue was dissolved in EtOAc, washed with water, dried and evaporated to give compound 8 (1.0 g, 100% yield). MS found for $C_{24}H_{19}ClFN_5O_2$ as (M+H)$^+$: 419.1.

Step 5:

From compound 8, following the procedure similar to that described in Step 4, Example 1, the titled compound 9 was prepared. MS found for $C_{24}H_{19}ClFN_5O_2$ as (M+H)$^+$: 464.1.

Example 34

N-{2-[N-(5-chloro(2-pyridyl))carbamoyl]-4-ethynylphenyl}[2-fluoro-4-(1-methyl(2-yl))phenyl]carboxamide

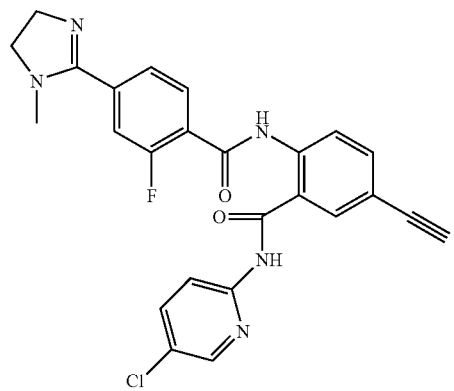

The titled compound was made by the procedure similar to that described in example 33.
MS found for $C_{25}H_{19}ClFN_5O_2$ as (M+H)$^+$: 476.1.

Example 35

Ethyl 1-{[4-(N-{2-[N-(5-chloro(2-pyridyl))carbamoyl]-4-ethynylphenyl}carbamoyl)-3-fluorophenyl]iminomethyl}piperidine-4-carboxylate

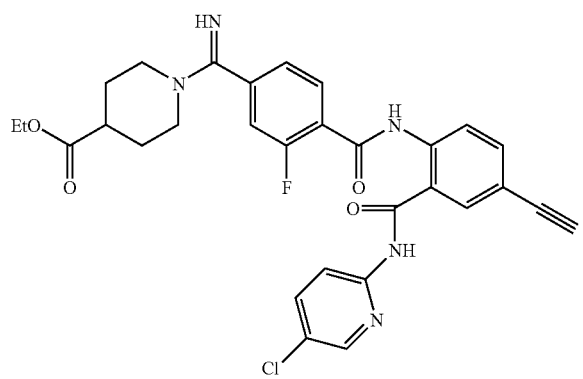

The titled compound was made by the procedure similar to that described in example 33.
MS found for $C_{30}H_{27}ClFN_5O_4$ as (M+H)$^+$: 576.1.

Example 36

Methyl 1-{[4-(N-{2-[N-(5-chloro(2-pyridyl))carbamoyl]-4-ethynylphenyl}carbamoyl)-3-fluorophenyl]iminomethyl}piperidine-4-carboxylate

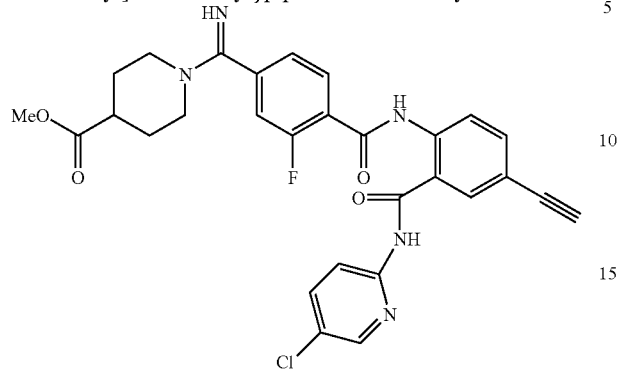

The titled compound was made by the procedure similar to that described in example 33.
MS found for $C_{29}H_{25}ClFN_5O_4$ as $(M+H)^+$: 562.2.

Example 37

1-{[4-(N-{2-[N-(5-chloro(2-pyridyl))carbamoyl]-4-ethynylphenyl}carbamoyl)-3-fluorophenyl]iminomethyl}piperidine-4-carboxylic acid

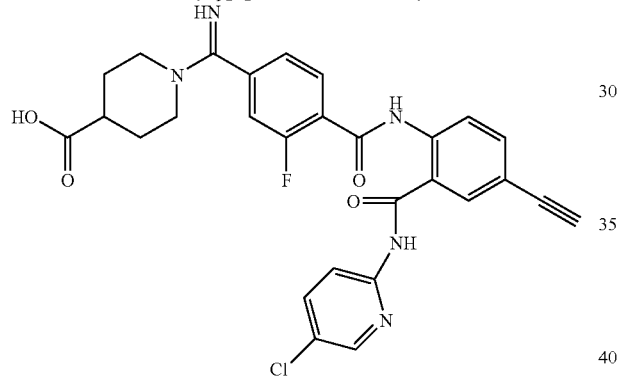

The titled compound was made by the procedure similar to that described in example 4.
MS found for $C_{28}H_{23}ClFN_5O_4$ as $(M+H)^+$: 548.1.

Example 38

1-{[4-(N-{2-[N-(5-chloro(2-pyridyl))carbamoyl]-4-ethynylphenyl}carbamoyl)-3-fluorophenyl]iminomethyl}piperidine-4-carboxamide

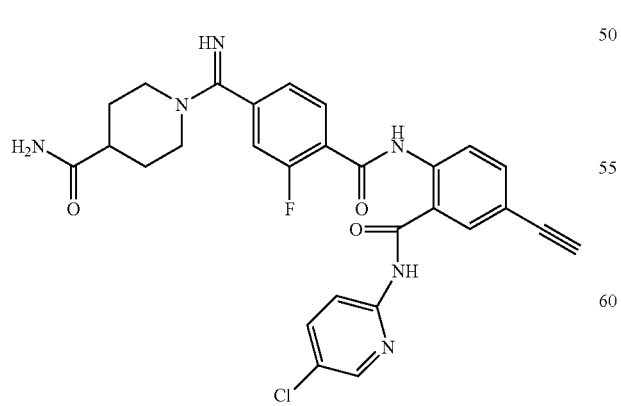

The titled compound was made by the procedure similar to that described in example 33.
MS found for $C_{28}H_{24}ClFN_6O_3$ as $(M+H)^+$: 547.1.

Example 39

N-{2-[N-(5-chloro(2-pyridyl))carbamoyl]-4-ethynylphenyl}(2-fluoro-4-{[4-(hydroxymethyl)piperidyl]iminomethyl}phenyl)carboxamide

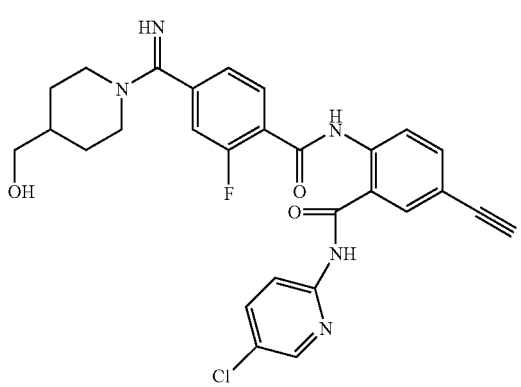

The titled compound was made by the procedure similar to that described in example 33.
MS found for $C_{28}H_{25}ClFN_5O_3$ as $(M+H)^+$: 534.1.

Example 40

N-{2-[N-(5-chloro(2-pyridyl))carbamoyl]-4-ethynylphenyl}[2-fluoro-4-(iminopiperidylmethyl)phenyl]carboxamide

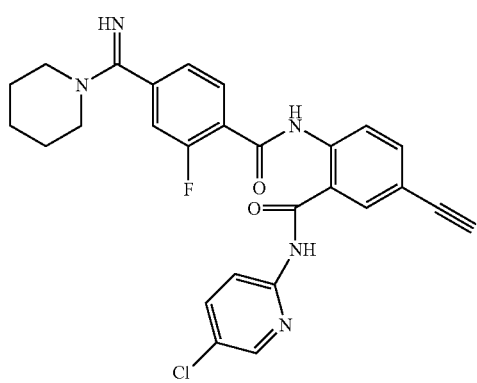

The titled compound was made by the procedure similar to that described in example 33.
MS found for $C_{27}H_{23}ClFN_5O_2$ as $(M+H)^+$: 504.1.

Example 41

[4-({[2-(dimethylamino)ethyl]methylamino}iminomethyl)-2-fluorophenyl]-N-{2-[N-(5-chloro(2-pyridyl))carbamoyl]-4-ethynylphenyl}carboxamide

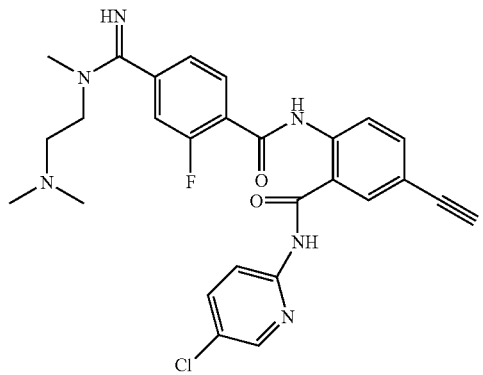

The titled compound was made by the procedure similar to that described in example 33.
MS found for $C_{27}H_{26}ClFN_6O_2$ as $(M+H)^+$: 521.1.

Example 42

[4-({[3-(dimethylamino)propyl]methylamino}iminomethyl)-2-fluorophenyl]-N-{2-[N-(5-chloro(2-pyridyl))carbamoyl]-4-ethynylphenyl}carboxamide

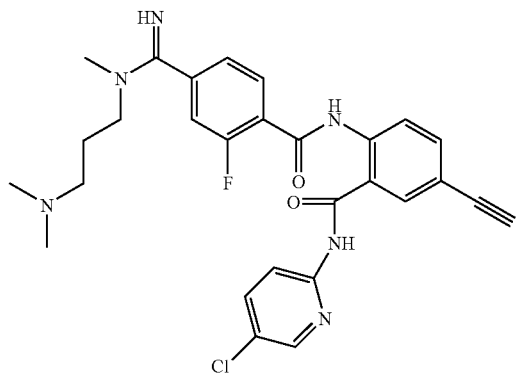

The titled compound was made by the procedure similar to that described in example 33.
MS found for $C_{28}H_{28}ClFN_6O_2$ as $(M+H)^+$: 535.2.

Example 43

{4-[(dimethylamino)iminomethyl]phenyl}-N-{2-[N-(5-chloro(2-pyridyl))carbamoyl]-4-ethynylphenyl}carboxamide

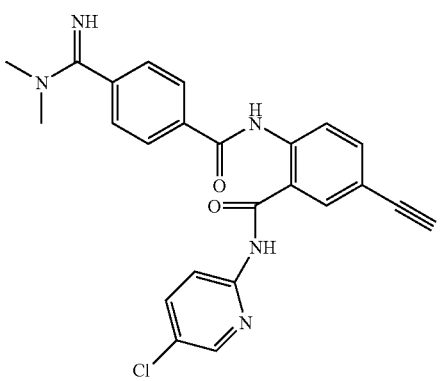

The titled compound was made by the procedure similar to that described in example 33.
MS found for $C_{24}H_{20}ClN_5O_2$ as $(M+H)^+$: 446.1.

Example 44

N-{2-[N-(5-chloro(2-pyridyl))carbamoyl]-4-ethynylphenyl}[4-(1-methyl(2-imidazolin-2-yl))phenyl]carboxamide

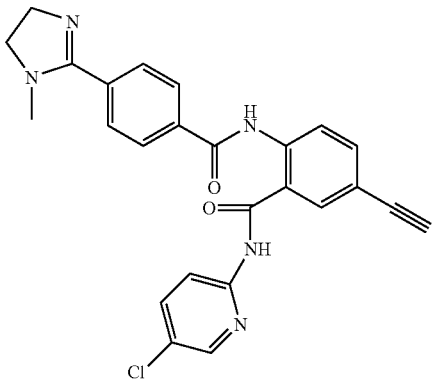

The titled compound was made by the procedure similar to that described in example 33.
MS found for $C_{25}H_{20}ClN_5O_2$ as $(M+H)^+$: 458.1.

Example 45

Ethyl 1-{[4-(N-{2-[N-(5-chloro(2-pyridyl))carbamoyl]-4-ethynylphenyl}carbamoyl)phenyl]iminomethyl}piperidine-4-carboxylate

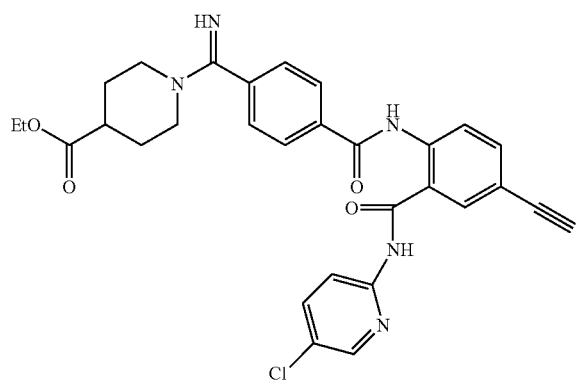

The titled compound was made by the procedure similar to that described in example 33.
MS found for $C_{30}H_{28}ClN_5O_4$ as $(M+H)^+$: 558.1.

Example 46

Methyl 1-{[4-(N-{2-[N-(5-chloro(2-pyridyl))carbamoyl]-4-ethynylphenyl}carbamoyl)phenyl]iminomethyl}piperidine-4-carboxylate

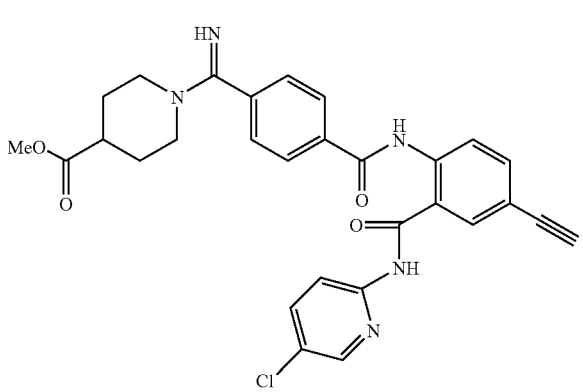

The titled compound was made by the procedure similar to that described in example 33.
MS found for $C_{29}H_{26}ClN_5O_4$ as $(M+H)^+$: 544.1.

Example 47

1-{[4-(N-{2-[N-(5-chloro(2-pyridyl))carbamoyl]-4-ethynylphenyl}carbamoyl)phenyl]iminomethyl}piperidine-4-carboxylic acid

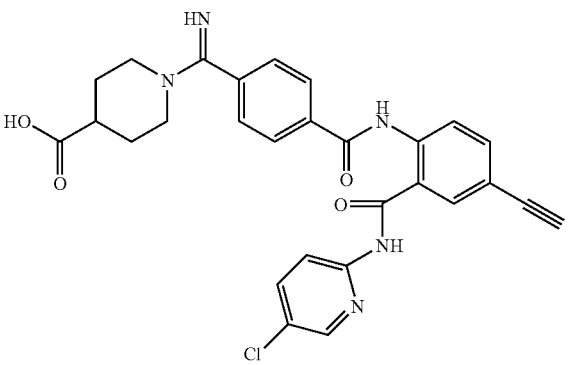

The titled compound was made by the procedure similar to that described in example 4.
MS found for $C_{28}H_{24}ClN_5O_4$ as $(M+H)^+$: 530.1.

Example 48

1-{[4-(N-{2-[N-(5-chloro(2-pyridyl))carbamoyl]-4-ethynylphenyl}carbamoyl)phenyl]iminomethyl}piperidine-4-carboxamide

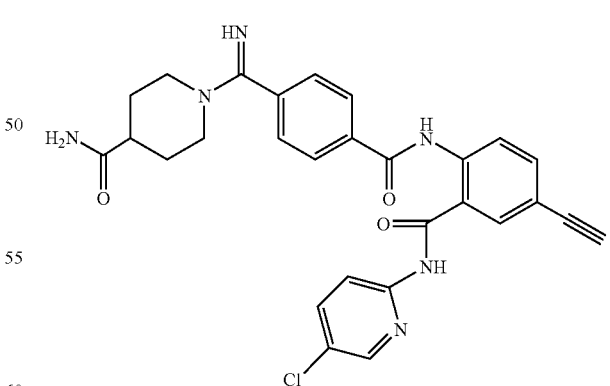

The titled compound was made by the procedure similar to that described in example 33.
MS found for $C_{28}H_{25}ClN_6O_3$ as $(M+H)^+$: 529.1.

Example 49

N-{2-[N-(5-chloro(2-pyridyl))carbamoyl]-4-ethynylphenyl}(4-{[4-(hydroxymethyl)piperidyl]iminomethyl}phenyl)carboxamide

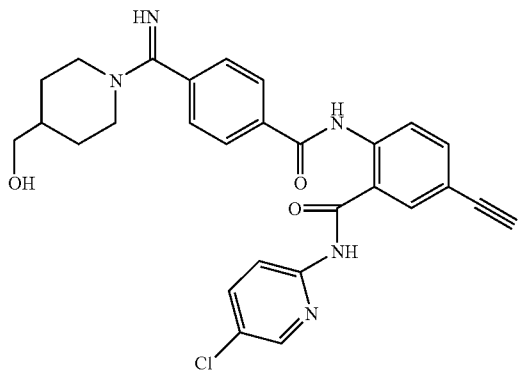

The titled compound was made by the procedure similar to that described in example 33.

MS found for $C_{28}H_{26}ClN_5O_3$ as $(M+H)^+$: 516.1.

Example 50

N-{2-[N-(5-chloro(2-pyridyl))carbamoyl]-4-ethynylphenyl}[4-(iminopiperidylmethyl)phenyl]carboxamide

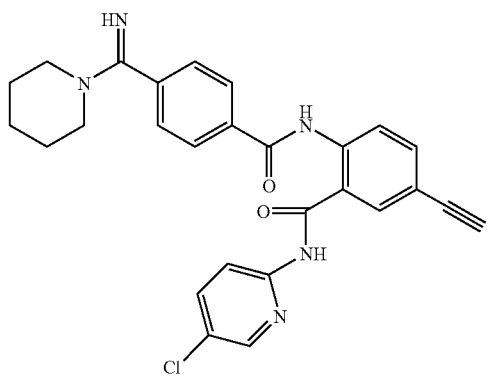

The titled compound was made by the procedure similar to that described in example 33.

MS found for $C_{27}H_{24}ClN_5O_2$ as $(M+H)^+$: 486.1.

Example 51

[4-({[2-(dimethylamino)ethyl]methylamino}iminomethyl)phenyl]-N-{2-[N-(5-chloro(2-pyridyl))carbamoyl]-4-ethynylphenyl}carboxamide

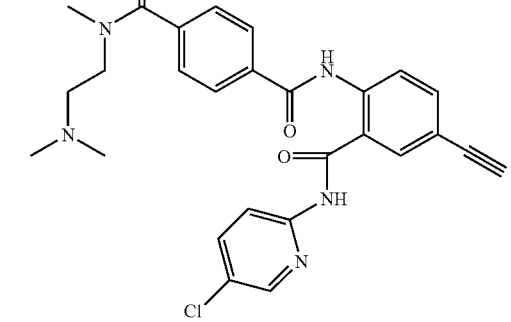

The titled compound was made by the procedure similar to that described in example 33.

MS found for $C_{27}H_{27}ClN_6O_2$ as $(M+H)^+$: 503.1.

Example 52

[4-({[3-(dimethylamino)propyl]methylamino}iminomethyl)phenyl]-N-{2-[N-(5-chloro(2-pyridyl))carbamoyl]-4-ethynylphenyl}carboxamide

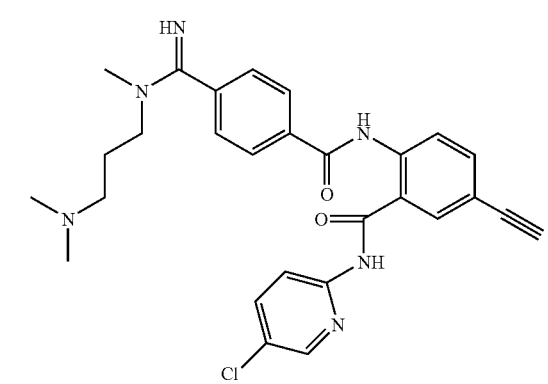

The titled compound was made by the procedure similar to that described in example 33.

MS found for $C_{28}H_{29}ClN_6O_2$ as $(M+H)^+$: 517.2.

Scheme 3

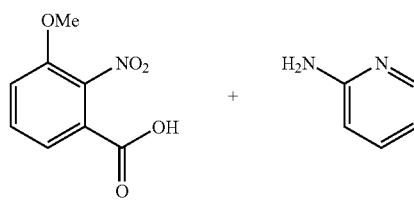
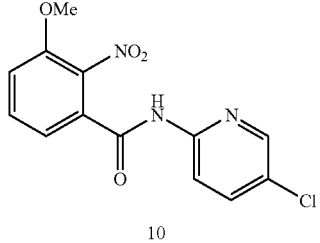
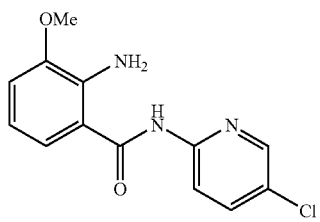
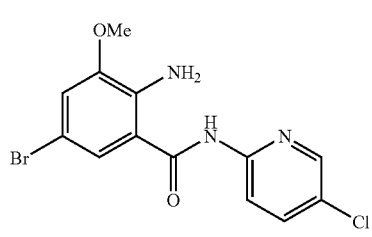
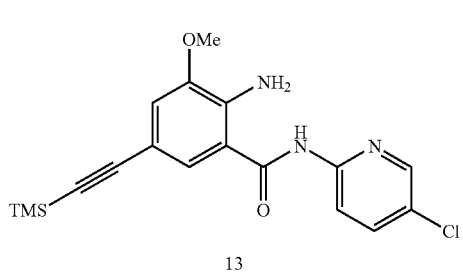
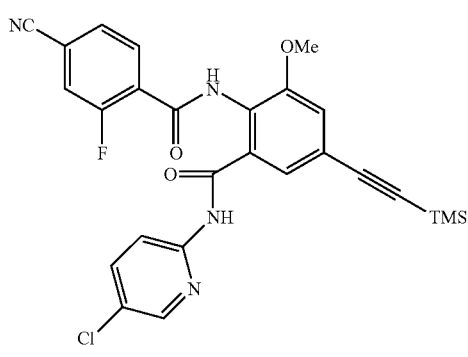
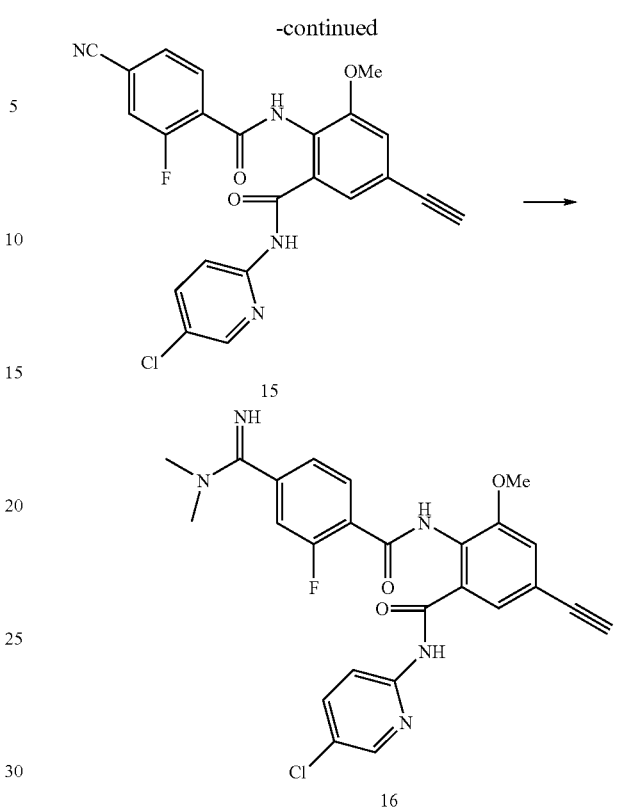

Example 53

{4-[(dimethylamino)iminomethyl]-2-fluorophenyl}-N-{2-[N-(5-chloro(2-pyridyl))carbamoyl]-4-ethynyl-6-methoxyphenyl}carboxamide (9)

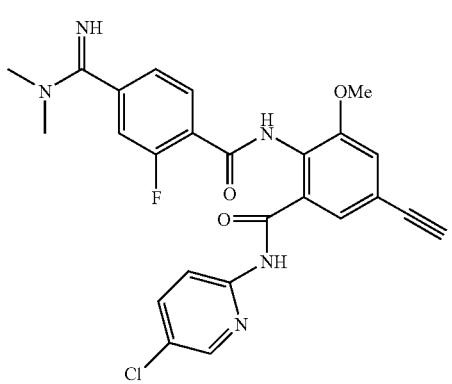

Step 1:

To a stirring solution of 2-amino-5-chloropyridine (6.5 g, 51 mmol) and 3-methoxy-2-nitrobenzoic acid (10.0 g, 50.8 mmol) in anhydrous THF (40 mL) and pyridine (16 mL) at 0° C. was added POCl$_3$ (15.3 g, 102 mmol) dropwise. The mixture was stirred at 0° C. for 20 min. Water (150 mL) was added and precipitate formed. The solid was collected by filtration, washed with water and dried to give compound 10 as a white solid (13.6 g, 88%). MS found for C$_{13}$H$_{10}$ClN$_3$O$_4$ as (M+Na)$^+$: 319.0.

Step 2:

To a solution of compound 10 (7.2 g, 23.5 mmol) in 1,4-dioxane (50 mL) and THF (50 mL) at 50° C. was added an aqueous solution of $Na_2S_2O_4$ (20 g, 117 mmol in 100 mL water). The mixture was stirred at 50° C. overnight. The two layers were separated. To the organic layer was added water and precipitate formed. The solid was collected by filtration and washed with water. After drying in vacuo, 5.4 g of compound 11 was obtained as a yellow solid in 83% yield. MS found for $C_{13}H_{12}ClN_3O_2$ as $(M+H)^+$: 278.

Step 3:

To a solution of compound 11 (4.82 g, 17.4 mmol) in toluene (100 mL) at 70° C. was added N-bromosuccinimide (3.3 g, 18.6 mmol) in portions. The mixture was stirred at 70° C.-75° C. for 15 min, cooled down and filtered through celite. The filtrate was washed with sat. $NaHCO_3$, sat. NaCl, dried and evaporated to give the crude compound 12 as dark brown solid (4.0 g, 65%). $^1$H NMR (DMSO-$d_6$, 400 MHz): δ 10.73 (s, 1H), 8.39 (d, 1H), 8.06 (d, 1H), 7.9 (dd, 1H), 7.56 (d, 1H), 7.04 (d, 1H), 6.24 (s, 2H). MS found for $C_{13}H_{11}BrClN_3O_2$ as $(M+H)^+$: 355.95, 358.0.

Step 4:

To a solution of compound 12 (3.0 g, 8.4 mmol) in $BuNH_2$ (15 mL) was added tetrakis(triphenylphosphine)Pd(0) (291 mg, 0.25 mmol), CuI (32 mg, 0.17 mmol) and (trimethylsilyl)acetylene (1.23 g, 12.6 mmol). The mixture was stirred under reflux for 2 h and cooled down to rt. The mixture was concentrated and passed through a short column of silica gel to give 3.4 g of compound 13. $^1$H NMR (DMSO-$d_6$, 400 MHz): δ 10.73 (s, 1H), 8.39 (d, 1H), 8.0 (d, 1H), 7.9 (dd, 1H), 7.56 (d, 1H), 6.91 (d, 1H), 6.51 (s, 2H), 3.81 (s, 3H), 0.18 (s, 9H). MS found for $C_{18}H_{20}ClN_3O_2Si$ as $(M+H)^+$: 374.1.

Step 5:

To a solution of compound 13 (2.6 g, 7.0 mmol) in THF (20 mL) was added 4-cyano-2-fluoro-bezoyl chloride (1.38 g, 7.5 mmol, prepared according to Step 4, Example 33). The mixture was stirred for 1 h. It was diluted with EtOAc, washed with sat $NaHCO_3$ and water. The organic layer was dried and evaporated to give compound 14 (2.5 g, 69% yield). MS found for $C_{26}H_{22}ClFN_4O_3Si$ as $(M+H)^+$: 521.

Step 6:

To a solution of compound 14 (2.25 g, 4.3 mmol) in THF (30 mL) was added tetrabutylammonium fluoride (1N solution in THF, 4.7 mL, 4.7 mmol). The mixture was stirred for 1 h, then concentrated. The residue was dissolved in EtOAc, washed with water, dried and evaporated. The crude material was triturated with 50% EtOAc/hexane to give compound 15 (1.85 g, 95% yield) as a solid. MS found for $C_{23}H_{14}ClFN_4O_3$ as $(M+H)^+$: 449.05.

Step 7:

From compound 15, following the procedure similar to that described in Step 4, Example 1, the titled compound 16 was prepared. MS found for $C_{25}H_{21}ClFN_5O_3$ as $(M+H)^+$: 494.1.

Example 54

N-{2-[N-(5-chloro(2-pyridyl))carbamoyl]-4-ethynyl-6-methoxyphenyl}[2-fluoro-4-(1-methyl(2-imidazolin-2-yl))phenyl]carboxamide

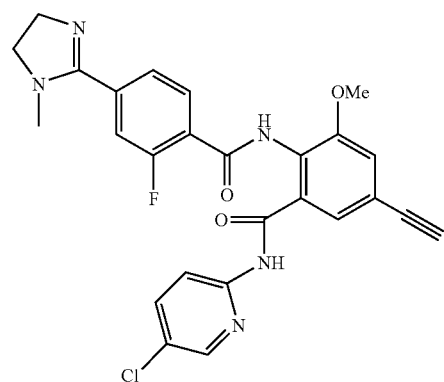

The titled compound was made by the procedure similar to that described in example 53.

MS found for $C_{26}H_{21}ClFN_5O_3$ as $(M+H)^+$: 506.1.

Example 55

Ethyl 1-{[4-(N-{2-[N-(5-chloro(2-pyridyl))carbamoyl]-4-ethynyl-6-methoxyphenyl}carbamoyl)-3-fluorophenyl]iminomethyl}piperidine-4-carboxylate

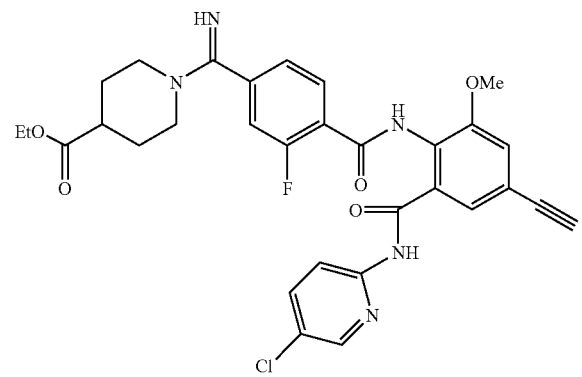

The titled compound was made by the procedure similar to that described in example 53.

MS found for $C_{31}H_{29}ClFN_5O_5$ as $(M+H)^+$: 606.2.

Example 56

Methyl 1-{[4-(N-{2-[N-(5-chloro(2-pyridyl))carbamoyl]-4-ethynyl-6-methoxyphenyl}carbamoyl)-3-fluorophenyl]iminomethyl}piperidine-4-carboxylate

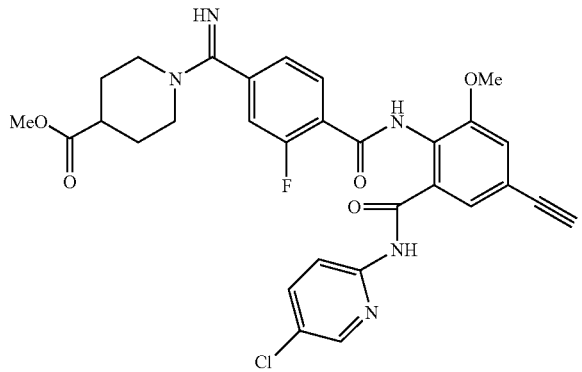

The titled compound was made by the procedure similar to that described in example 53.

MS found for $C_{30}H_{27}ClFN_5O_5$ as $(M+H)^+$: 592.2.

Example 57

1-{[4-(N-{2-[N-(5-chloro(2-pyridyl))carbamoyl]-4-ethynyl-6-methoxyphenyl}carbamoyl)-3-fluorophenyl]iminomethyl}piperidine-4-carboxylic Acid

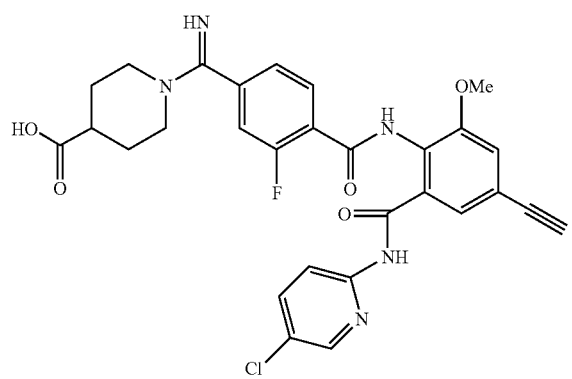

The titled compound was made by the procedure similar to that described in example 4.

MS found for $C_{29}H_{25}ClFN_5O_5$ as $(M+H)^+$: 578.1.

Example 58

1-{[4-(N-{2-[N-(5-chloro(2-pyridyl))carbamoyl]-4-ethynyl-6-methoxyphenyl}carbamoyl)-3-fluorophenyl]iminomethyl}piperidine-4-carboxamide

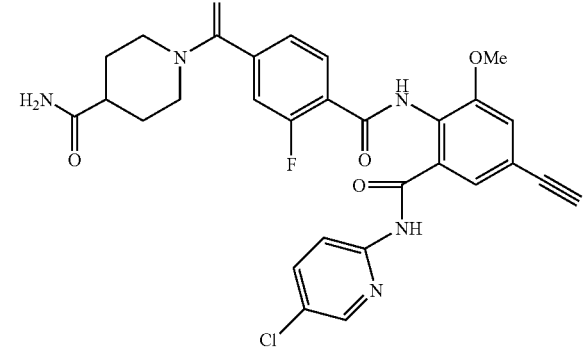

The titled compound was made by the procedure similar to that described in example 53.

MS found for $C_{29}H_{26}ClFN_6O_4$ as $(M+H)^+$: 577.1.

Example 59

N-{2-[N-(5-chloro(2-pyridyl))carbamoyl]-4-ethynyl-6-methoxyphenyl}(2-fluoro-4-{[4-(hydroxymethyl)piperidyl]iminomethyl}phenyl)carboxamide

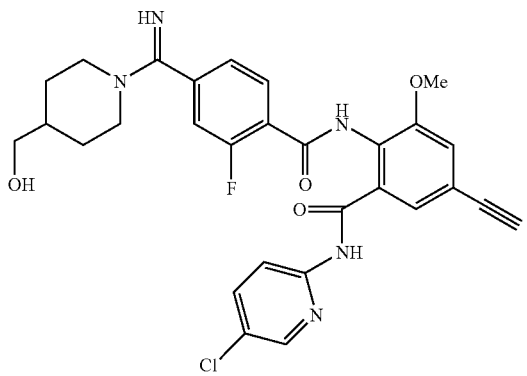

The titled compound was made by the procedure similar to that described in example 53.

MS found for $C_{29}H_{27}ClFN_5O_4$ as $(M+H)^+$: 564.2.

Example 60

N-{2-[N-(5-chloro(2-pyridyl))carbamoyl]-4-ethynyl-6-methoxyphenyl})[2-fluoro-4-(iminopiperidylmethyl)phenyl]carboxamide

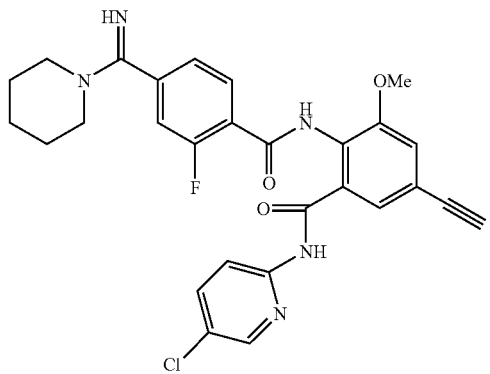

The titled compound was made by the procedure similar to that described in example 53.

MS found for $C_{28}H_{25}ClFN_5O_3$ as (M+H)$^+$: 534.1.

Example 61

N-{2-[N-(5-chloro(2-pyridyl))carbamoyl]-4-ethynyl-6-methoxyphenyl}[2-fluoro-4-(iminopiperidylmethyl)phenyl]carboxamide

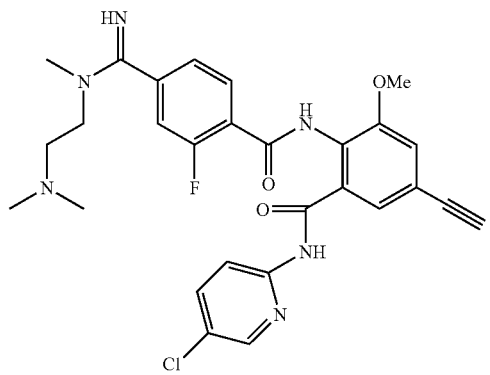

The titled compound was made by the procedure similar to that described in example 53.

MS found for $C_{28}H_{28}ClFN_6O_3$ as (M+H)$^+$: 551.2.

Example 62

[4-({[3-(dimethylamino)propyl]methylamino}iminomethyl)-2-fluorophenyl]-N-{2-[N-(5-chloro(2-pyridyl))carbamoyl]-4-ethynyl-6-methoxyphenyl}carboxamide

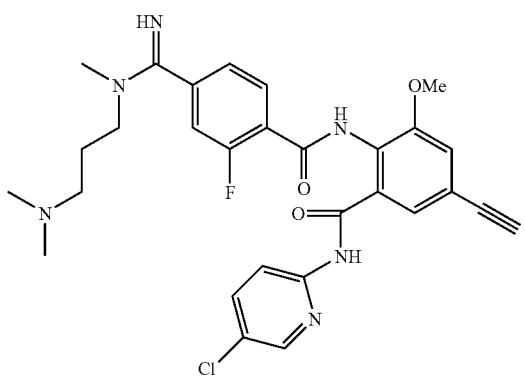

The titled compound was made by the procedure similar to that described in example 53.

MS found for $C_{29}H_{30}ClFN_6O_3$ as (M+H)$^+$: 565.2.

Example 63

N-{2-[N-(5-chloro(2-pyridyl))carbamoyl]-4-ethynyl-6-methoxyphenyl}{4-[(ethylmethylamino)iminomethyl]-2-fluorophenyl}carboxamide

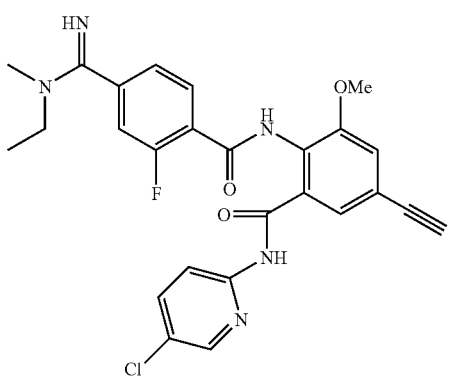

The titled compound was made by the procedure similar to that described in example 53.

MS found for $C_{26}H_{23}ClFN_5O_3$ as (M+H)$^+$: 508.1.

Example 64

[4-(azetidinyl iminomethyl)-2-fluorophenyl]-N-{2-[N-(5-chloro(2-pyridyl))carbamoyl]-4-ethynyl-6-methoxyphenyl}carboxamide

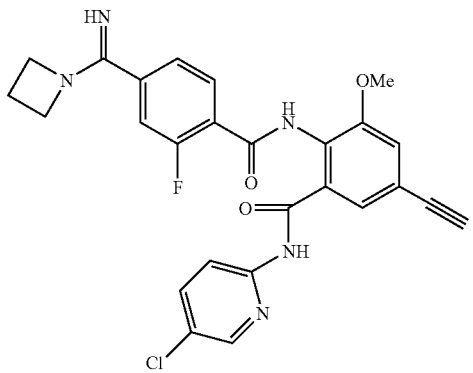

The titled compound was made by the procedure similar to that described in example 53.
MS found for $C_{26}H_{21}ClFN_5O_3$ as $(M+H)^+$: 506.1.

Example 65

[4-(azetidinylazetidinylidenemethyl)-2-fluorophenyl]-N-{2-[N-(5-chloro(2-pyridyl))carbamoyl]-4-ethynyl-6-methoxyphenyl}carboxamide

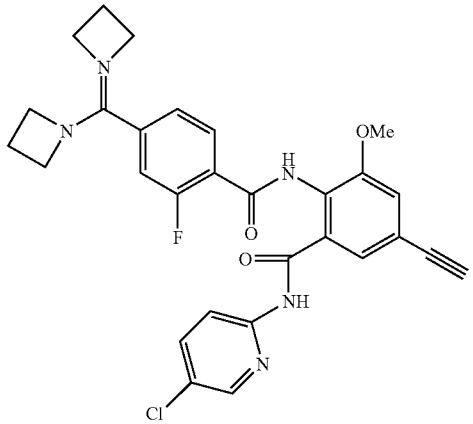

The titled compound was made by the procedure similar to that described in example 53.
MS found for $C_{29}H_{26}ClFN_5O_3$ as $M^+$: 546.1.

Example 66

(4-[(dimethylamino)iminomethyl]phenyl)-N-{2-[N-(5-chloro(2-pyridyl))carbamoyl]-4-ethynyl-6-methoxyphenyl}carboxamide

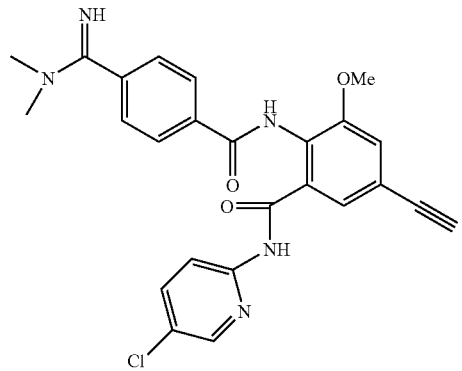

The titled compound was made by the procedure similar to that described in example 53.
MS found for $C_{25}H_{22}ClN_5O_3$ as $(M+H)^+$: 476.1.

Example 67

N-{2-[N-(5-chloro(2-pyridyl))carbamoyl]-4-ethynyl-6-methoxyphenyl}[4-(1-methyl(2-yl))phenyl]carboxamide

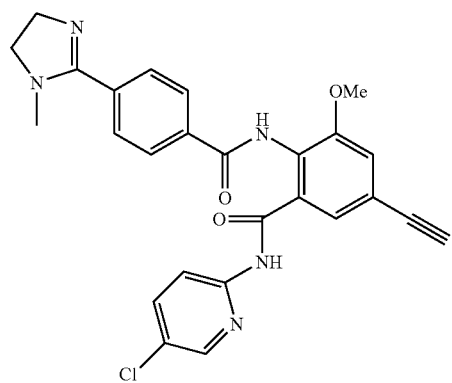

The titled compound was made by the procedure similar to that described in example 53.
MS found for $C_{26}H_{22}ClN_5O_3$ as $(M+H)^+$: 488.1.

Example 68

Ethyl 1-{[4-(N-{2-[N-(5-chloro(2-pyridyl))carbamoyl]-4-ethynyl-6-methoxyphenyl}carbamoyl)phenyl]iminomethyl}piperidine-4-carboxylate

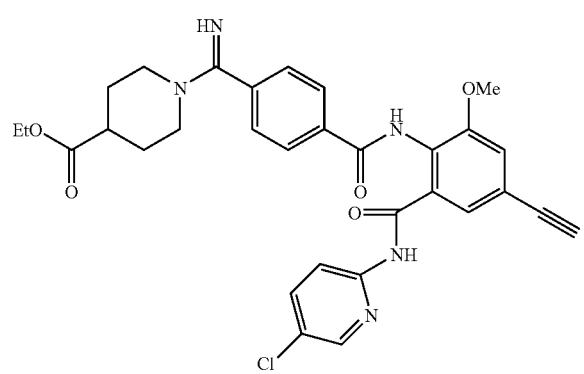

The titled compound was made by the procedure similar to that described in example 53.

MS found for $C_{31}H_{30}ClN_5O_5$ as $(M+H)^+$: 588.2.

Example 69

Methyl 1-{[4-(N-{2-[N-(5-chloro(2-pyridyl))carbamoyl]-4-ethynyl-6-methoxyphenyl}carbamoyl)phenyl]iminomethyl}piperidine-4-carboxylate

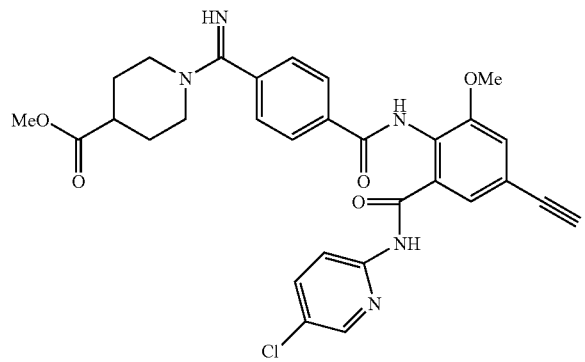

The titled compound was made by the procedure similar to that described in example 53.

MS found for $C_{30}H_{28}ClN_5O_5$ as $(M+H)^+$: 574.2.

Example 70

1-{[4-(N-{2-[N-(5-chloro(2-pyridyl))carbamoyl]-4-ethynyl-6-methoxyphenyl}carbamoyl)phenyl]iminomethyl}piperidine-4-carboxylic acid

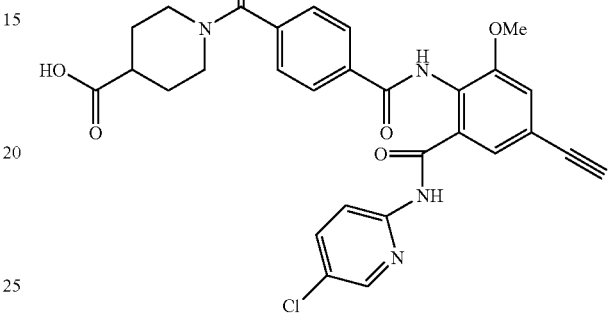

The titled compound was made by the procedure similar to that described in example 4.

MS found for $C_{29}H_{26}ClN_5O_5$ as $(M+H)^+$: 560.1.

Example 71

1-{[4-(N-{2-[N-(5-chloro(2-pyridyl))carbamoyl]-4-ethynyl-6-methoxyphenyl}carbamoyl)phenyl]iminomethyl}piperidine-4-carboxamide

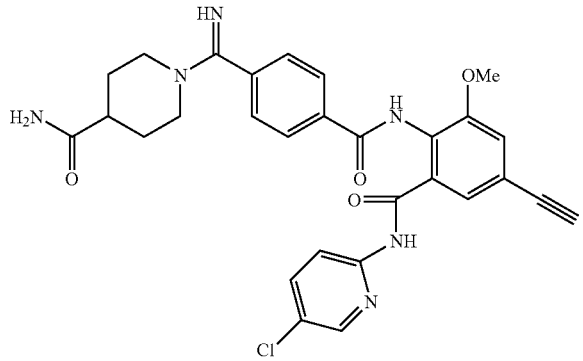

The titled compound was made by the procedure similar to that described in example 53.

MS found for $C_{29}H_{27}ClN_6O_4$ as $(M+H)^+$: 559.1.

Example 72

N-{2-[N-(5-chloro(2-pyridyl))carbamoyl]-4-ethynyl-6-methoxyphenyl)(4-([4-(hydroxymethyl)piperidyl]iminomethyl}phenyl)carboxamide

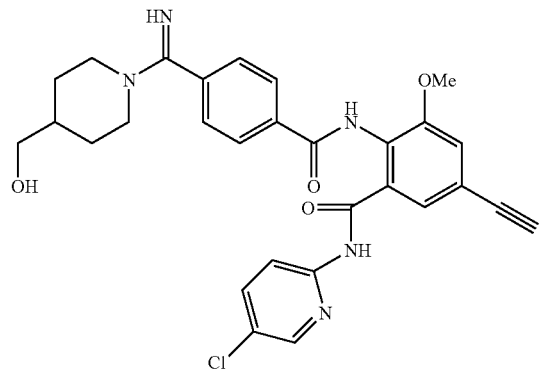

The titled compound was made by the procedure similar to that described in example 53.

MS found for $C_{29}H_{28}ClN_5O_4$ as $(M+H)^+$: 546.1.

Example 73

N-{2-[N-(5-chloro(2-pyridyl))carbamoyl]-4-ethynyl-6-methoxyphenyl}[4-(iminopiperidylmethyl)phenyl]carboxamide

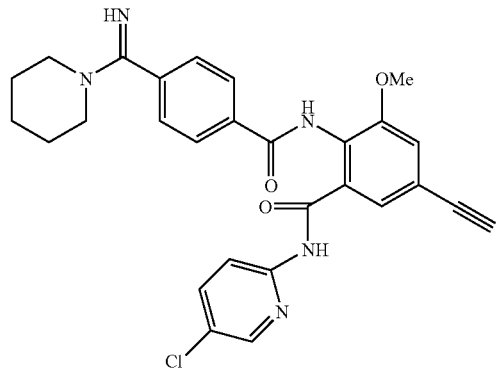

The titled compound was made by the procedure similar to that described in example 53.

MS found for $C_{28}H_{26}ClN_5O_3$ as $(M+H)^+$: 516.1.

Example 74

[4-({[2-(dimethylamino)ethyl]methylamino}iminomethyl)phenyl]-N-{2-[N-(5-chloro(2-pyridyl))carbamoyl]-4-ethynyl-6-methoxyphenyl}carboxamide

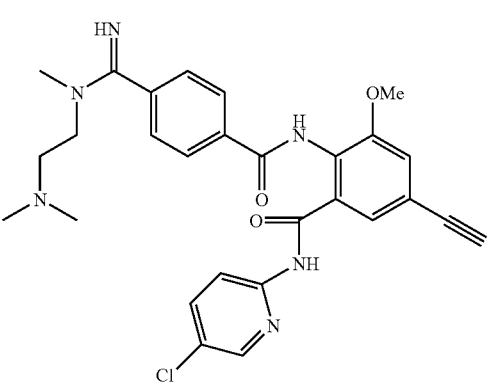

The titled compound was made by the procedure similar to that described in example 53.

MS found for $C_{28}H_{29}ClN_6O_3$ as $(M+H)^+$: 533.2.

Example 75

[4-({[3-(dimethylamino)propyl]methylamino}iminomethyl)phenyl]-N-{2-[N-(5-chloro(2-pyridyl))carbamoyl]-4-ethynyl-6-methoxyphenyl}carboxamide

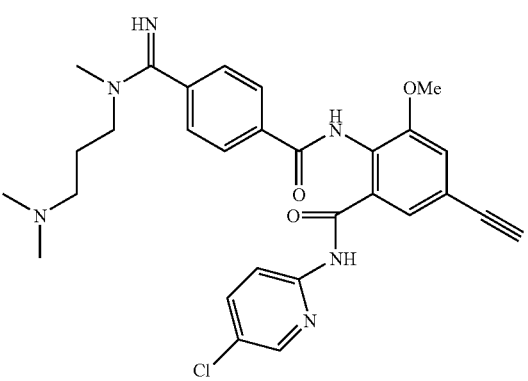

The titled compound was made by the procedure similar to that described in example 53.

MS found for $C_{29}H_{31}ClN_6O_3$ as $(M+H)^+$: 547.2.

Example 76

N-{2-[N-(5-chloro(2-pyridyl))carbamoyl]-4-ethynyl-6-methoxyphenyl}{4-[(ethylmethylamino)iminomethyl]phenyl}carboxamide

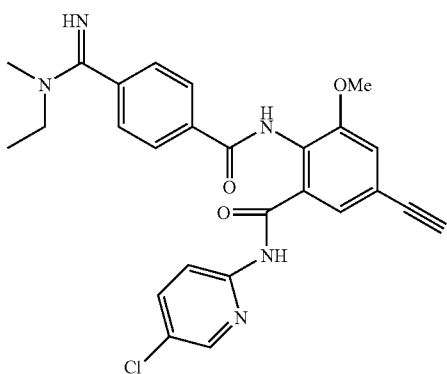

The titled compound was made by the procedure similar to that described in example 53.

MS found for $C_{26}H_{24}ClN_5O_3$ as $(M+H)^+$: 490.1.

Example 77

[4-(azetidinyliminomethyl)phenyl]-N-{2-[N-(5-chloro(2-pyridyl))arbamoyl]-4-ethynyl-6-methoxyphenyl}carboxamide

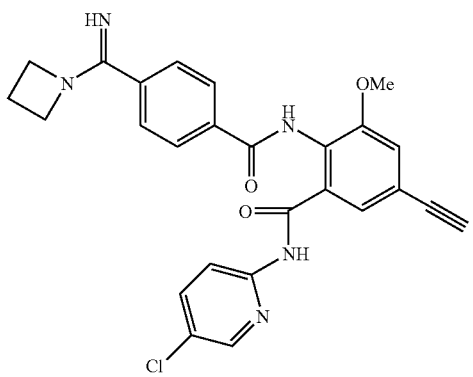

The titled compound was made by the procedure similar to that described in example 53.

MS found for $C_{26}H_{22}ClN_5O_3$ as $(M+H)^+$: 488.1.

Example 78

[4-(azetidinylazetidinylidenemethyl)phenyl]-N-{2-[N-(5-chloro(2-pyridyl))carbamoyl]-4-ethynyl-6-methoxyphenyl}carboxamide

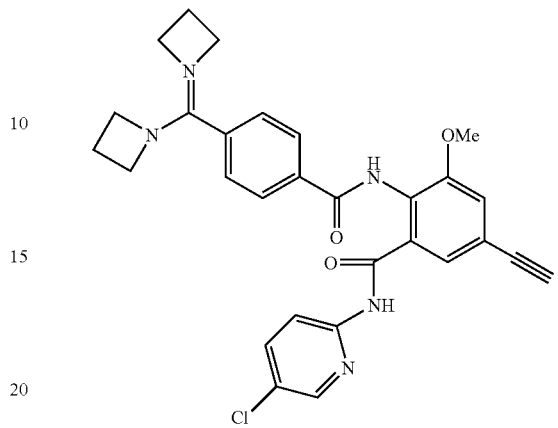

The titled compound was made by the procedure similar to that described in example 53.

MS found for $C_{29}H_{27}ClN_5O_3$ as $M^+$: 528.1.

Scheme 4

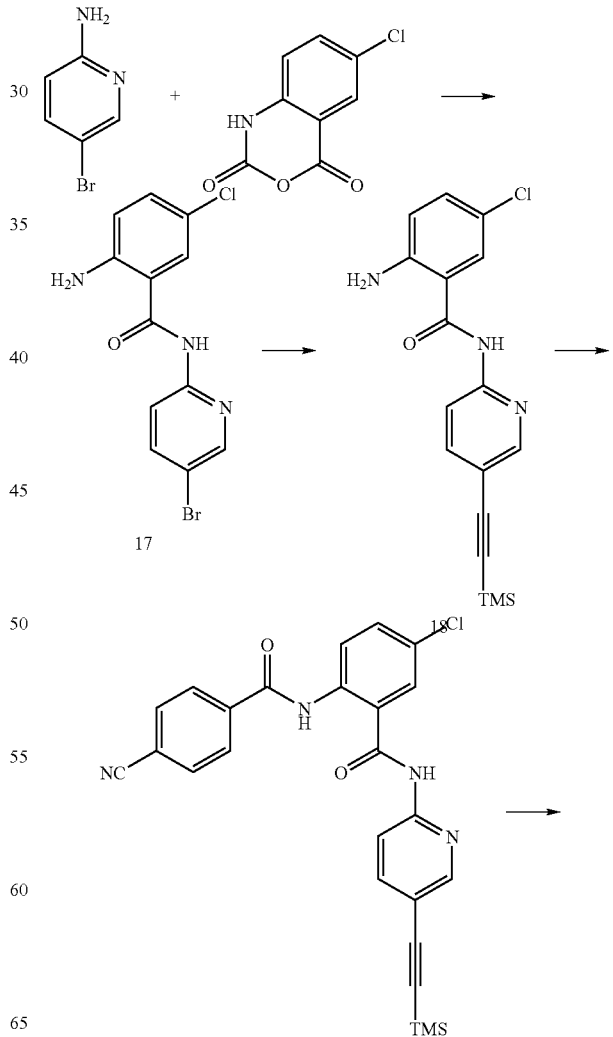

-continued

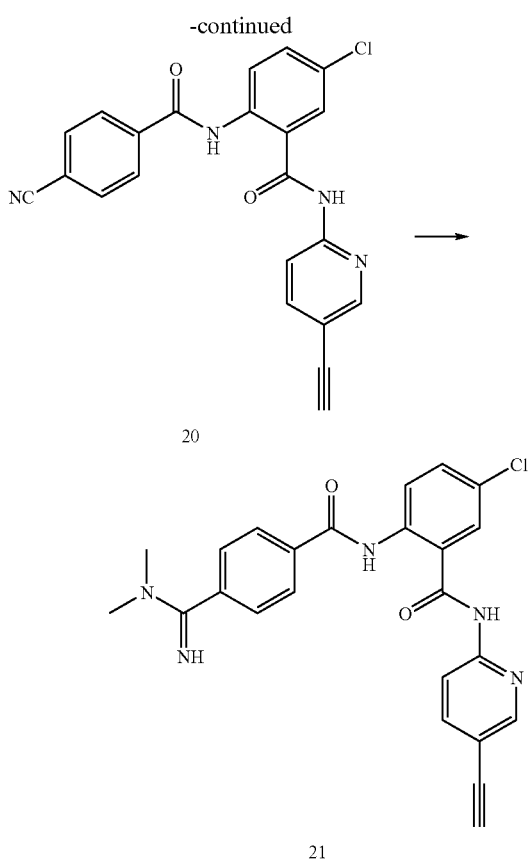

Example 79

{4-[(dimethylamino)iminomethyl]phenyl}-N-{4-chloro-2-[N-(5-ethynyl(2-pyridyl))carbamoyl]phenyl}-carboxamide

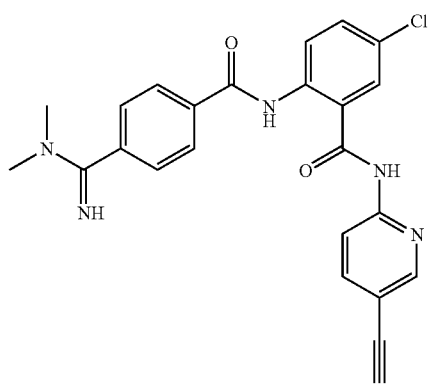

Step 1:

A solution of 2-amino-5-bromopyridine (10.0 g, 58.0 mmol) in 200 mL THF was treated with NaH (6.00 g, 145 mmol) in several small portions over which time the reaction became cloudy and yellow-brown. After 30 min 5-chloroisatoic anhydride (12.00 g, 61.0 mmol) was added resulting in a thick, white suspension. After 40 min the reaction was diluted with water, filtered and aspirated to dryness affording the desired product as a light violet powder containing trace impurities (no yield calculated). MS found for $C_{12}H_9BrClN_3O$ as $(M+H)^+$: 326.0.

Step 2:

Aryl bromide 17 (5.00 g, 15 mmol) was combined with $Pd(PhCN)_2Cl_2$ (0.18 g, 0.46 mmol), CuI (0.59 g, 0.31 mmol) and $t-Bu_3P$ (0.23 g, 0.92 mmol) in 15 mL dioxane which was then degassed with argon for 3 min. The reaction mixture was then treated with trimethylsilylacetylene (2.6 mL, 18 mmol) and diisopropylamine (3.2 mL, 23 mmol), then stirred overnight at rt during which time the color changed from beige to black. The following day the mixture was concentrated, then filtered through a plug of silica gel (2 in×3 in) and eluted with dichloromethane. Concentration of the filtrate afforded a brown solid which was used immediately for Step 3. MS found for $C_{17}H_{18}N_3OSi$ as $(M+H)^+$: 344.1.

Step 3:

Aniline 18 (15 mmol theoretical) was diluted with 35 mL of THF then treated with 4-cyanobenzoyl chloride (2.50 g, 15 mmol) and stirred until the starting aniline was consumed (TLC). The reaction was then diluted with hexane until a flocculent precipitate was formed. The solid was then filtered, washed with hexanes and aspirated to dryness affording the desired product 19 as a brown powder (4.04 g, 56%).

Step 4:

Trimethylsilylalkene 19 (4.02 g, 8.50 mmol) was diluted with 10 mL of THF then treated with tetrabutylammonium fluoride (1 M solution in THF, 10 mL, 10 mmol) during which time the reaction changed from a beige suspension to a brown solution. The reaction was stirred until no starting material was present by TLC, then it was diluted with water (150 mL), the solid filtered, then washed sequentially with water, methanol and diethyl ether affording 20 (3.03 g, 89%) as a beige powder. MS found for $C_{22}H_{13}ClN_4O_2$ as $(M+H)^+$: 401.1.

Step 5:

Nitrile 20 (1.6 g, 4.0 mmol) was diluted with dioxane (20 mL) and treated with triethyl amine (2.2 mL, 16 mmol) then placed under an atmosphere of hydrogen sulfide overnight. Then next day the reaction was determined to be complete by HPLC then concentrated in vacuo. The resulting solid was then diluted with acetone (20 mL) and methyl iodide (2.0 mL, 32 mmol), then refluxed until the starting material was consumed. The resulting imidate was the concentrated to a yellow powder, then diluted with THF (40 mL) affording an approximately 0.1 M solution.

Dimethyl amine (2 M in THF, 0.5 mL, 1 mmol) and acetic acid (0.44 mL, 1.5 mmol) were diluted with THF (2 mL) and combined with 2.0 mL of the above imidate stock solution (0.2 mmol) and stirred overnight. The following day the reaction was determined to be complete by HPLC, then concentrated and the crude oil purified by preparative RP-HPLC affording amidine 4 as a TFA salt. MS found for $C_{24}H_{20}ClN_5O_2$ as $(M+H)^+$: 446.1.

Example 80

N-{4-chloro-2-[N-(5-ethynyl(2-pyridyl))carbamoyl]phenyl}[4-(1-methyl (2-imidazolin-2-yl))phenyl]-carboxamide

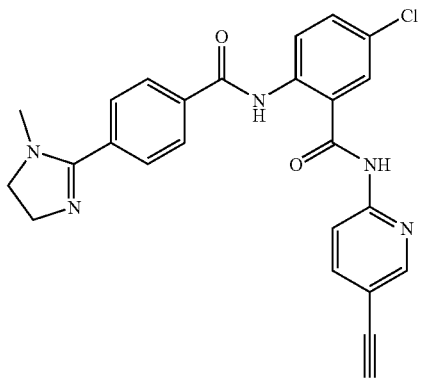

The titled compound was made by the procedure similar to that described in example 79.

MS found for $C_{25}H_{20}ClN_5O_2$ as $(M+H)^+$: 458.1.

Example 81

N-{2-[N-(5-ethynyl(2-pyridyl))carbamoyl]-4-chlorophenyl}[4-(iminopyrrolidinylmethyl)phenyl]carboxamide

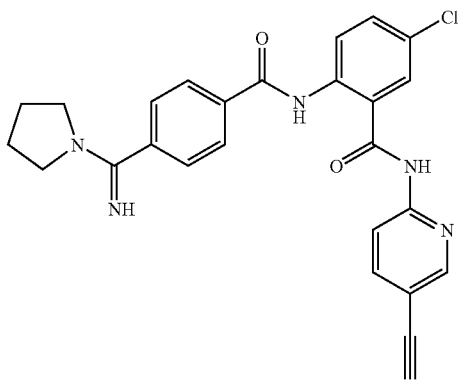

The titled compound was made by the procedure similar to that described in example 79.

MS found for $C_{26}H_{22}ClN_5O_2$ as $(M+H)^+$: 472.1

Example 82

N-{2-[N-(5-ethynyl(2-pyridyl))carbamoyl]-4-chlorophenyl}[4-(piperidyliminomethyl)phenyl]carboxamide

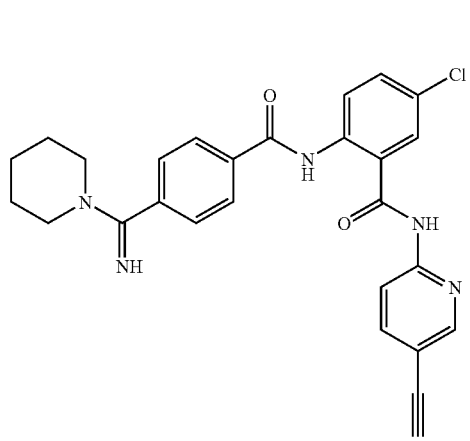

The titled compound was made by the procedure similar to that described in example 79.

MS found for $C_{27}H_{24}ClN_5O_2$ as $(M+H)^+$: 486.1

Example 83

Ethyl 1-{[4-(N-{4-chloro-2-[N-(5-ethynyl(2-pyridyl))carbamoyl]phenyl}carbamoyl)phenyl]iminomethyl}piperidine4-carboxylate The titled compound was made by the procedure similar to that described in example 79.

MS found for $C_{30}H_{28}ClN_5O_4$ as $(M+H)^+$: 558.2.

Example 84

1-{[4-(N-{4-chloro-2-[N-(5-ethynyl(2-pyridyl))carbamoyl]phenyl}carbamoyl)phenyl]iminomethyl}-piperidine-4-carboxamide

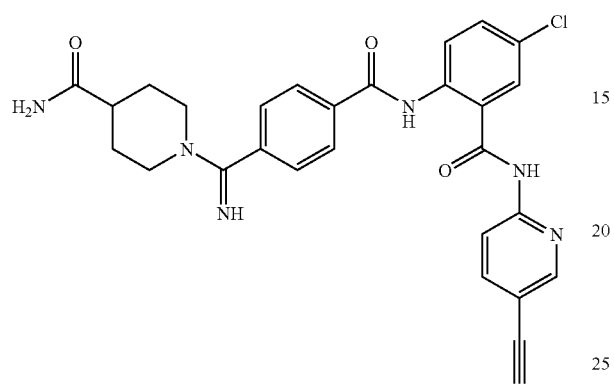

The titled compound was made by the procedure similar to that described in example 79.

MS found for $C_{28}H_{25}ClN_6O_3$ as $(M+H)^+$: 529.1.

Example 85

{4-[(N-ethylmethylamino)iminomethyl]phenyl}-N-{4-chloro-2-[N-(5-ethynyl(2-pyridyl))carbamoyl]phenyl}-carboxamide

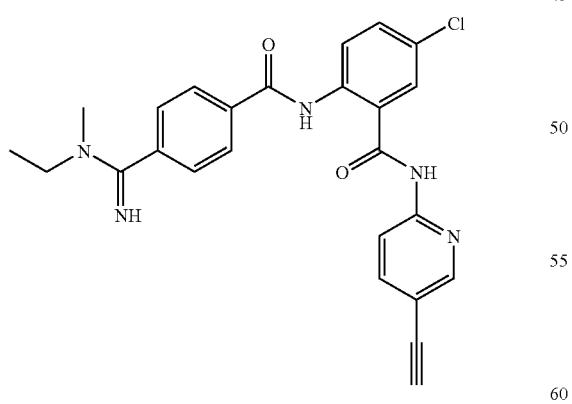

The titled compound was made by the procedure similar to that described in example 79.

MS found for $C_{25}H_{22}ClN_5O_2$ as $(M+H)^+$: 460.1.

Example 86

{4-[(N-methylpropylamino)iminomethyl]phenyl}-N-{4-chloro-2-[N-(5-ethynyl(2-pyridyl))carbamoyl]phenyl}-carboxamide

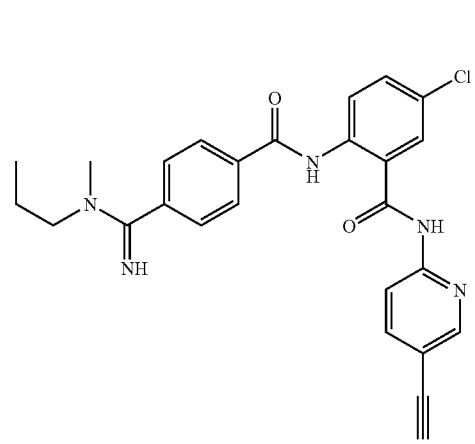

The titled compound was made by the procedure similar to that described in example 79.

MS found for $C_{26}H_{22}ClN_5O_2$ as $(M+H)^+$: 474.1.

Example 87

{4-[Azetidinylazetidinylidenemethyl]phenyl}-N-{4-chloro-2-[N-(5-ethynyl(2-pyridyl))carbamoyl]phenyl}-carboxamide

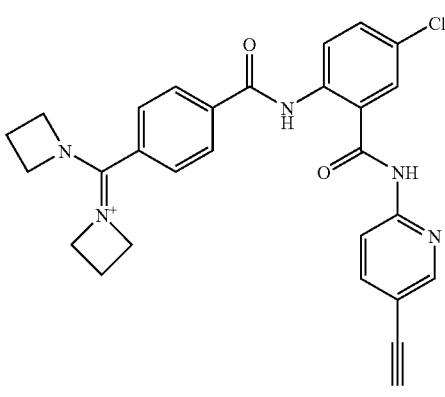

The titled compound was made by the procedure similar to that described in example 79.

MS found for $C_{28}H_{25}ClN_5O_2$ as $(M)+$: 498.2.

Example 88

[4-({[2-(dimethylamino)ethyl]methylamino}iminomethyl)phenyl]-N-{4-chloro-2-[N-(5-ethynyl(2-pyridyl))carbamoyl]phenyl}carboxamide

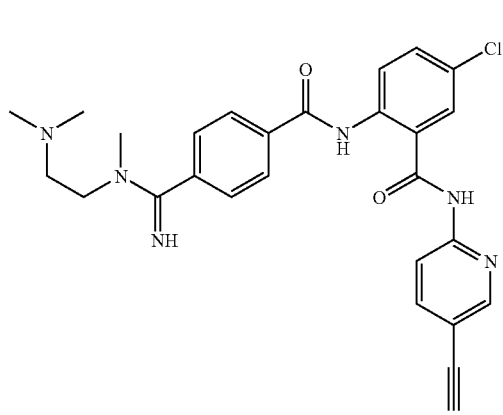

The titled compound was made by the procedure similar to that described in example 79.

MS found for $C_{27}H_{27}ClN_6O_2$ as $(M+H)^+$: 503.2.

Example 89

{4-[(N-methyl-2-propynylamino)iminomethyl]phenyl}-N-{4-chloro-2-[N-(5-ethynyl(2-pyridyl))carbamoyl]phenyl}-carboxamide

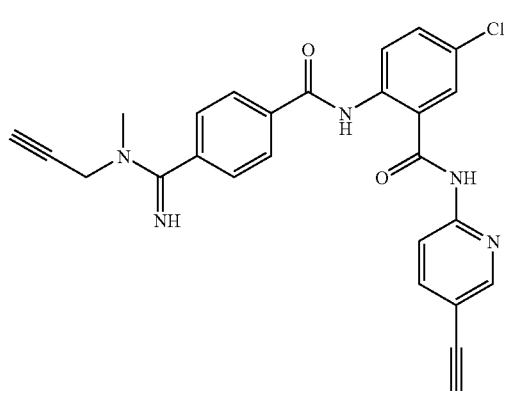

The titled compound was made by the procedure similar to that described in example 79.

MS found for $C_{26}H_{20}ClN_5O_2$ as $(M+H)^+$: 470.1.

Example 90

{4-[(N-methyl-2-cyanoethylamino)iminomethyl]phenyl}-N-{4-chloro-2-[N-(5-ethynyl(2-pyridyl))carbamoyl]phenyl}-carboxamide

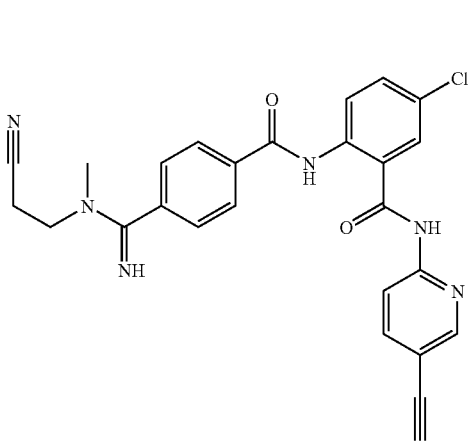

The titled compound was made by the procedure similar to that described in example 79.

MS found for $C_{26}H_{21}ClN_6O_2$ as $(M+H)^+$: 457.3.

Example 91

{4-[(dimethylamino)iminomethyl]-2-fluorophenyl}-N-{4-chloro-2-[N-(5-ethynyl(2-pyridyl))carbamoyl]phenyl}-carboxamide

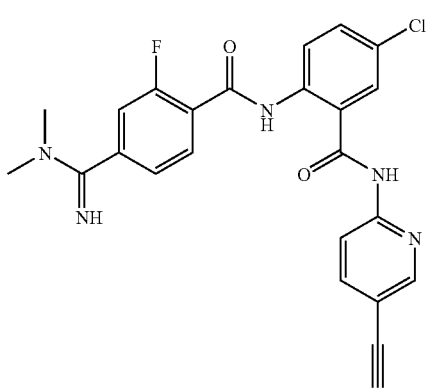

The titled compound was made by the procedure similar to that described in example 79.

MS found for $C_{24}H_{19}ClFN_5O_2$ as $(M+H)^+$: 464.1.

Example 92

N-{2-[N-(5-ethynyl(2-pyridyl))carbamoyl]-4-chlorophenyl}[4-(iminopyrrolidinylmethyl)-2-fluorophenyl]carboxamide

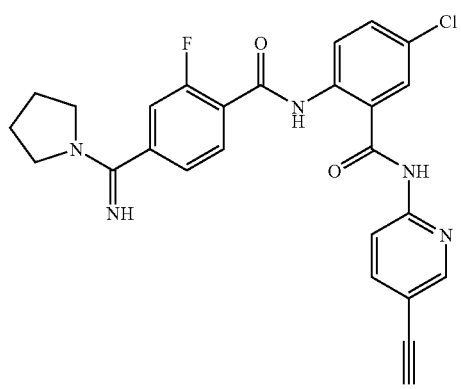

The titled compound was made by the procedure similar to that described in example 79.

MS found for $C_{26}H_{21}ClFN_5O_2$ as $(M+H)^+$: 490.1

Example 93

Ethyl 1-{[4-(N-{4-chloro-2-[N-(5-ethynyl(2-pyridyl))carbamoyl]phenyl}carbamoyl)-3-fluorophenyl]iminomethyl}piperidine-4-carboxylate

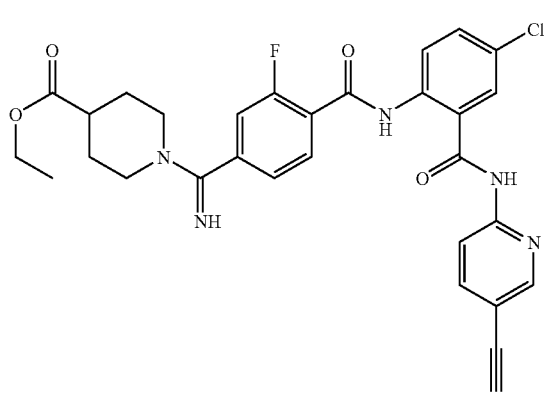

The titled compound was made by the procedure similar to that described in example 79.

MS found for $C_{30}H_{27}ClFN_5O_4$ as $(M+H)^+$: 576.2.

Example 94

1-{[4-(N-{4-chloro-2-[N-(5-ethynyl(2-pyridyl))carbamoyl]phenyl}carbamoyl)-3-fluorophenyl]iminomethyl}piperidine-4-carboxamide

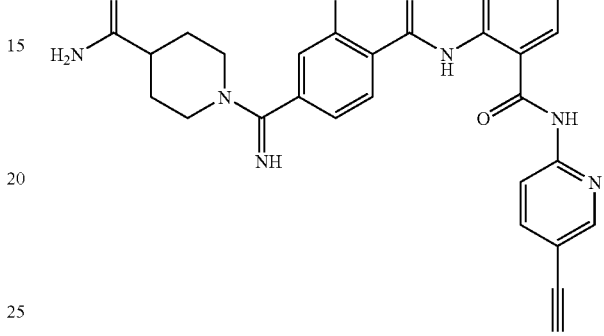

The titled compound was made by the procedure similar to that described in example 79.

MS found for $C_{28}H_{24}ClFN_6O_3$ as $(M+H)^+$: 547.1.

Example 95

N-{4-chloro-2-[N-(5-ethynyl(2-pyridyl))carbamoyl]phenyl}[4-(1-methyl(2-imidazolin-2-yl))-2-fluorophenyl]-carboxamide

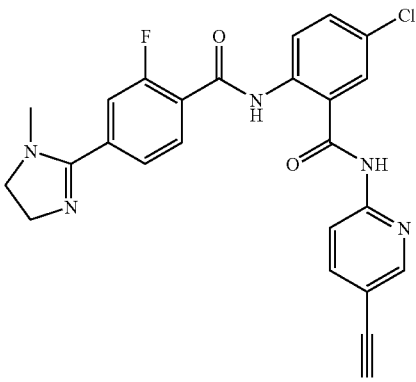

The titled compound was made by the procedure similar to that described in example 79.

MS found for $C_{25}H_{19}ClFN_5O_2$ as $(M+H)^+$: 476.1.

Example 96

{4-[(N-methyl(phenylmethyl)amino)iminomethyl]-2-fluorophenyl}-N-{4-chloro-2-[N-(5-ethynyl(2-pyridyl))carbamoyl]phenyl}-carboxamide

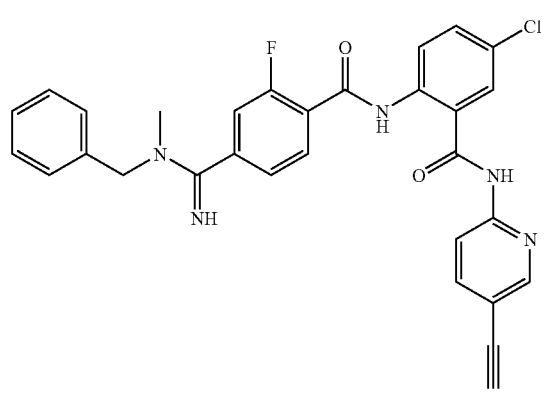

The titled compound was made by the procedure similar to that described in example 79.
MS found for $C_{30}H_{23}ClFN_5O_2$ as $(M+H)^+$: 540.1.

Example 97

{4-[(N-(2-methoxyethyl)methylamino)iminomethyl]-2-fluorophenyl}-N-{4-chloro-2-[N-(5-ethynyl(2-pyridyl))carbamoyl]phenyl}-carboxamide

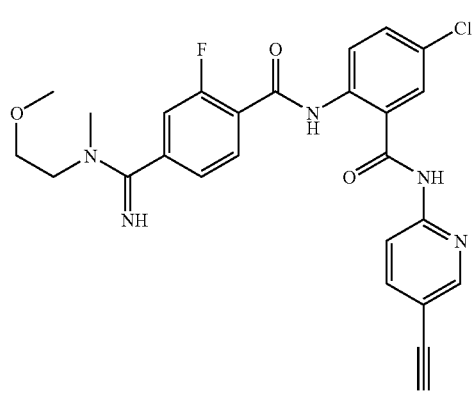

The titled compound was made by the procedure similar to that described in example 79.
MS found for $C_{26}H_{23}ClFN_5O_3$ as $(M+H)^+$: 508.1.

Example 98

{4-[(N-methyl(furanylmethyl)amino)iminomethyl]-2-fluorophenyl}-N-{4-chloro-2-[N-(5-ethynyl(2-pyridyl))carbamoyl]phenyl}-carboxamide

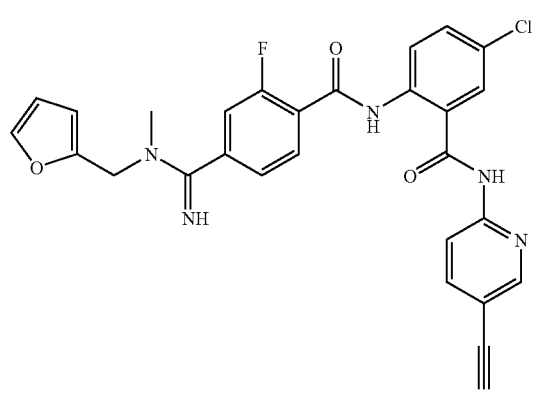

The titled compound was made by the procedure similar to that described in example 79.
MS found for $C_{28}H_{21}ClFN_5O_3$ as $(M+H)^+$: 530.1.

Example 99

N-{4-chloro-2-[N-(5-ethynyl (2-pyridyl))carbamoyl]phenyl}[4-(11-(2-hydroxyethyl)(2-imidazolin-2-yl))-2-fluorophenyl]-carboxamide

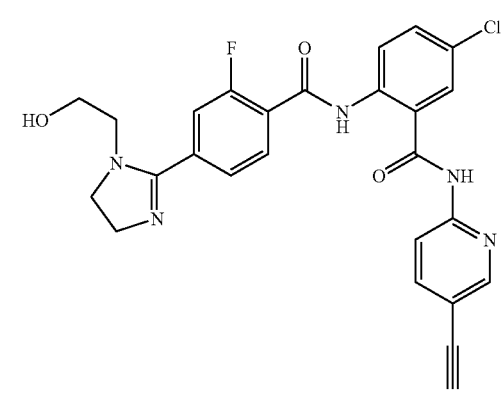

The titled compound was made by the procedure similar to that described in example 79.
MS found for $C_{26}H_{21}ClFN_5O_3$ as $(M+H)^+$: 506.1.

Example 100

N-{4-chloro-2-[N-(5-ethynyl(2-pyridyl))carbamoyl]phenyl}[4-(1-propyl(2-imidazolin-2-yl))-2-fluorophenyl]-carboxamide

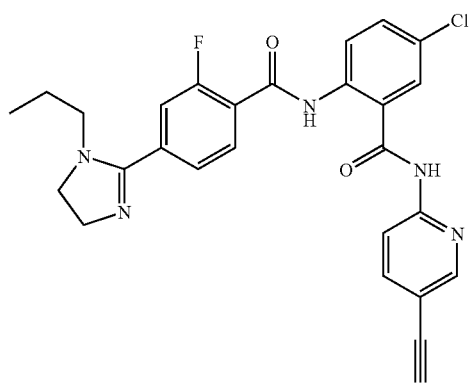

The titled compound was made by the procedure similar to that described in example 79.

MS found for $C_{27}H_{23}ClFN_5O_2$ as $(M+H)^+$: 504.1.

Example 101

{4-[(N-(2-[1,3]Dioxolan-2-yl-ethyl)methylamino)iminomethyl]-2-fluorophenyl}-N-{4-chloro-2-[-N-(5-ethynyl(2-pyridyl))carbamoyl]phenyl}-carboxamide

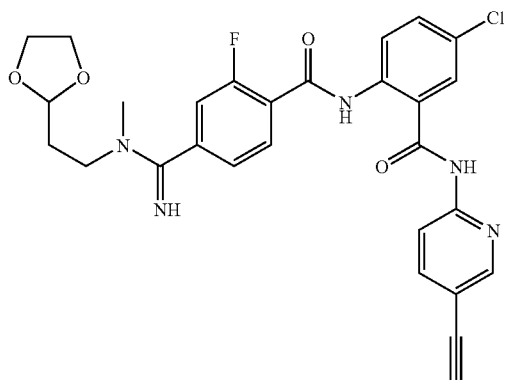

The titled compound was made by the procedure similar to that described in example 79.

MS found for $C_{28}H_{25}ClFN_5O_4$ as $(M+H)^+$: 550.2.

Example 102

1-{[4-(N-{4-chloro-2-[N-(5-ethynyl(2-pyridyl))carbamoyl]phenyl}carbamoyl)-3-fluorophenyl]iminomethyl}-4-phenylpiperazine

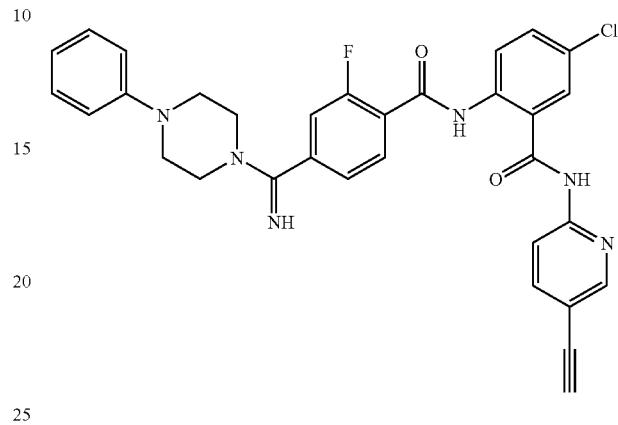

The titled compound was made by the procedure similar to that described in example 79.

MS found for $C_{32}H_{26}ClFN_6O_2$ as $(M+H)^+$: 581.2.

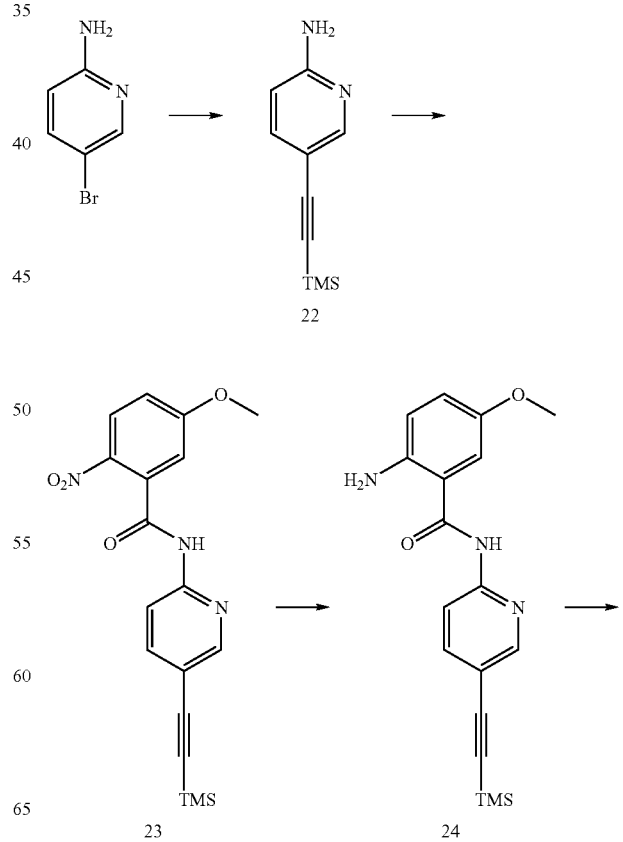

Scheme 5

-continued

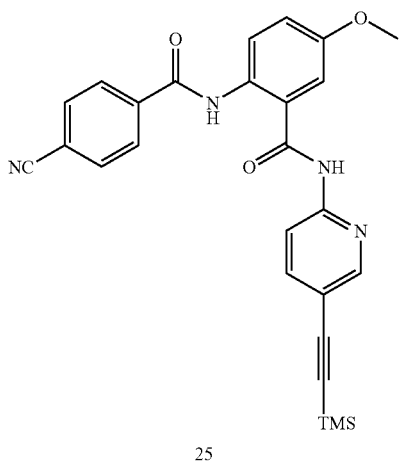

25

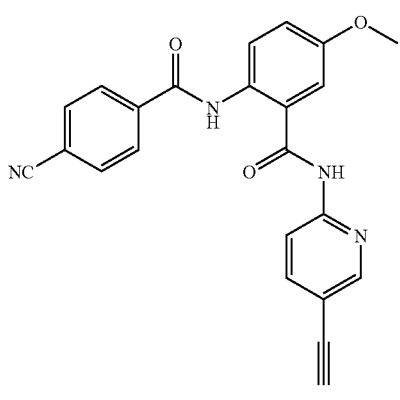

26

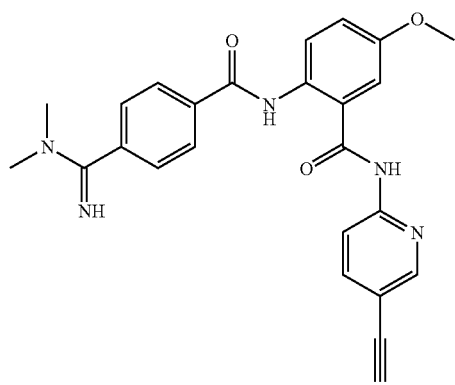

27

Example 103

{4-[(dimethylamino)iminomethyl]phenyl}-N-{4-methoxy-2-[N-(5-ethynyl(2-pyridyl))carbamoyl]phenyl}-carboxamide

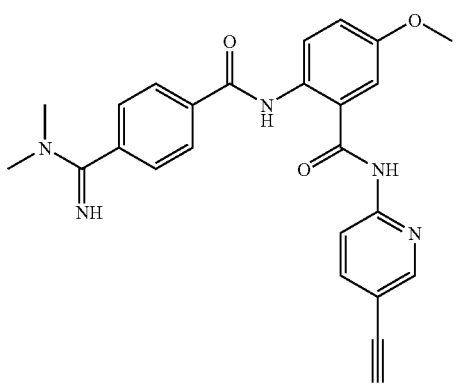

Step 1:

A stirring solution of 2-amino-5-bromopyridine (50 g, 290 mmol) in dioxane (300 mL) was treated with Pd(Ph CN)$_2$ (3.20 g, 8.70 mmol) and CuI (1.44 g, 7.60 mmol), then degassed with argon for 3 minutes. The solution was then treated with PBu$_3$ (4.20 g, 17.4 mmol), trimethylsilyl acetylene (48 mL, 346 mmol) and finally diisopropylamine (30.0 mL, 436 mmol) was added dropwise to the light beige suspension which changed to orange and finally dark brown as the reaction progressed. After one hour the reaction was concentrated to a volume of approximately 70 mL then filtered through a plug of silica gel and eluted with 2 L of diethyl ether. This was then concentrated at which time the desired product crystallized. The crystals were then diluted with hexanes (to aid in transfer), filtered and washed with hexanes affording 40 g (73%) of 22 as beige crystalline solid. MS found for $C_{10}H_{14}N_2Si$ as (M+H)$^+$: 191.1.

Step 2:

Aniline 22 (10.00 g, 53 mmol) was dissolved in pyridine (20 mL), cooled to 0° C., then treated with POCl$_3$ dropwise during which time the reaction changed from colorless to light orange. The reaction was stirred 10 min then diluted with 10 volumes of water and 10 mL triethyl amine to give a light orange, filterable precipitate which was collected and dried overnight by aspiration (14.77 g, 76%). $^1$H NMR (DMSO-d$_6$, 400 MHz): δ 11.31 (s, 1H), 8.41 (s, 1H), 8.16 (m, 2H), 7.92 (m, 1H), 7.19 (m, 2H), 3.88 (s, 3H), 0.21 (s, 9H).

Step 3:

Nitroarene 23 (8.6 g, 23 mmol) was dissolved in ethyl acetate (50 mL) then treated with tin(II) chloride dihydrate (21 g, 93 mmol) and heated to 60° C. for 30 min at which time if was found to be complete by TLC. The reaction was cooled to rt then treated slowly with saturated aqueous K$_2$CO$_3$ until no more precipitate formed. The mixture was then filtered through a pad of celite and concentrated in vacuo affording the desired aniline (24) as an orange semi-solid (7.32 g, 94%).

MS found for $C_{18}H_{21}N_3O_2Si$ as (M+H)$^+$: 340.1.

Step 4:

Aniline 24 (3.24 g, 9.56 mmol) was dissolved in THF (30 mL) and treated with 4-cyanobenzoyl chloride (1.73 g, 10.5 mmol) in one portion. After one hour the reaction was concentrated and diluted with a 1:1 mixture of diethyl ether and hexanes (50 mL) and filtered affording a quantitative yield of the desired amide as an orange solid. MS found for $C_{26}H_{24}N_4O_3Si$ as $(M+H)^+$: 469.2.

Step 5:

From compound 25, following a procedure similar to that described in Step 4, Example 79, the titled compound 26 was prepared. MS found for $C_{23}H_{16}N_4O_3$ as $(M+H)^+$: 396.1.

Step 6:

From compound 26, following a procedure similar to that described in Step 5, Example 79, the titled compound 27 was prepared. MS found for $C_{25}H_{23}N_5O_3$ as $(M+H)^+$: 442.1.

Example 104

{4-[(dimethylamino)iminomethyl]phenyl}-N-{4-methoxy-2-[N-(5-ethynyl(2-pyridyl))carbamoyl]phenyl}-carboxamide

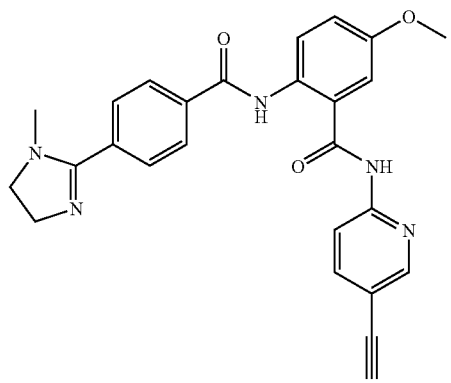

The titled compound was made by the procedure similar to that described in Example 103. MS found for $C_{26}H_{23}N_5O_3$ as $(M+H)^+$: 454.2.

Example 105

N-{2-[N-(5-ethynyl(2-pyridyl))carbamoyl]-4-methoxyphenyl}[4-(iminopyrrolidinylmethyl)phenyl]carboxamide

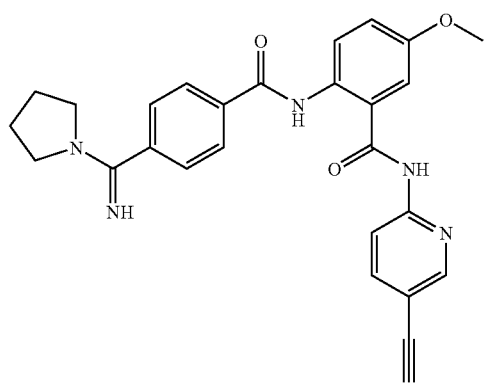

The titled compound was made by the procedure similar to that described in Example 103. MS found for $C_{27}H_{25}N_5O_3$ as $(M+H)^+$: 468.2.

Example 106

N-{2-[N-(5-ethynyl(2-pyridyl))carbamoyl]-4-methoxyphenyl}[4-(iminopiperidylmethyl)phenyl]carboxamide

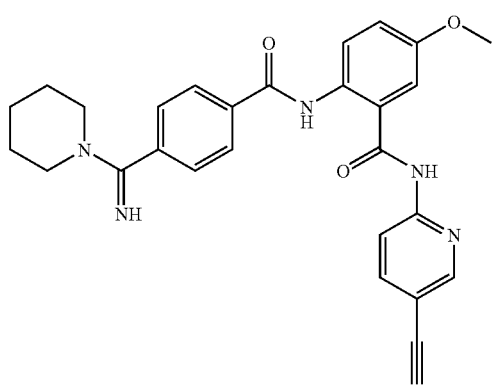

The titled compound was made by the procedure similar to that described in Example 103. MS found for $C_{28}H_{27}N_5O_3$ as $(M+H)^+$: 482.2.

Example 107

Ethyl 1-{[4-(N-{4-methoxy-2-[N-(5-ethynyl(2-pyridyl))carbamoyl]phenyl}carbamoyl)phenyl]iminomethyl}-piperidine-4-carboxylate

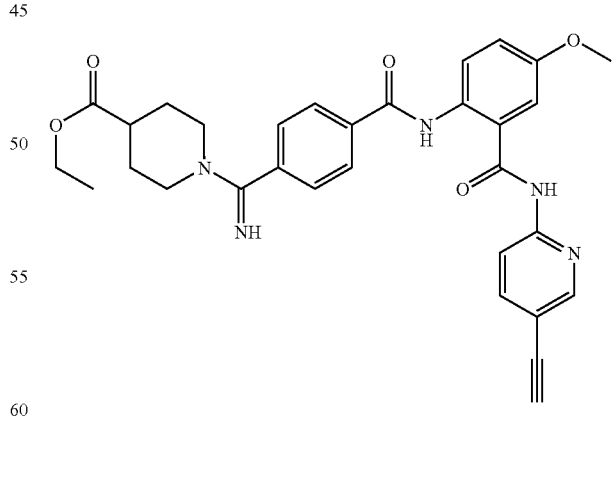

The titled compound was made by the procedure similar to that described in Example 103. MS found for $C_{31}H_{31}N_5O_5$ as $(M+H)^+$: 554.2.

Example 108

{4-[(dimethylamino)iminomethyl]-2-fluorophenyl}-N-{4-methoxy-2-[N-(5-ethynyl(2-pyridyl))carbamoyl]phenyl}-carboxamide

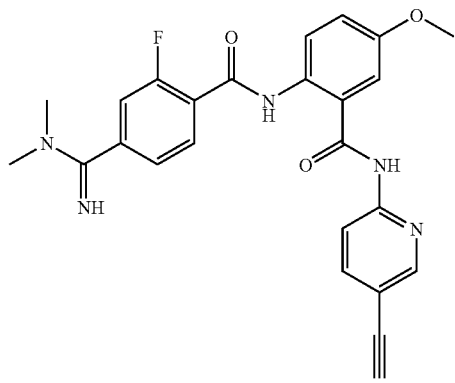

The titled compound was made by the procedure similar to that described in Example 103. MS found for $C_{25}H_{22}FN_5O_3$ as $(M+H)^+$: 460.1.

Example 109

N-{4-methoxy-2-[N-(5-ethynyl(2-pyridyl))carbamoyl]phenyl}[4-(1-methyl(2-imidazolin-2-yl))-2-fluorophenyl]-carboxamide

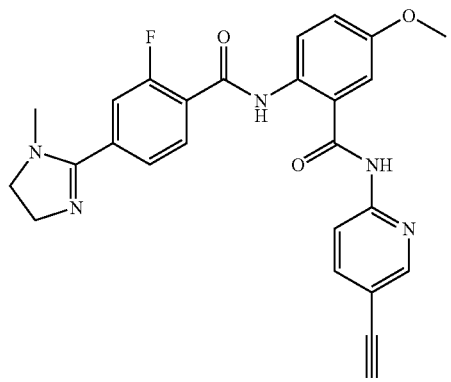

The titled compound was made by the procedure similar to that described in Example 103. MS found for $C_{26}H_{22}FN_5O_3$ as $(M+H)^+$: 472.2.

Example 110

N-{2-[N-(5-ethynyl(2-pyridyl))carbamoyl]-4-methoxyphenyl}[4-(iminopiperidinylmethyl)-2-fluorophenyl]carboxamide

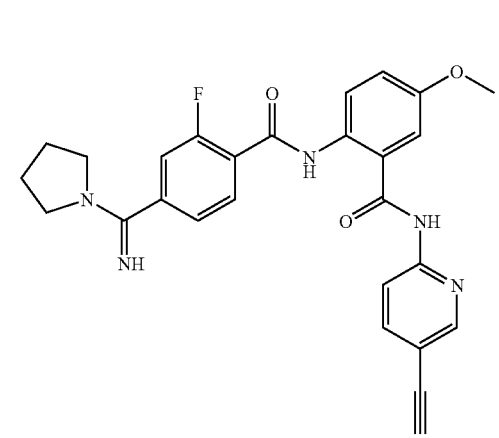

The titled compound was made by the procedure similar to that described in Example 103. MS found for $C_{27}H_{24}FN_5O_3$ as $(M+H)^+$: 486.2.

Example 111

N-{2-[N-(5-ethynyl(2-pyridyl))carbamoyl]-4-chlorophenyl}[4-(iminopiperidinylmethyl)-2-fluorophenyl]carboxamide

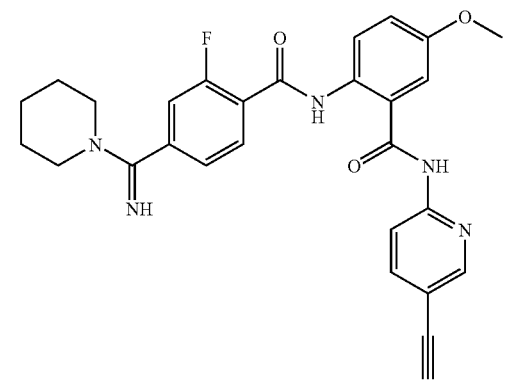

The titled compound was made by the procedure similar to that described in Example 103. MS found for $C_{28}H_{26}FN_5O_3$ as $(M+H)^+$: 500.2.

Example 112

Ethyl 1-{[4-(N-{4-methoxy-2-[N-(5-ethynyl (2-pyridyl))carbamoyl]phenyl}carbamoyl)-3-fluorophenyl]iminomethyl}piperidine-4-carboxylate

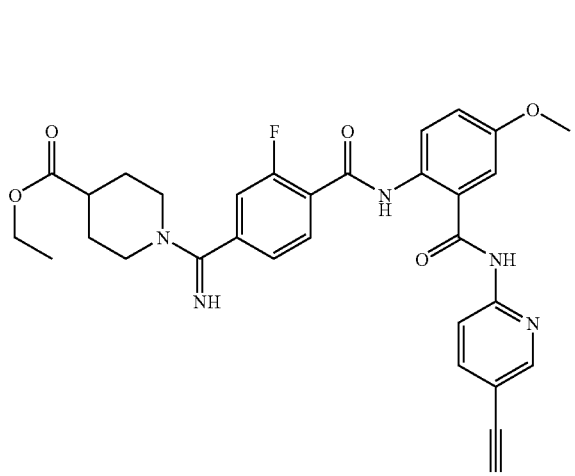

The titled compound was made by the procedure similar to that described in Example 103. MS found for $C_{31}H_{30}FN_5O_5$ as $(M+H)^+$: 572.2.

Example 113

{4-[(N-methylethylamino)iminomethyl]-2-fluorophenyl}-N-{4-methoxy-2-[N-(5-ethynyl(2-pyridyl))carbamoyl]phenyl}-carboxamide

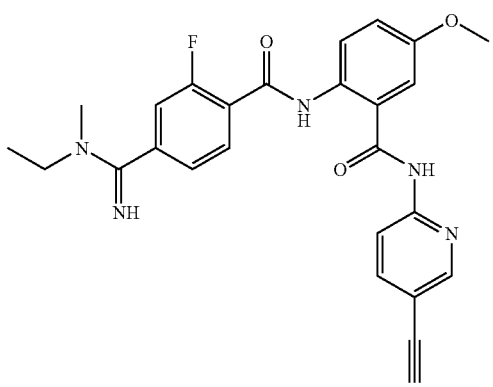

The titled compound was made by the procedure similar to that described in Example 103. MS found for $C_{26}H_{24}FN_5O_3$ as $(M+H)^+$: 474.2.

Example 114

{4-[(N-propylmethylamino)iminomethyl]-2-fluorophenyl}-N-{4-methoxy-2-[N-(5-ethynyl(2-pyridyl))carbamoyl]phenyl}-carboxamide

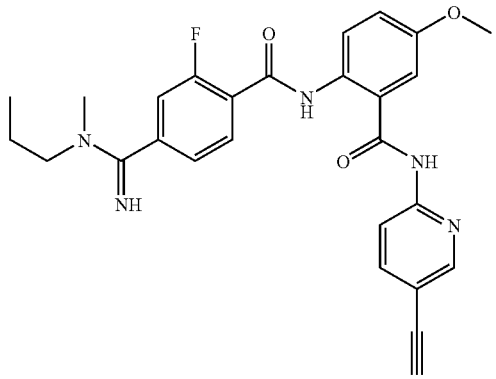

The titled compound was made by the procedure similar to that described in Example 103. MS found for $C_{27}H_{26}FN_5O_3$ as $(M+H)^+$: 488.2.

Example 115

{4-[Azetidinyiminomethyl]-2-fluorophenyl}-N-{4-methoxy-2-[N-(5-ethynyl(2-pyridyl))carbamoyl]phenyl}-carboxamide

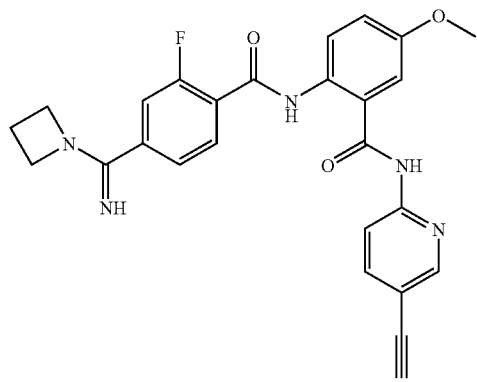

The titled compound was made by the procedure similar to that described in Example 103. MS found for $C_{26}H_{22}FN_5O_3$ as $(M+H)^+$: 473.1.

Scheme 6

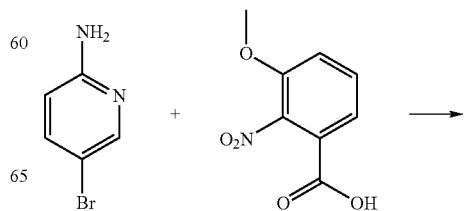

-continued
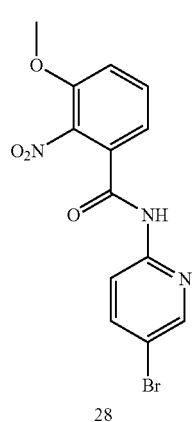 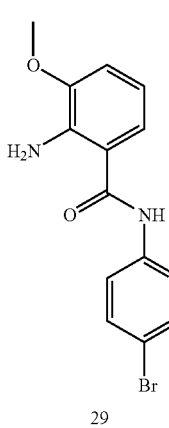 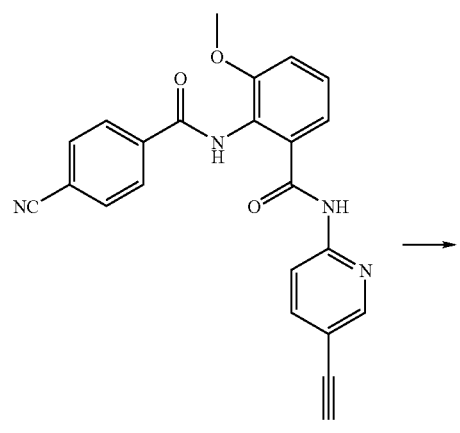
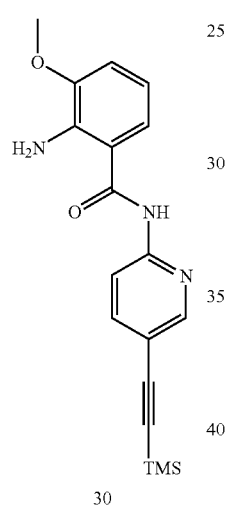 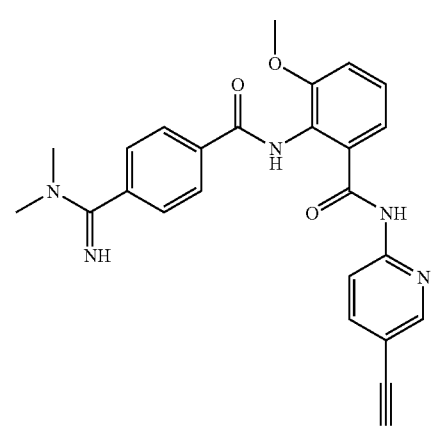
Example 116
{4-[(dimethylamino)iminomethyl]phenyl}-N-{6-methoxy-2-[N-(5-ethynyl (2-pyridyl))carbamoyl]phenyl}-carboxamide
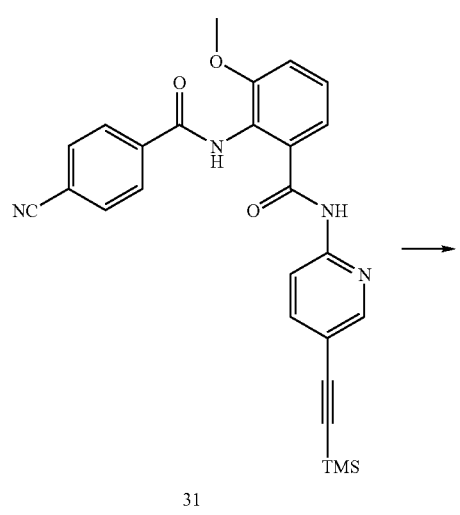 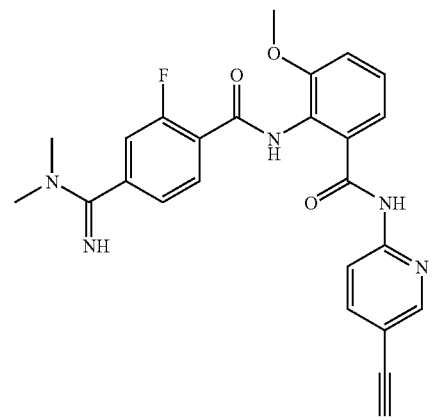

Step 1:

From 2-amino-5-bromopyridine and 3-methoxy-2-nitrobenzoic acid, following the procedure similar to that described in Step 2, Example 103, the titled compound 28 was prepared. $^1$H NMR (DMSOd$_6$, 400 MHz): δ 11.41 (s, 1H), 8.48 (s, 1H), 8.00 (s, 2H), 7.64 (t, 1H), 7.49 (d, 1H), 7.39 (d, 1H), 3.84 (s, 3H).

Step 2:

Nitrobenzamide 28 (15.83 g, 45 mmol) was diluted with THF (150 mL), dioxane (150 mL), and water (225 mL). To the stirring solution was added sodium hydrosulfite (39.0 g, 225 mmol) and the mixture heated to 60° C. for 3 hrs. The reaction mixture was then diluted with ca. 500 mL of water and filtered. The solids were then diluted with aq sodium bicarbonate and extracted thrice with ethyl acetate, the combined organic fractions then dried over magnesium sulfate. After filtration of the drying agent the solution was concentrated affording desired aniline 29 (10.76 g, 74%) as an off white solid. MS found for $C_{13}H_{12}BrN_3O_2$ as (M+H)$^+$: 322.0.

Step 3:

Aniline 29 (6.00 g, 19 mmol) was diluted with n-butylamine (30 mL) and trimethylsilylacetylene (6 mL, 38 mmol), then degassed with argon for 3 min. Tetrakis(triphenylphosphine)Pd(0) (0.14 g, 0.12 mmol) was then added and the reaction refluxed overnight. The next day the reaction was recharged with trimethylsilylacetylene (6 mL, 38 mmol) and heated overnight. The following day the starting material was completely consumed and the reaction was concentrated, partitioned between water and ethyl acetate, separated, and the organic phase concentrated. The crude brown oil was then purified by filtration through a 4 in.×2 in. plug of silica gel eluted with 15% ethyl acetate/hexanes affording alkyne 30 (1.69 g) in 26% yield. MS found for $C_{18}H_{21}N_3O_2Si$ as (M+H)$^+$: 340.2.

Step 4:

From compound 30, following a procedure similar to that described in Step 3, Example 79, the titled compound 31 was prepared. MS found for $C_{26}H_{24}N_4O_3Si$ as (M+H)$^+$: 469.2.

Step 5:

From compound 31, following a procedure similar to that described in Step 4, Example 79, the titled compound 32 was prepared. MS found for $C_{23}H_{16}N_4O_3$ as (M+H)$^+$: 397.0.

Step 6:

From compound 32, following a procedure similar to that described in Step 5, Example 79, the titled compound 33 was prepared. MS found for $C_{25}H_{23}N_5O_3$ as (M+H)$^+$: 442.1.

Example 117

{4-[(dimethylamino)iminomethyl]phenyl}-N-{6-methoxy-2-[N-(5-ethynyl(2-pyridyl))carbamoyl]phenyl}-carboxamide

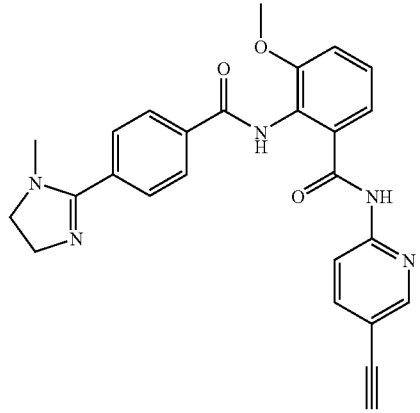

The titled compound was made by the procedure similar to that described in Example 116. MS found for $C_{27}H_{26}N_5O_3$ as (M+H)$^+$: 454.1.

Example 118

N-{2-[N-(5-ethynyl(2-pyridyl))carbamoyl]-6-methoxyphenyl}[4-(iminopyrrolidinylmethyl)phenyl]carboxamide

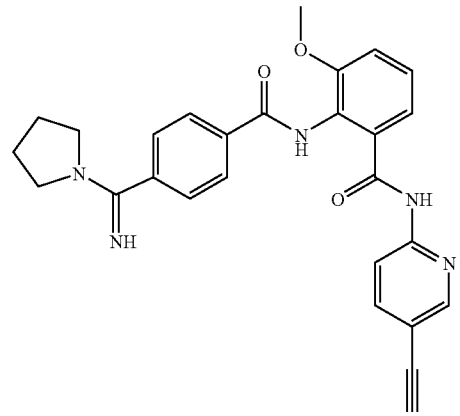

The titled compound was made by the procedure similar to that described in Example 116. MS found for $C_{27}H_{25}N_5O_3$ as (M+H)$^+$: 468.1.

Example 119

N-{2-[N-(5-ethynyl(2-pyridyl))carbamoyl]-6-methoxyphenyl}[4-(iminopiperidylmethyl)phenyl]carboxamide

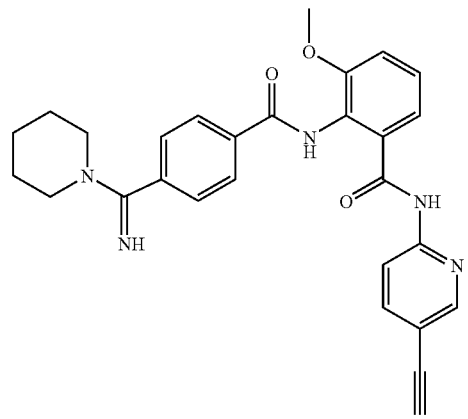

The titled compound was made by the procedure similar to that described in Example 116. MS found for $C_{28}H_{27}N_5O_3$ as (M+H)$^+$: 482.2.1

Example 120

Ethyl 1-{[4-(N-{6-methoxy-2-[N-(5-ethynyl(2pyridyl))carbamoyl]phenyl}carbamoyl)phenyl]iminomethyl}-piperidine-4-carboxylate

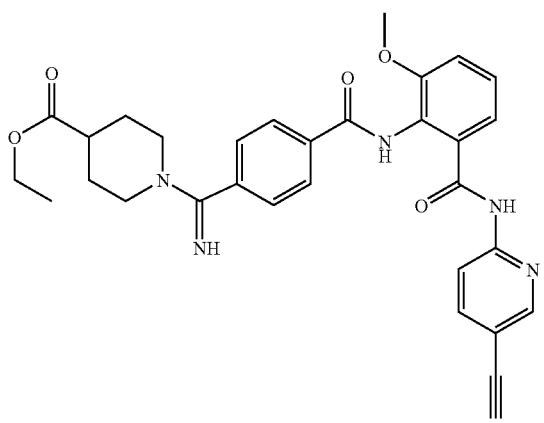

The titled compound was made by the procedure similar to that described in Example 116. MS found for $C_{31}H_{31}N_5O_5$ as $(M+H)^+$: 554.2.

Example 121

{4-[(N-ethylmethylamino)iminomethyl]phenyl}-N-{6-methoxy-2-[N-(5-ethynyl(2-pyridyl))carbamoyl]phenyl}-carboxamide

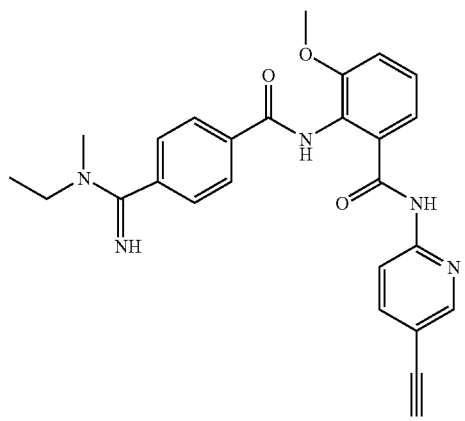

The titled compound was made by the procedure similar to that described in Example 1116. MS found for $C_{26}H_{25}N_5O_3$ as $(M+H)^+$: 456.1.

Example 122

{4-[(N-methylpropylamino)iminomethyl]phenyl}-N-{6-methoxy-2-[N-(5-ethynyl(2-pyridyl))carbamoyl]phenyl}-carboxamide

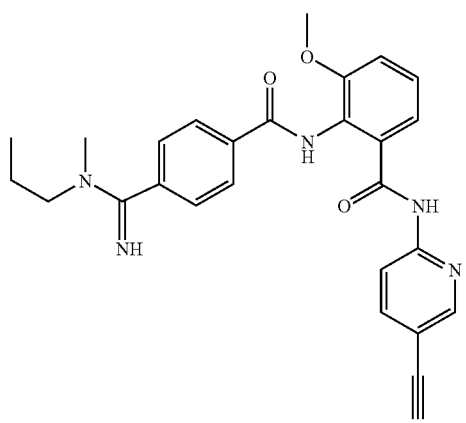

The titled compound was made by the procedure similar to that described in Example 116. MS found for $C_{27}H_{27}N_5O_3$ as $(M+H)^+$: 470.2.

Example 123

{4-[Azetidinyliminomethyl]phenyl}-N-{6-methoxy-2-[N-(5-ethynyl(2-pyridyl))carbamoyl]phenyl}-carboxamide

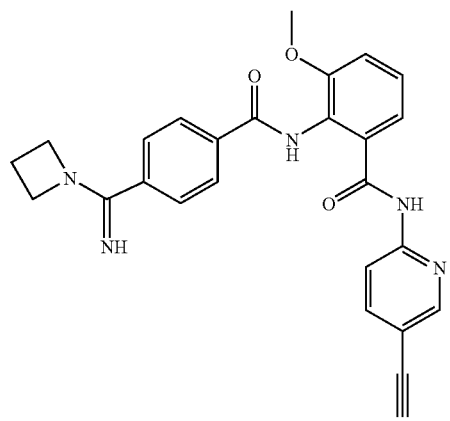

The titled compound was made by the procedure similar to that described in Example 116. MS found for $C_{26}H_{23}N_5O_3$ as $(M+H)^+$: 454.1.

Example 124

{4-[Azetidinylazetidinylidenemethyl]phenyl}-N-{6-methoxy-2-[N-(5-ethynyl(2-pyridyl))carbamoyl]phenyl}-carboxamide

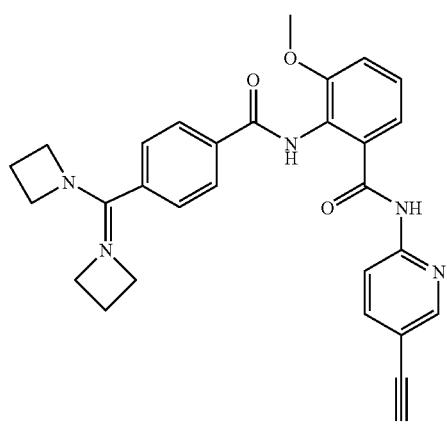

The titled compound was made by the procedure similar to that described in Example 116. MS found for $C_{29}H_{28}N_5O_3$ as (M)+: 494.1.

Example 125

[4-({[2-(dimethylamino)ethyl]methylamino}iminomethyl)phenyl]-N-{6-methoxy-2-[N-(5-ethynyl(2-pyridyl))carbamoyl]phenyl}carboxamide

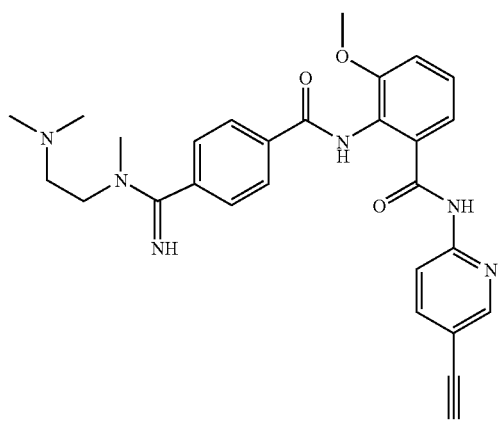

The titled compound was made by the procedure similar to that described in Example 116. MS found for $C_{28}H_{30}N_6O_3$ as (M+H)+: 499.2.

Example 126

{4-[(N-methyl-2-propynylamino)iminomethyl]phenyl}-N-{6-methoxy-2-[N-(5-ethynyl (2-pyridyl))carbamoyl]phenyl}-carboxamide

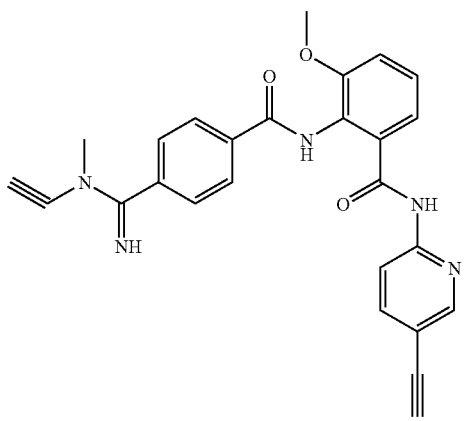

The titled compound was made by the procedure similar to that described in Example 116. MS found for $C_{27}H_{23}N_5O_3$ as (M+H)+: 466.1.

Scheme 7

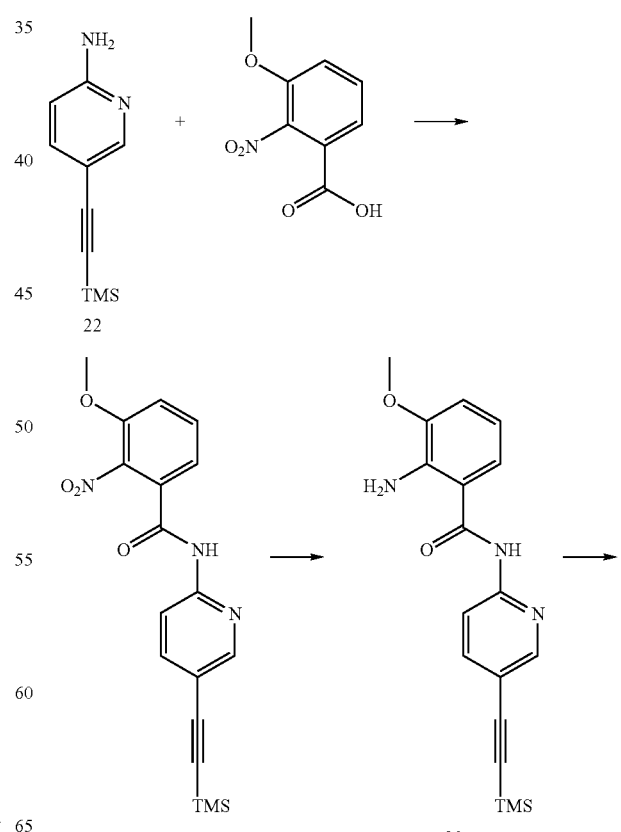

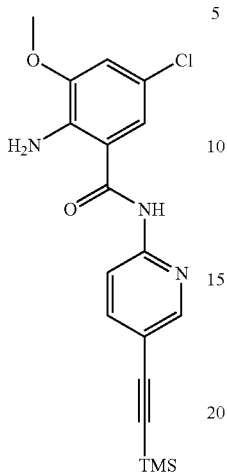

35

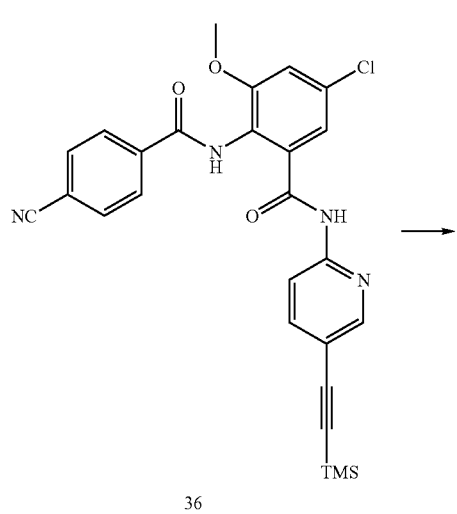

36

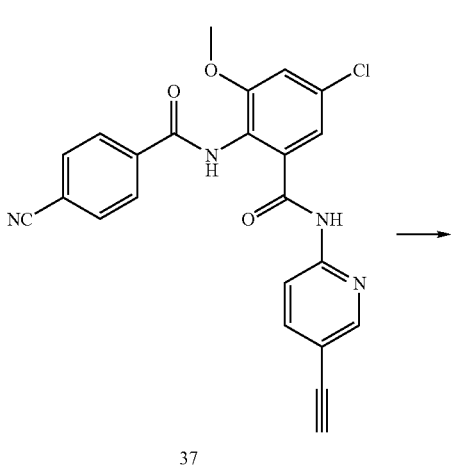

37

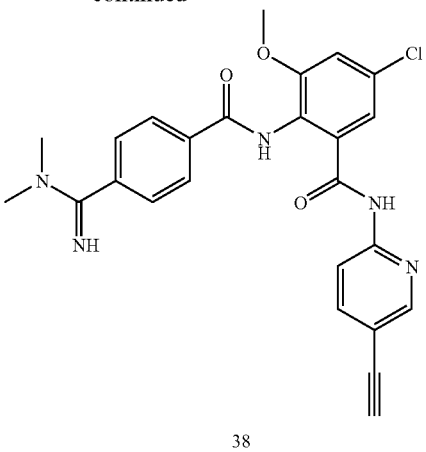

38

Example 127

{4-[(dimethylamino)iminomethyl]phenyl}-N-{4-chloro-6-methoxy-2-[N-(5-ethynyl(2-pyridyl))carbamoyl]phenyl}-carboxamide

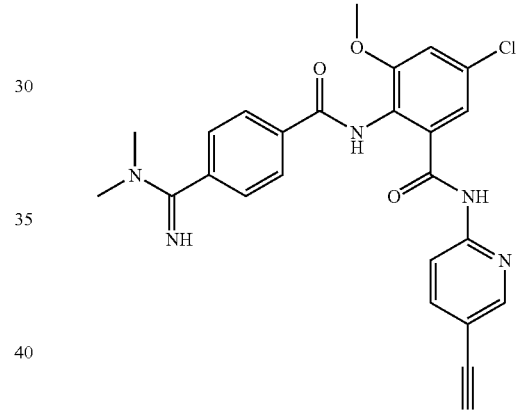

Step 1:

From amine 22 and 3-methoxy-2-nitrobenzoic acid, following the procedure similar to that described in Step 2, Example 103, the titled compound 34 was prepared. $^1$H NMR (DMSO-$d_6$, 400 MHz): δ 11.49 (s, 1H), 8.03 (m, 1H) 7.95 (m, 1H), 7.75 (m, 1H), 7.63 (m, 1H), 7.49 (m, 1H), 7.40 (m, 1H) 3.89 (s, 3H), 0.18 (s, 9H).

Step 2:

From compound 34, following the procedure similar to that described in Step 2, Example 116, the titled compound 30 was prepared. MS found for $C_{18}H_{21}N_3OSi$ as $(M+H)^+$: 340.0.

Step 3:

Aniline 30 (6.25 g, 19.4 mmol) was diluted with toluene (80 mL), treated with N-chlorosuccinamide (2.71 g, 20.3 mmol) and heated to 60° C. for 2 hrs during which time the appearance of the reaction changed from a light orange suspension to dark orange and finally black. The mixture was then concentrated and purified by filtration through a plug of silica gel (3 in.×2 in.) eluting with dichloromethane affording 5.7 g (83%) of 35 as a beige solid. MS found for $C_{18}H_{20}ClN_3O_2Si$ as $(M+H)^+$: 374.0.

Step 4:

From compound 35, following the procedure similar to that described in Step 3, Example 79, the titled compound 36 was prepared. MS found for $C_{26}H_{23}ClN_4O_3Si$ as $(M+H)^+$: 503.1.

Step 5:

From compound 36, following the procedure similar to that described in Step 4, Example 79, the titled compound 37 was prepared. MS found for $C_{23}H_{15}ClN_4O_3$ as $(M+H)^+$: 431.1.

Step 6:

From compound 37, following the procedure similar to that described in Step 5, Example 79, the titled compound 38 was prepared. MS found for $C_{25}H_{23}N_5O_3$ as $(M+H)^+$: 476.0.

Example 128

N-{4-chloro-6-methoxy-2-[N-(5-ethynyl(2-pyridyl))carbamoyl]phenyl}[4-(1-methyl(2-imidazolin-2-yl))phenyl]-carboxamide

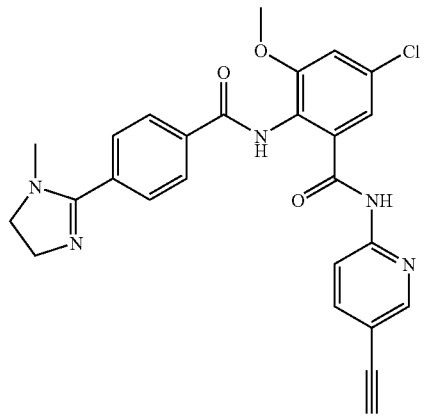

The titled compound was made by the procedure similar to that described in Example 127. MS found for $C_{26}H_{22}ClN_5O_3$ as $(M+H)^+$: 488.1.

Example 129

N-{2-[N-(5-ethynyl(2-pyridyl))carbamoyl]-4-chloro-6-methoxyphenyl}[4-(iminopyrrolidinylmethyl)phenyl]carboxamide

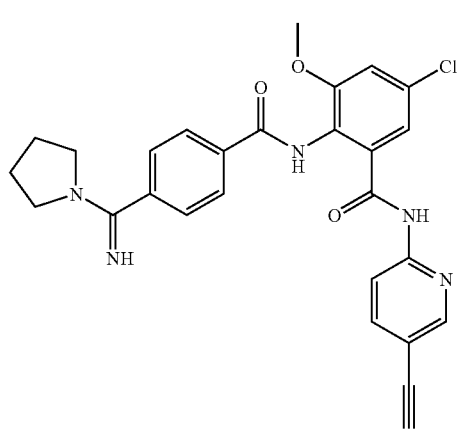

The titled compound was made by the procedure similar to that described in Example 127. MS found $C_{27}H_{24}ClN_5O_3$ as $(M+H)^+$: 502.1.

Example 130

N-{2-[N-(5-ethynyl(2-pyridyl))carbamoyl]-4-chloro-6-methoxyphenyl}[4-(iminopiperidylmethyl)phenyl]carboxamide

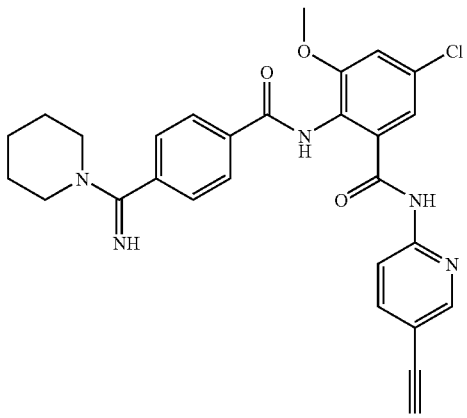

The titled compound was made by the procedure similar to that described in Example 127. MS found for $C_{28}H_{26}ClN_5O_3$ as $(M+H)^+$: 516.1.

Example 131

Ethyl 1-{[4-(N-{4-chloro-6-methoxy-2-[N-(5-ethynyl(2-pyridyl))carbamoyl]phenyl}carbamoyl)phenyl]iminomethyl}-piperidine-4-carboxylate

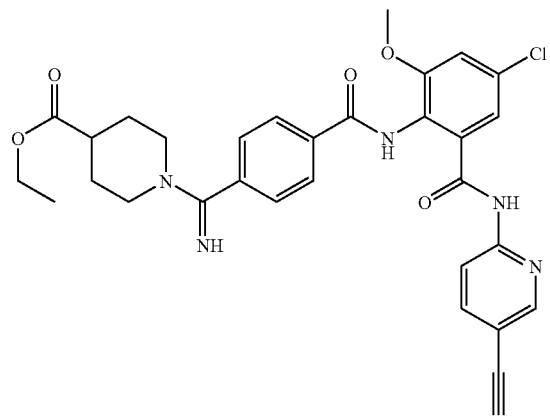

The titled compound was made by the procedure similar to that described in Example 127. MS found for $C_{31}H_{30}ClN_5O_5$ as $(M+H)^+$: 588.2.

Example 132

1-{[4-(N-{4-chloro-6-methoxy-2-[N-(5-ethynyl(2-pyridyl))carbamoyl]phenyl}carbamoyl)phenyl]iminomethyl}-piperidine-4-carboxylate Acid

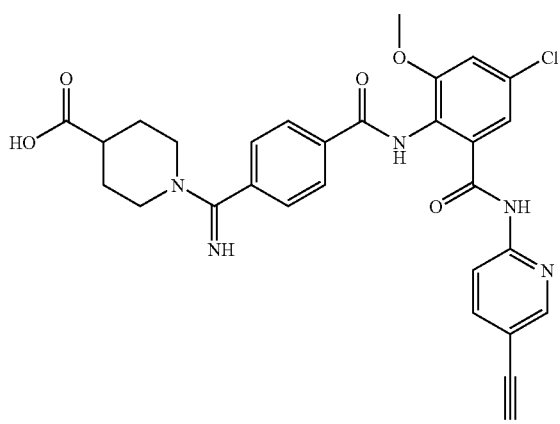

The titled compound was made by the procedure similar to that described in Example 127. MS found for $C_{29}H_{26}ClN_5O_5$ as $(M+H)^+$: 560.1

Example 133

{4-[(N-ethylmethylamino)iminomethyl]phenyl}-N-{4-chloro-6-methoxy-2-[N-(5-ethynyl(2-pyridyl))carbamoyl]phenyl}-carboxamide

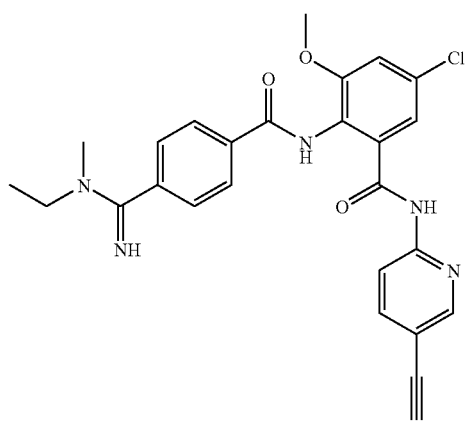

The titled compound was made by the procedure similar to that described in Example 127. MS found for $C_{26}H_{24}ClN_6O_3$ as $(M+H)^+$: 490.1

Example 134

{4-[(N-methylpropylamino)iminomethyl]phenyl}-N-{4-chloro-6-methoxy-2-[N-(5-ethynyl(2pyridyl))carbamoyl]phenyl}-carboxamide

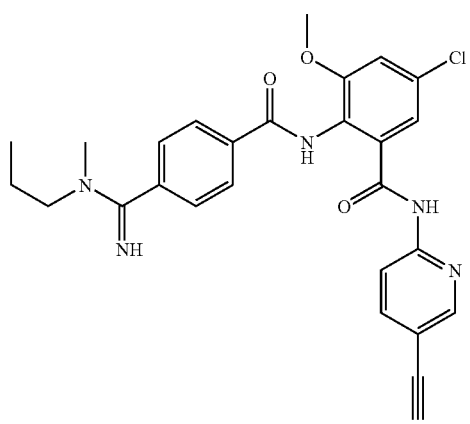

The titled compound was made by the procedure similar to that described in Example 127. MS found for $C_{27}H_{26}ClN_5O_3$ as $(M+H)^+$: 504.1.

Example 135

{4-[Azetidinylazetidinylidenemethyl]phenyl}-N-{4-chloro-6-methoxy-2-[N-(5-ethynyl (2-pyridyl))carbamoyl]phenyl}-carboxamide

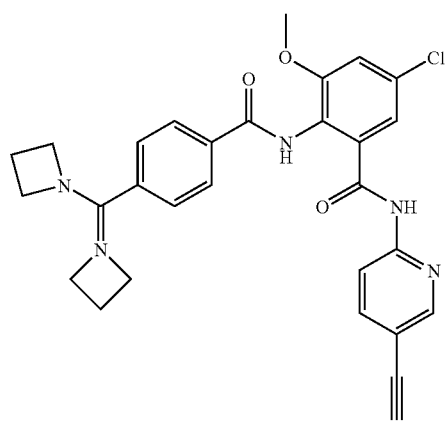

The titled compound was made by the procedure similar to that described in Example 127. MS found for $C_{29}H_{27}ClN_5O_3$ as $(M)+$: 528.1.

Example 136

1-{[4-(N-{4-chloro-6-methoxy-2-[N-(5-ethynyl(2-pyridyl))carbamoyl]phenyl}carbamoyl)phenyl]iminomethyl}-piperidine-4-carboxamide

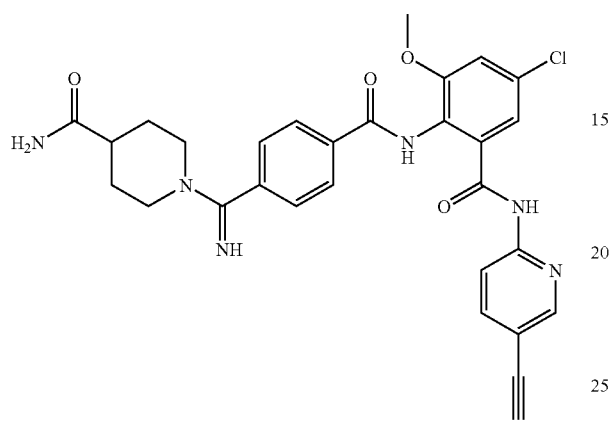

The titled compound was made by the procedure similar to that described in Example 127. MS found for $C_{29}H_{27}ClN_6O_4$ as $(M+H)^+$: 559.2.

Example 137

{4-[(dimethylamino)iminomethyl]-2-fluorophenyl}-N-{4-chloro-6-methoxy-2-[N-(5-ethynyl(2-pyridyl))carbamoyl]phenyl}-carboxamide

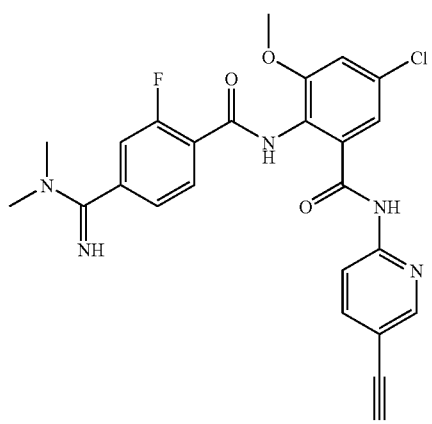

The titled compound was made by the procedure similar to that described in Example 127. MS found for $C_{25}H_{21}ClFN_5O_3$ as $(M+H)^+$: 494.1.

Example 138

N-{4-chloro-6-methoxy-2-[N-(5-ethynyl (2-pyridyl))carbamoyl]phenyl}[4-(1-methyl(2-imidazolin-2-yl))-2-fluorophenyl]-carboxamide

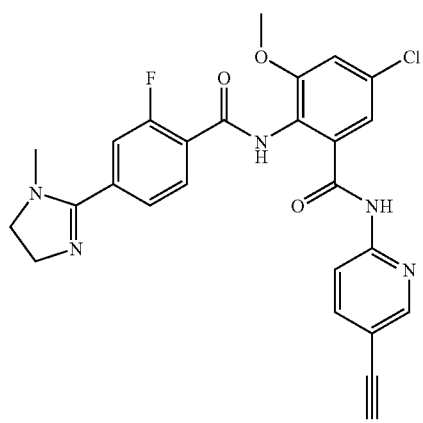

The titled compound was made by the procedure similar to that described in Example 127. MS found for $C_{26}H_{21}ClFN_5O_3$ as $(M+H)^+$: 506.1.

Example 139

N-{2-[N-(5-ethynyl(2-pyridyl))carbamoyl]-4-chloro-6-methoxyphenyl}[4-(iminopyrrolidinylmethyl)-2-fluorophenyl]carboxamide

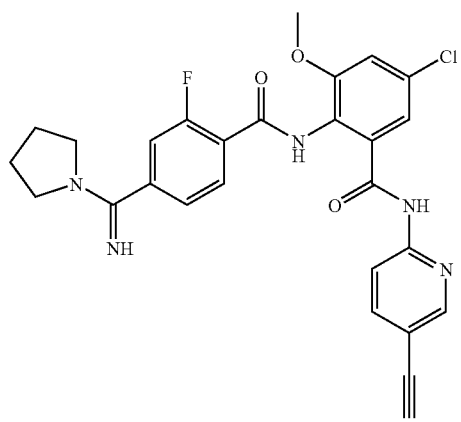

The titled compound was made by the procedure similar to that described in Example 127. MS found for $C_{27}H_{23}ClFN_5O_3$ as $(M+H)^+$: 520.1.

Example 140

N-{4-chloro-6-methoxy-2-[N-(5-ethynyl(2-pyridyl))carbamoyl]phenyl}[4-(1-methyl(2-imidazolin-2-yl))-2-fluorophenyl]-carboxamide

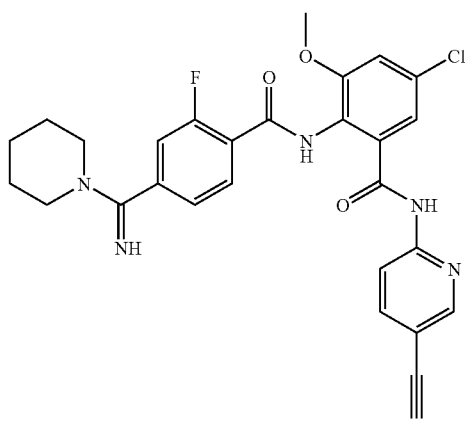

The titled compound was made by the procedure similar to that described in Example 127. MS found for $C_{28}H_{25}ClFN_5O_3$ as $(M+H)^+$: 534.1.

Example 141

Ethyl 1-{[4-(N-{4-chloro-6-methoxy-2-[N-(5-ethynyl(2-pyridyl))carbamoyl]phenyl}carbamoyl)-2-fluorophenyl]iminomethyl}-piperidine-4-carboxylate

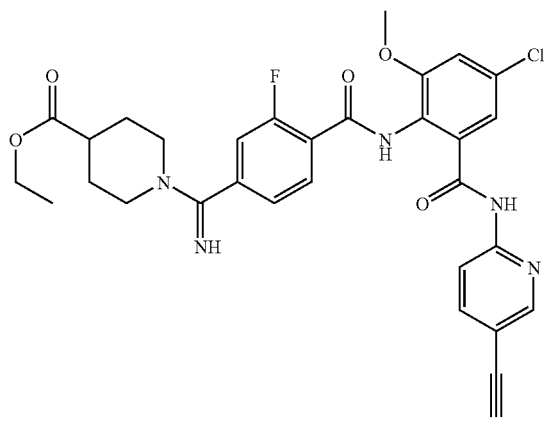

The titled compound was made by the procedure similar to that described in Example 127. MS found for $C_{31}H_{29}ClFN_5O_5$ as $(M+H)^+$: 606.2.

Example 142

1-{[4-(N-{4-chloro-6-methoxy-2-[N-(5-ethynyl(2-pyridyl))carbamoyl]phenyl}carbamoyl)-2-fluorophenyl]iminomethyl}-piperidine-4-carboxylic acid

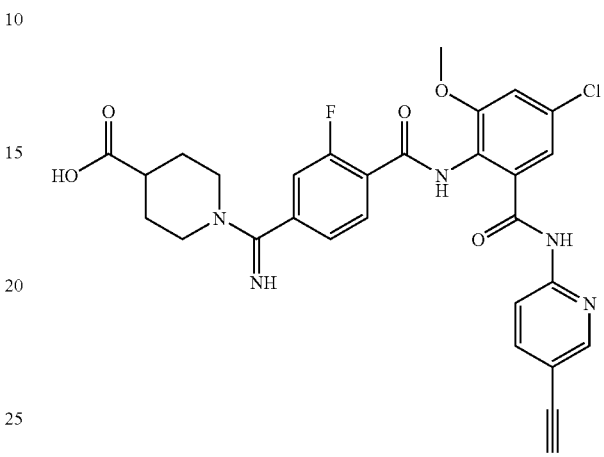

The titled compound was made by the procedure similar to that described in Example 127. MS found for $C_{29}H_{25}ClFN_5O_5$ as $(M+H)^+$: 578.1.

Example 143

{4-[azetidinyliminomethyl]-2-fluorophenyl}-N-{4-chloro-6-methoxy-2-[N-(5-ethynyl(2-pyridyl))carbamoyl]phenyl}-carboxamide

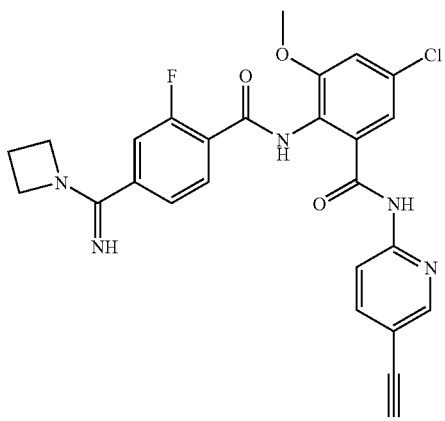

The titled compound was made by the procedure similar to that described in Example 127. MS found for $C_{26}H_{21}ClFN_5O_3$ as $(M+H)^+$: 506.1.

Example 144

{4-[Azetidinyliminomethyl]-2-fluorophenyl}-N-{4-chloro-6-methoxy-2-[N-(5-ethynyl(2-pyridyl))carbamoyl]phenyl}-carboxamide

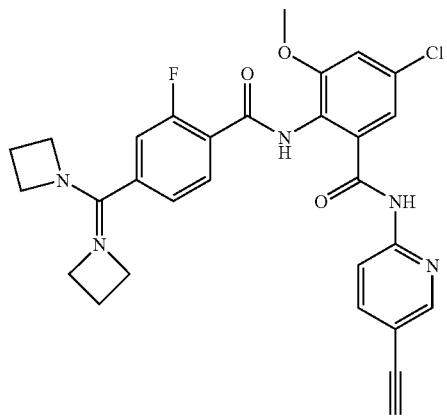

The titled compound was made by the procedure similar to that described in Example 127. MS found for $C_{29}H_{26}ClFN_5O_3$ as (M)+: 546.1.

Example 145

{4-[(N-ethylmethylamino)iminomethyl]-2-fluorophenyl}-N-{4-chloro-6-methoxy-2-[N-(5-ethynyl(2-pyridyl))carbamoyl]phenyl}-carboxamide

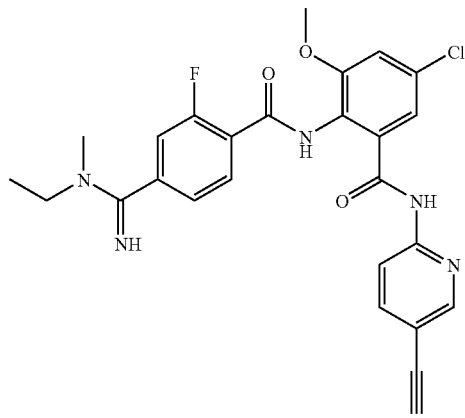

The titled compound was made by the procedure similar to that described in Example 127. MS found for $C_{26}H_{23}ClFN_5O_3$ as (M+H)$^+$: 508.2.

Example 146

{4-[(N-methylpropylamino)iminomethyl]-2-fluorophenyl}-N-{4-chloro-6-methoxy-2-[N-(5-ethynyl)2-pyridyl))carbamoyl]phenyl}-carboxamide

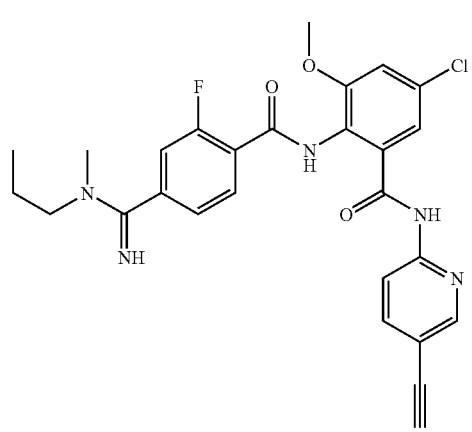

The titled compound was made by the procedure similar to that described in Example 127. MS found for $C_{27}H_{25}ClFN_5O_3$ as (M+H)$^+$: 522.1.

Example 147

[4-({[2-(dimethylamino)ethyl]methylamino}iminomethyl)-2-fluorophenyl]-N-{4-chloro-6-methoxy-2-[N-(5-ethynyl(2-pyridyl))carbamoyl]phenyl}carboxamide

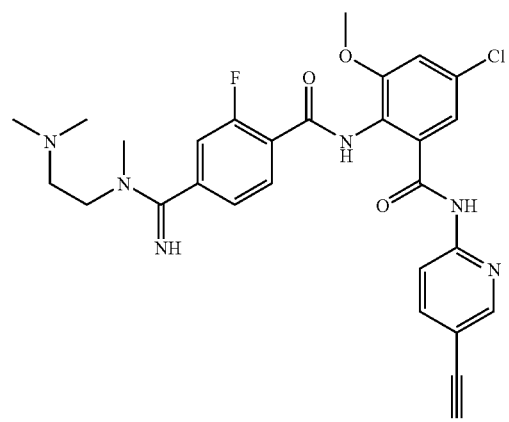

The titled compound was made by the procedure similar to that described in Example 127. MS found for $C_{28}H_{28}ClFN_6O_3$ as (M+H)$^+$: 551.3.

Example 148

1-{[4-(N-{4-chloro-6-methoxy-2-[N-(5-ethynyl(2-pyridyl))carbamoyl]-2-fluorophenyl}carbamoyl)phenyl]iminomethyl}-piperidine-4-carboxamide

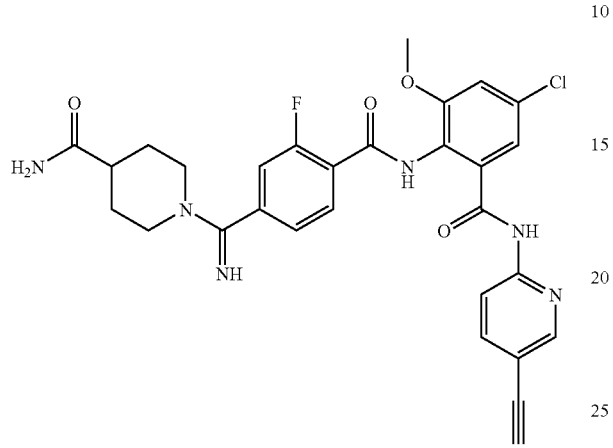

The titled compound was made by the procedure similar to that described in Example 127. MS found for $C_{29}H_{26}ClFN_6O_4$ as $(M+H)^+$: 577.1.

Example 149

{4-[(N-methyl(furanylmethyl)amino)iminomethyl]-2-fluorophenyl}-N-{4-chloro-6-methoxy-2-[N-(5-ethynyl(2-pyridyl))carbamoyl]phenyl}-carboxamide

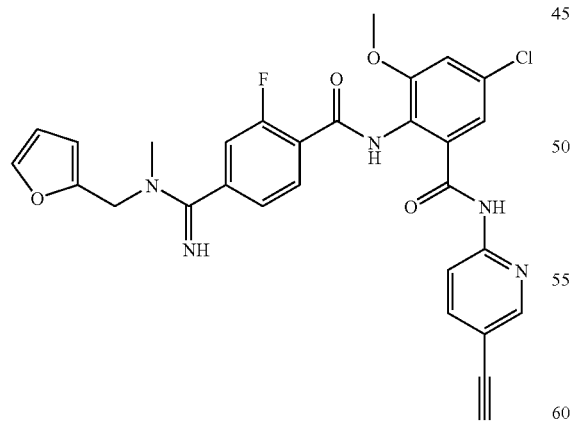

The titled compound was made by the procedure similar to that described in Example 127. MS found for $C_{29}H_{23}ClFN_5O_4$ as $(M+H)^+$: 560.0.

Example 150

{4-[(dimethylamino)iminomethyl]phenyl}-N-{2-[N-(5-ethynyl(2-pyridyl))carbamoyl]phenyl}-carboxamide

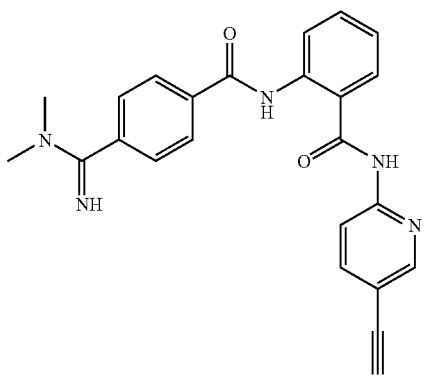

The titled compound was made by the procedure similar to that described in Example 103. MS found for $C_{24}H_{21}N_5O_2$ as $(M+H)^+$: 412.1.

Example 151

N-{2-[N-(5-ethynyl(2-pyridyl))carbamoyl]phenyl}[4-(1-methyl(2-imidazolin-2-yl))phenyl]-carboxamide

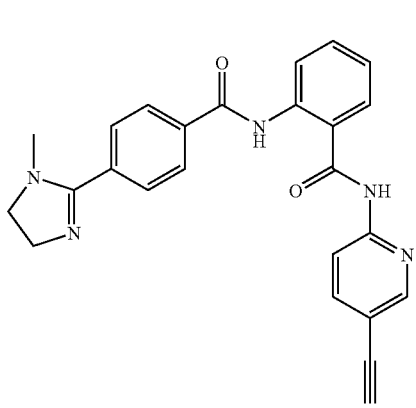

The titled compound was made by the procedure similar to that described in Example 103. MS found for $C_{25}H_{21}N_5O_2$ as $(M+H)$: 424.1.

Example 152

N-{2-[N-(5-ethynyl(2-pyridyl))carbamoyl]}[4-(iminopyrrolidinylmethyl)phenyl]carboxamide

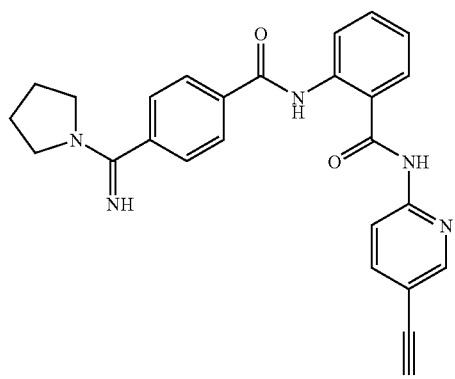

The titled compound was made by the procedure similar to that described in Example 103. MS found for $C_{26}H_{23}N_5O_2$ as $(M+H)^+$: 438.2.

Example 153

N-{2-[N-(5-ethynyl(2-pyridyl))carbamoyl]}[4-(iminopiperidylmethyl)phenyl]carboxamide

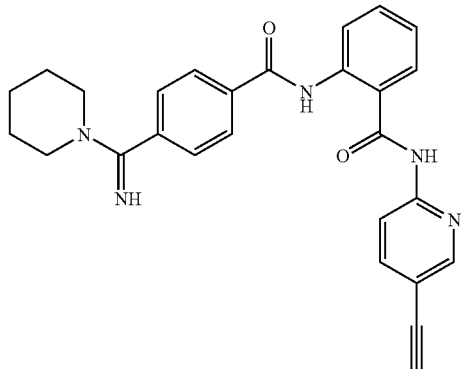

The titled compound was made by the procedure similar to that described in Example 103. MS found for $C_{27}H_{25}N_5O_2$ as $(M+H)^+$: 452.2.

Example 154

Ethyl 1-{[4-(N-{2-[N-(5-ethynyl(2-pyridyl))carbamoyl]phenyl}carbamoyl)phenyl]iminomethyl}-piperidine-4-carboxylate

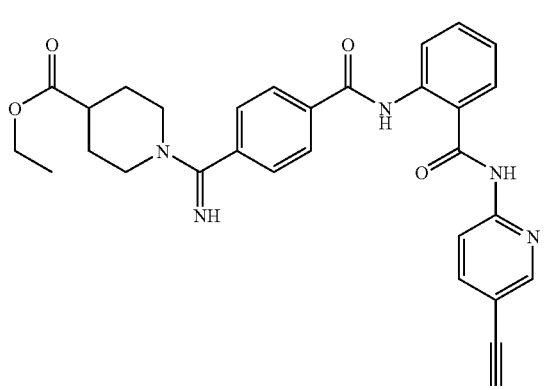

The titled compound was made by the procedure similar to that described in Example 103. MS found for $C_{30}H_{29}N_5O_4$ as $(M+H)^+$: 524.2.

Example 155

N-{4-chloro-2-[N-(5-ethynyl(2-pyridyl))carbamoyl]phenyl}[4-(1-propyl(2-imidazolin-2-yl))phenyl]-carboxamide

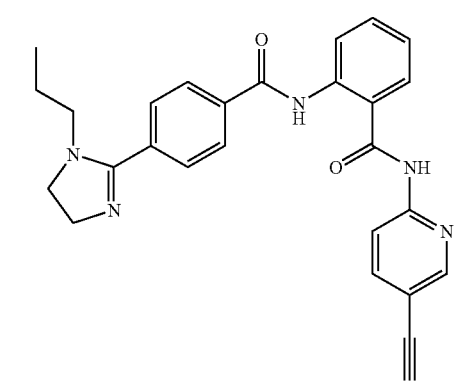

The titled compound was made by the procedure similar to that described in Example 103. MS found for $C_{27}H_{25}N_5O_2$ as $(M+H)^+$: 452.2.

Example 156

N-{4-chloro-2-[N-(5-ethynyl(2-pyridyl))carbamoyl]phenyl}[4-(1-(2-hydroxy)ethyl(2-imidazolin-2-yl))phenyl]-carboxamide

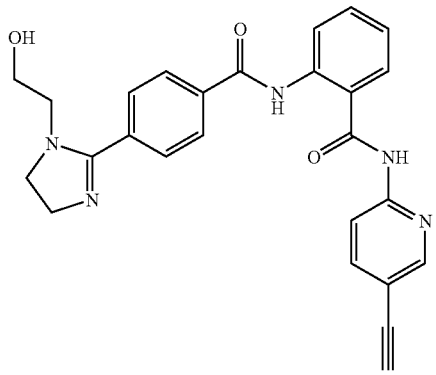

The titled compound was made by the procedure similar to that described in Example 103. MS found for $C_{26}H_{23}N_5O_3$ as $(M+H)^+$: 454.1.

Example 157

{4-[(dimethylamino)iminomethyl]phenyl}-N-{2-[N-(5-(1-propynyl)(2-pyridyl))carbamoyl]phenyl}-carboxamide

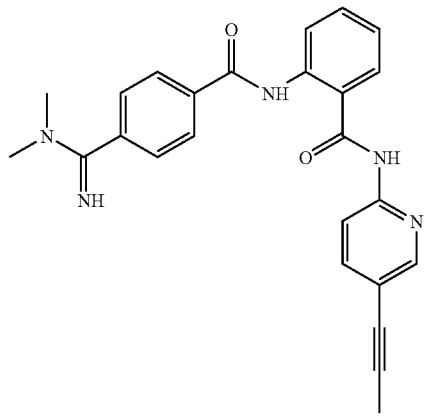

The titled compound was made by the procedure similar to that described in Example 103. MS found for $C_{25}H_{23}N_5O_2$ as $(M+H)^+$: 426.2.

Example 158

N-{2-[N-(5-(1-propynyl)(2-pyridyl))carbamoyl]phenyl}[4-(1-methyl(2-imidazolin-2-yl))phenyl]-carboxamide

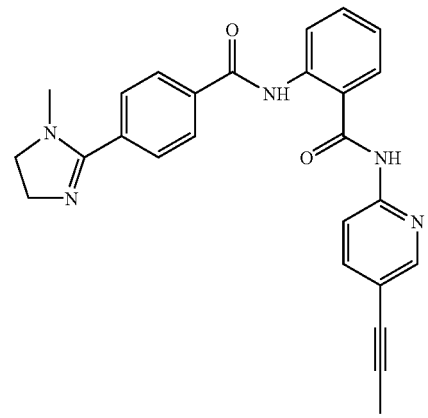

The titled compound was made by the procedure similar to that described in Example 103. MS found for $C_{26}H_{23}N_5O_2$ as $(M+H)^+$: 438.1.

Example 159

N-{2-[N-(5-(11-propynyl)(2-pyridyl)) carbamoyl]}[4-(iminopyrrolidinylmethyl)phenyl]carboxamide

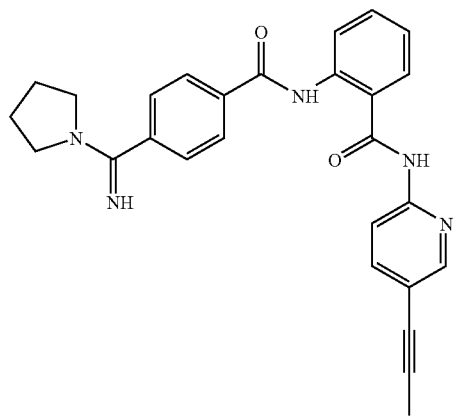

The titled compound was made by the procedure similar to that described in Example 103. MS found for $C_{28}H_{28}N_4O_2$ as $(M+H)^+$: 0.452.2.

Example 160

N-{2-[N-(5-(1-propynyl)(2-pyridyl))carbamoyl]}[4-(iminopiperidylmethyl)phenyl]carboxamide

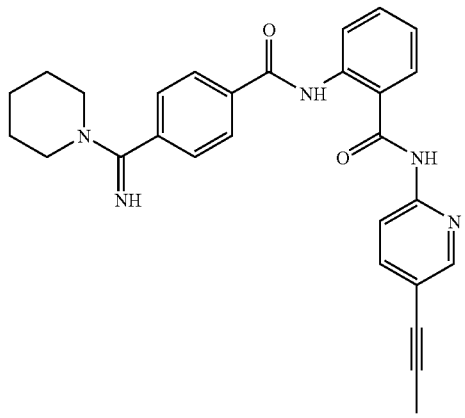

The titled compound was made by the procedure similar to that described in Example 103. MS found for $C_{29}H_{28}N_4O_2$ as $(M+H)^+$: 466.2.

Example 161

Ethyl 1-{[4-(N-{2-[N-(5-(1-propynyl)(2-pyridyl))carbamoyl]phenyl}carbamoyl)phenyl]iminomethyl}-piperidine-4-carboxylate

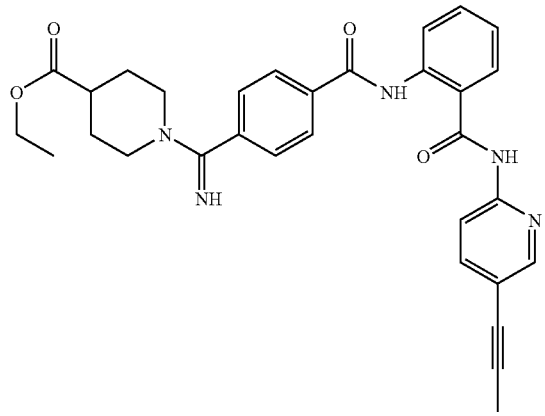

The titled compound was made by the procedure similar to that described in Example 103. MS found for $C_{32}H_{32}N_4O_4$ as $(M+H)^+$: 538.2.

Example 162

{4-[(N-methyl(furanylmethyl)amino)iminomethyl]phenyl}-N-{2-[N-(5-(1-propynyl)(2-pyridyl))carbamoyl]phenyl}-carboxamide

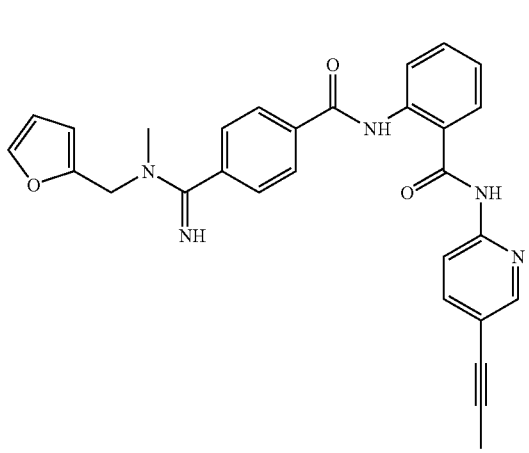

The titled compound was made by the procedure similar to that described in Example 103. MS found for $C_{30}H_{26}N_4O_3$ as $(M+H)^+$: 492.2.

Example 163

N-{2-[N-(5-(propynyl)(2-pyridyl))carbamoyl]phenyl}[4-(1-propyl(2-imidazolin-2-yl))phenyl]-carboxamide

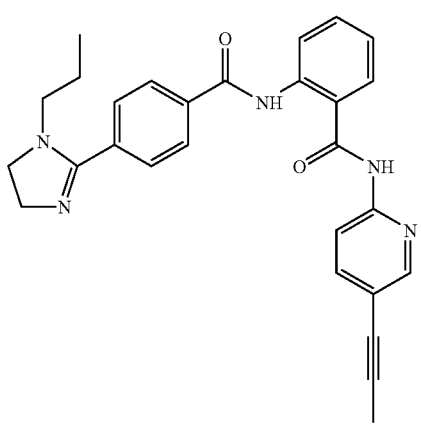

The titled compound was made by the procedure similar to that described in Example 103. MS found for $C_{29}H_{28}N_4O_2$ as $(M+H)^+$: 466.2.

Example 164

N-{2-[N-(5-(propynyl)(2-pyridyl))carbamoyl]phenyl}[4-(1-(2-hydroxyethyl)(2-imidazolin-2-yl))phenyl]-carboxamide

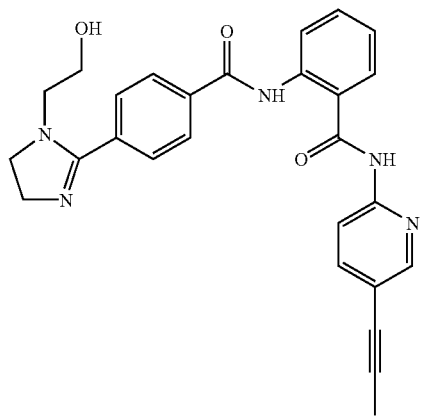

The titled compound was made by the procedure similar to that described in Example 103. MS found for $C_{28}H_{26}N_4O_3$ as $(M+H)^+$: 468.2.

Example 165

{4-[(dimethylamino)iminomethyl]phenyl}-N-{4-chloro-2-[N-(4-ethynylphenyl)carbamoyl]phenyl}-carboxamide

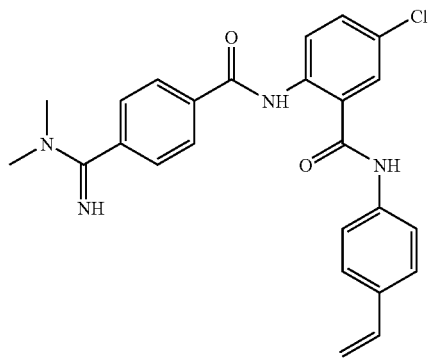

The titled compound was made by the procedure similar to that described in Example 79.
MS found for $C_{25}H_{23}ClN_4O_2$ as $(M+H)^+$: 447.2.

Example 166

N-{4-chloro-2-[N-(4-ethenylphenyl)carbamoyl]phenyl}[4-(1-methyl(2-imidazolin-2-yl))phenyl]-carboxamide

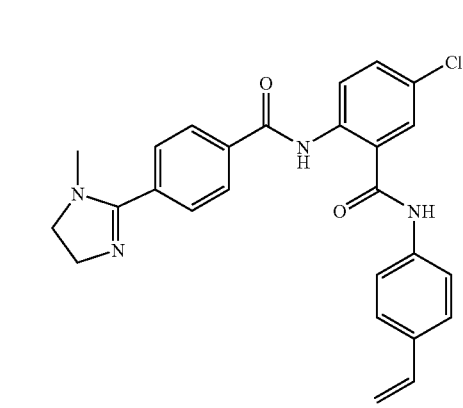

The titled compound was made by the procedure similar to that described in Example 79.
MS found for $C_{26}H_{23}ClN_4O_2$ as $(M+H)^+$: 459.2.

Example 167

N-{2-[N-(4-ethenylphenylcarbamoyl]-4-chlorophenyl}[4-(iminopyrrolidinylmethyl)phenyl]carboxamide

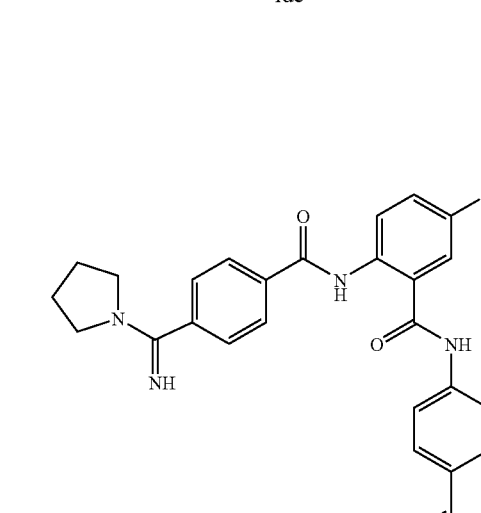

The titled compound was made by the procedure similar to that described in Example 79.
MS found for $C_{27}H_{25}ClN_4O_2$ as $(M+H)^+$: 473.2.

221

Example 168

N-{2-[N-(4-ethenylphenyl)carbamoyl]-4-chlorophenyl}[4-(iminopiperidylmethyl)phenyl]carboxamide

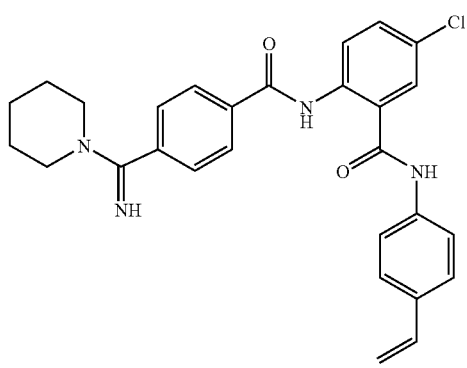

The titled compound was made by the procedure similar to that described in Example 79.
MS found for $C_{28}H_{27}ClN_4O_2$ as (M+H)$^+$: 487.2.

Example 169

Ethyl 1-{[4-(N-{4-chloro-2-[N-(4-ethenylphenyl)carbamoyl)phenyl]iminomethyl}-piperidine-4-carboxylate

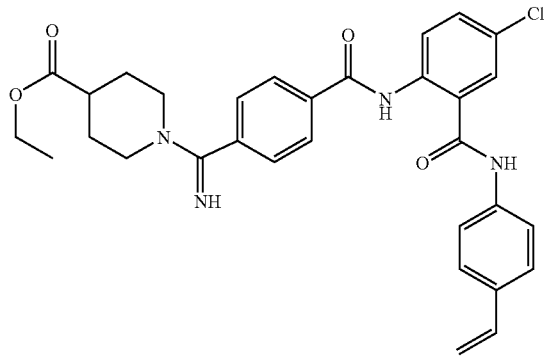

The titled compound was made by the procedure similar to that described in Example 79.
MS found for $C_{31}H_{31}ClN_4O_4$ as (M+H)$^+$: 559.2.

222

Example 170

{4-[(N-ethylmethylamino)iminomethyl]phenyl}N-{4-chloro-2-[N-(4-ethenylphenyl)carbamoyl]phenyl}-carboxamide

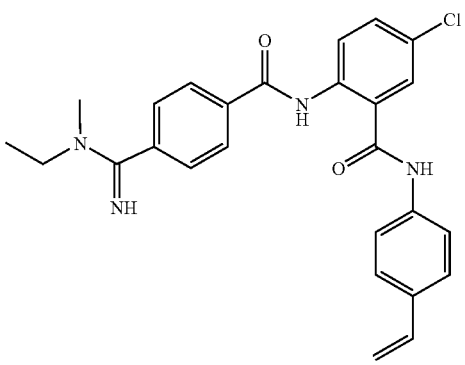

The titled compound was made by the procedure similar to that described in Example 79.
MS found for $C_{26}H_{25}ClN_4O_2$ as (M+H)$^+$: 461.2.

Example 171

{4-[(N-methylpropylamino)iminomethyl]phenyl}-N-{4-chloro-2-[N-(4-ethenylphenyl)carbamoyl]phenyl}-carboxamide

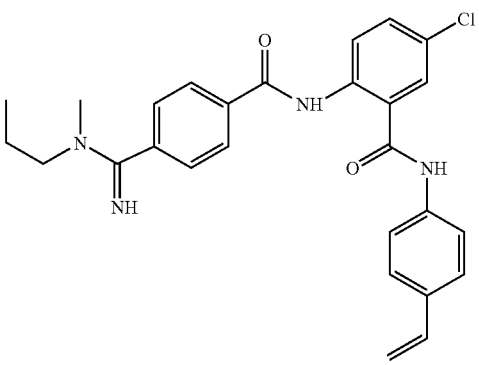

The titled compound was made by the procedure similar to that described in Example 79.
MS found for $C_{27}H_{27}ClN_4O_2$ as (M+H)$^+$: 475.2.

Example 172

[4-({[2-(dimethylamino)ethyl]methylamino}iminomethyl)phenyl]-N-{4-chloro-2-[N-(4-ethenylphenyl)carbamoyl]phenyl}carboxamide

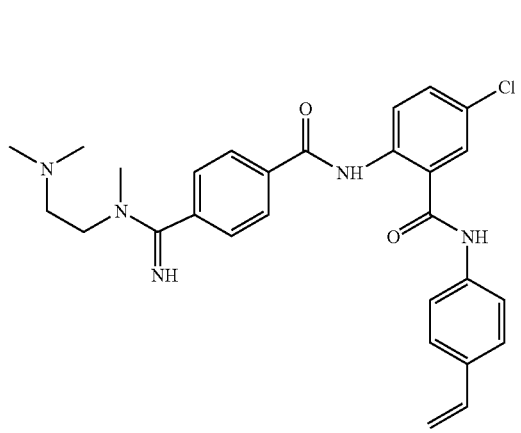

The titled compound was made by the procedure similar to that described in Example 79.
MS found for $C_{28}H_{30}ClN_5O_2$ as $(M+H)^+$: 504.2.

Example 173

1-{[4-(N-{4-chloro-2-[N-(4-ethenylphenyl)carbamoyl)phenyl]iminomethyl}-piperidine-4-carboxamide

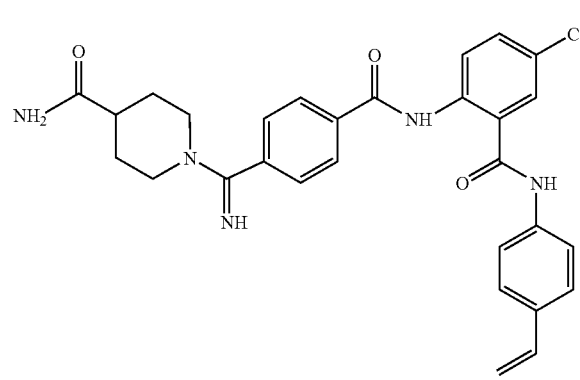

The titled compound was made by the procedure similar to that described in Example 79.
MS found for $C_{29}H_{28}ClN_5O_3$ as $(M+H)^+$: 530.2.

Example 174

[4-({[2-(methoxy)ethyl]methylamino}iminomethyl)phenyl]-N-{4-chloro-2-[N-(4-ethenylphenyl)carbamoyl]phenyl}carboxamide

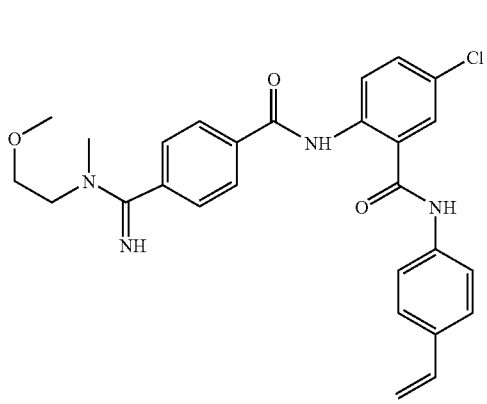

The titled compound was made by the procedure similar to that described in Example 79.
MS found for $C_{27}H_{27}ClN_4O_3$ as $(M+H)^+$: 491.2.

Example 175

{4-[(N-methyl-2-propynylamino)iminomethyl]phenyl}-N-{4-chloro-2-[N-(4-ethenylphenyl)carbamoyl]phenyl}-carboxamide

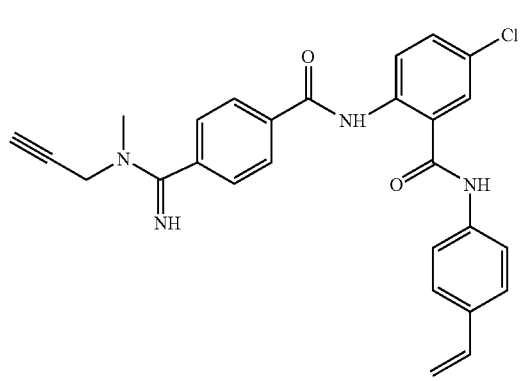

The titled compound was made by the procedure similar to that described in Example 79.
MS found for $C_{27}H_{23}ClN_4O_2$ as $(M+H)^+$: 471.2.

Example 176

{4-[Azetidinylazetidinylidenemethyl]phenyl}-N-{4-chloro-2-[N-(4-ethenylphenyl)carbamoyl]phenyl}-carboxamide

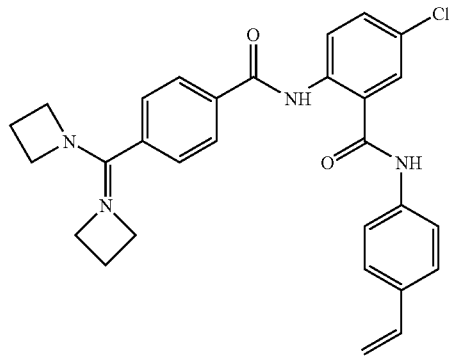

The titled compound was made by the procedure similar to that described in Example 79.

MS found for $C_{29}H_{28}ClN_4O_2$ as (M)+: 499.2.

Example 177

{4-[(N-methyl(furanylmethyl)amino)iminomethyl]phenyl}-N-{4-chloro-2-[N-(4-ethenylphenyl)carbamoyl]phenyl}-carboxamide

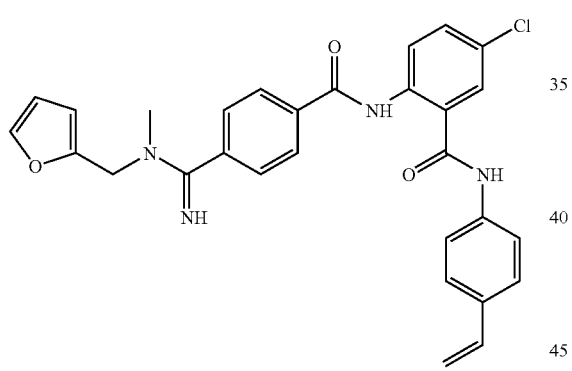

The titled compound was made by the procedure similar to that described in Example 79.

MS found for $C_{29}H_{25}ClN_4O_3$ as (M+H)+: 513.2.

Scheme 8:

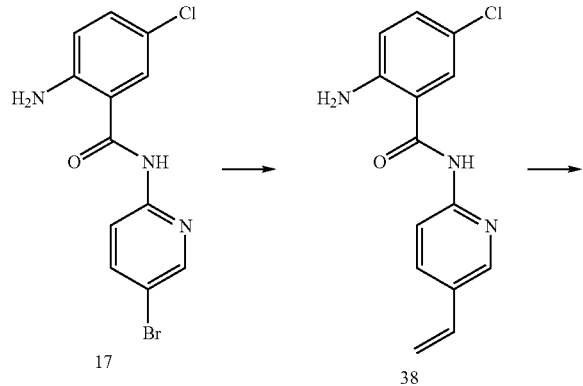

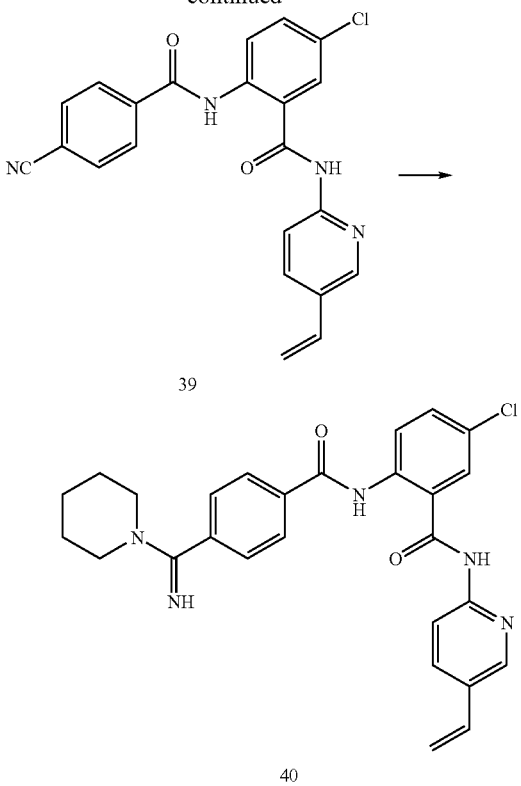

Example 178

N-{2-[N-(5-ethenyl(2-pyridyl))carbamoyl]-4-chlorophenyl}[4-(iminopiperidylmethyl)phenyl]carboxamide

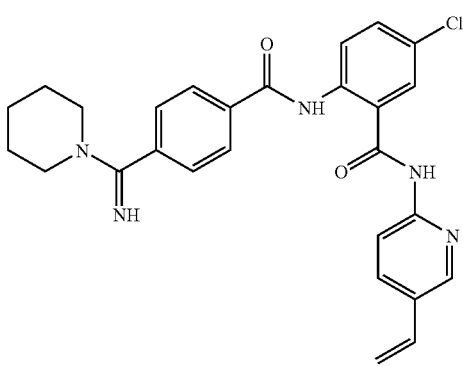

Step 1:

Bromide 17 (1.00 g, 3.07 mmol) was diluted with toluene (10 mL) then degassed with argon for 5 min. Then, it was treated with tributyl vinyl tin (0.99 mL, 3.38 mmol) and tetrakis(triphenylphosphine)Pd(0) (0.32 g, 0.31 mmol) and stirred at 80° C. overnight. The following day the reaction diluted with aqueous potassium fluoride and ethyl acetate, separated, and the aqueous phase extracted with ethyl acetate again. The combined organic layers were dried over magnesium sulfate, then concentrated and purified by filtration through a plug of silica gel eluted with dichloromethane affording, after concentration, a quantitative amount of the desired alkene as a light yellow solid contaminated with a small amount of tin byproducts. $^1$H NMR (DMSO-d$_6$, 400 MHz): δ 10.12 (s, 1H), 7.64 (m, 3H), 7.39 (d, 2H), 7.20 (m, 1H), 6.75 (m, 1H), 6.67 (m, 1H), 6.44 (s, 2H), 5.72 (d, 1H), 5.18 (d, 1H).

Step 2:

From compound 38, following a procedure similar to that described in Step 3, Example 79, the titled compound 39 was prepared. $^1$H NMR (DMSO-d$_6$, 400 MHz): δ 11.23 (m, 2H), 8.40 (s, 1H), 8.12-7.90 (m, 7H), 7.89 (s, 1H), 7.64 (m, 1H), 6.73 (m, 1H), 5.90 (d, 1H), 5.30 (d, 1H).

Step 3:

From compound 40, following a procedure similar to that described in Step 5, Example 79, the titled compound 41 was prepared. MS found for C$_{27}$H$_{26}$ClN$_5$O$_2$ as (M+H)$^+$: 488.2.

Example 179

Ethyl 1-{[4-(N-{4-chloro-2-[N-(5-ethenyl(2-pyridyl))carbamoyl]phenyl}carbamoyl)phenyl]iminomethyl}-piperidine-4-carboxylate

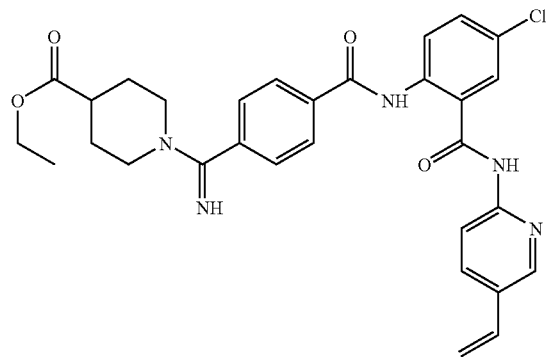

The titled compound was made by the procedure similar to that described in Example 178. MS found for C$_{30}$H$_{30}$ClN$_5$O$_4$ as (M+H)$^+$: 560.2.

Example 180

{4-[(N-ethylmethylamino)iminomethyl]phenyl}-N-{4-chloro-2-[N-(5-ethenyl(2-pyridyl))carbamoyl]phenyl}-carboxamide

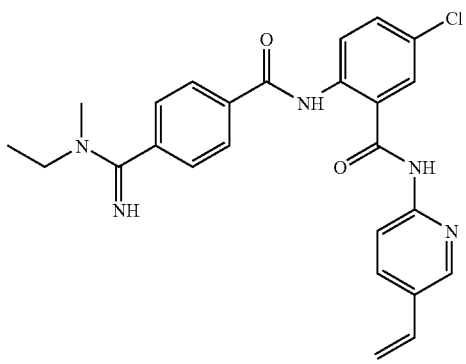

The titled compound was made by the procedure similar to that described in Example 178. MS found for C$_{25}$H$_{24}$ClN$_5$O$_2$ as (M+H)$^+$: 462.2.

Example 181

{4-[(N-methyl(furanylmethyl)amino)iminomethyl]phenyl}-N-{4-chloro-2-[N-(5-ethenyl(2-pyridyl))carbamoyl]phenyl}-carboxamide

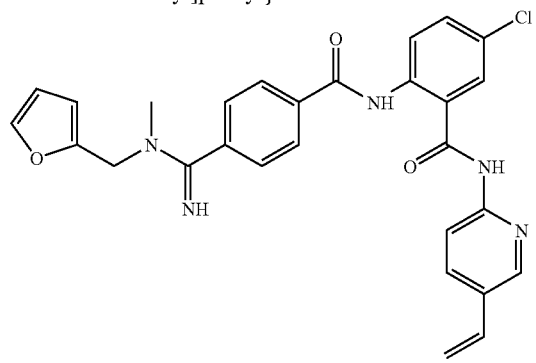

The titled compound was made by the procedure similar to that described in Example 178. MS found for C$_{28}$H$_{24}$ClN$_5$O$_3$ as (M+H)$^+$: 514.2.

Example 182

[4-({[2-methoxyethyl]methylamino}iminomethyl)phenyl]-N-{4-chloro-2-[N-(5-ethenyl(2-pyridyl))carbamoyl]phenyl}carboxamide

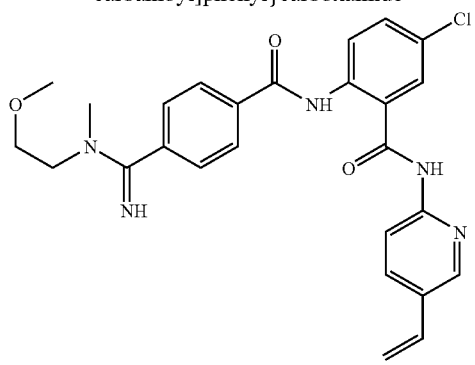

The titled compound was made by the procedure similar to that described in Example 178. MS found for C$_{26}$H$_{26}$ClN$_5$O$_3$ as (M+H)$^+$: 492.2.

Example 183

{4-[(N-methylpropylamino)iminomethyl]phenyl}-N-{4-chloro-2-[N-(5-ethenyl(2-pyridyl))carbamoyl]phenyl}-carboxamide

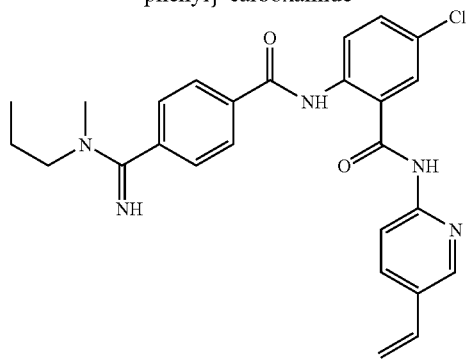

The titled compound was made by the procedure similar to that described in Example 178. MS found for C$_{26}$H$_{26}$ClN$_5$O$_2$ as (M+H)$^+$: 476.2.

Scheme 9

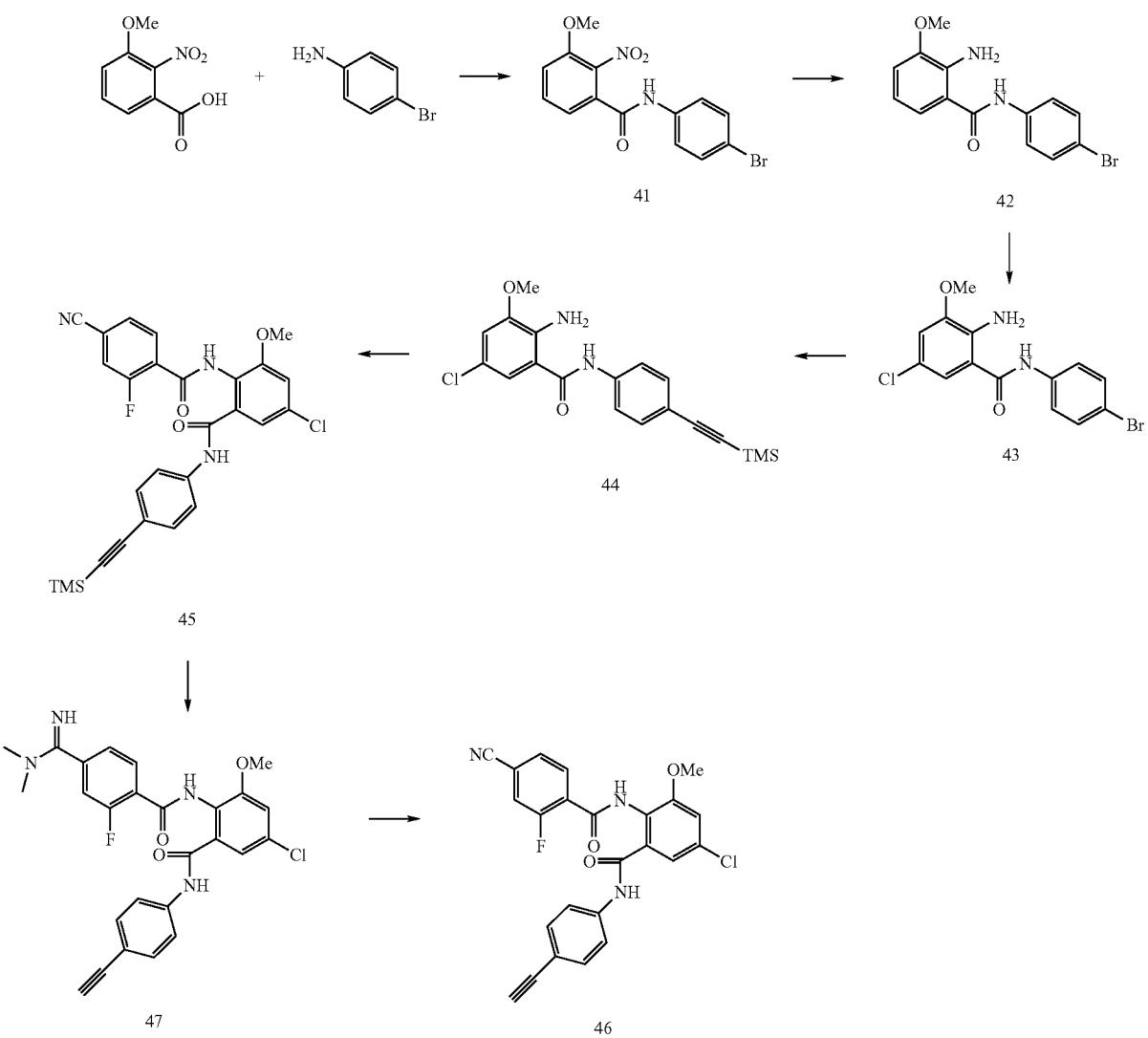

Example 184

{4-[(dimethylamino)iminomethyl]-2-fluorophenyl}-N-{4-chloro-2-[N-(4-ethynylphenyl)carbamoyl]-6-methoxyphenyl}carboxamide

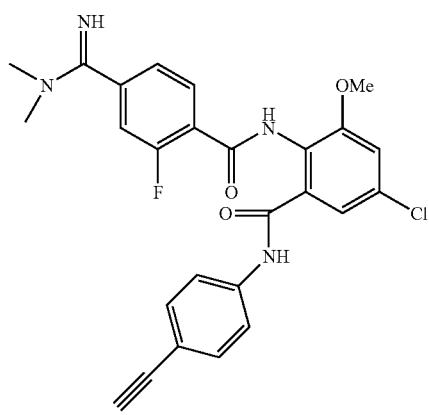

Step 1:

To a stirring solution of 4-bromoaniline (4.3 g, 25 mmol) and 3-methoxy-2-nitro-benzoic acid (5.0 g, 25 mmol) in anhydrous THF (20 mL) and pyridine (9.4 mL, 100 mmol) at 0° C. was added $POCl_3$ (7.65 g, 50 mmol) dropwise. The mixture was stirred at 0° C. for 20 min. Water (400 mL) was added and precipitate formed. The solid was collected by filtration, washed with water and dried to give compound 41 as a light brown solid (8.5 g, 97%). MS found for $C_{14}H_{11}BrN_2O_4$ as $(M+Na)^+$: 373.1.

Step 2:

To a solution of compound 41 (8.1 g, 23 mmol) in 1,4-dioxane (40 mL) and THF (40 mL) at 50° C. was added an aqueous solution of $Na_2S_2O_4$ (24 g, 174 mmol in 80 mL water). The mixture was stirred at 50° C. overnight. The two layers were separated. To the organic layer was added water and precipitate formed. The solid was collected by filtration and washed with water. After dried in vacco, 4.1 g of compound 42 was obtained as a yellow solid in 55% yield. MS found for $C_{14}H_{13}BrN_2O_2$ as $(M+Na)^+$: 343.0.

Step 3:

To a solution of compound 42 (2.8 g, 8.7 mmol) in toluene (50 mL) at 70° C. was added N-chlorosuccinimide (1.2 g, 9.0 mmol) in portions. The mixture was stirred at 70° C.-75° C. for 20 min, cooled down and washed with sat. NaHCO$_3$, sat. NaCl, dried and evaporated to give 3.5 g of the crude compound 43 as a dark brown solid. MS found for C$_{14}$H$_{12}$BrClN$_2$O$_2$ as (M+Na)$^+$: 377.0.

Step 4:

To a solution of compound 43 (3.5 g, 10 mmol) in BuNH$_2$ (15 mL) was added tetrakis(triphenylphosphine)Pd(0) (231 mg, 0.2 mmol), CuI (57 mg, 0.3 mmol) and (trimethylsilyl)acetylene (1.47 g, 15 mmol). The mixture was stirred under reflux for 2 h and cooled down to rt. The mixture was concentrated and purified by silica gel chromatography (eluted with 20% EtOAc in Hexane) to give 2.4 g of compound 44 in 65% yield. MS found for C$_{19}$H$_{21}$ClN$_2$$_{12}$Si as (M+H)$^+$: 373.1.

Step 5:

To a solution compound 44 (1.0 g, 2.7 mmol) in THF (20 mL) was added 4-cyano-2-fluoro-bezoyl chloride (512 mg, 2.8 mmol, prepared according to Step 4, Example 33). The mixture was stirred for 1 h. Water (100 mL) was added. The resulted precipitate was collected by filtration and dried to give compound 45 (1.2 g, 91% yield). MS found for C$_{27}$H$_{23}$ClFN$_3$O$_3$Si as (M+Na)$^+$: 542.0.

Step 6:

To a solution of compound 45 (1.0 g, 1.9 mmol) in THF (20 mL) was added tetrabutylammonium fluoride (1N solution in THF, 2.7 mL). The mixture was stirred for 1 h. Water (100 mL) was added. The resulted precipitate was collected by filtration and dried to give 930 mg of compound 46. MS found for C$_{24}$H$_{15}$ClFN$_3$O$_3$ as (M+Na)$^+$: 470.0.

Step 7:

From compound 46, following the procedure similar to that described in Step 4, Example 1, the titled compound 47 was prepared. MS found for C$_{26}$H$_{22}$ClFN$_4$O$_3$ as (M+H)$^+$: 493.1.

Example 185

N-{4-chloro-2-[N-(4-ethynylphenyl)carbamoyl]-6-methoxyphenyl}[2-fluoro-4-(1-methyl(2-imidazolin-2-yl))phenyl]carboxamide

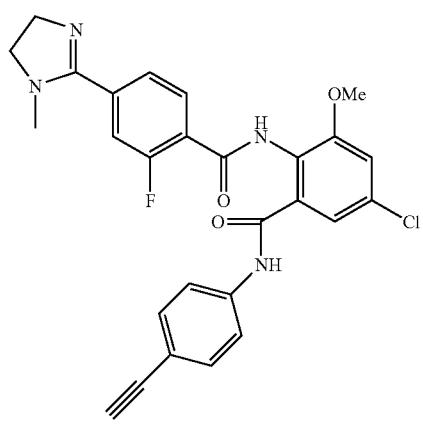

The titled compound was made by the procedure similar to that described in example 184. MS found for C$_{27}$H$_{22}$ClFN$_4$O$_3$ as (M+H)$^+$: 505.1.

Example 186

Ethyl 1-{[4-(N-{4-chloro-2-[N-(4-ethynylphenyl)carbamoyl]-6-methoxyphenyl}carbamoyl)-3-fluorophenyl]iminomethyl}piperidine-4-carboxylate

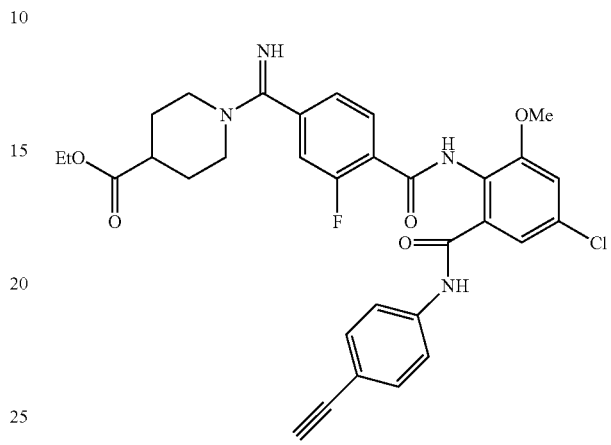

The titled compound was made by the procedure similar to that described in example 184. MS found for C$_{32}$H$_{30}$ClFN$_4$O$_5$ as (M+H)$^+$: 605.2.

Example 187

Methyl 1-{[4-(N-{4-chloro-2-[N-(4-ethynylphenyl)carbamoyl]-6-methoxyphenyl}carbamoyl)-3-fluorophenyl]iminomethyl}piperidine-4-carboxylate

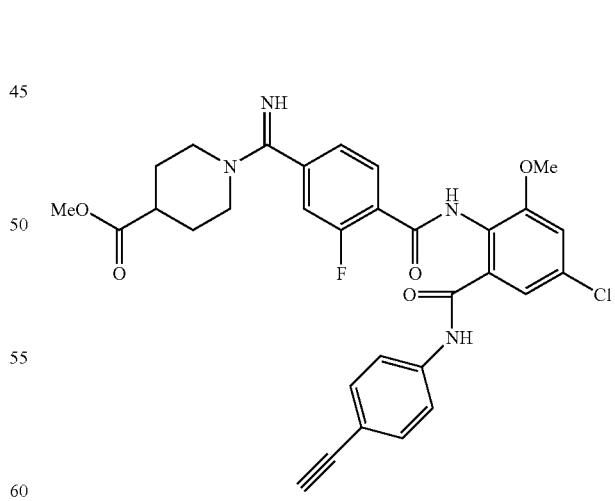

The titled compound was made by the procedure similar to that described in example 184. MS found for C$_{31}$H$_{28}$ClFN$_4$O$_5$ as (M+H)$^+$: 591.2.

Example 188

1-{[4-(N-4-chloro-2-[N-(4-ethynylphenyl)carbamoyl]-6-methoxyphenylcarbamoyl)-3-fluorophenyl]iminomethyl}piperidine-4-carboxylic Acid

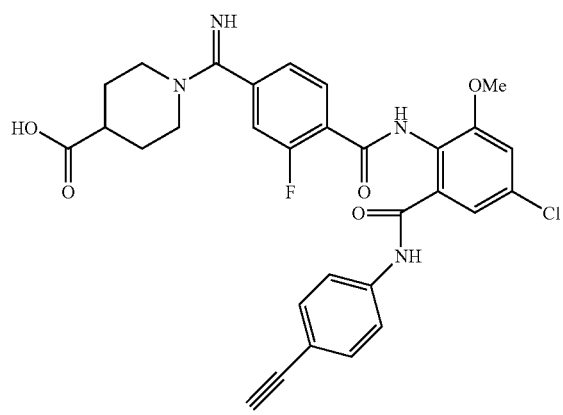

The titled compound was made by the procedure similar to that described in example 184. MS found for $C_{30}H_{26}ClFN_4O_5$ as $(M+H)^+$: 577.2.

Example 189

1-{[4-(N-(4-chloro-2-[N-(4-ethynylphenyl)carbamoyl]-6-methoxyphenylcarbamoyl)-3-fluorophenyl]iminomethyl}piperidine-4-carboxamide

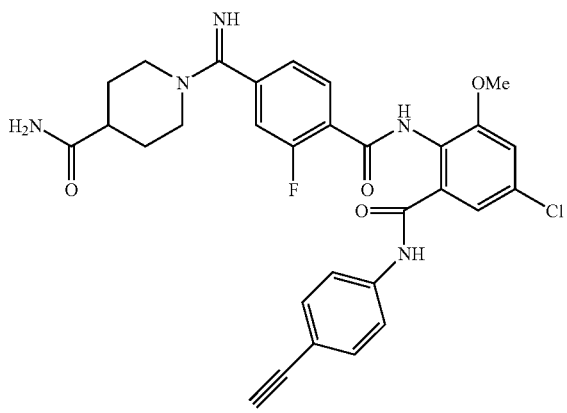

The titled compound was made by the procedure similar to that described in example 184. MS found for $C_{30}H_{27}ClFN_5O_4$ as $(M+H)^+$: 576.2.

Example 190

N-{4-chloro-2-[N-(4-ethynylphenyl)carbamoyl]-6-methoxyphenyl}(2-fluoro-4-{[4-(hydroxymethyl)piperidyl]iminomethyl}phenyl)carboxamide

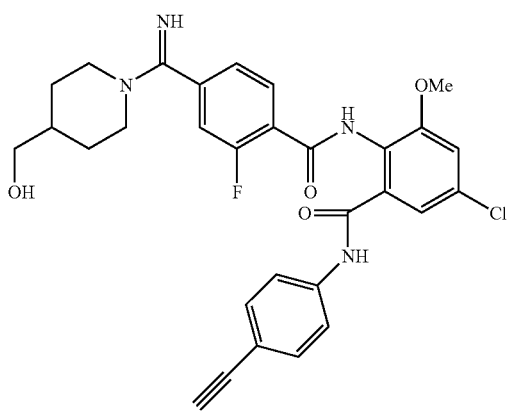

The titled compound was made by the procedure similar to that described in example 184. MS found for $C_{30}H_{28}ClFN_4O_4$ as $(M+H)^+$: 563.2.

Example 191

[4-({[2-(dimethylamino)ethyl]methylamino}iminomethyl)-2-fluorophenyl]-N-{4-chloro-2-[N-(4-ethynylphenyl)carbamoyl]-6-methoxyphenyl}carboxamide

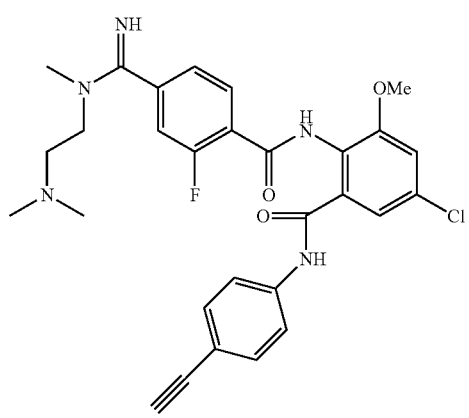

The titled compound was made by the procedure similar to that described in example 184. MS found for $C_{29}H_{29}ClFN_5O_3$ as $(M+H)^+$: 550.2.

Example 192

N-{4-chloro-2-[N-(4-ethynylphenyl)carbamoyl]-6-methoxyphenyl}{4-[(ethylmethylamino)iminomethyl]-2-fluorophenyl}carboxamide

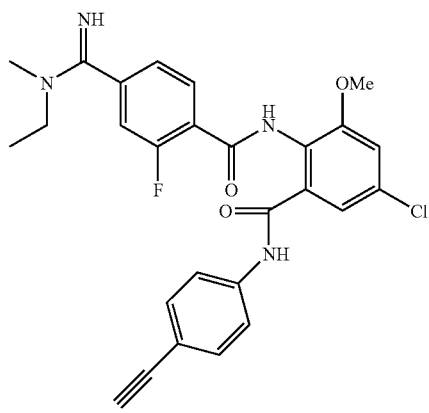

The titled compound was made by the procedure similar to that described in example 184. MS found for $C_{27}H_{24}ClFN_4O_3$ as $(M+H)^+$: 507.1.

Example 193

[4-({[3-(dimethylamino)propyl]methylamino}iminomethyl)-2-fluorophenyl-N-{4-chloro-2-[N-(4-ethynylphenyl)carbamoyl]-6-methoxyphenyl}carboxamide

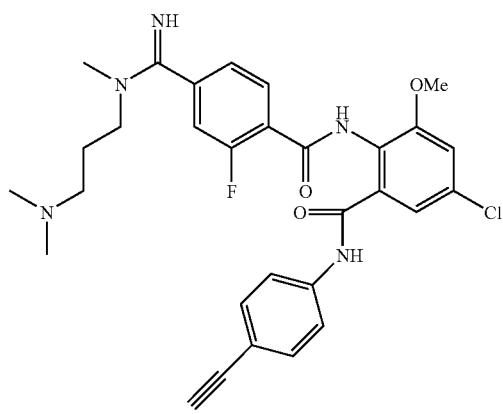

The titled compound was made by the procedure similar to that described in example 184. MS found for $C_{30}H_{31}ClFN_5O_3$ as $(M+H)^+$: 564.2.

Example 194

N-{4-chloro-2-[N-(4-ethynylphenyl)carbamoyl]-6-methoxyphenyl}[2-fluoro-4-(iminopiperidylmethyl)phenyl]carboxamide

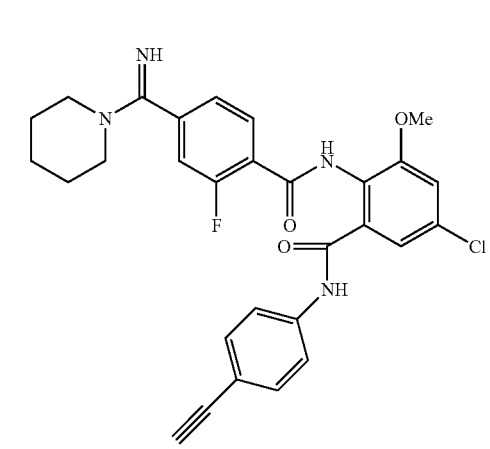

The titled compound was made by the procedure similar to that described in example 184. MS found for $C_{29}H_{26}ClFN_4O_3$ as $(M+H)^+$: 533.2.

Example 195

N-{4-chloro-2-[N-(4-ethynylphenyl)carbamoyl]-6-methoxyphenyl}[4-(azetidinyliminomethyl)-2-fluorophenyl)phenyl]carboxamide

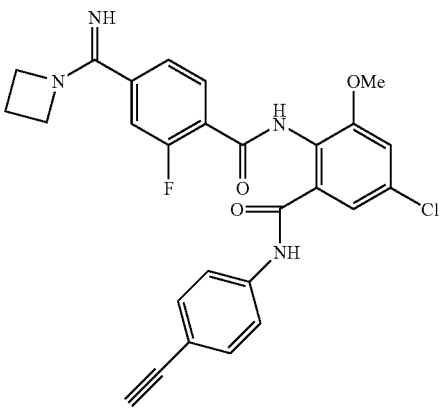

The titled compound was made by the procedure similar to that described in example 184. MS found for $C_{27}H_{22}ClFN_4O_3$ as $(M+H)^+$: 505.1.

Example 196

N-{4-chloro-2-[N-(4-ethynylphenyl)carbamoyl]-6-methoxyphenyl}[4-(azetidinylazetidinylidenem-ethyl)-2-fluorophenyl]carboxamide

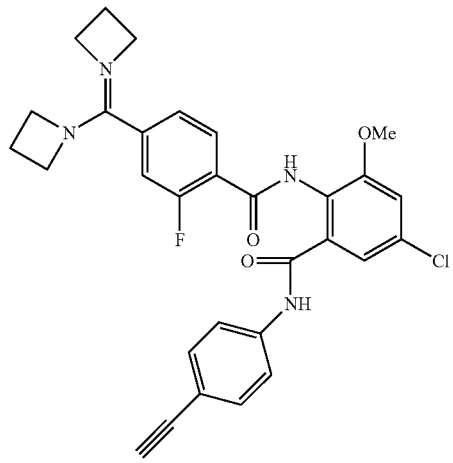

The titled compound was made by the procedure similar to that described in example 184. MS found for $C_{30}H_{27}ClFN_4O_3$ as $M^+$: 545.2.

Example 197

N-{4-chloro-2-[N-(4-ethynylphenyl)carbamoyl]-6-methoxyphenyl}[4-(1-methyl(2-imidazolin-2-yl))phenyl]-carboxamide

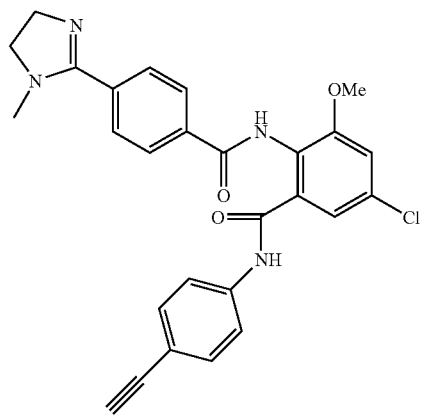

The titled compound was made by the procedure similar to that described in example 184. MS found for $C_{27}H_{23}ClN_4O_3$ $(M+H)^+$: 487.1.

Example 198

Ethyl 1-{[4-(N-{4-chloro-2-[N-(4-ethynylphenyl)carbamoyl]-6-methoxyphenyl}carbamoyl)phenyl]iminomethyl}-piperidine-4-carboxylate

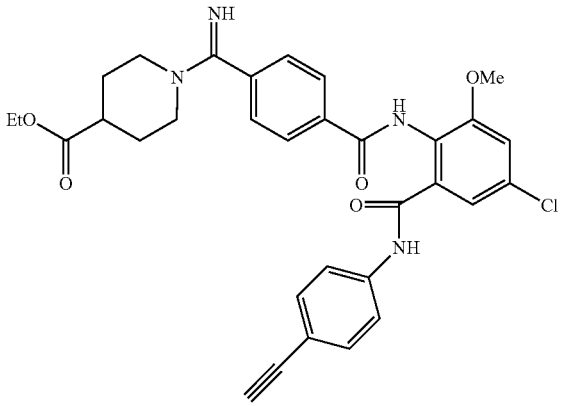

The titled compound was made by the procedure similar to that described in example 184. MS found for $C_{32}H_{31}ClN_4O_5$ as $(M+H)^+$: 587.2.

Example 199

Methyl 1-{[4-(N-{4-chloro-2-[N-(4-ethynylphenyl)carbamoyl]-6-methoxyphenyl}carbamoyl)phenyl]iminomethyl}-piperidine-4-carboxylate

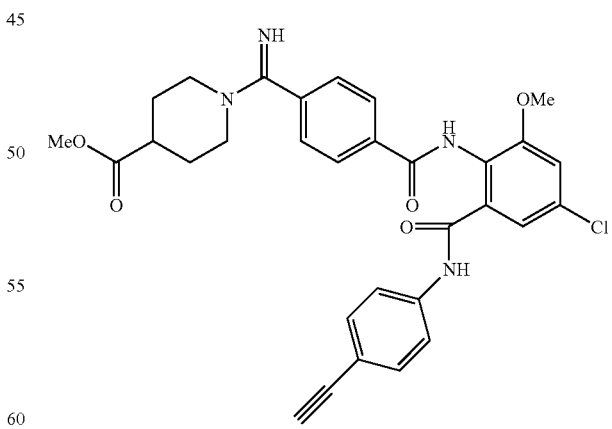

The titled compound was made by the procedure similar to that described in example 184. MS found for $C_{31}H_{29}ClN_4O_5$ as $(M+H)^+$: 573.2.

Example 200

1-{[4-(N-{4-chloro-2-[N-(4-ethynylphenyl)carbamoyl]-6-methoxyphenyl}carbamoyl)phenyl]iminomethyl}-piperidine-4-carboxylic acid

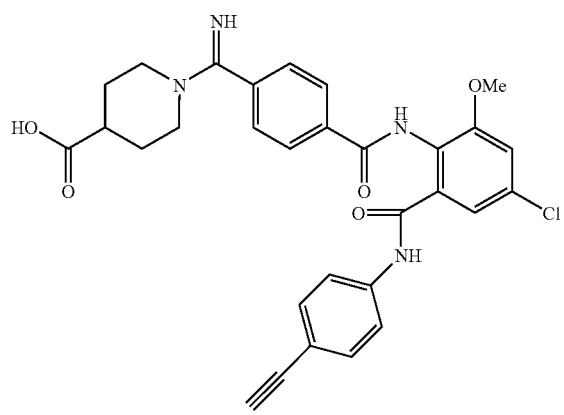

The titled compound was made by the procedure similar to that described in example 4.

MS found for $C_{30}H_{27}ClN_4O_5$ as $(M+H)^+$: 559.2.

Example 201

{4-[(dimethylamino)iminomethyl]phenyl}-N-{4-chloro-2-[N-(4-ethynylphenyl)carbamoyl]-6methoxyphenyl}carboxamide

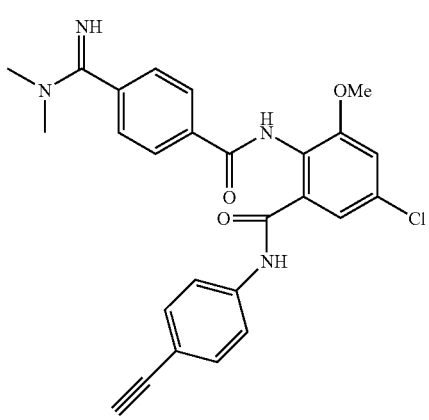

The titled compound was made by the procedure similar to that described in example 184. MS found for $C_{26}H_{23}ClN_4O_3$ as $(M+H)^+$: 475.1.

Example 202

N-{4-chloro-2-[N-(4-ethynylphenyl)carbamoyl]-6-methoxyphenyl}{4-[(ethylmethylamino)iminomethyl]phenyl}carboxamide

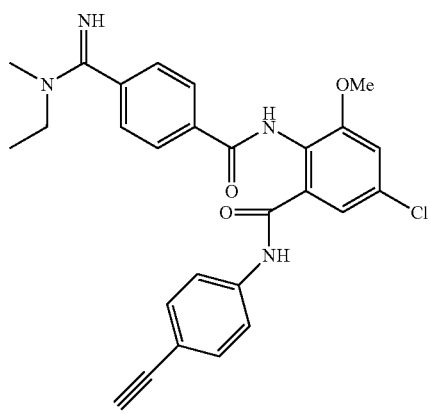

The titled compound was made by the procedure similar to that described in example 184. MS found for $C_{27}H_{25}ClN_4O_3$ as $(M+H)^+$: 489.1.

Example 203

[4-({[2-(dimethylamino)ethyl]methylamino}iminomethyl)phenyl]-N-{4-chloro-2-[N-(4-ethynylphenyl)carbamoyl]-6-methoxyphenyl}carboxamide

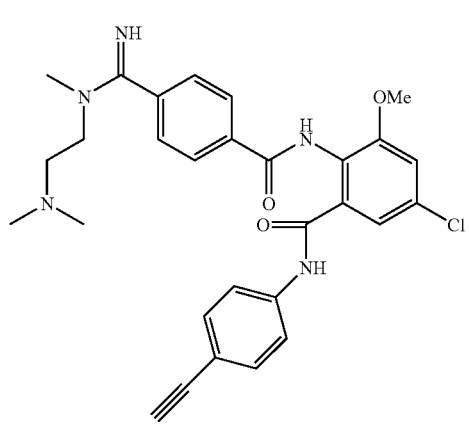

The titled compound was made by the procedure similar to that described in example 184. MS found for $C_{29}H_{30}ClN_5O_3$ as $(M+H)^+$: 532.2.

Example 204

[4-({[3-(dimethylamino)propyl]methylamino}iminomethyl)phenyl]-N-{4-chloro-2-[N-(4-ethynylphenyl)carbamoyl]-6-methoxyphenyl}carboxamide

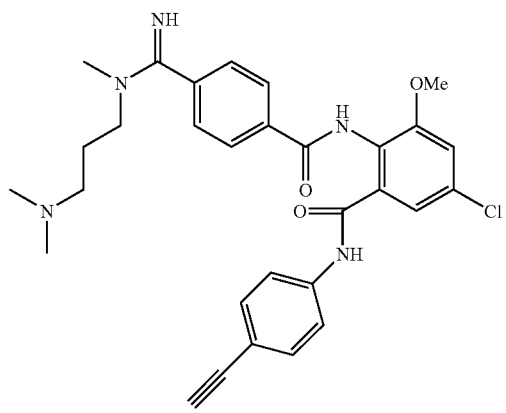

The titled compound was made by the procedure similar to that described in example 184. MS found for $C_{30}H_{32}ClN_5O_3$ as $(M+H)^+$: 546.2.

Example 205

N-{4-chloro-2-[N-(4-ethynylphenyl)carbamoyl]-6-methoxyphenyl}[4-(iminopiperidylmethyl)phenyl]carboxamide

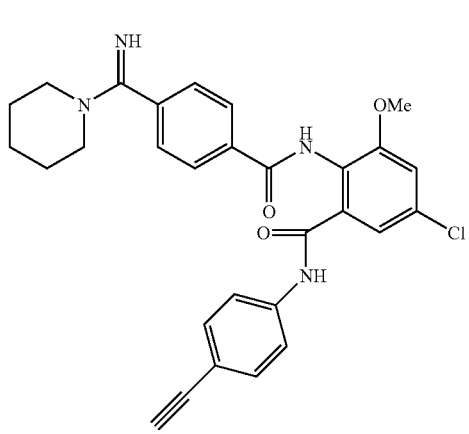

The titled compound was made by the procedure similar to that described in example 184. MS found for $C_{29}H_{27}ClN_4O_3$ as $(M+H)^+$: 515.2.

Example 206

N-{4-chloro-2-[N-(4-ethynylphenyl)carbamoyl]-6-methoxyphenyl}[4-(azetidinyliminomethyl)phenyl)phenyl]carboxamide

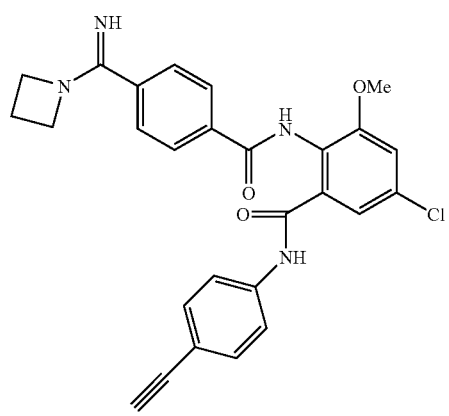

The titled compound was made by the procedure similar to that described in example 184. MS found for $C_{27}H_{23}ClN_4O_3$ as $(M+H)^+$: 487.1.

Example 207

N-{4-chloro-2-[N-(4-ethynylphenyl)carbamoyl]-6-methoxyphenyl}[4-(azetidinylazetidinylidenemethyl)phenyl]carboxamide

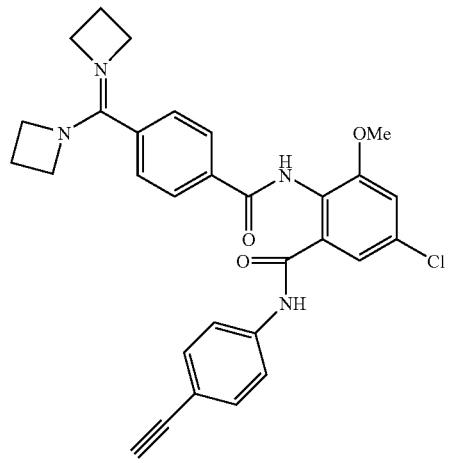

The titled compound was made by the procedure similar to that described in example 184. MS found for $C_{30}H_{28}ClN_4O_3$ as $M^+$: 527.2.

Scheme 10

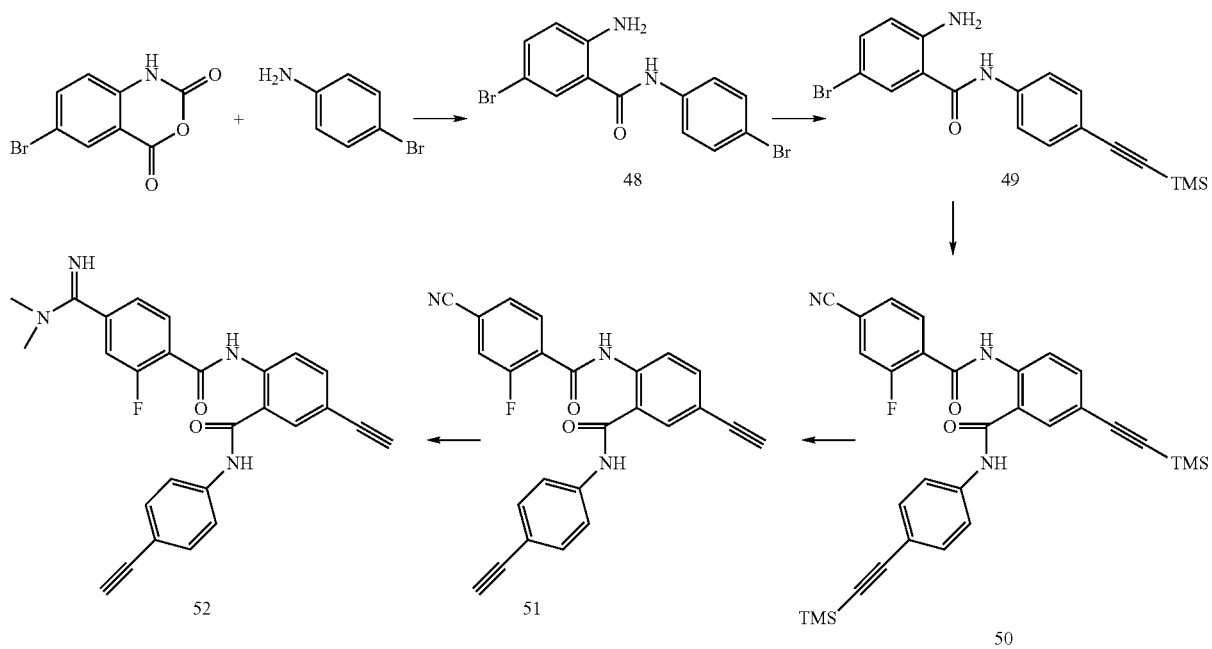

Example 208

{4-[(dimethylamino)iminomethyl]-2-fluorophenyl}-N-{4-ethynyl-2-[N-(4-ethynylphenyl)carbamoyl]phenyl}carboxamide (52)

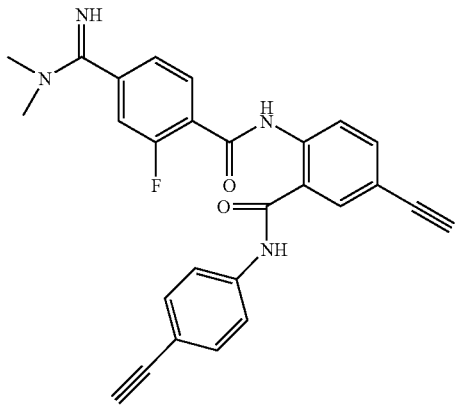

Step 1:

To a solution of 4-bromoaniline (3.4 g, 20 mmol) in anhydrous THF (40 mL) at −78° C. was added Lithium bis(trimethylsilyl)amide (1 N solution in THF, 42 mL) via a double ended needle. The mixture was stirred at −78° C. for 30 min. To this solution, a suspension of 5-bromoisatoic anhydride (4.84 g, 20 mmol) in anhydrous THF (30 mL) was added via a double ended needle. The mixture was stirred at −78° C. for 20 min and then warmed up to rt and stirred overnight. The reaction was quenched with sat. NH$_4$Cl (100 mL). The organic layer was diluted with EtOAc, washed with sat. NH$_4$Cl, sat. NaCl, dried and evaporated to give compound 48 as an offwhite solid (7.1 g, 97%).

Step 2:

To a solution of compound 48 (3.67 g, 10 mmol) in BuNH$_2$ (15 mL) was added tetrakis(triphenylphosphine)Pd (0) (460 mg, 0.4 mmol), CuI (114 mg, 0.6 mmol) and (trimethylsilyl)acetylene (3.27 mL, 30 mmol). The mixture was stirred under reflux for 3 h and cooled down to rt. The mixture was concentrated and purified by silica gel chromatography (eluted with 20% EtOAc in Hexane) to give 1.2 g of compound 49 in 30% yield. $^1$H NMR (DMSO-d$_6$, 400 MHz): δ 10.218 (s, 1H), 7.72-7.69 (m, 3H), 7.39-7.37 (d, 2H), 7.24-7.21 (dd, 1H), 6.7 (s, 2H), 6.69-6.67 (d, 1H), 0.19 (s, 9H), 0.17 (s 9H). MS found for C$_{23}$H$_{28}$N$_2$OSi$_2$ as (M+H)$^+$: 405.2.

Step 3:

To a solution compound 49 (610 mg, 1.5 mmol) in THF (20 mL) was added 4-cyano-2-fluoro-bezoyl chloride (304 mg, 1.7 mmol, prepared according to Step 4, Example 33). The mixture was stirred for 1 h before it was concentrated. The residue was dissolved in EtOAc, washed with sat. NaCl, dried and evaporated to give compound 50 (810 mg, 97% yield). MS found for C$_{31}$H$_{30}$FN$_3$O$_2$Si$_2$ as (M+Na)$^+$: 574.2.

Step 4:

To a solution of compound 50 (800 mg, 1.47 mmol) in THF (20 mL) was added tetrabutylammonium fluoride (1 N solution in THF, 1.5 mL). The mixture was stirred for 1 h. The mixture was concentrated. The residue was dissolved in EtOAc, washed with sat. NaCl and dried. The organic solution was concentrated and during which time precipitate formed. The solid was collected by filtration to give compound 51 (430 mg, 73%). MS found for C$_{25}$H$_{14}$FN$_3$O$_2$ as (M+Na)$^+$: 430.0.

Step 5:

From compound 51, following the procedure similar to that described in Step 4, Example 1, the titled compound 52 was prepared. $^1$H NMR (DMSO-d$_6$, 400 MHz): δ 11.43 (d, 1H), 10.74 (s, 1H), 9.40 (s, 1H), 9.06 (s, 1H), 8.37, (d, 1H), 8.01 (t, 1H), 7.96 (d, 1H), 7.43-7.67 (m, 4H), 7.56-7.54 (d, 1H), 7.45-7.43 (d, 2H), 4.31 (s, 1H), 4.12 (s, 1H), 3.18 (s, 3H), 2.95 (s, 3H). MS found for C$_{27}$H$_{21}$FN$_4$O$_2$ as (M+H)$^+$: 453.1.

Example 209

N-{4-ethynyl-2-[N-(4-ethynylphenyl)carbamoyl]phenyl}[2-fluoro-4-(1-methyl(2-imidazolin-2-yl))phenyl]carboxamide

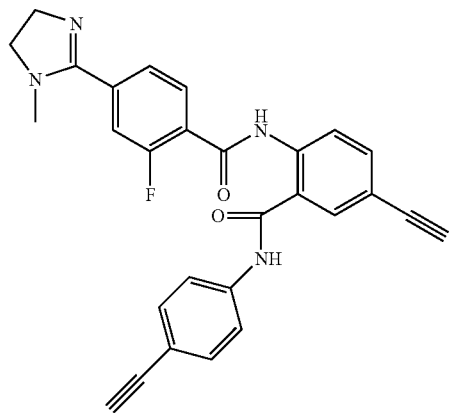

The titled compound was made by the procedure similar to that described in example 208. MS found for $C_{28}H_{21}FN_4O_2$ as $(M+H)^+$: 565.1.

Example 210

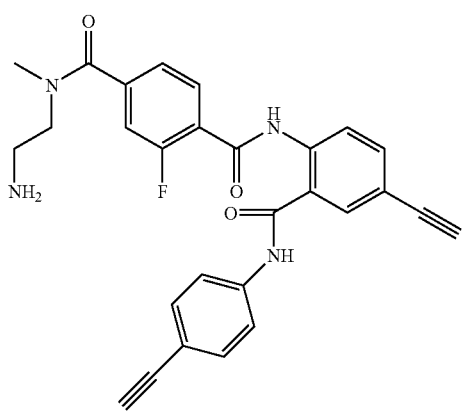

The titled compound was obtained from the preparation of the compound in example 209.
MS found for $C_{28}H_{23}FN_4O_3$ as $(M+H)^+$: 583.1.

Example 211

Ethyl 1-{[4-(N-{4-ethynyl-2-[N-(4-ethynylphenyl)carbamoyl]phenyl}carbamoyl)-3-fluorophenyl]iminomethyl}piperidine-4-carboxylate

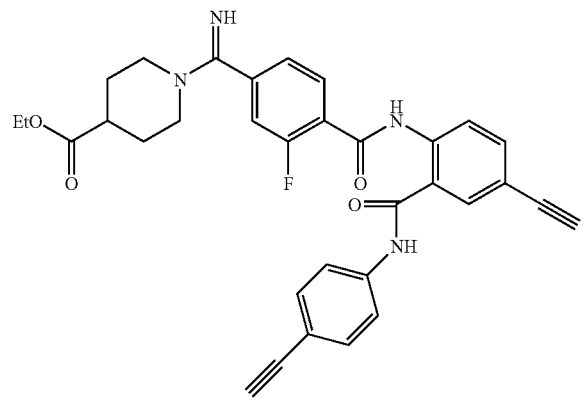

The titled compound was made by the procedure similar to that described in example 208. MS found for $C_{33}H_{29}FN_4O_4$ as $(M+H)^+$: 565.2.

Example 212

Methyl 1-{[4-(N-{4-ethynyl-2-[N-(4-ethynylphenyl)carbamoyl]phenyl}carbamoyl)-3-fluorophenyl]iminomethyl}piperidine-4-carboxylate

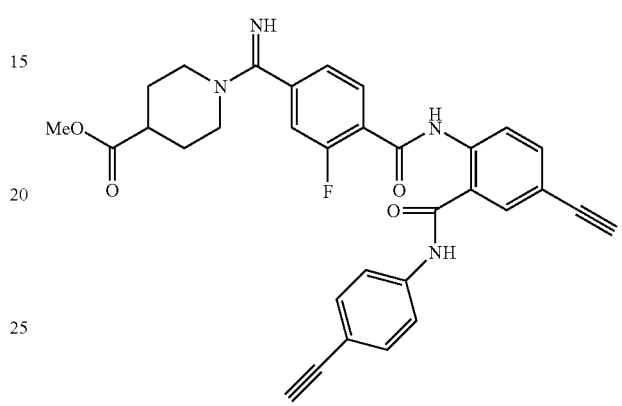

The titled compound was made by the procedure similar to that described in example 208. MS found for $C_{32}H_{29}FN_4O_4$ as $(M+H)^+$: 551.2.

Example 213

1-{[4-(N-{4-ethynyl-2-[N-(4-ethynylphenyl)carbamoyl]phenyl}carbamoyl)-3-fluorophenyl]iminomethyl}piperidine-4-carboxylic acid

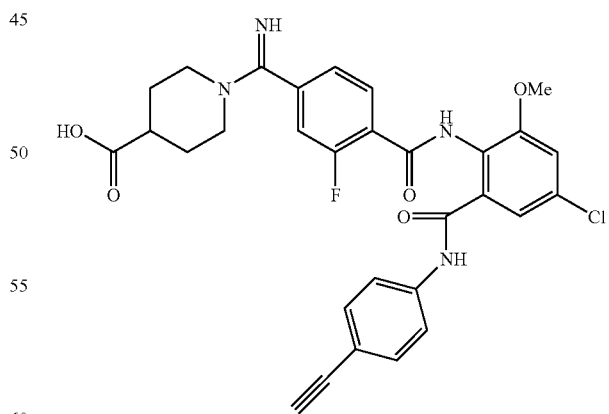

The titled compound was made by the procedure similar to that described in example 4.
MS found for $C_{31}H_{25}FN_4O_4$ as $(M+H)^+$: 537.2.

Example 214

[4-({[2-(dimethylamino)ethyl]methylamino}iminomethyl)-2-fluorophenyl]-N-{4-ethynyl-2-[N-(4-ethynylphenyl)carbamoyl]phenyl}carboxamide

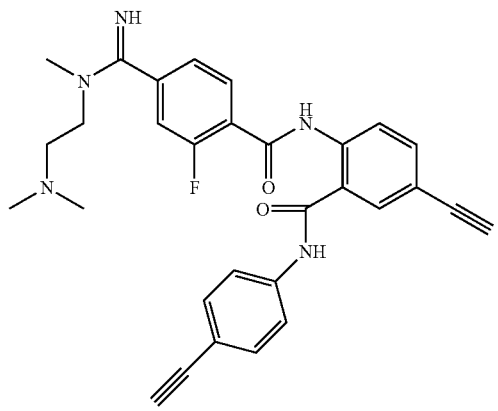

The titled compound was made by the procedure similar to that described in example 208. MS found for $C_{30}H_{28}FN_5O_2$ as $(M+H)^+$: 510.2.

Example 215

N-{4-ethynyl-2-[N-(4-ethynylphenyl)carbamoyl]phenyl)}-{4-[(ethylmethylamino)iminomethyl]-2-fluorophenyl}carboxamide

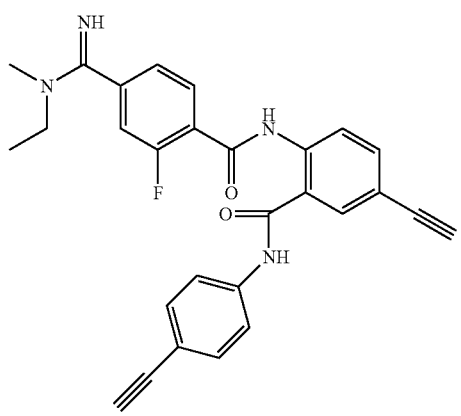

The titled compound was made by the procedure similar to that described in example 208. MS found for $C_{28}H_{23}FN_4O_2$ as $(M+H)^+$: 467.1.

Example 216

[4-({[3-(dimethylamino)propyl]methylamino}iminomethyl)-2-fluorophenyl]-N-{4-ethynyl-2-[N-(4-ethynylphenyl)carbamoyl]phenyl}carboxamide

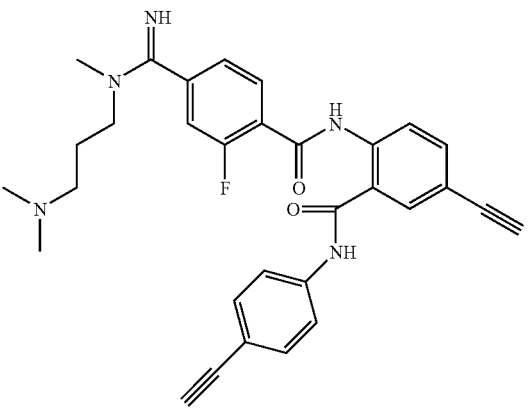

The titled compound was made by the procedure similar to that described in example 208. MS found for $C_{31}H_{30}FN_5O_2$ as $(M+H)^+$: 524.2.

Example 217

N-{4-ethynyl-2-[N-(4-ethynylphenyl)carbamoyl]phenyl}[4-(azetidinyliminomethyl)-2-fluorophenyl)phenyl]carboxamide

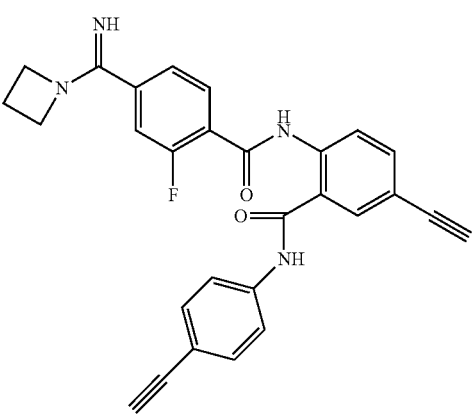

The titled compound was made by the procedure similar to that described in example 208. MS found for $C_{28}H_{21}FN_4O_2$ as $(M+H)^+$: 465.2.

Example 218

N-{4-ethynyl-2-[N-(4-ethynylphenyl)carbamoyl]phenyl}[4-(azetidinylazetidinylidenemethyl)-2-fluorophenyl]carboxamide

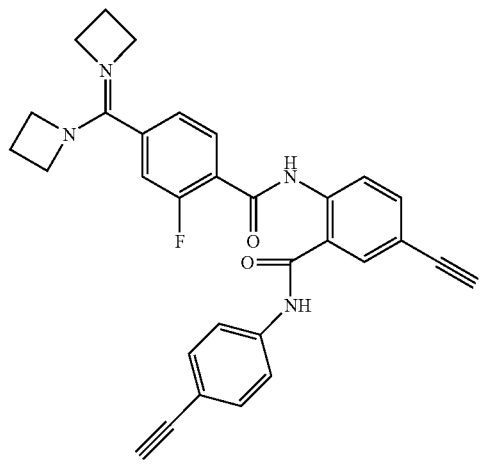

The titled compound was made by the procedure similar to that described in example 208. MS found for $C_{31}H_{26}FN_4O_2$ as $M^+$: 505.2.

Example 219

(4-{[(2-methoxyethyl)methylamino]iminomethyl}-2-fluorophenyl)-N-{4-ethynyl-2-[N-(4-ethynylphenyl)carbamoyl]phenyl}carboxamide

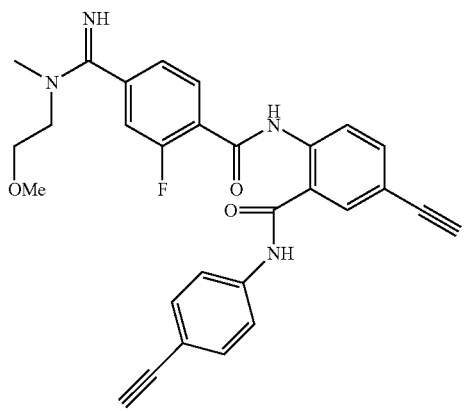

The titled compound was made by the procedure similar to that described in example 208. MS found for $C_{29}H_{25}FN_4O_3$ as $(M+H)^+$: 497.2.

Example 220

(4-{[(2-methoxyethyl)methylamino] iminomethyl}-2-fluorophenyl)-N-{4-ethynyl-2-[N-(4-ethynylphenyl)carbamoyl]phenyl}carboxamide

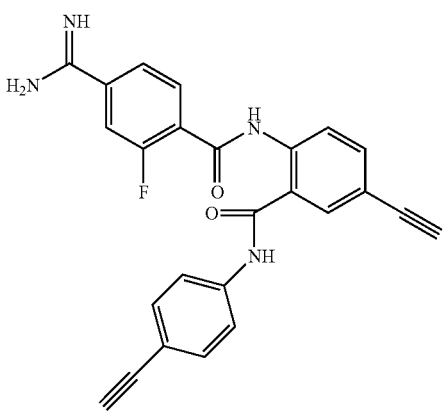

The titled compound was made by the procedure similar to that described in example 208. MS found for $C_{25}H_{17}FN_4O_2$ as $(M+H)^+$: 425.1.

Example 221

N-{4-ethynyl-2-[N-(4-ethynylphenyl)carbamoyl]phenyl}[4-(1-methyl(2-imidazolin-2-yl))phenyl]carboxamide

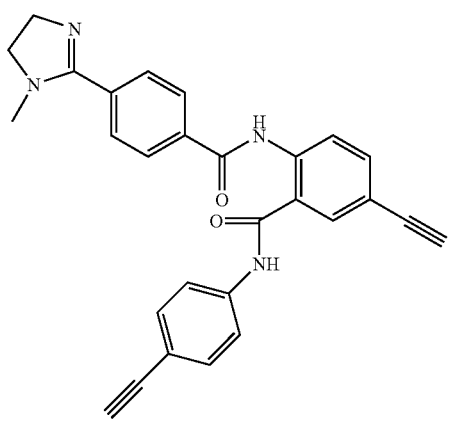

The titled compound was made by the procedure similar to that described in example 208. MS found for $C_{28}H_{22}N_4O_2$ $(M+H)^+$: 447.2.

Example 222

Methyl 1-{[4-(N-{4-ethynyl-2-[N-(4-ethynylphenyl)carbamoyl]phenyl}carbamoyl)phenyl]iminomethyl}-piperidine-4-carboxylate

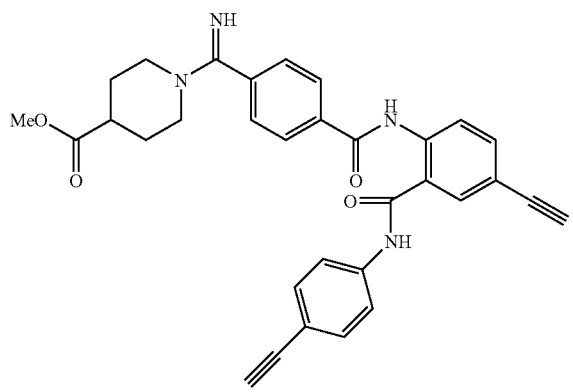

The titled compound was made by the procedure similar to that described in example 208. MS found for C$_{32}$H$_{28}$N$_4$O$_4$ as (M+H)$^+$: 533.3.

Example 223

1-{[4-(N-{4-ethynyl-2-[N-(4-ethynylphenyl)carbamoyl]phenyl}carbamoyl)phenyl]iminomethyl}-piperidine-4-carboxylic Acid

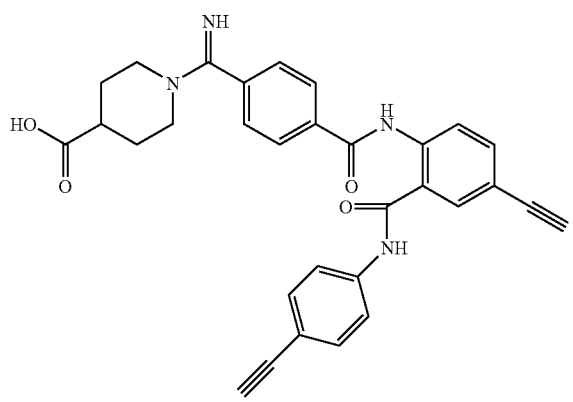

The titled compound was made by the procedure similar to that described in example 4.
MS found for C$_{31}$H$_{26}$N$_4$O$_4$ as (M+H)$^+$: 519.2.

Example 224

{4-[(dimethylamino)iminomethyl]phenyl}-N-{4-ethynyl-2-[N-(4-ethynylphenyl)carbamoyl]phenyl}carboxamide

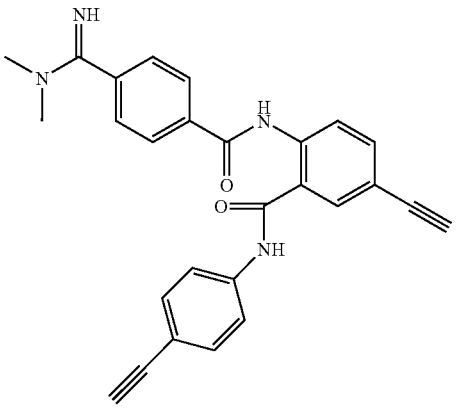

The titled compound was made by the procedure similar to that described in example 208. MS found for C$_{27}$H$_{22}$N$_4$O$_2$ as (M+H)$^+$: 435.2.

Example 225

N-{4-ethynyl-2-[N-(4-ethynylphenyl)carbamoyl]phenyl}{4-[(ethylmethylamino)iminomethyl]phenyl}carboxamide

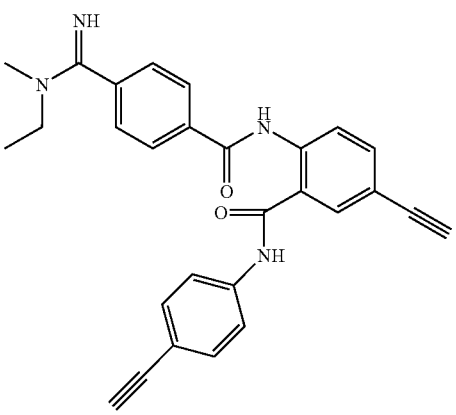

The titled compound was made by the procedure similar to that described in example 208. MS found for C$_{28}$H$_{24}$N$_4$O$_2$ as (M+H)$^+$: 449.2.

Example 226

[4-({[2-(dimethylamino)ethyl]methylamino}iminomethyl)phenyl]-N-{4-ethynyl-2-[N-(4-ethynylphenyl)carbamoyl]phenyl}carboxamide

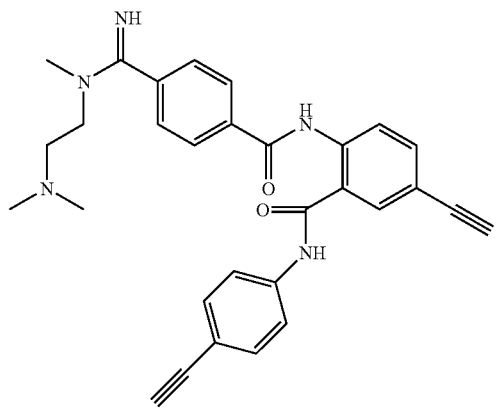

The titled compound was made by the procedure similar to that described in example 208. MS found for $C_{30}H_{29}N_5O_2$ as $(M+H)^+$: 492.3.

Example 227

[4-({[3-(dimethylamino)propyl]methylamino}iminomethyl)phenyl]-N-{4-ethynyl-2-[N-(4-ethynylphenyl)carbamoyl]phenyl}carboxamide

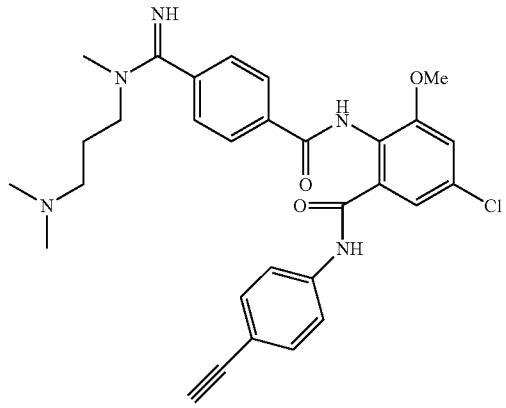

The titled compound was made by the procedure similar to that described in example 208. MS found for $C_{31}H_{31}N_5O_2$ as $(M+H)^+$: 506.2.

Example 228

N-{4-ethynyl-2-[N-(4-ethynylphenyl)carbamoyl]phenyl}[4-(iminopiperidylmethyl)phenyl]carboxamide

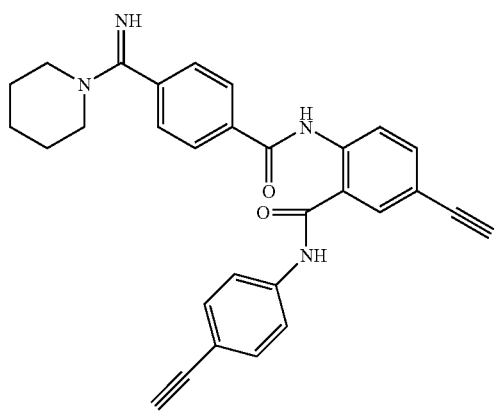

The titled compound was made by the procedure similar to that described in example 208. MS found for $C_{30}H_{26}N_4O_2$ as $(M+H)^+$: 475.2.

Example 229

N-{4-ethynyl-2-[N-(4-ethynylphenyl)carbamoyl]phenyl}[4-(azetidinyliminomethyl)phenyl)phenyl]carboxamide

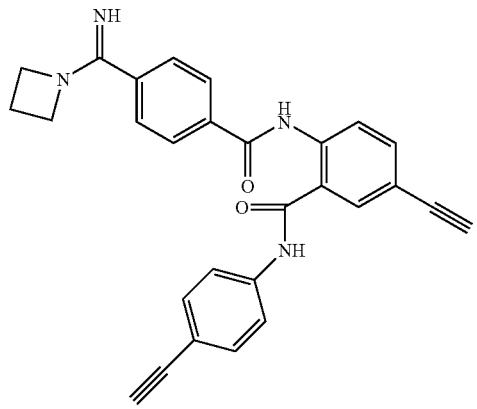

The titled compound was made by the procedure similar to that described in example 208. MS found for $C_{28}H_{22}N_4O_2$ as $(M+H)^+$: 447.2.

Scheme 11

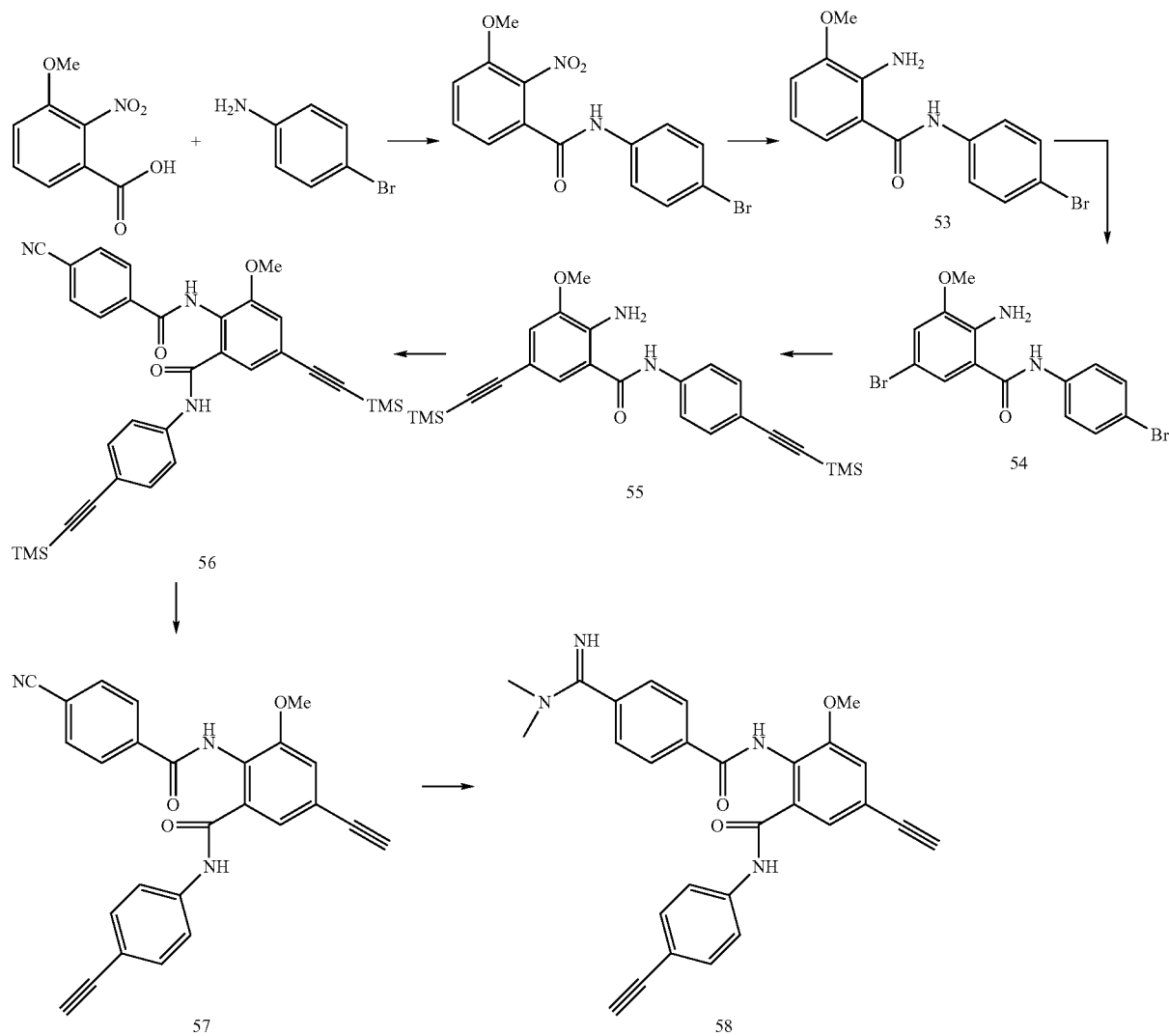

Example 230

{4-[(dimethylamino)iminomethyl]-2-fluorophenyl}-
N-{4-chloro-2-[N-(4-ethynylphenyl)carbamoyl]-6-
methoxyphenyl}carboxamide

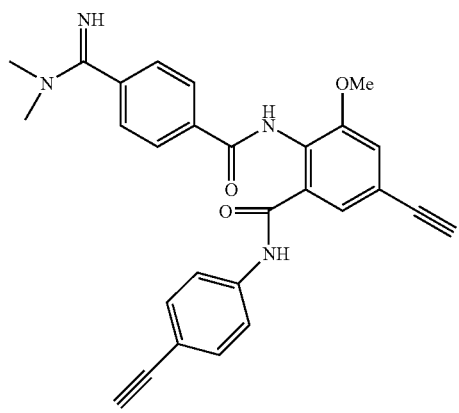

Step 1:

To a stirring solution of 4- bromoaniline (8.6 g, 50 mmol) and 3-methoxy-2-nitro-benzoic acid (10.0 g, 50 mmol) in anhydrous THF (40 mL) and pyridine (18.8 mL) at 0° C. was added $POCl_3$ (15.3 g, 100 mmol) dropwise. The mixture was stirred at 0° C. for 20 min. Water (500 mL) was added and precipitate formed. The solid was isolateded by filtration and dissolved in a mixture of 1,4-dioxane (100 mL) and THF (100 mL). Then, an aqueous solution of $Na_2S_2O_4$ (48 g, 348 mmol in 200 mL water) was added to the mixture. It was stirred at overnight. The two layers were separated. To the organic layer was added water and precipitate formed. The solid was collected by filtration and washed with water. After dried in vacco, 9.5 g of compound 53 was obtained as a gray solid in 60% yield for two steps.

Step 2:

To a solution of compound 53 (5.0 g, 15.6 mmol) in toluene (90 mL) at 70° C. was added N-bromosuccinimide (3.0 g, 17.1 mmol) in portions. The mixture was stirred at 70° C.-75° C. for 20 min, cooled down and washed with sat. $NaHCO_3$, sat. NaCl, dried and evaporated to give 6.3 g (100%) of the crude compound 54 as a dark brown solid. MS found for $C_{14}H_{12}Br_2N_2O_2$ as $(M+H)^+$: 401.0.

Step 3:

To a solution of compound 54 (3.2 g, 8 mmol) in $BuNH_2$ (15 mL) was added tetrakis(triphenylphosphine)Pd(0) (370 mg, 0.32 mmol), CuI (91 mg, 0.5 mmol) and (trimethylsilyl)acetylene (5.2 mL, 48 mmol). The mixture was stirred under reflux for 2 h and cooled down to rt. The mixture was concentrated and purified by silica gel chromatography (eluted with 10% EtOAc in Hexane) to give 1.63 g of compound 55 in 47% yield. MS found for $C_{24}H_{30}N_2O_2Si_2$ as $(M+H)^+$: 435.2.

Step 4:

To a solution compound 55 (1.5 g, 3.8 mmol) in THF (20 mL) was added 4-cyanobezoyl chloride (627 mg, 3.8 mmol) and pyridine (530 mL, 6.9 mmol). The mixture was stirred for 1 h and then concentrated. The residue was dissolved in EtOAc, washed with sat. $NaHCO_3$, water, dried and evaporated to give compound 56 (2.0 g, 100% yield).

Step 5:

To a solution of compound 56 (1.8 g, 3.2 mmol) in MeOH (20 mL) was added $K_2CO_3$ (4.4 g, 32 mmol). The mixture was stirred for 1 h and then concentrated. The residue was dissolved in EtOAc, washed with sat. $NaHCO_3$, water, 1 N HCl, sat. NaCl, dried and evaporated to give compound 57 (830 mg, 62% yield).

Step 6:

From compound 57, following the procedure similar to that described in Step 4, Example 1, the titled compound 58 was prepared. MS found for $C_{28}H_{24}N_4O_3$ as $(M+H)^+$: 465.2.

Example 231

[4-({[2-(dimethylamino)ethyl]amino}iminomethyl)phenyl]-N-{4-ethynyl-2-[N-(4-ethynylphenyl)carbamoyl]-6-methoxyphenyl}carboxamide

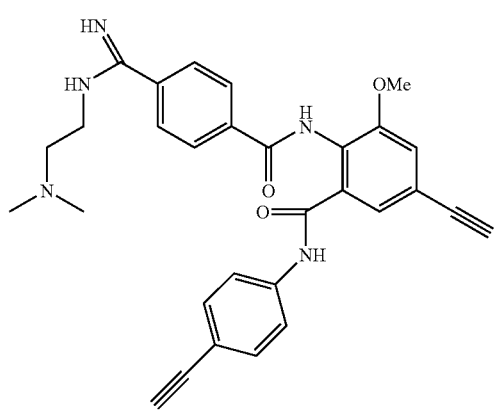

The titled compound was made by the procedure similar to that described in example 230. MS found for $C_{30}H_{29}N_5O_3$ as $(M+H)^+$: 508.3.

Example 232

N-{4-ethynyl-2-[N-(4-ethynylphenyl)carbamoyl]-6-methoxyphenyl}{4-[(ethylmethylamino)iminomethyl]phenyl}carboxamide

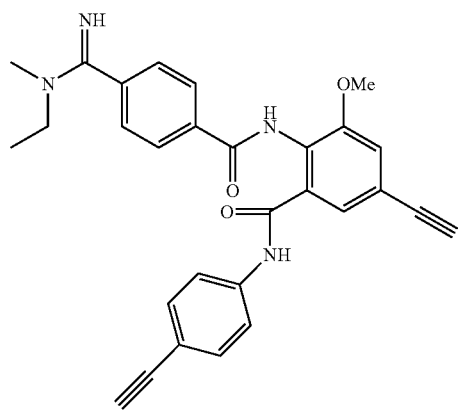

The titled compound was made by the procedure similar to that described in example 230. MS found for $C_{29}H_{26}N_4O_3$ as $(M+H)^+$: 479.2.

Example 233

{4-[(dimethylamino)iminomethyl]phenyl}-N-{2-[N-(4-ethynylphenyl)carbamoyl]-6-methoxyphenyl}carboxamide

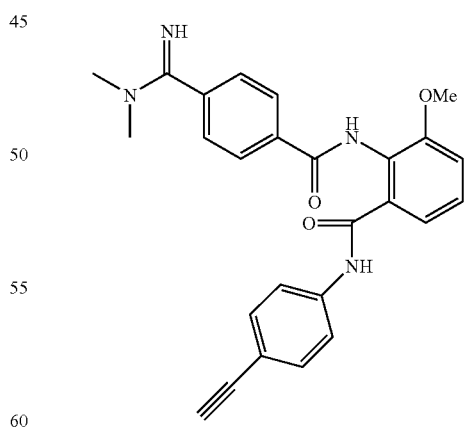

The titled compound was made by the procedure similar to that described in example 1.

MS found for $C_{26}H_{24}N_4O_3$ as $(M+H)^+$: 441.2.

Example 234

N-{2-[N-(4-ethynylphenyl)carbamoyl]-6-methoxyphenyl}[4-(1-methyl(2-imidazolin-2-yl))phenyl]carboxamide

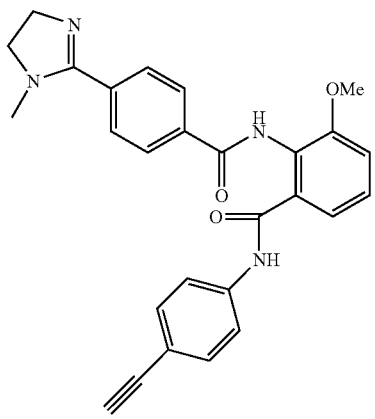

The titled compound was made by the procedure similar to that described in example 1.
MS found for $C_{27}H_{24}N_4O_3$ as $(M+H)^+$: 453.2.

Example 235

{4-[(dimethylamino)iminomethyl]-2-fluorophenyl}-N-{2-[N-(4-ethynylphenyl)carbamoyl]-6-methoxyphenyl}carboxamide

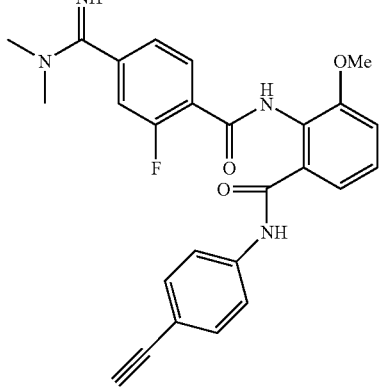

The titled compound was made by the procedure similar to that described in example 1.
MS found for $C_{26}H_{23}FN_4O_3$ as $(M+H)^+$: 459.1.

Example 236

N-{2-[N-(4-ethynylphenyl)carbamoyl]-6-methoxyphenyl}[2-fluoro-4-(1-methyl(2-imidazolin-2-yl))phenyl]carboxamide

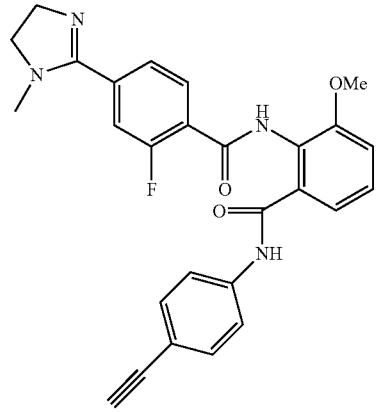

The titled compound was made by the procedure similar to that described in example 1.
MS found for $C_{27}H_{23}FN_4O_3$ as $(M+H)^+$: 471.1.

Scheme 11

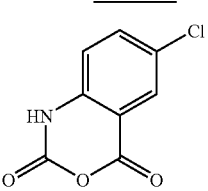

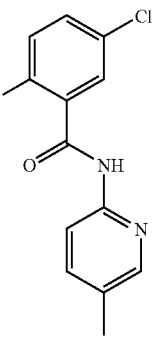

-continued

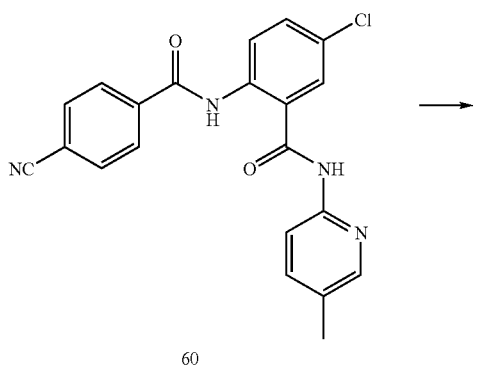

60

Example 237

{4-[(dimethylamino)iminomethyl]phenyl}-N-{4-chloro-2[N-(5-methyl(2-pyridyl))carbamoyl]phenyl}-carboxamide

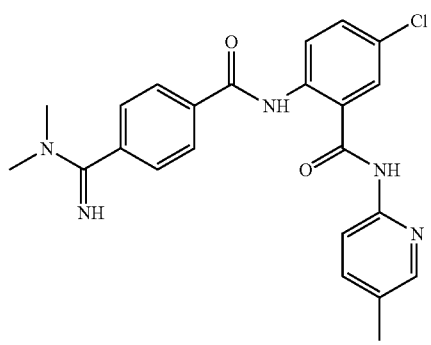

Step 1:

From 5-chloroisatoic anhydride and 2-amino-5-methylpyridine, following the procedure similar to that described in Step 1, Example 79, the titled compound 59 was prepared. MS found for $C_{13}H_{12}ClN_3O$ as $(M+H)^+$: 262.0.

Step 2:

From compound 59, following the procedure similar to that described in Step 3, Example 79, the titled compound 60 was prepared. MS found for $C_{21}H_{15}ClN_4O_2$ as $(M+H)^+$: 391.1.

Step 3:

From compound 60, following the procedure similar to that described in Step 3, Example 79, the titled compound 61 was prepared. MS found for $C_{23}H_{22}ClN_5O_2$ as $(M+H)^+$: 436.2.

Example 238

N-{4-chloro-2-[N-(5-methyl(2-pyridyl))carbamoyl]phenyl}[4-(1-methyl(2-imidazolin-2-yl))phenyl]-carboxamide

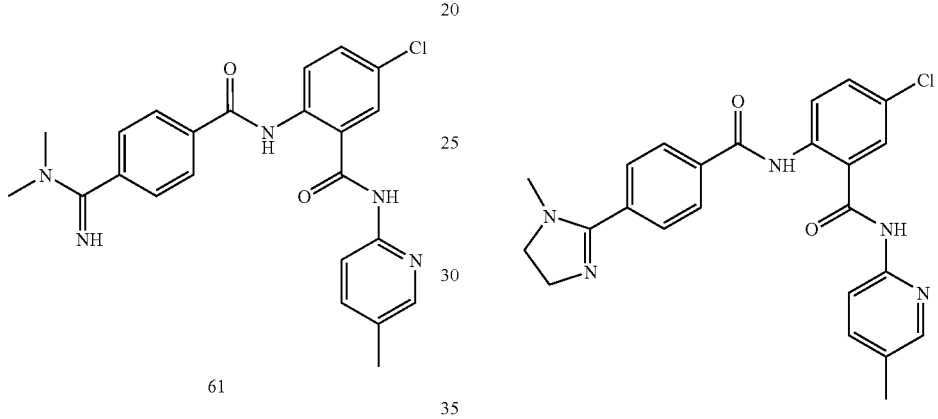

The titled compound was made by the procedure similar to that described in example 1.

MS found for $C_{24}H_{22}ClN_5O_2$ as $(M+H)^+$: 448.2.

Example 239

N-{2-[N-(5-methyl(2-pyridyl))carbamoyl]-4-chlorophenyl}[4-(iminopyrrolidinylmethyl)phenyl]carboxamide

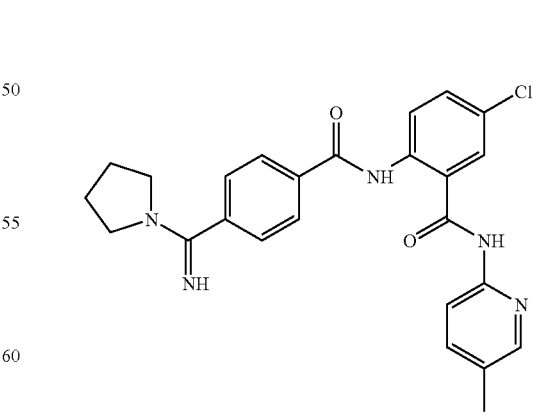

The titled compound was made by the procedure similar to that described in example 1.

MS found for $C_{25}H_{24}ClN_5O_2$ as $(M+H)^+$: 462.2.

Example 240

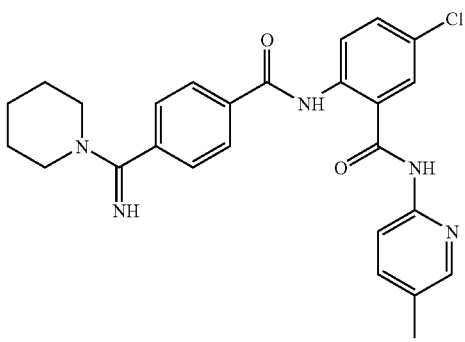

The titled compound was made by the procedure similar to that described in example 1.

MS found for $C_{26}H_{26}ClN_5O_2$ as $(M+H)^+$: 476.2.

Biological Activity Examples

Evaluation of the compounds of this invention is guided by in vitro protease activity assays (see below) and in vivo studies to evaluate antithrombotic efficacy, and effects on hemostasis and hematological parameters.

The compounds of the present invention are dissolved in buffer to give solutions containing concentrations such that assay concentrations range from 0 to 100 µM. In the assays for thrombin, prothrombinase and factor Xa, a synthetic chromogenic substrate is added to a solution containing test compound and the enzyme of interest and the residual catalytic activity of that enzyme is determined spectrophotometrically. The $IC_{50}$ of a compound is determined from the substrate turnover. The $IC_{50}$ is the concentration of test compound giving 50% inhibition of the substrate turnover. The compounds of the present invention desirably have an $IC_{50}$ of less than 500 nM in the factor Xa assay, preferably less than 200 nM, and more preferred compounds have an $IC_{50}$ of about 100 nM or less in the factor Xa assay. The compounds of the present invention desirably have an $IC_{50}$ of less than 4.0 µM in the prothrombinase assay, preferably less than 200 nM, and more preferred compounds have an $IC_{50}$ of about 10 nM or less in the prothrombinase assay. The compounds of the present invention desirably have an $IC_{50}$ of greater than 1.0 µM in the thrombin assay, preferably greater than 10.0 µM, and more preferred compounds have an $IC_{50}$ of greater than 100.0 µM in the thrombin assay.

Amidolytic Assays for Determining Protease Inhibition Activity

The factor Xa and thrombin assays are performed at room temperature, in 0.02 M TrisHCl buffer, pH 7.5, containing 0.15 M NaCl. The rates of hydrolysis of the para-nitroanilide substrate S-2765 (Chromogenix) for factor Xa, and the substrate Chromozym TH (Boehringer Mannheim) for thrombin following preincubation of the enzyme with inhibitor for 5 minutes at room temperature, and were determined using the Softmax 96-well plate reader (Molecular Devices), monitored at 405 nm to measure the time dependent appearance of p-nitroaniline.

The prothrombinase inhibition assay is performed in a plasma free system with modifications to the method described by Sinha, U. et al., Thromb. Res., 75, 427-436 (1994). Specifically, the activity of the prothrombinase complex is determined by measuring the time course of thrombin generation using the p-nitroanilide substrate Chromozym TH. The assay consists of preincubation (5 minutes) of selected compounds to be tested as inhibitors with the complex formed from factor Xa (0.5 nM), factor Va (2 nM), phosphatidyl serine:phosphatidyl choline (25:75, 20 µM) in 20 mM TrisHCl buffer, pH 7.5, containing 0.15 M NaCl, 5 mM $CaCl_2$ and 0.1% bovine serum albumin. Aliquots from the complex-inhibitor mixture are added to prothrombin(1 nM) and Chromozym TH (0.1 mM). The rate of substrate cleavage is monitored at 405 nm for two minutes. Eight different concentrations of inhibitor are assayed in duplicate. A standard curve of thrombin generation by an equivalent amount of untreated complex are used for determination of percent inhibition.

Antithrombotic Efficacy in a Rabbit Model of Venous Thrombosis

A rabbit deep vein thrombosis model as described by Hollenbach, S. et al., Thromb. Haemost. 71, 357-362 (1994), is used to determine the in-vivo antithrombotic activity of the test compounds. Rabbits are anesthetized with I.M. injections of Ketamine, Xylazine, and Acepromazine cocktail. A standardized protocol consists of insertion of a thrombogenic cotton thread and copper wire apparatus into the abdominal vena cava of the anesthetized rabbit. A non-occlusive thrombus is allowed to develop in the central venous circulation and inhibition of thrombus growth is used as a measure of the antithrombotic activity of the studied compounds. Test agents or control saline are administered through a marginal ear vein catheter. A femoral vein catheter is used for blood sampling prior to and during steady state infusion of test compound. Initiation of thrombus formation begins immediately after advancement of the cotton thread apparatus into the central venous circulation. Test compounds are administered from time=30 min to time=150 min at which the experiment is terminated. The rabbits are euthanized and the thrombus excised by surgical dissection and characterized by weight and histology. Blood samples are analyzed for changes in hematological and coagulation parameters.

Effects of Compounds in Rabbit Venous Thrombosis model

Administration of compounds in the rabbit venous thrombosis model demonstrates antithrombotic efficacy at the higher doses evaluated. There are no significant effects of the compound on the aPTT and PT prolongation with the highest dose (100 µg/kg+2.57 lg/kg/min). Compounds have no significant effects on hematological parameters as compared to saline controls. All measurements are an average of all samples after steady state administration of vehicle or (D)-Arg-Gly-Arg-thiazole. Values are expressed as mean ±SD.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

The above examples have been depicted solely for the purpose of exemplification and are not intended to restrict the scope or embodiments of the invention. The invention is further illustrated with reference to the claims that follow thereto.

What is claimed is:

1. A compound of formula Ia:

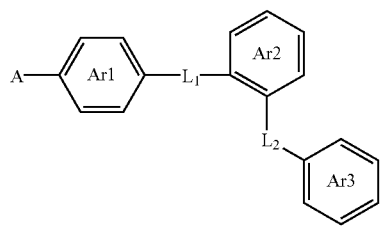

wherein:

Ar1 is independently selected from the group consisting of:

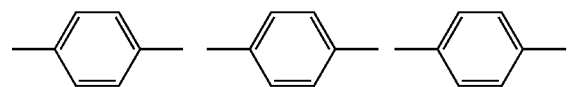
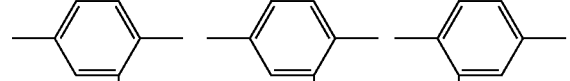
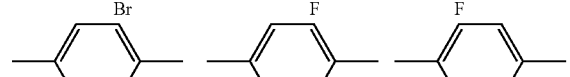
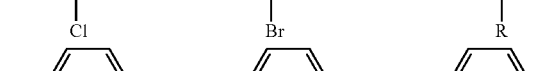
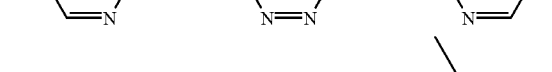
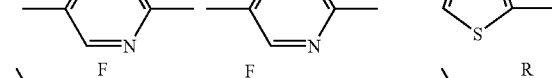
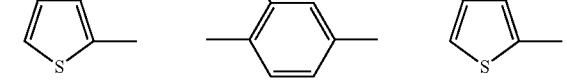

each R is independently selected from the group consisting of Cl, OMe, NHMe, —NMe$_2$, —OCH$_2$CH$_2$OMe, —OCH$_2$CH$_2$NMe$_2$, —SMe, —SO$_2$Me,

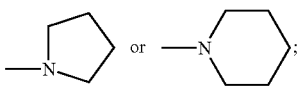

L1 is a direct link, —CONH, —CH$_2$NH, or —NHCO—;
L2 is —CONH, or —NHCO;
Ar3 is

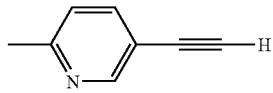

Ar2 is independently selected from the group consisting of:

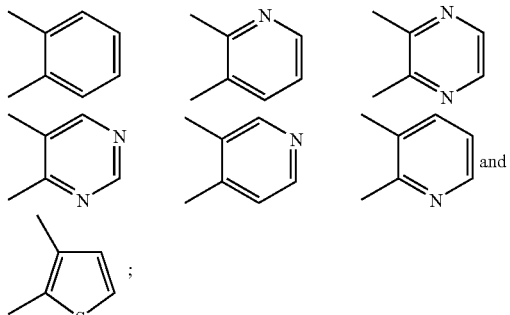

Ar2 may be optionally substituted with 0-3 R$^{1d}$ group; each R$^{1d}$ is independently selected from the group consisting of:

H, —Me, —F, —Cl, —Br, I, —CH$_3$, —CF$_3$, —CN, —CO$_2$H, —CO$_2$Me, —CO$_2$Et, —CONH$_2$, —CONHMe, —CONMe$_2$, —CH$_2$NMe$_2$, —COMe, —CH$_2$COOH,

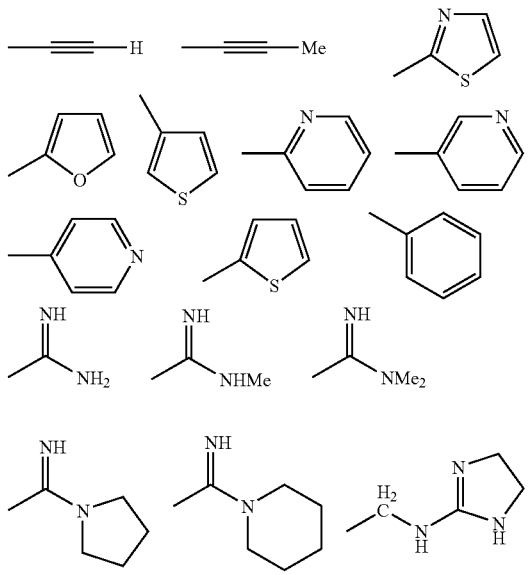

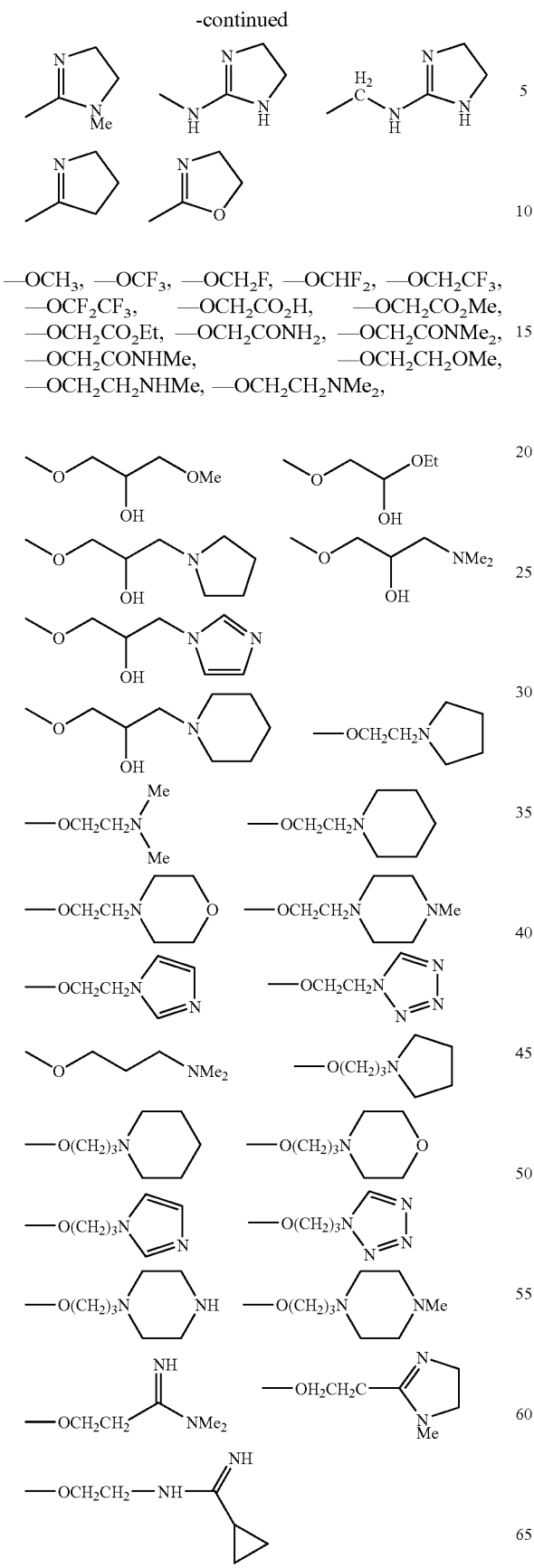
—OCH₃, —OCF₃, —OCH₂F, —OCHF₂, —OCH₂CF₃, —OCF₂CF₃, —OCH₂CO₂H, —OCH₂CO₂Me, —OCH₂CO₂Et, —OCH₂CONH₂, —OCH₂CONMe₂, —OCH₂CONHMe, —OCH₂CH₂OMe, —OCH₂CH₂NHMe, —OCH₂CH₂NMe₂,
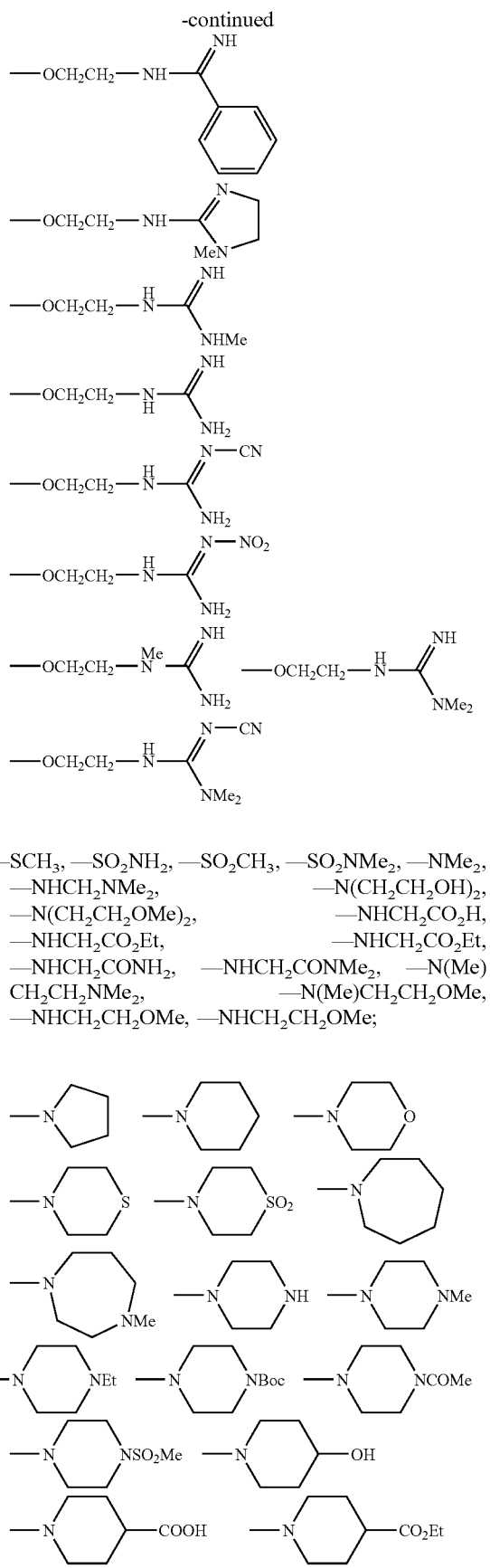
—SCH₃, —SO₂NH₂, —SO₂CH₃, —SO₂NMe₂, —NMe₂, —NHCH₂NMe₂, —N(CH₂CH₂OH)₂, —N(CH₂CH₂OMe)₂, —NHCH₂CO₂H, —NHCH₂CO₂Et, —NHCH₂CO₂Et, —NHCH₂CONH₂, —NHCH₂CONMe₂, —N(Me)CH₂CH₂NMe₂, —N(Me)CH₂CH₂OMe, —NHCH₂CH₂OMe, —NHCH₂CH₂OMe;

-continued
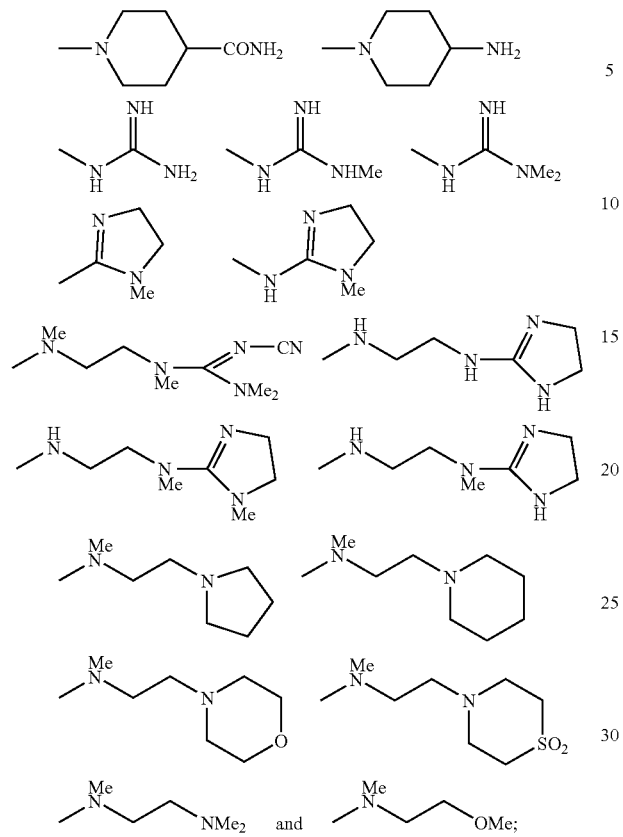
A is independently selected from the group consisting of:
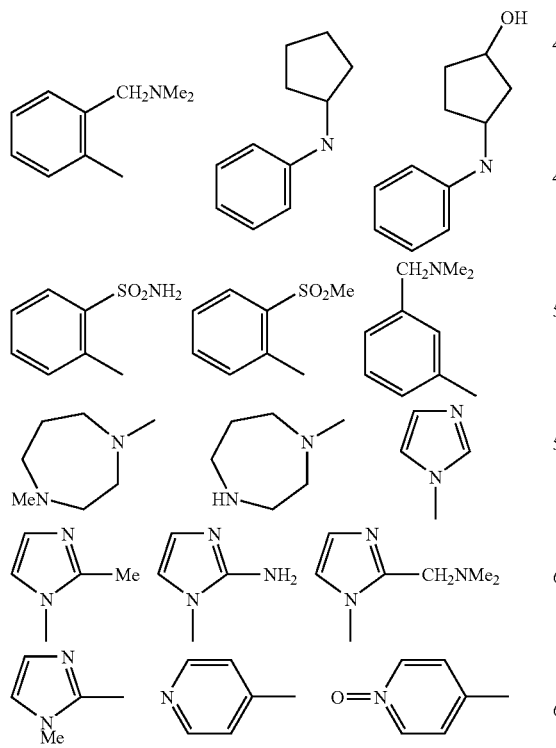
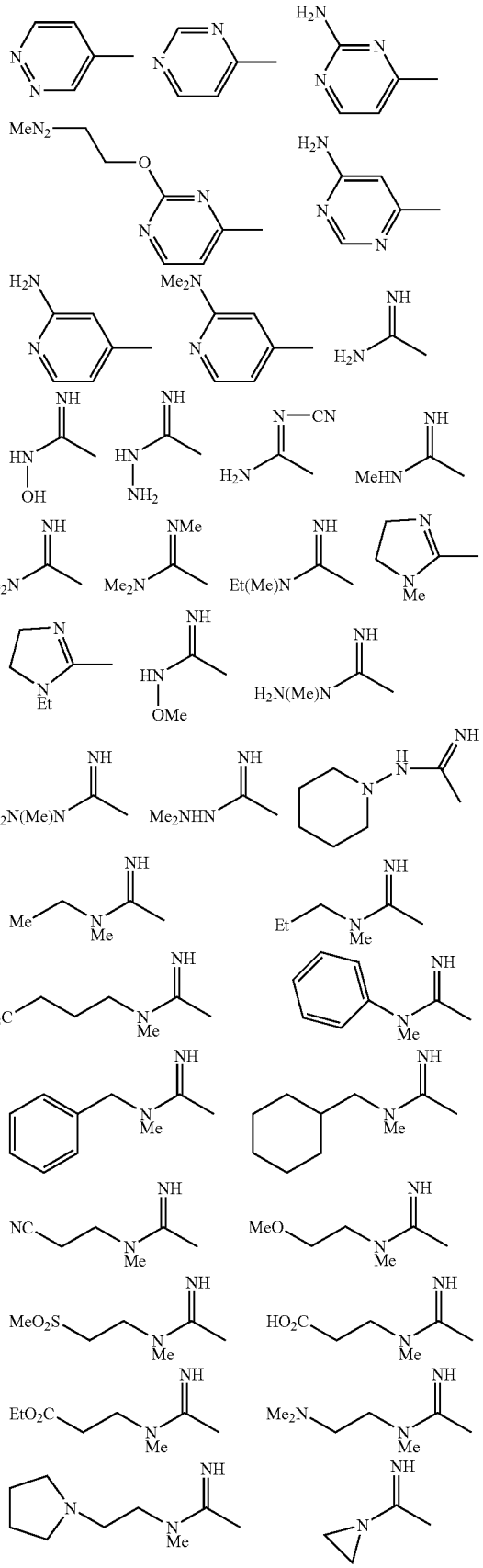

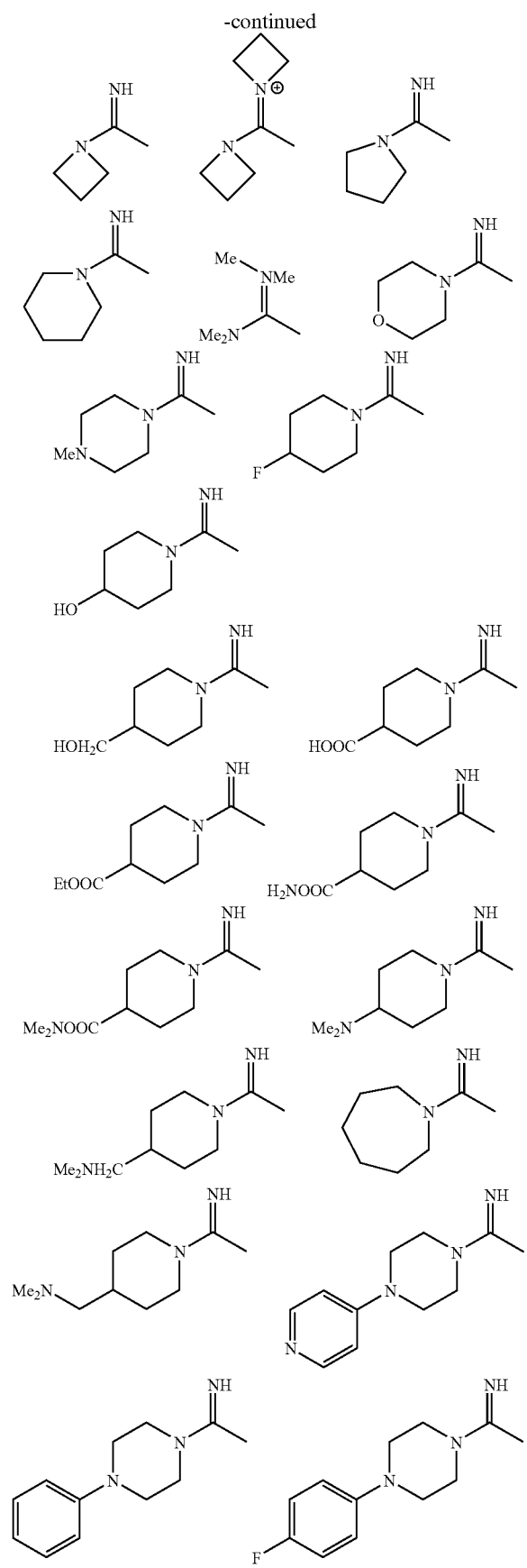
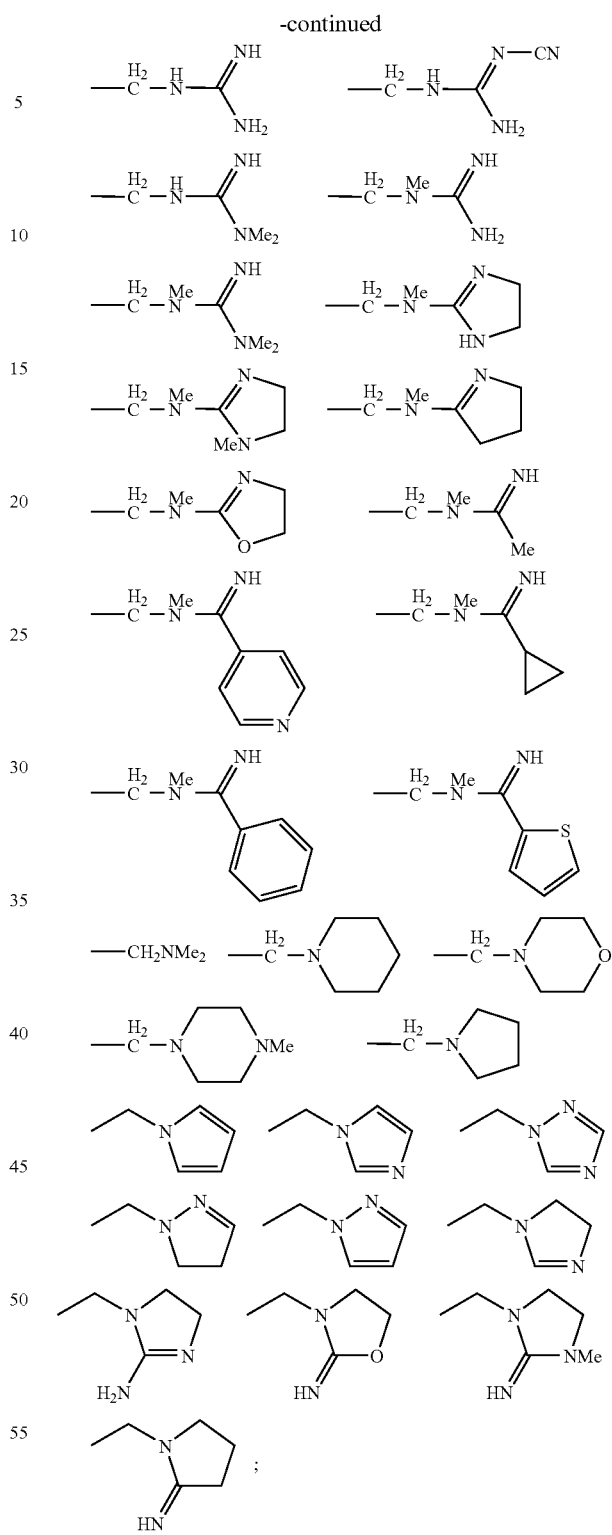
and all pharmaceutically acceptable isomers, salts, hydrates, solvates and prodrugs derivatives thereof.
2. The compound according to claim 1 wherein L1 or L2 is —CONH.
3. The compound according to claim 1, wherein Ar1 is independently selected from the group consisting of:

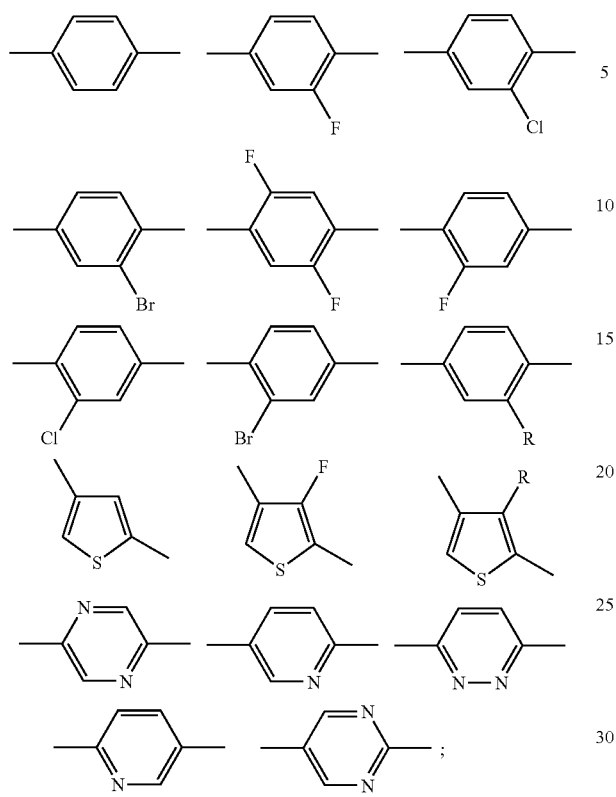

each R is independently selected from the group consisting of Cl, OMe, NHMe, —NMe$_2$, —OCH$_2$CH$_2$OMe, —OCH$_2$CH$_2$NMe$_2$, —SMe, —SO$_2$Me,

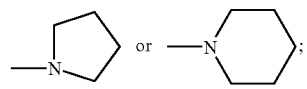

Ar3 is

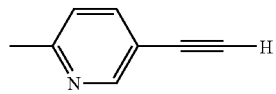

Ar2 may be optionally substituted with 0-3 R$^{1d}$ groups; each R$^{1d}$ is independently selected from the group consisting of:

H, —Me, —Cl, —Br, —OCH$_3$, —OCF$_3$, —OCH$_2$F, —OCHF$_2$, —OCH$_2$CF$_3$, —OCF$_2$CF$_3$, —OCH$_2$CO$_2$H, —OCH$_2$CO$_2$Me, —OCH$_2$CO$_2$Et, —OCH$_2$CONH$_2$, —OCH$_2$CONMe$_2$, —OCH$_2$CONHMe, —OCH$_2$CH$_2$OMe, —OCH$_2$CH$_2$NMe$_2$,

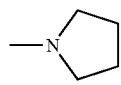 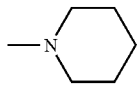 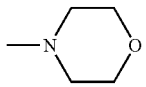

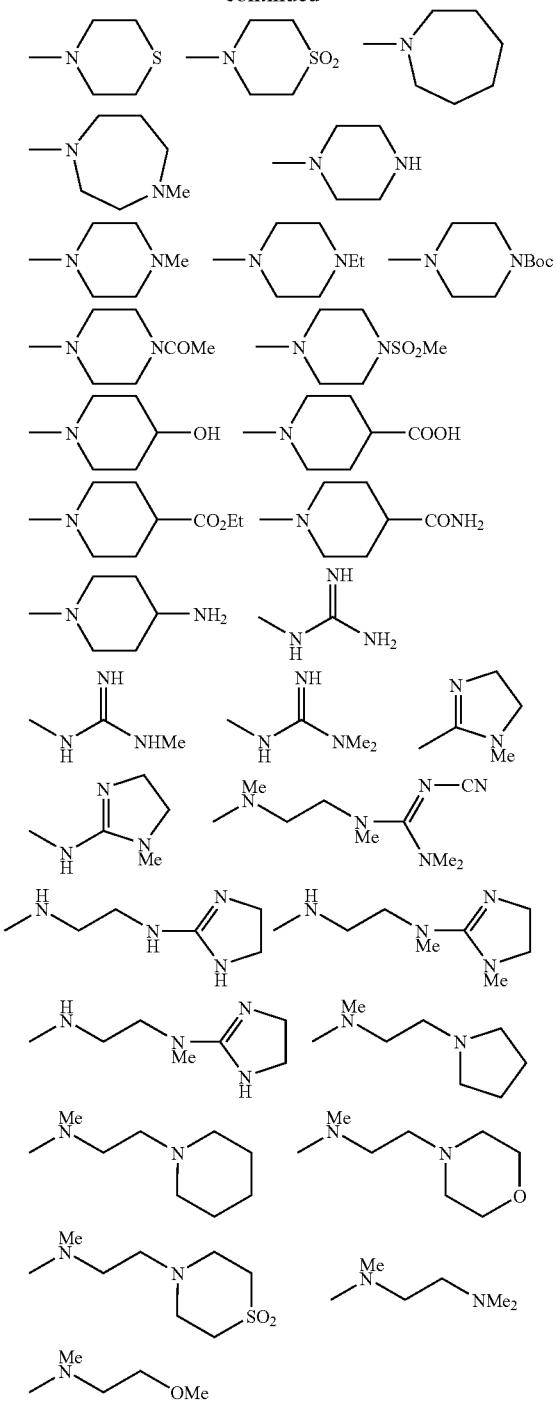

—F, —I, —CH$_2$—CF$_3$—CN, —CO$_2$H, —CO$_2$Me, —CO$_2$Et, —CONH$_2$, —CONHMe, —CONMe$_2$, —CH$_2$NH$_2$, —CH$_2$NHMe, —CH$_2$NMe$_2$, —COMe, —CH$_2$COOH, —CH$_2$COOEt,

 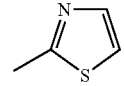 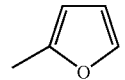

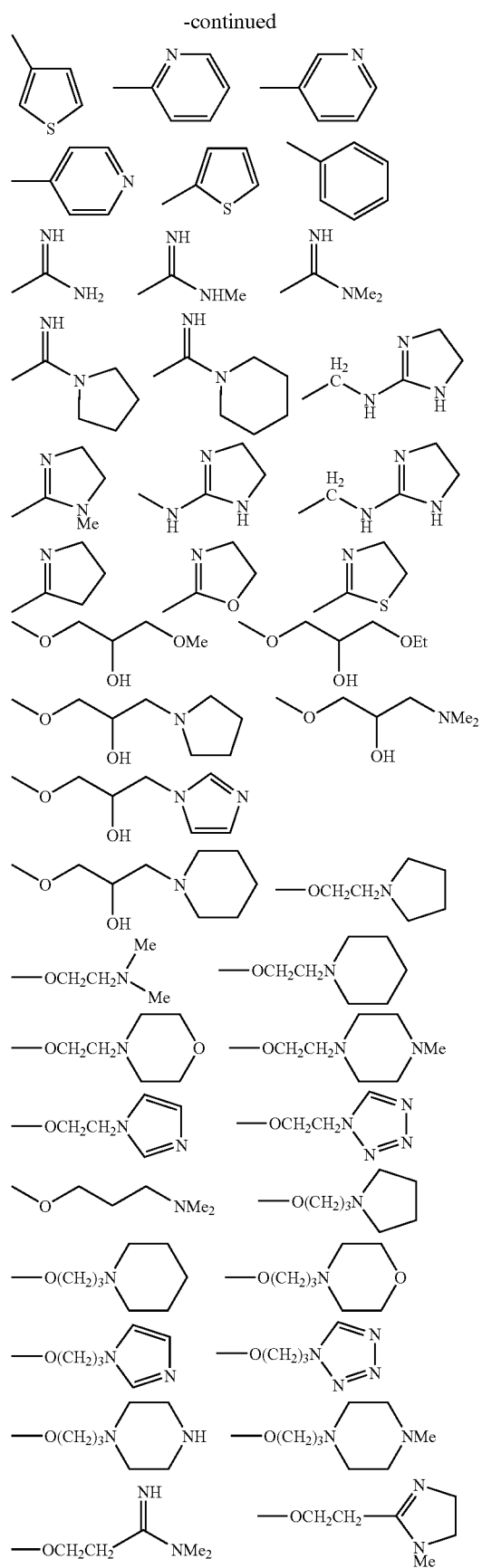
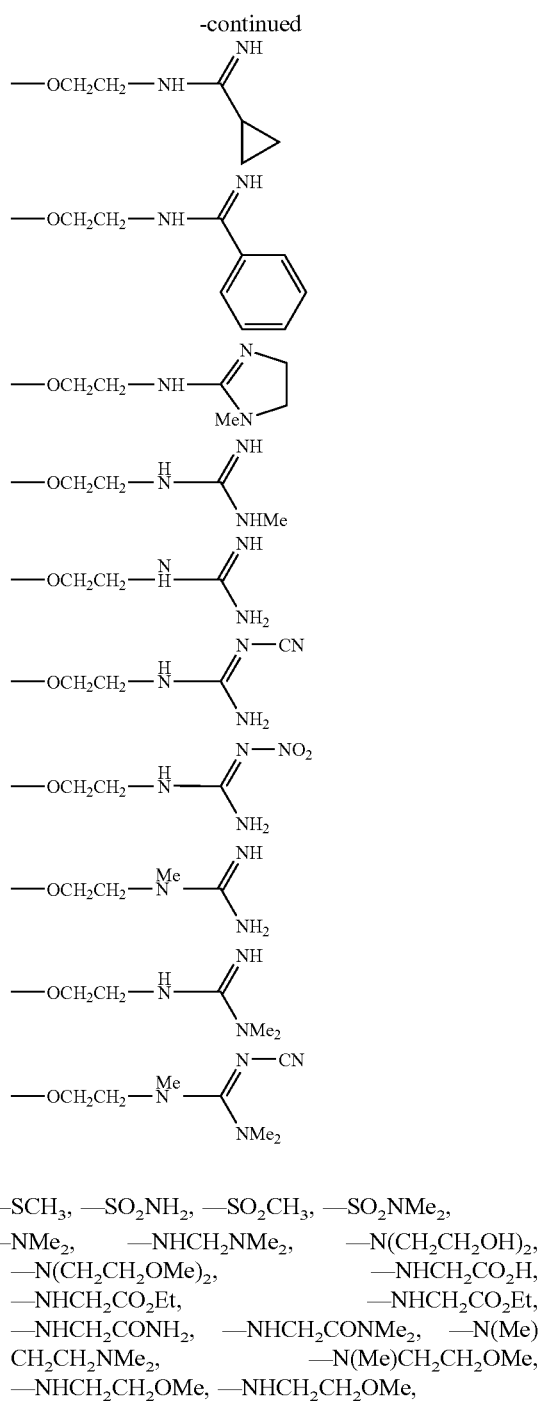
—SCH$_3$, —SO$_2$NH$_2$, —SO$_2$CH$_3$, —SO$_2$NMe$_2$, —NMe$_2$, —NHCH$_2$NMe$_2$, —N(CH$_2$CH$_2$OH)$_2$, —N(CH$_2$CH$_2$OMe)$_2$, —NHCH$_2$CO$_2$H, —NHCH$_2$CO$_2$Et, —NHCH$_2$CO$_2$Et, —NHCH$_2$CONH$_2$, —NHCH$_2$CONMe$_2$, —N(Me)CH$_2$CH$_2$NMe$_2$, —N(Me)CH$_2$CH$_2$OMe, —NHCH$_2$CH$_2$OMe, —NHCH$_2$CH$_2$OMe,
A is independently selected from the group consisting of:
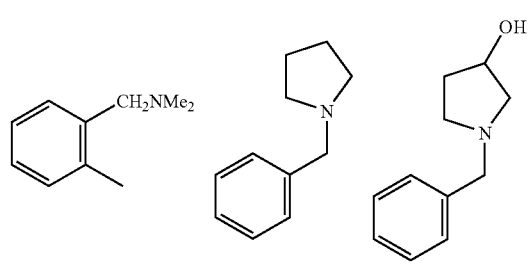

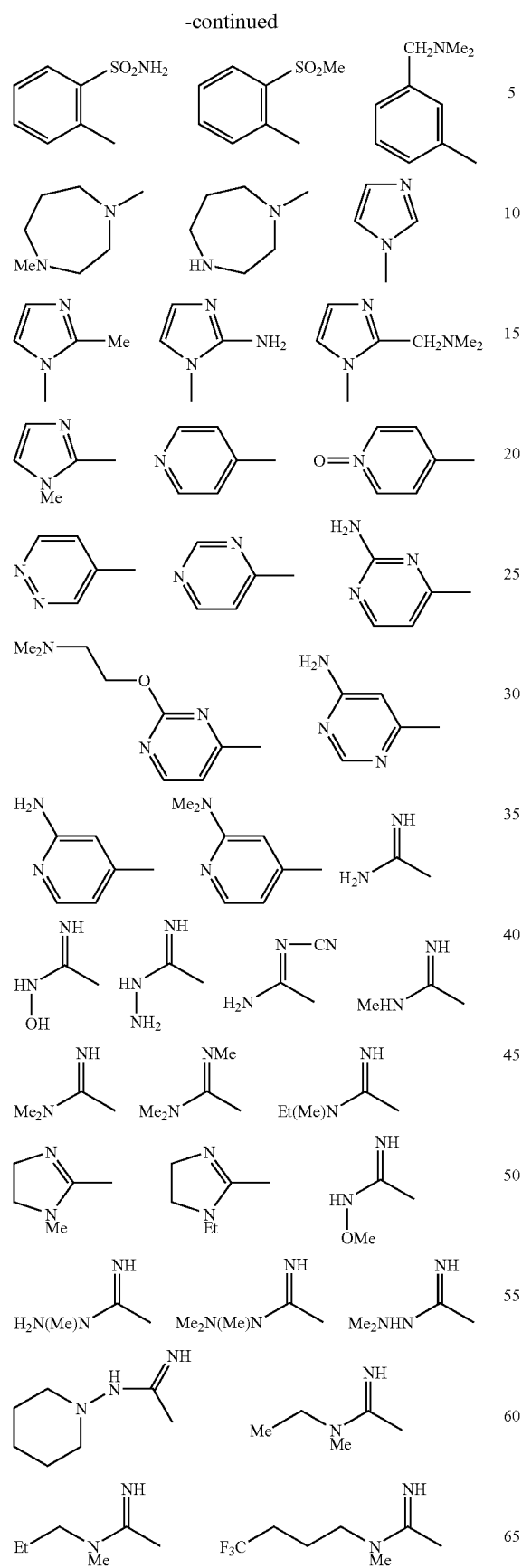
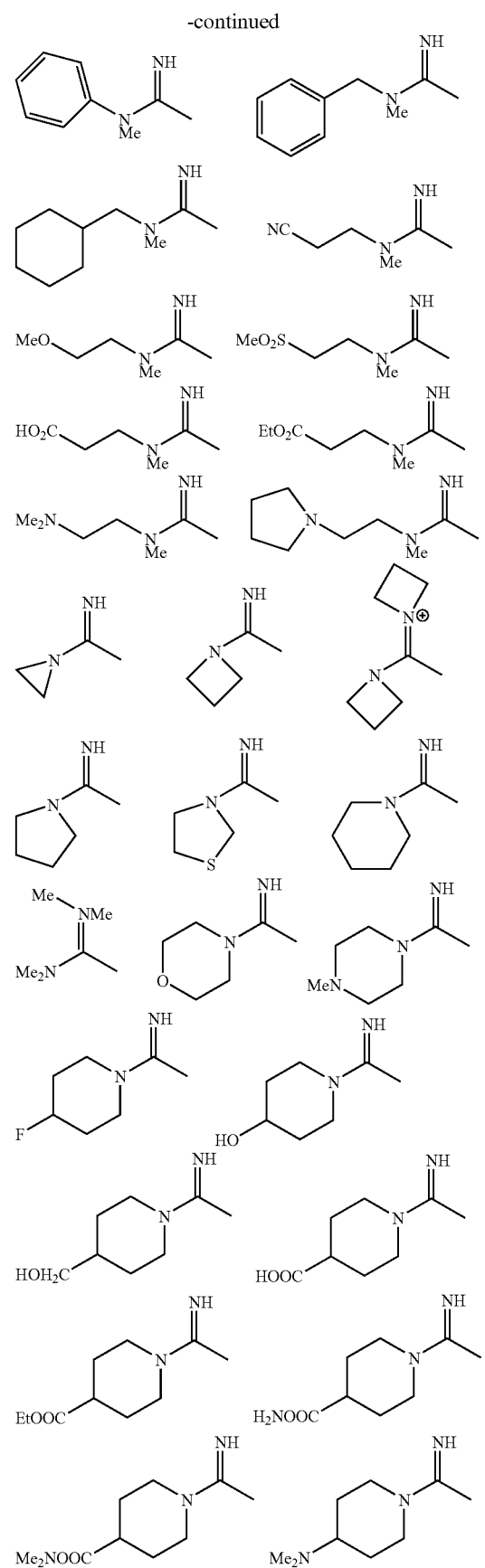

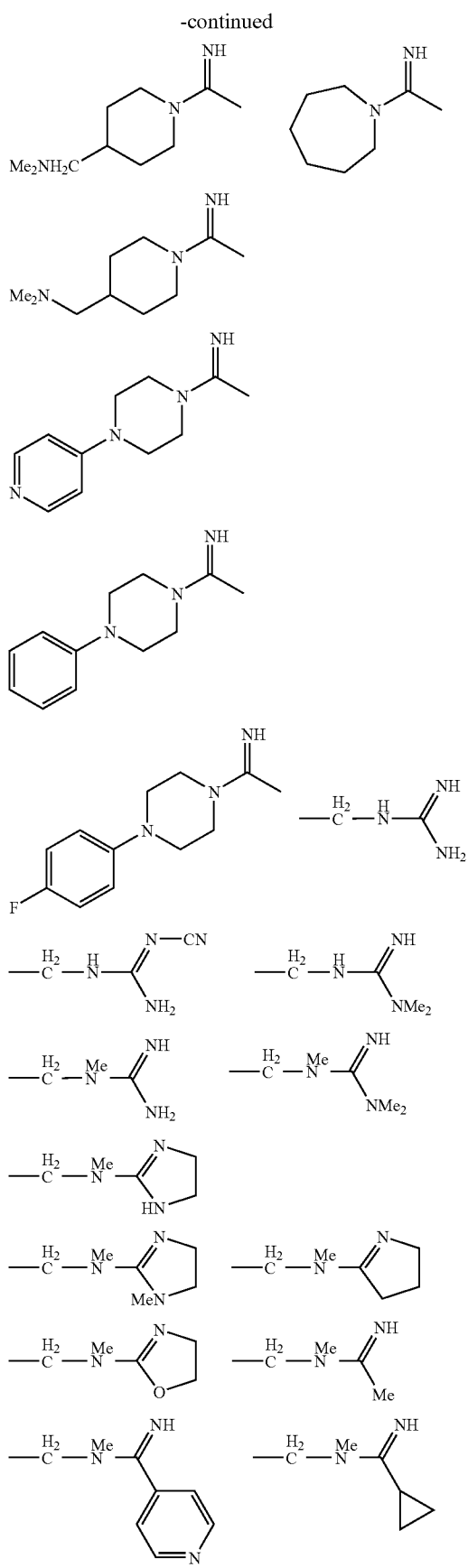
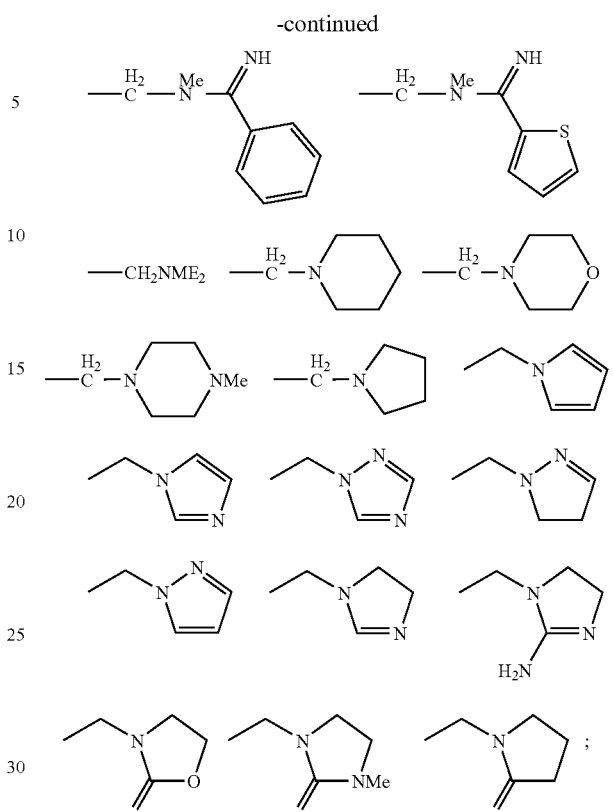
and all pharmaceutically acceptable isomers, salts, hydrates, solvates, and prodrug derivatives therof.
4. The compound according to claim 1 having the formula:
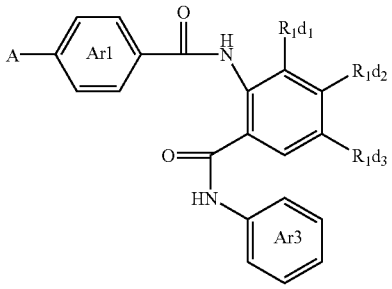
and
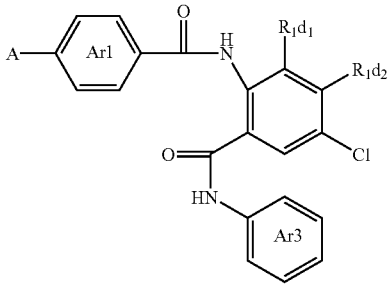

wherein:

Ar1 is independently selected from the group consisting of:

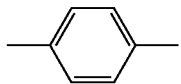 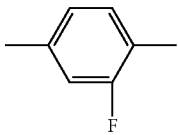

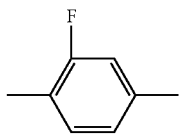 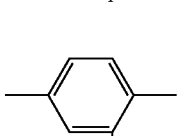

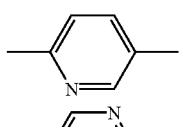 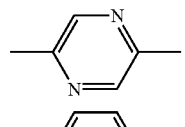

 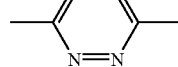

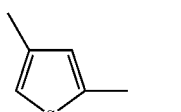 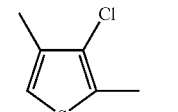

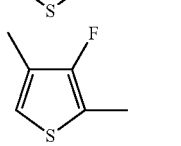 and 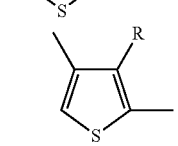

each R is independently selected from the group consisting of Me, OMe, $NH_2$, NHMe, —$NME_2$, —SMe, —$SO_2Me$, —$OCH_2CH_2OMe$, —$OCH_2CH_2NMe_2$,

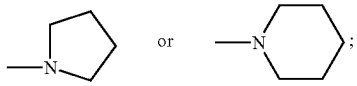

Ar3 is

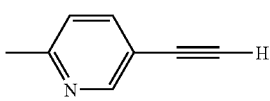

each $R^{1d1}$ is independently selected from the group consisting of:

H, —Me, —Cl, —$OCH_3$, —$OCF_3$, —$OCH_2F$, —$OCHF_2$, —$OCH_2CF_3$, —$OCF_2CF_3$, —$OCH_2CO_2H$, —$OCH_2CO_2Me$, —$OCH_2CO_2Et$, —$OCH_2CONH_2$, —$OCH_2CONMe_2$, —$OCH_2CONHMe$, —$OCH_2CH_2OMe$, —$OCH_2CH_2NMe_2$,

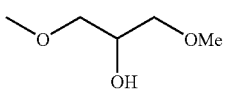 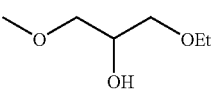

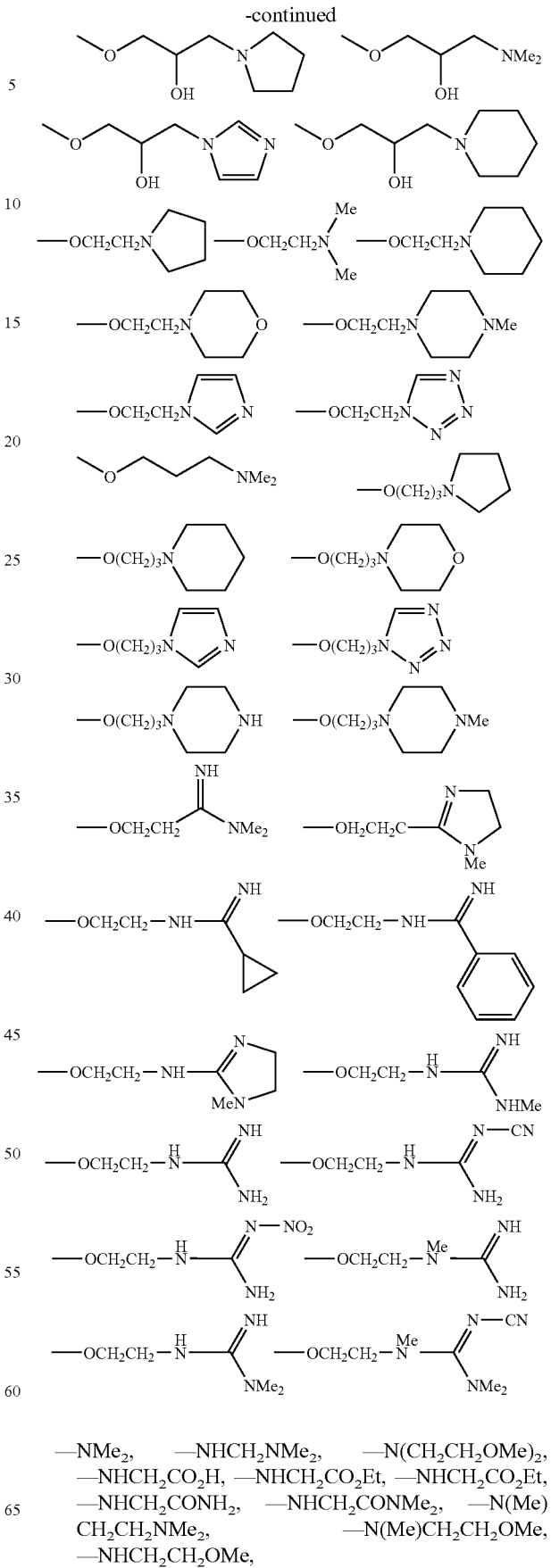

—$NMe_2$, —$NHCH_2NMe_2$, —$N(CH_2CH_2OMe)_2$, —$NHCH_2CO_2H$, —$NHCH_2CO_2Et$, —$NHCH_2CO_2Et$, —$NHCH_2CONH_2$, —$NHCH_2CONMe_2$, —$N(Me)CH_2CH_2NMe_2$, —$N(Me)CH_2CH_2OMe$, —$NHCH_2CH_2OMe$,

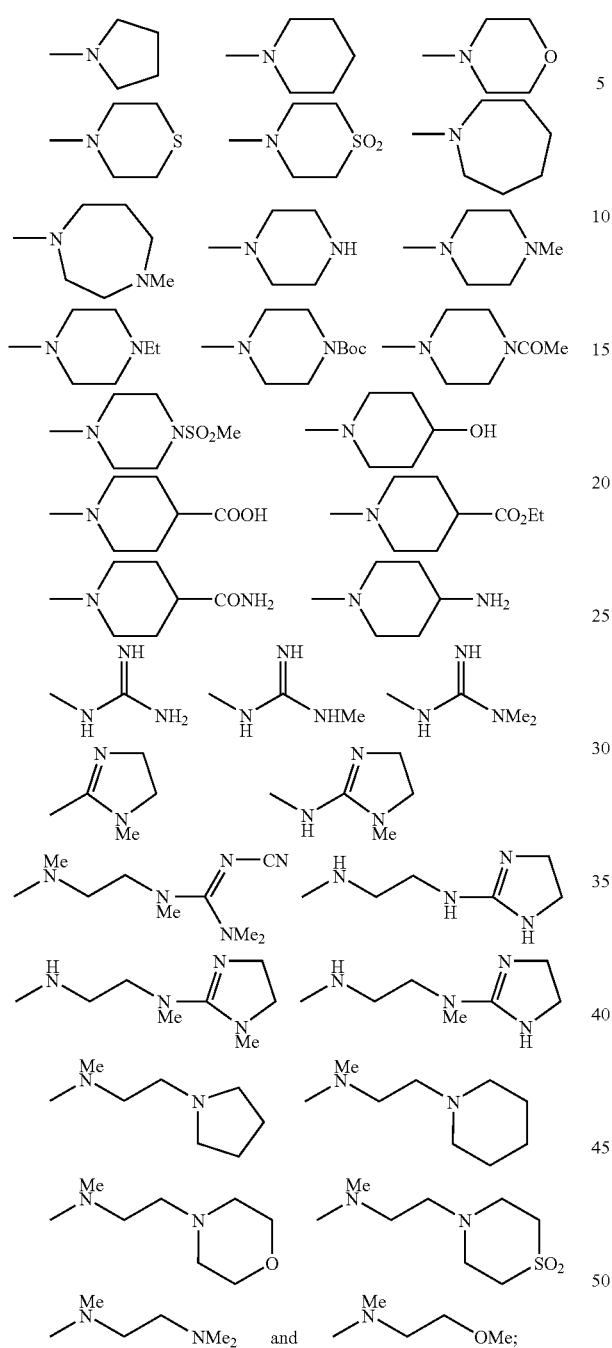
each $R^{1d2}$ and $R^{1d3}$ is independently selected from the group consisting of:
H, —Me, —F, —Cl, —Br, —I, —CH$_2$—CF$_3$, —CN, —CO$_2$H, —CO$_2$Me, —CO$_2$Et, —CONH$_2$, —CONHMe, —CONMe$_2$, —CH$_2$NH$_2$, —CH$_2$NHMe, —CH$_2$NMe$_2$, —COMe, —CH$_2$COOH, —CH$_2$COOEt,
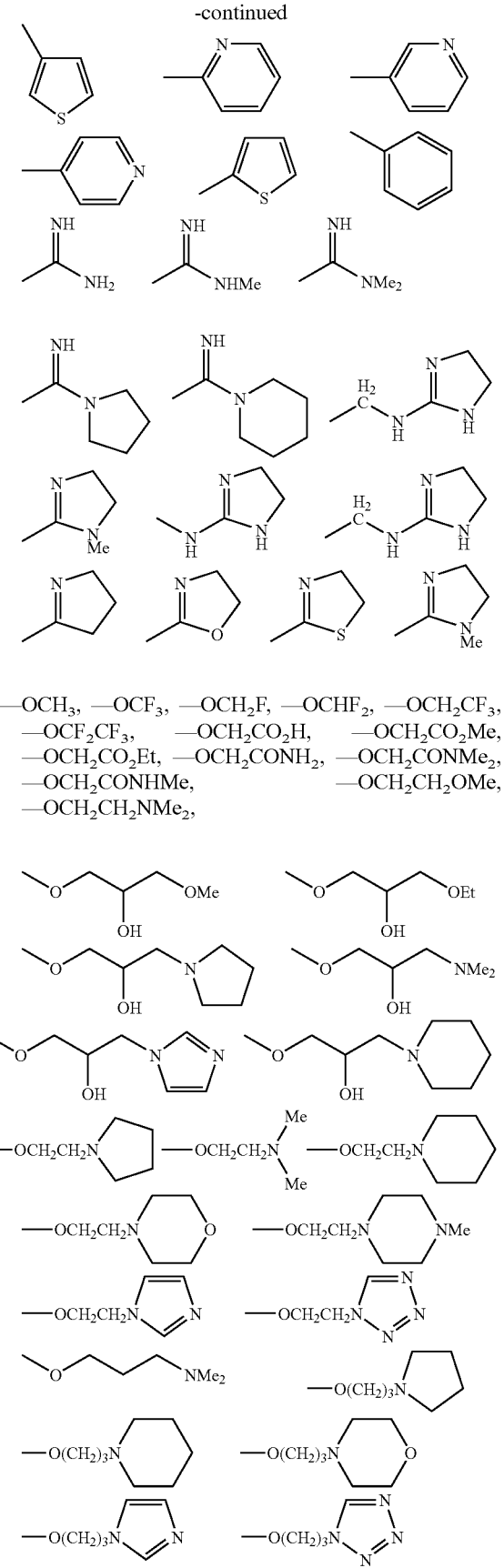
—OCH$_3$, —OCF$_3$, —OCH$_2$F, —OCHF$_2$, —OCH$_2$CF$_3$, —OCF$_2$CF$_3$, —OCH$_2$CO$_2$H, —OCH$_2$CO$_2$Me, —OCH$_2$CO$_2$Et, —OCH$_2$CONH$_2$, —OCH$_2$CONMe$_2$, —OCH$_2$CONHMe, —OCH$_2$CH$_2$OMe, —OCH$_2$CH$_2$NMe$_2$, -continued
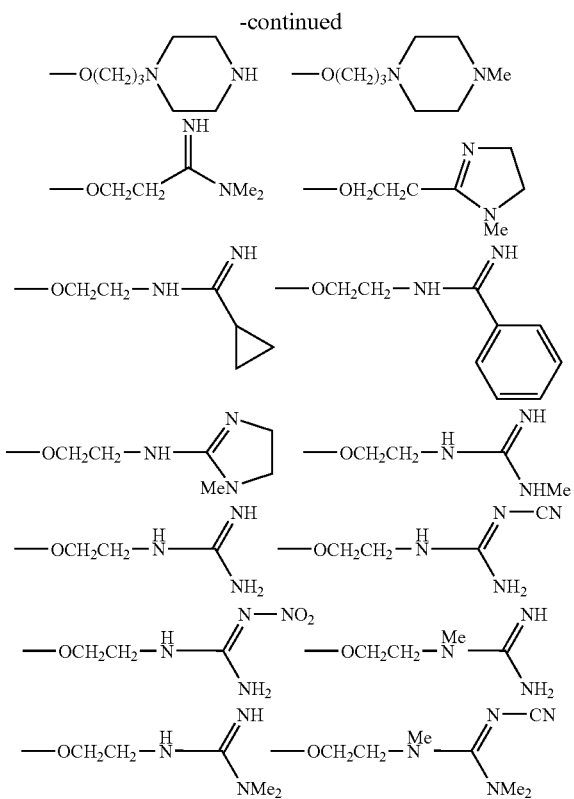
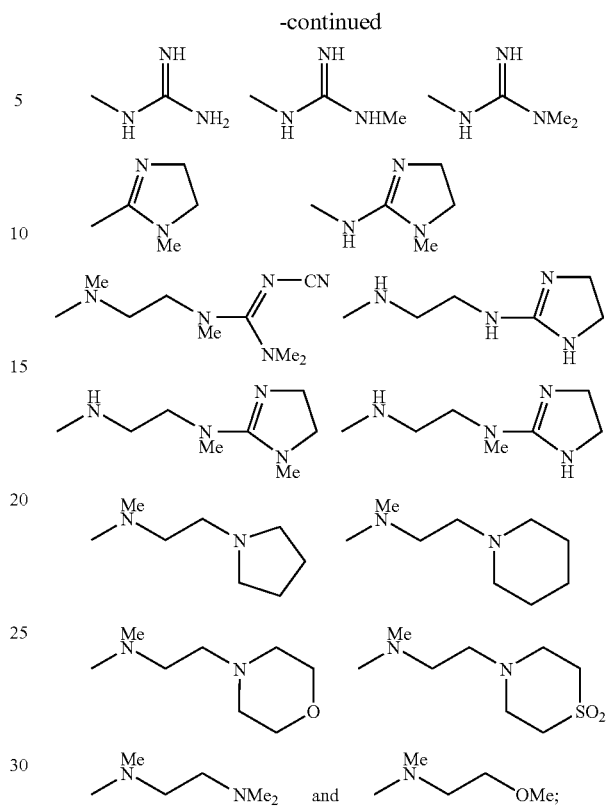
—SCH₃, —SO₂NH₂, —SO₂CH₃, —SO₂NMe₂, —SCH₂CH₂OMe, —SO₂CH₂CH₂OMe, —SO₂NH₂, —SO₂CH₃, —SO₂NMe₂, —SO₂CH₂CH₂NMe, —NMe₂, —NHCH₂CH₂NMe₂, —N(CH₂CH₂OH)₂, —N(CH₂CH₂OMe)₂, —NHCH₂CO₂H, —NHCH₂CO₂Et, —NHCH₂CO₂Et, —NHCH₂CONH₂, —NHCH₂CONMe₂, —N(Me)CH₂CH₂NMe₂, —N(Me)CH₂CH₂OMe;
and A is independently selected from the group consisting of:
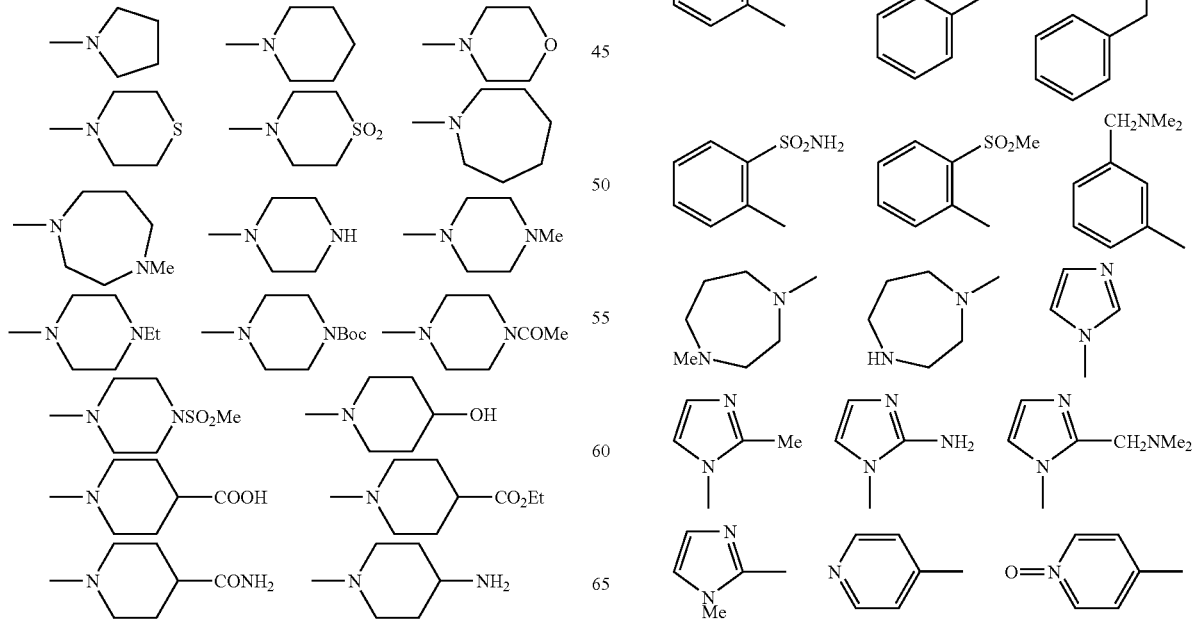

-continued
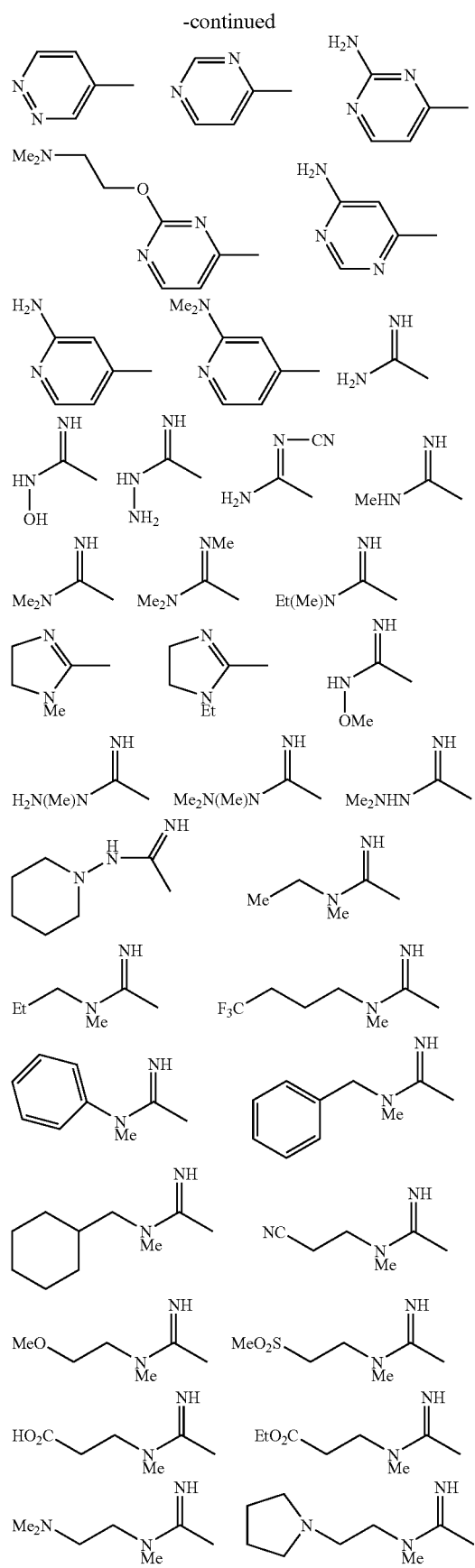
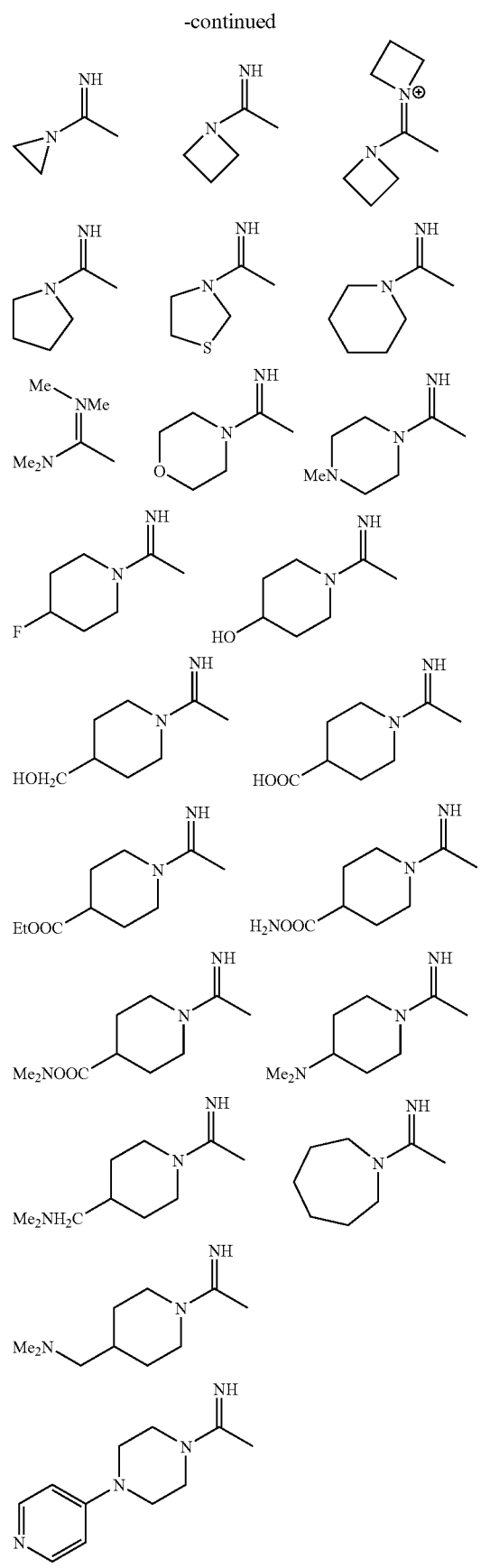

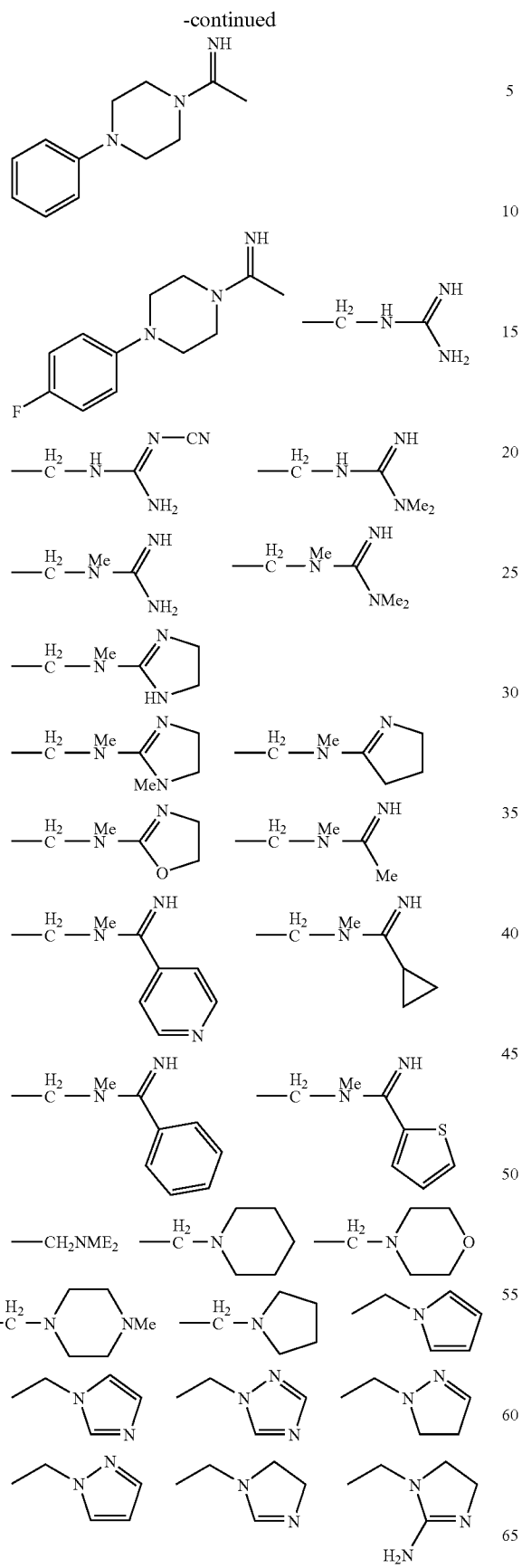
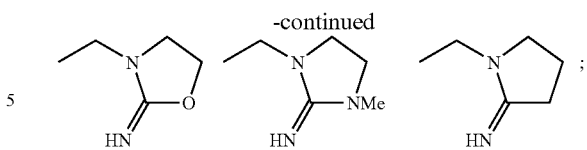
and all pharmaceutically acceptable isomers, salts, hydrates, solvates and prodrug derivatives thereof.
5. The compound according to claim 1, having the formula:
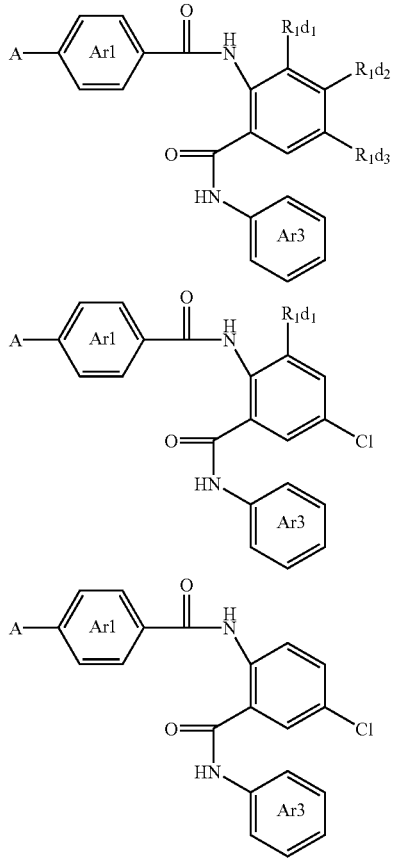
wherein Ar1 is independently selected from the group consisting of:

-continued

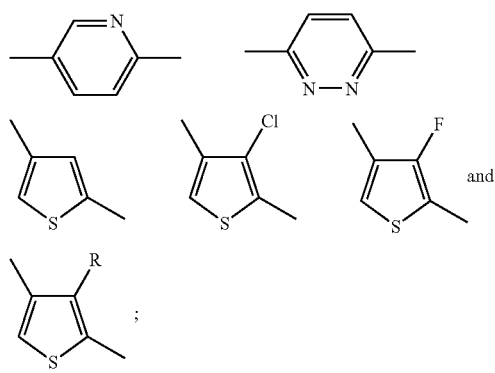

each R is independently selected from the group consisting of Cl, OMe, NHMe, —NMe$_2$, —OCH$_2$CH$_2$OMe, —OCH$_2$CH$_2$NMe$_2$,

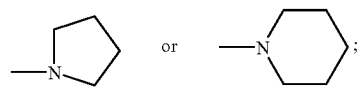

Ar3 is

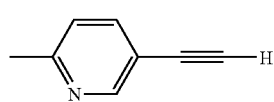

each R$^{1d1}$ is independently selected from the group consisting of H, —Me, —Cl, —OCH$_3$, —OCH$_2$CH$_2$OMe, —OCH$_2$CH$_2$NMe$_2$, —NMe$_2$, —N(Me)CH$_2$CH$_2$NMe$_2$, —N(Me)CH$_2$CH$_2$OMe,

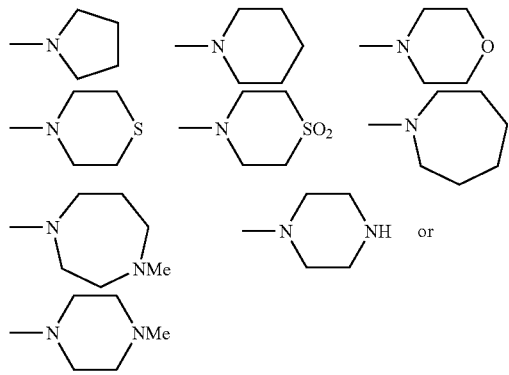

each R$^{1d1}$ and R$^{1d3}$ is independently selected from the group consisting of:
H, —C≡CH, —Me, —F, —Cl, —Br, —CF$_3$, —CN, —CO$_2$H, —CO$_2$Me, —CO$_2$Et, —CONH$_2$, —CH$_2$NMe$_2$, —COMe, —NMe$_2$, —SMe, —SCH$_2$CH$_2$OMe, —SO$_2$CH$_2$CH$_2$OMe, —SCH$_3$, —SO$_2$NH$_2$, —SO$_2$CH$_3$, —SO$_2$NMe$_2$, and —SO$_2$CH$_2$CH$_2$NMe$_2$;

and A is independently selected from the group consisting of:

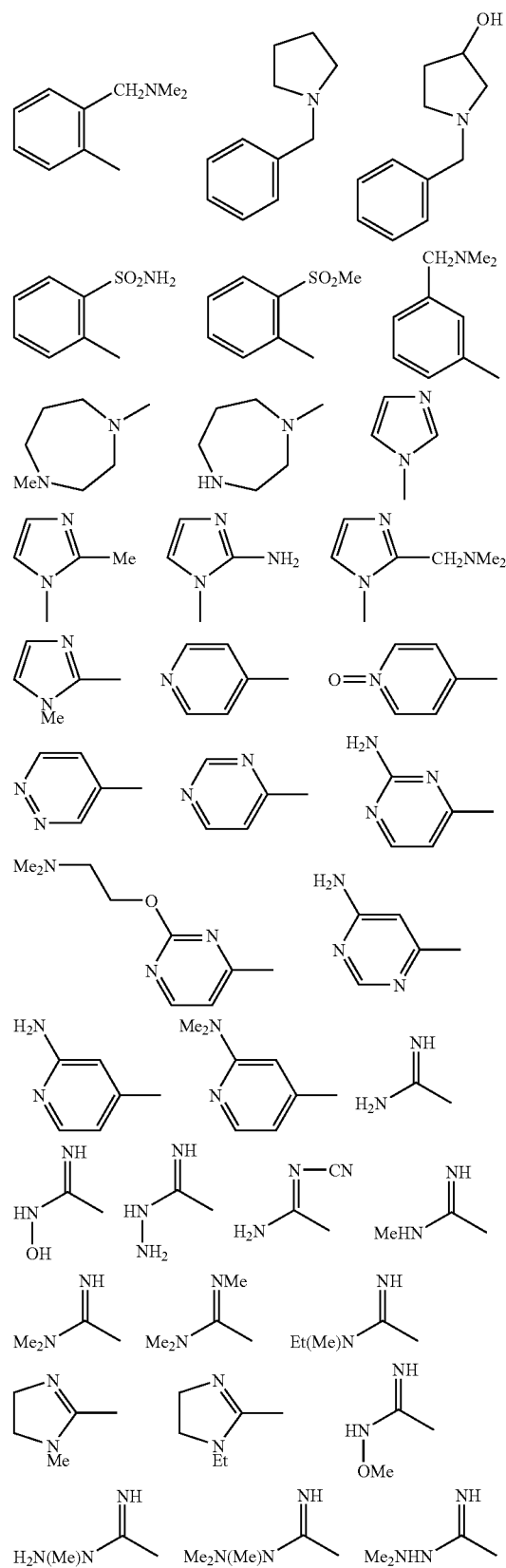

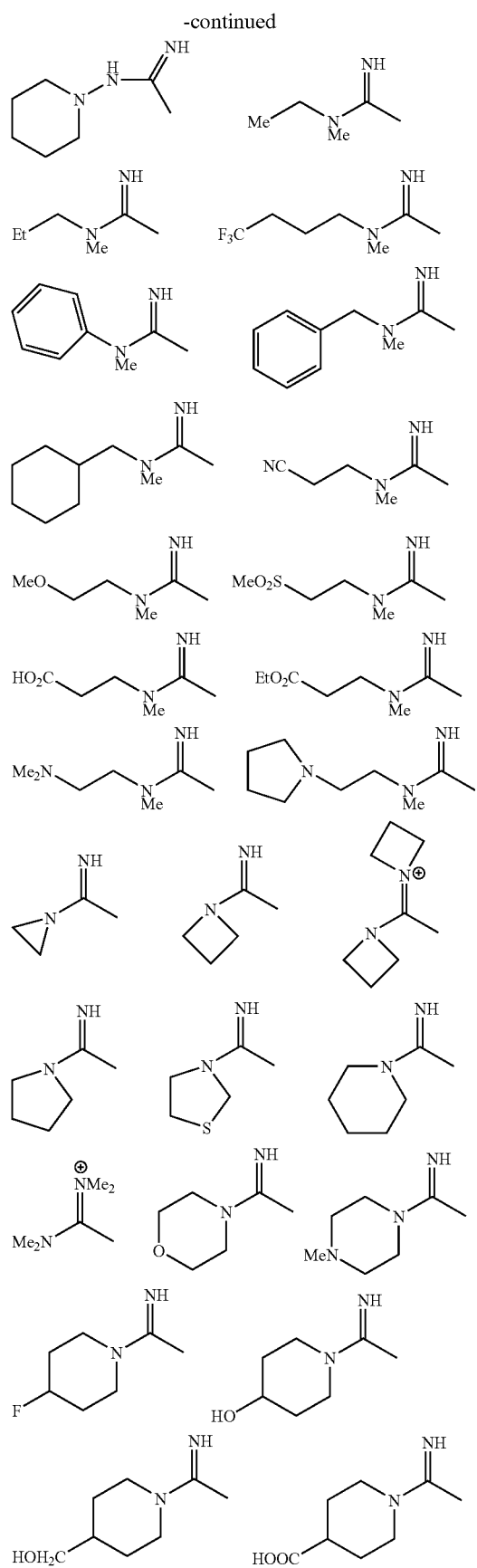
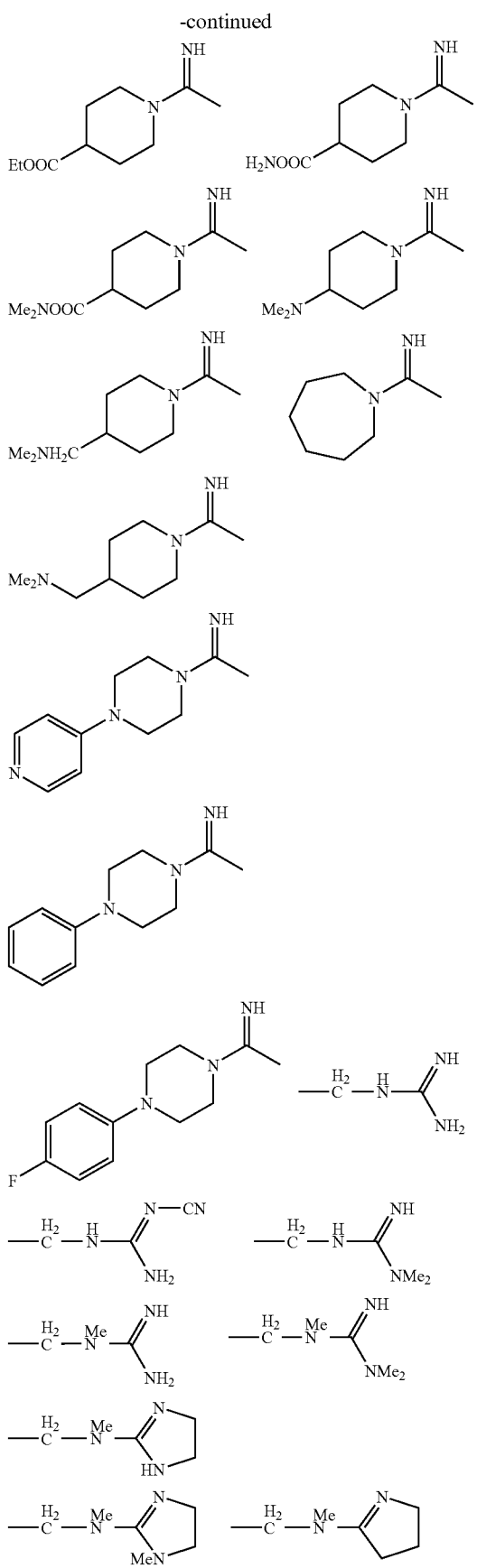

-continued
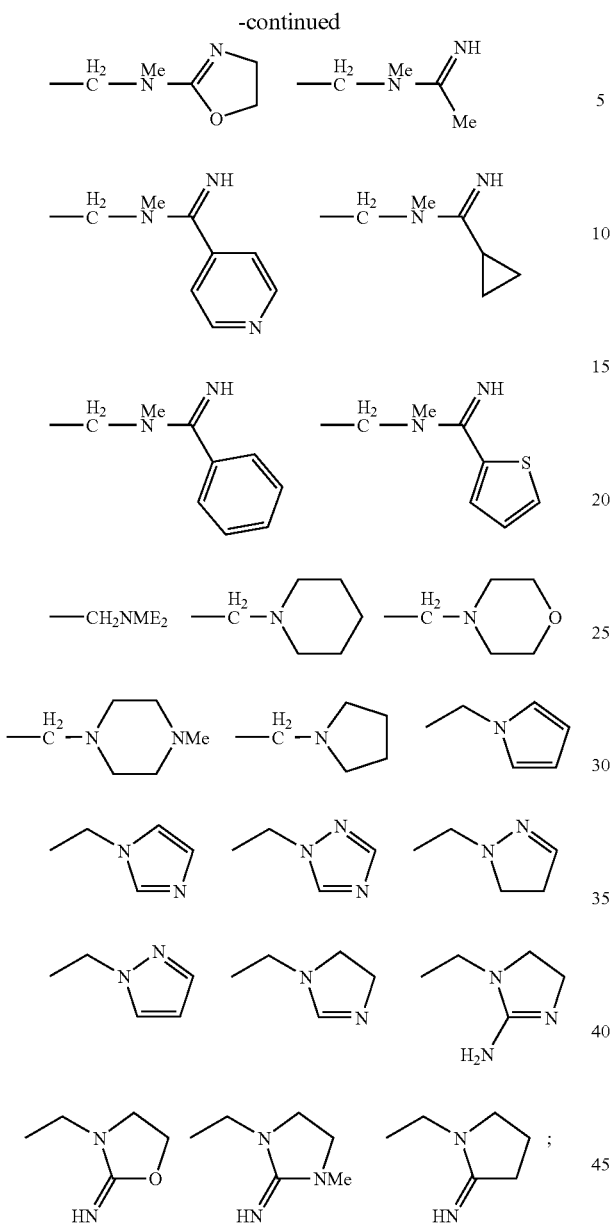
and pharmaceutically acceptable isomers salts, hydrates, solvates and prodrug derivatives thereof.
6. The compound according to claim 1 having the formula:
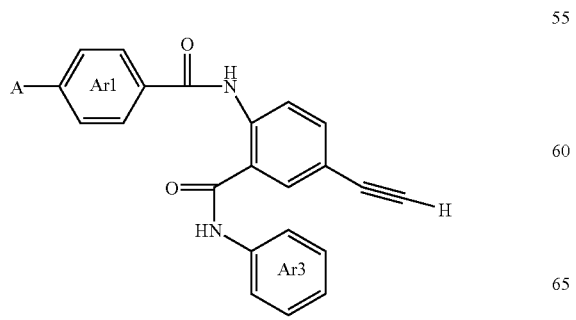
-continued
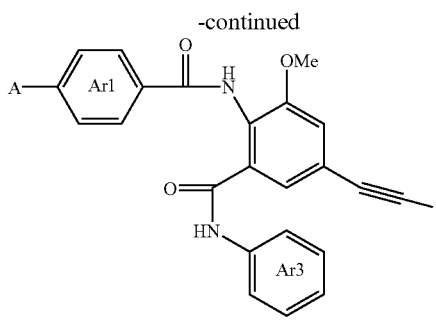
wherein:
Ar1 is independently selected from the group consisting of:
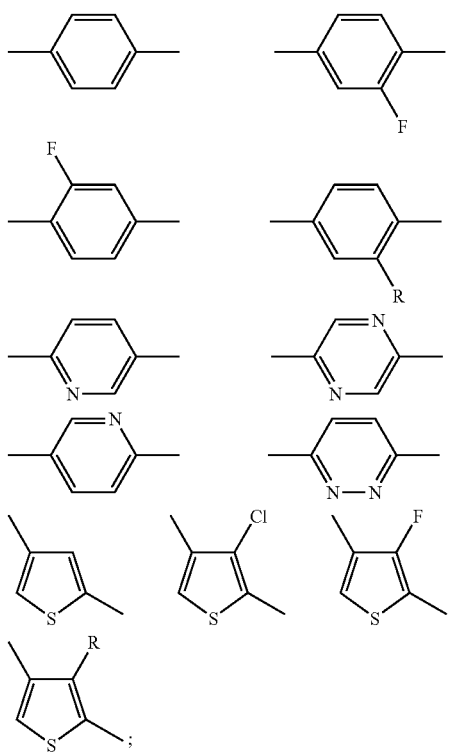
each R is independently selected from the group consisting of Cl, OMe, NHMe, —NMe$_2$, —OCH$_2$CH$_2$OMe, —OCH$_2$CH$_2$NMe$_2$,
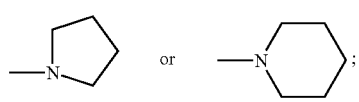
Ar3 is
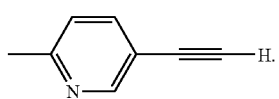

7. The compound according to claim 1 having the formula:
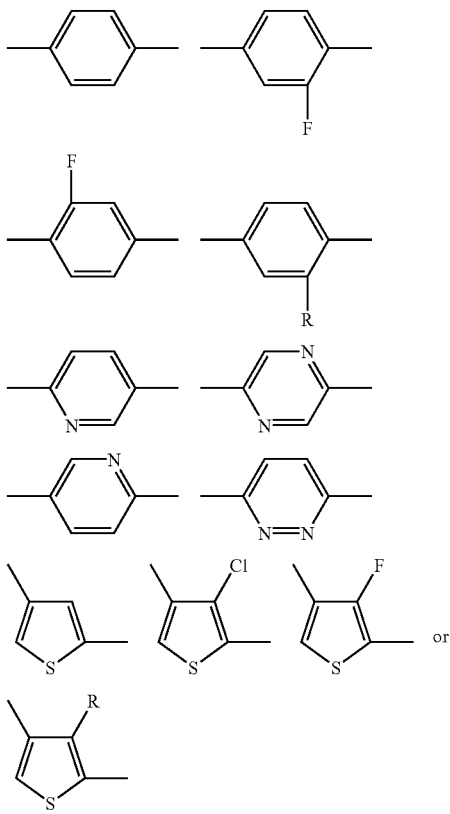
wherein:
Ar1 is independently selected from the group consisting of:
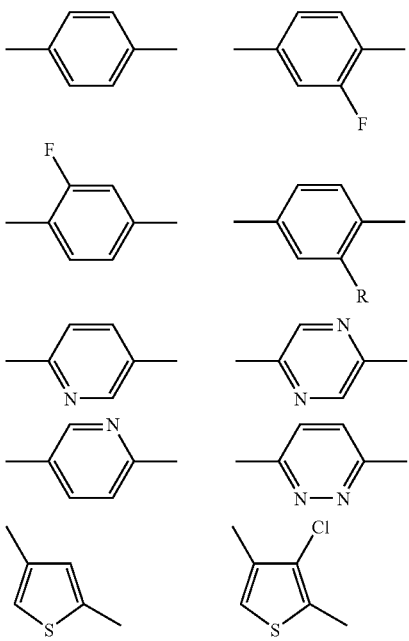
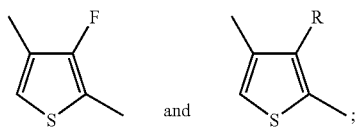
each R is independently selected from the group consisting of —Cl, —OMe, —NHMe, —NMe$_2$, —OCH$_2$CH$_2$OMe, —OCH$_2$CH$_2$NMe$_2$,
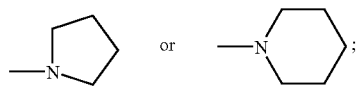
and A is independently selected from the group consisting of:
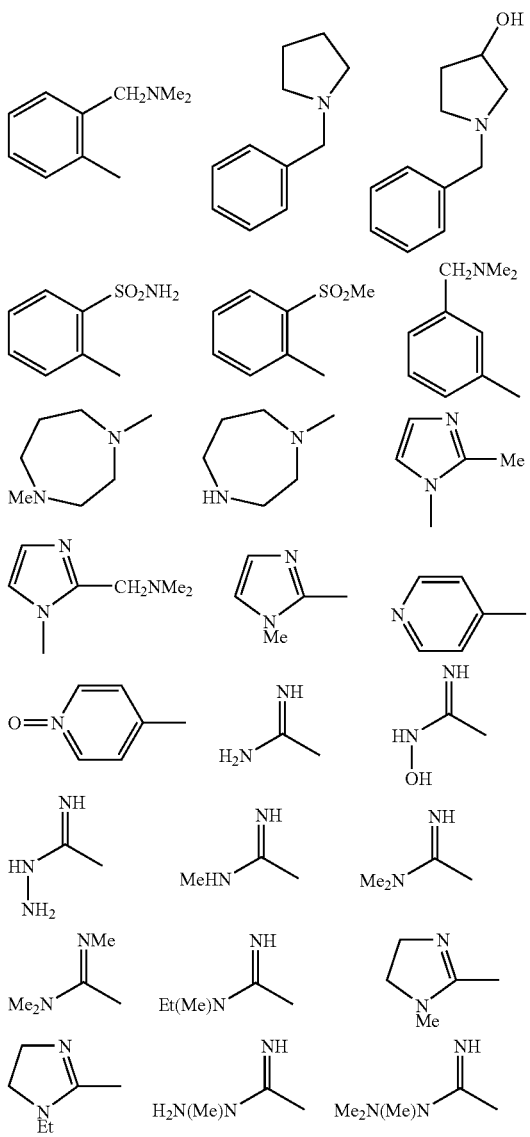

-continued
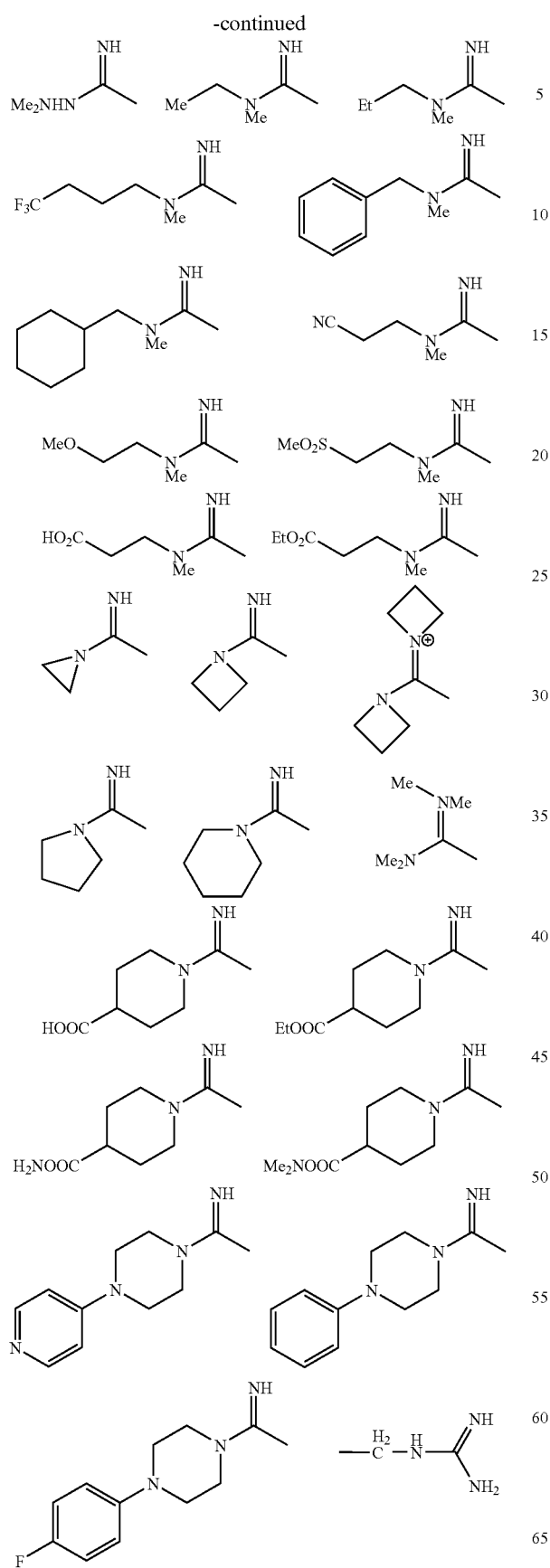
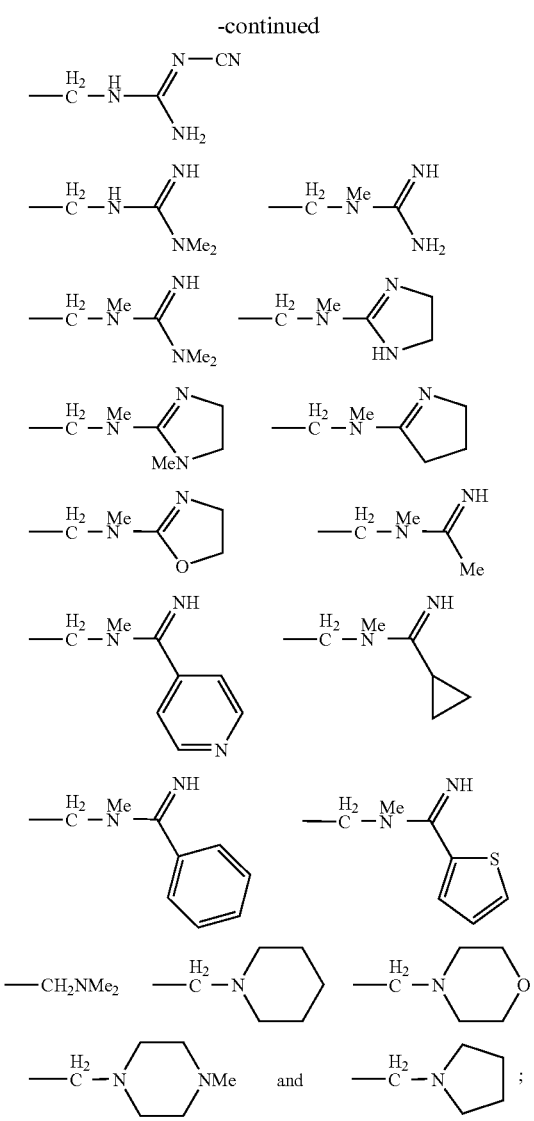
and all pharmaceutically acceptable isomers, salts, hydrates, solvates and prodrug derivatives thereof.
8. The compound according to claim 1 having the formula:
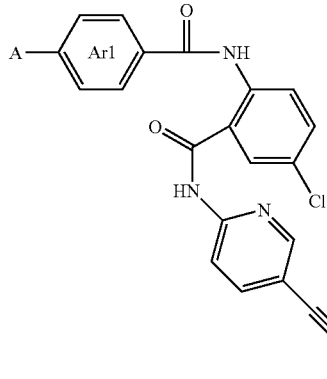

301
-continued
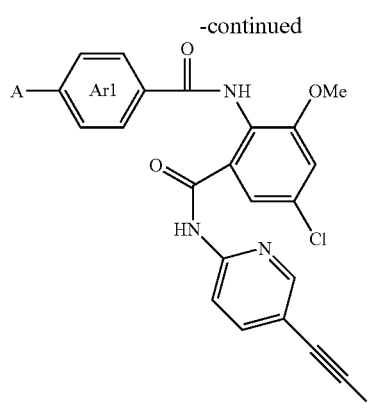
wherein:
Ar1 is independently
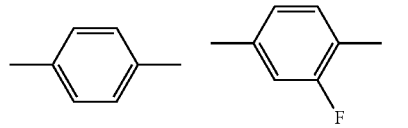
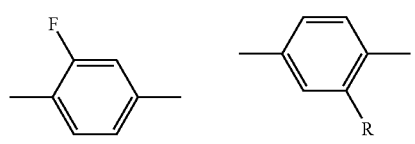
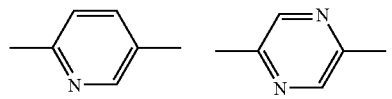
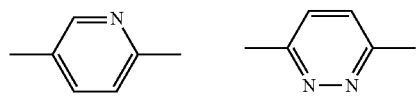
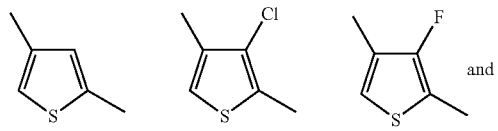 and
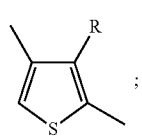;
each R is independently selected from the group consisting of —Cl, —OMe, —NMe$_2$, —OCH$_2$CH$_2$OMe, —OCH$_2$CH$_2$NMe$_2$,
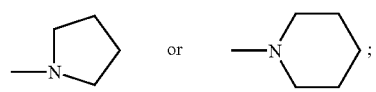;
302
A is independently selected from the group consisting of:
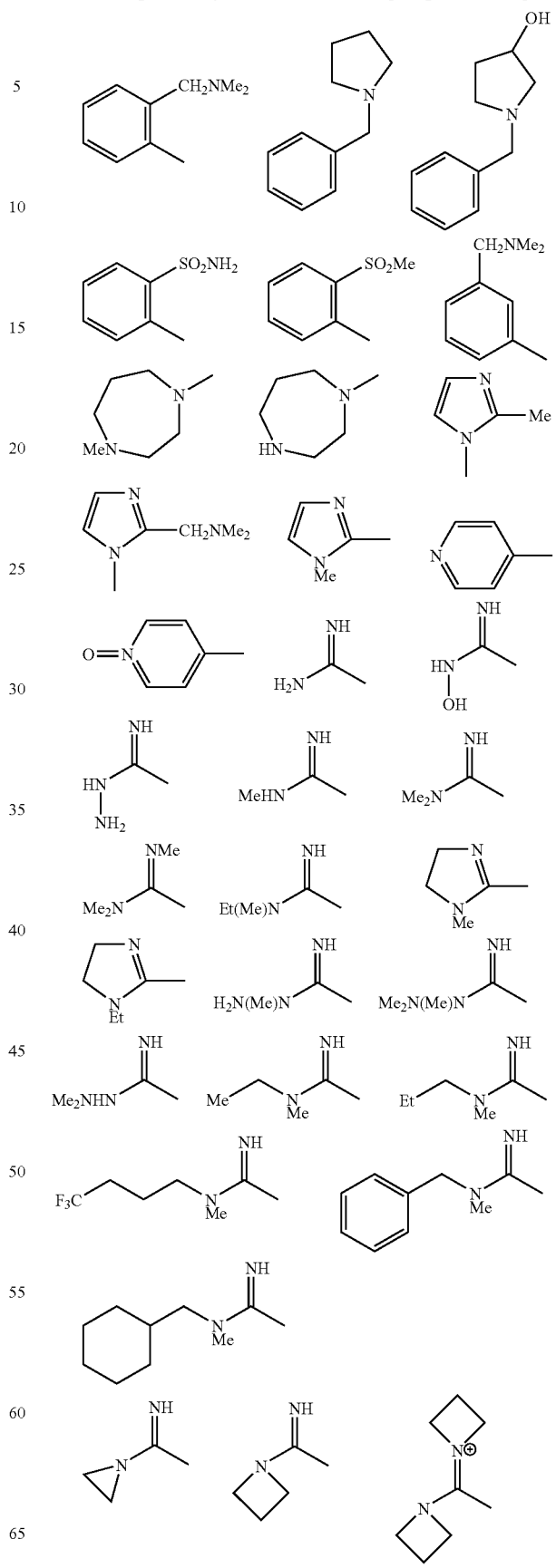

-continued

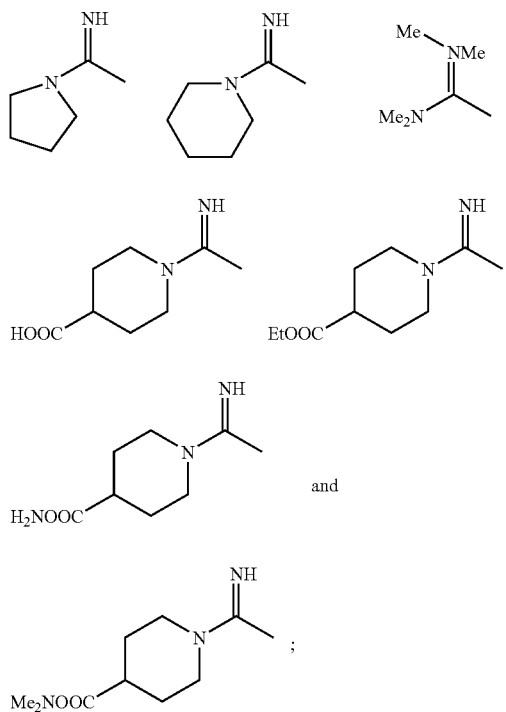

and all pharmaceutically acceptable isomers, salts, hydrates, solvates and prodrug derivatives thereof.

9. The compound according to claim 1 having the formula

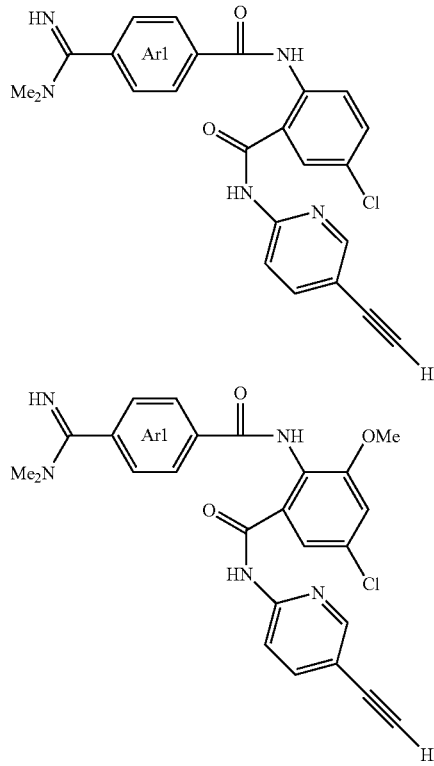

wherein
Ar1 is independently selected from the group consisting of:

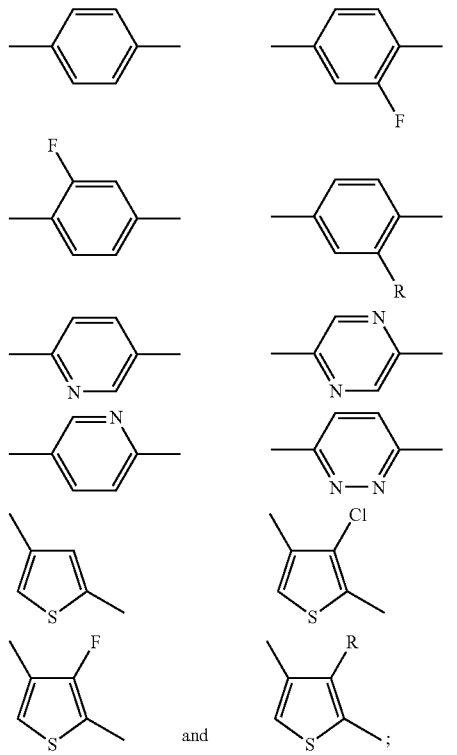

each R is independently selected from the group consisting of —Cl, —OMe, —NHMe, —NMe$_2$, —OCH$_2$CH$_2$OMe, and —OCH$_2$CH$_2$NMe$_2$;

A is independently selected from the group consisting of:

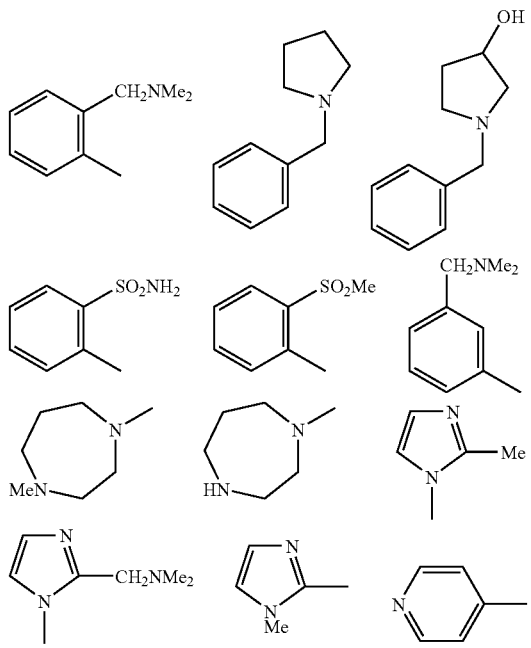

-continued

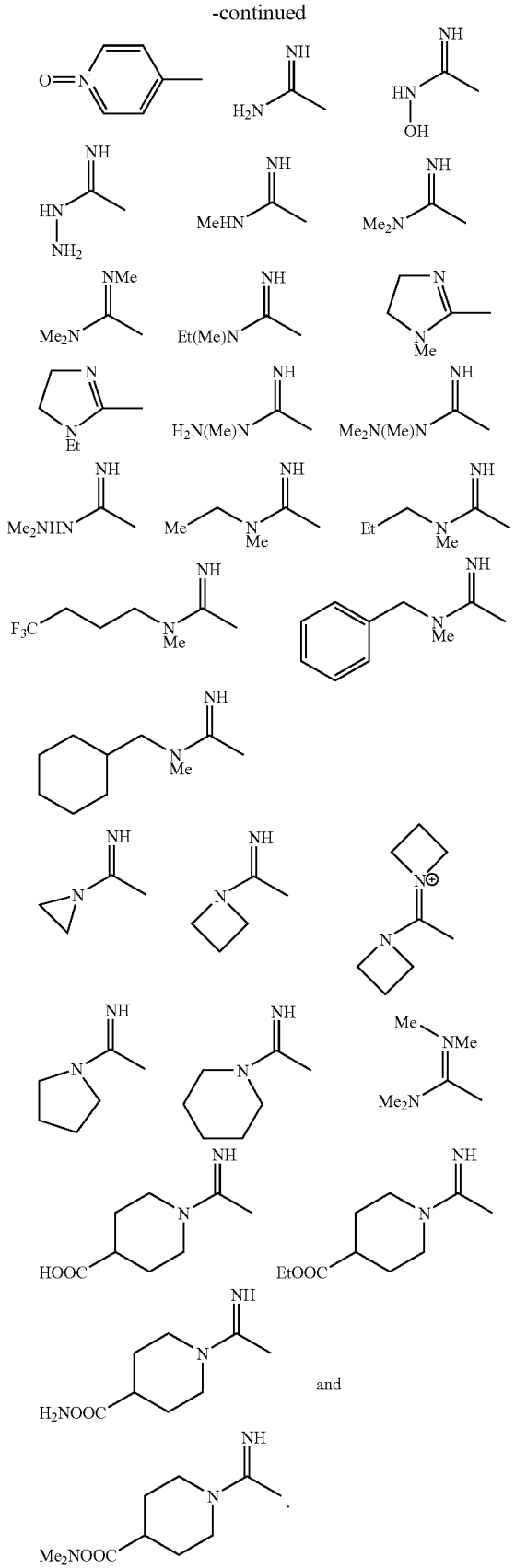

and

10. The compound according to claim 1 having the formula

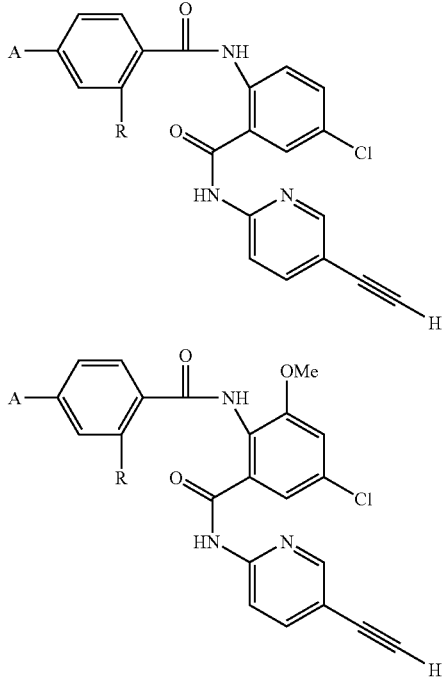

wherein
each R is independently selected from the group consisting of —H, —F, —Cl, —OMe, —NMe$_2$, —OCH$_2$CH$_2$OMe, —OCH$_2$CH$_2$NMe$_2$,

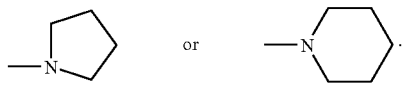

11. The compound according to claim 1 having the formula:

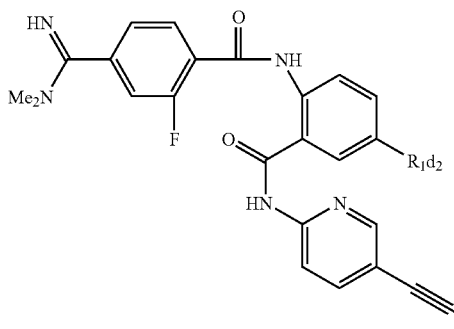

wherein
each $R^{1d2}$ is independently selected from the group consisting of:
H, —C≡CH, —C—≡—CH, —Me, —F, —Cl, —Br, —CF$_3$, —CN, —CO$_2$H, —CO$_2$Me, —CO$_2$Et, —CONH$_2$, —CH$_2$NMe$_2$, —COMe, —NMe$_2$, —SMe, —SCH$_2$CH$_2$OMe, —SO$_2$CH$_2$CH$_2$OMe, —SCH$_3$, —SO$_2$NH$_2$, —SO$_2$CH$_3$, —SO$_2$NMe$_2$, and —SO$_2$CH$_2$CH$_2$NMe$_2$.

12. The compound according to claim 1 having the formula:

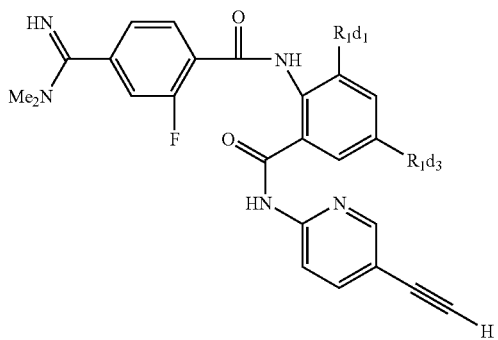

wherein:
each $R^{1d1}$ is independently selected from the group consisting of H, OMe, and NMe$_2$:
each $R^{1d3}$ is independently selected from the group consisting of Cl, Br, —C≡CH, and —C═══—CH;
and all pharmaceutically acceptable isomers, salts, hydrates, solvates and prodrug derivatives thereof.

13. The compound according to claim 1 having the formula:

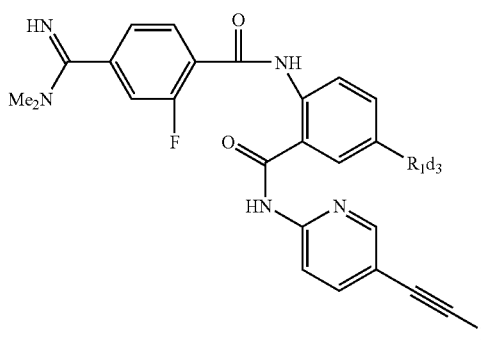

wherein:
each $R^{1d3}$ is independently selected from the group consisting of Cl, Br, —C≡CH, and C═══—CH;
and all pharmaceutically acceptable isomers, salts, hydrates, solvates and prodrug derivatives thereof.

14. The compound according to claim 1 having the formula:

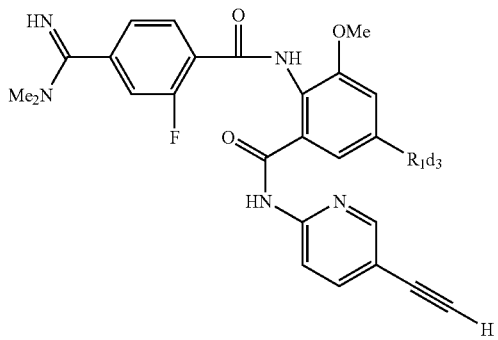

wherein:
each $R^{1d3}$ is independently selected from the group consisting of Cl, Br, —C≡CH, and C═══—CH;
and all pharmaceutically acceptable isomers, salts, hydrates, solvates and prodrug derivatives thereof.

15. The compound according to claim 1 having the formula:

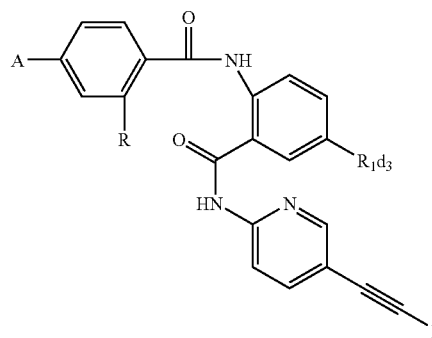

wherein:
each R is independently selected from the group consisting of —H, —F, —Cl, —OMe, —NMe$_2$, —OCH$_2$CH$_2$OMe, —OCH$_2$CH$_2$NMe$_2$,

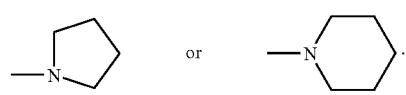

each $R^{1d3}$ is independently selected from the group consisting of Cl, Br, —C≡CH, and C═══—CH.

16. The compound according to claim 1 having the formula:

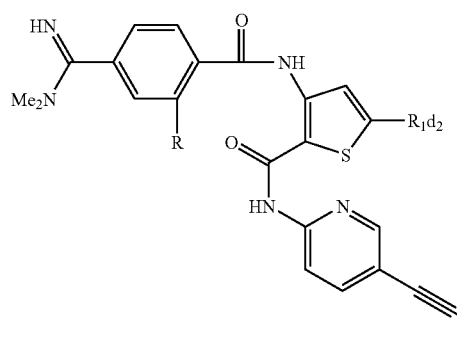

wherein:
each R is independently selected from the group consisting of —H, —F, —Cl, —OMe, —NMe$_2$, —OCH$_2$CH$_2$OMe, —OCH$_2$CH$_2$NMe$_2$,

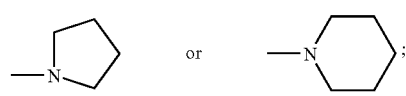

each $R^{1d2}$ is independently selected from the group consisting of Cl, Br, —C≡CH, and C═══—CH;

and all pharmaceutically acceptable isomers, salts, hydrates, solvates and prodrug derivatives thereof.

17. The compound according to claim 1 having the formula:

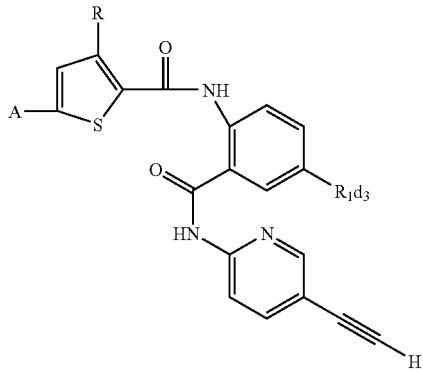

wherein:
each R is independently selected from the group consisting of —H, —F, —Cl, —OMe, —NMe₂, —OCH₂CH₂OMe, —OCH₂CH₂NMe₂,

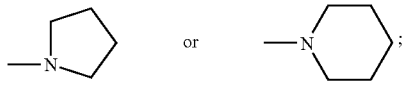

each R$^{1d3}$ is independently selected from the group consisting of Cl, Br, —C≡CH, and C—≡—CH.

18. The compound according to claim 1 having the formula:

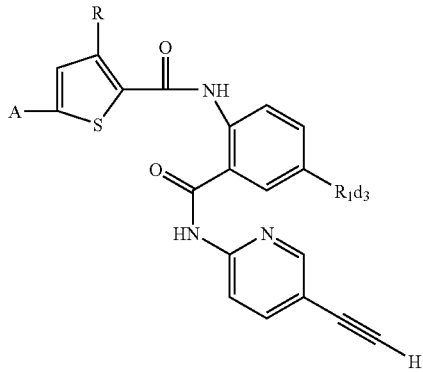

wherein:
each R is independently selected from the group consisting of —H, —F, —Cl, —OMe, —SMe, —NMe₂, —OCH₂CH₂OMe, —OCH₂CH₂NMe₂,

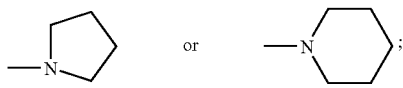

each R$^{1d3}$ is independently selected from the group consisting of Cl, Br, —C≡CH, and C—≡—CH.

19. The compound according to claim 1 having the formula:

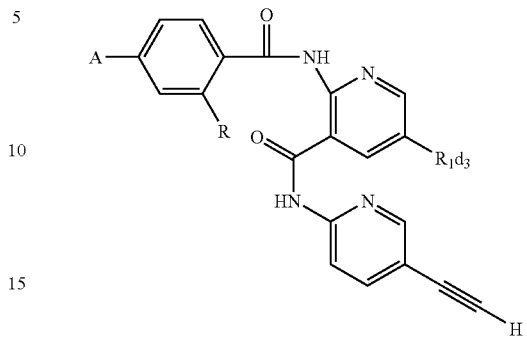

wherein:
each R is independently selected from the group consisting of Cl, OMe, —NMe₂, —OCH₂CH₂OMe, —OCH₂CH₂NMe₂,

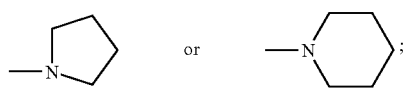

each R$^{1d3}$ is independently selected from the group consisting of Cl, Br, —C≡CH, and C—≡—CH.

20. The compound according to claim 1 selected from the group consisting of:
{4-[(dimethylamino)iminomethyl]phenyl}-N-{4-chloro-2-[N-(5-ethynyl(2-pyridyl))carbamoyl]phenyl}-carboxamide;
N-{4-chloro-2-[N-(5-ethynyl(2-pyridyl))carbamoyl]phenyl}[4-(1-methyl(2-imidazolin-2-yl))phenyl]-carboxamide;
N-(2-[N-(5-ethynyl(2-pyridyl))carbamoyl]-4-chlorophenyl}[4-(iminopyrrolidinylmethyl)phenyl]carboxamide;
N-{2-[N-(5-ethynyl(2-pyridyl))carbamoyl]-4-chlorophenyl}[4-(piperidyliminomethyl)phenyl]carboxamide;
ethyl 1-{[4-(N-{4-chloro-2-[N-(5-ethynyl(2-pyridyl))carbamoyl]phenyl}carbamoyl)phenyl]iminomethyl}-piperidine-4-carboxylate;
1-{[4-(N-{4-chloro-2-[N-(5-ethynyl(2-pyridyl))carbamoyl]phenyl}carbamoyl)phenyl]iminomethyl}-piperidine-4-carboxamide;
{4-[(N-ethylmethylamino)iminomethyl]phenyl}-N-{4-chloro-2-[N-(5-ethynyl(2-pyridyl))carbamoyl]phenyl}-carboxamide;
{4-[(N-methylpropylamino)iminomethyl]phenyl}-N-{4-chloro-2-[N-(5-ethynyl(2-pyridyl))carbamoyl]phenyl}-carboxamide;
{4-[Azetidinylazetidinylidenemethyl]phenyl}-N-{4-chloro-2-[N-(5-ethynyl(2-pyridyl))carbamoyl]phenyl}-carboxamide;
[4-({[2-(dimethylamino)ethyl]methylamino}iminomethyl)phenyl]-N-{4-chloro-2-[N-(5-ethynyl(2-pyridyl))carbamoyl]phenyl}carboxamide;
{4-[(N-methyl-2-propynylamino)iminomethyl]phenyl}-N-{4-chloro-2-[N-(5-ethynyl(2-pyridyl))carbamoyl]phenyl}-carboxamide;

{4-[(N-methyl-2-cyanoethylamino)iminomethyl]phenyl}-N-(4-chloro-2-[N-(5-ethynyl(2-pyridyl))carbamoyl]phenyl}-carboxamide;

{4-[(dimethylamino)iminomethyl]-2-fluorophenyl}-N-{4-chloro-2-[N-(5-ethynyl(2-pyridyl))carbamoyl]phenyl}-carboxamide;

N-{2-[N-(5-ethynyl(2-pyridyl))carbamoyl]-4-chlorophenyl}[4-(iminopyrrolidinylmethyl)-2-fluorophenyl]carboxamide;

ethyl 1-{[4-(N-{4-chloro-2-[N-(5-ethynyl(2-pyridyl))carbamoyl]phenyl}carbamoyl)-3-fluorophenyl]iminomethyl}piperidine-4-carboxylate;

1-{[4-(N-{4-chloro-2-[N-(5-ethynyl(2-pyridyl))carbamoyl]phenyl}carbamoyl)-3-fluorophenyl]iminomethyl}piperidine-4-carboxamide;

N-{4-chloro-2-[N-(5-ethynyl(2-pyridyl))carbamoyl]phenyl}[4-(1-methyl(2-imidazolin-2-yl))-2-fluorophenyl]-carboxamide;

{4-[(N-methyl(phenylmethyl)amino)iminomethyl]-2-fluorophenyl}-N-{4-chloro-2-[N-(5-ethynyl(2-pyridyl))carbamoyl]phenyl}-carboxamide;

{4-[(N-(2-methoxyethyl)methylamino)iminomethyl]-2-fluorophenyl}-N-{4-chloro-2-[N-(5-ethynyl(2-pyridyl))carbamoyl]phenyl}-carboxamide;

{4-[(N-methyl(furanylmethyl)amino)iminomethyl]-2-fluorophenyl}-N-{4-chloro-2-[N-(5-ethynyl(2-pyridyl))carbamoyl]phenyl}-carboxamide;

N-(4-chloro-2-[N-(5-ethynyl(2-pyridyl))carbamoyl]phenyl}[4-(1-(2-hydroxyethyl)(2-imidazolin-2-yl))-2-fluorophenyl]-carboxamide;

N-{4-chloro-2-[N-(5-ethynyl(2-pyridyl))carbamoyl]phenyl}[4-(1-propyl(2-imidazolin-2-yl))-2-fluorophenyl]-carboxamide;

{4-[(N-(2-[1,3]Dioxolan-2-yl-ethyl)methylamino)iminomethyl]-2-fluorophenyl}-N-{4-chloro-2-[N-(5-ethynyl(2-pyridyl))carbamoyl]phenyl}-carboxamide;

1-{[4-(N-{4-chloro-2-[N-(5-ethynyl(2-pyridyl))carbamoyl]phenyl}carbamoyl)-3-fluorophenyl]iminomethyl}-4-phenylpiperazine;

{4-[(dimethylamino)iminomethyl]phenyl}-N-{4-methoxy-2-[N-(5-ethynyl(2-pyridyl))carbamoyl]phenyl}-carboxamide;

{4-[(dimethylamino)iminomethyl]phenyl}-N-{4-methoxy-2-[N-(5-ethynyl(2-pyridyl))carbamoyl]phenyl}-carboxamide;

N-{2-[N-(5-ethynyl(2-pyridyl))carbamoyl]-4-methoxyphenyl}[4-(iminopyrrolidinylmethyl)phenyl]carboxamide;

N-{2-[N-(5-ethynyl(2-pyridyl))carbamoyl]-4-methoxyphenyl}[4-(iminopiperidylmethyl)phenyl]carboxamide;

ethyl 1-{[4-(N-{4-methoxy-2-[N-(5-ethynyl(2-pyridyl))carbamoyl]phenyl}carbamoyl)phenyl]iminomethyl}-piperidine-4-carboxylate;

(4-[(dimethylamino)iminomethyl]-2-fluorophenyl}-N-{4-methoxy-2-[N-(5-ethynyl(2-pyridyl))carbamoyl]phenyl}-carboxamide;

N-{4-methoxy-2-[N-(5-ethynyl(2-pyridyl))carbamoyl]phenyl}[4-(1-methyl(2-imidazolin-2-yl))-2-fluorophenyl-carboxamide;

N-{2-[N-(5-ethynyl(2-pyridyl))carbamoyl]-4-methoxyphenyl}[4-(iminopyrrolidinylmethyl)-2-fluorophenyl]carboxamide;

N-{2-[N-(5-ethynyl(2-pyridyl))carbamoyl]-4-chlorophenyl}[4-(iminopiperidinylmethyl)-2-fluorophenyl]carboxamide;

ethyl 1-{[4-(N-{4-methoxy-2-[N-(5-ethynyl(2-pyridyl))carbamoyl]phenyl}carbamoyl)-3-fluorophenyl]iminomethyl}piperidine-4-carboxylate;

{4-[(N-methylethylamino)iminomethyl]-2-fluorophenyl}-N-{4-methoxy-2-[N-(5-ethynyl(2-pyridyl))carbamoyl]phenyl}carboxamide;

{4-[(N-propylmethylamino)iminomethyl]-2-fluorophenyl}-N-4-methoxy-2-[N-(5-ethynyl(2-pyridyl))carbamoyl]phenyl}carboxamide;

{4-[Azetidinyliminomethyl]-2-fluorophenyl}-N-{4-methoxy-2-[N-(5-ethynyl(2-pyridyl))carbamoyl]phenyl}carboxamide;

{4-[(dimethylamino)iminomethyl]phenyl}-N-{6-methoxy-2-[N-(5-ethynyl(2-pyridyl))carbamoyl]phenyl}carboxamide;

{4-[(dimethylamino)iminomethyl]phenyl}-N-{6-methoxy-2-[N-(5-ethynyl(2-pyridyl))carbamoyl]phenyl}-carboxamide;

N-{2-[N-(5-ethynyl(2-pyridyl))carbamoyl]-6-methoxyphenyl}[4-(iminopyrrolidinylmethyl)phenyl]carboxamide;

N-{2-[N-(5-ethynyl(2-pyridyl))carbamoyl]-6-methoxyphenyl}[4-(iminopiperidylmethyl)phenyl]carboxamide;

ethyl 1-{[4-(N-{6-methoxy-2-[N-(5-ethynyl(2-pyridyl))carbamoyl]phenyl}carbamoyl)phenyl]iminomethyl}-piperidine-4-carboxylate;

{4-[(N-ethylmethylamino)iminomethyl]phenyl}-N-6-methoxy-2-[N-(5-ethynyl(2-pyridyl))carbamoyl]phenyl}-carboxamide;

{4-[(N-methylpropylamino)iminomethyl]phenyl}-N-{6-methoxy-2-[n-(5-ethynyl(2-pyridyl))carbamoyl]phenyl}-carboxamide;

{4-[Azetidinyliminomethyl]phenyl}-N-{6-methoxy-2-[N-(5-ethynyl(2-pyridyl))carbamoyl]phenyl}-carboxamide;

{4-[Azetidinylazetidinylidenemethyl]phenyl}-N-{6-methoxy-2-[N-(5-ethynyl(2-pyridyl))carbamoyl]phenyl}-carboxamide;

[4-({[2-(dimethylamino)ethyl]methylamino}iminomethyl)phenyl]-N-{6-methoxy-2-[N-(5-ethynyl(2-pyridyl))carbamoyl]phenyl}carboxamide;

{4-[(N-methyl-2-propynylamino)iminomethyl]phenyl}-N-{6-methoxy-2-[N-(5-ethynyl(2-pyridyl))carbamoyl]phenyl}-carboxamide;

{4-[(dimethylamino)iminomethyl]phenyl}-N-{4-chloro-6-methoxy-2-[N-(5-ethynyl(2-pyridyl))carbamoyl]phenyl}-carboxamide;

N-{4-chloro-6-methoxy-2-[N-(5-ethynyl(2-pyridyl))carbamoyl]phenyl}[4-(1-methyl(2-imidazolin-2-yl))phenyl]-carboxamide;

N-{2-[N-(5-ethynyl(2-pyridyl))carbamoyl]-4-chloro-6-methoxyphenyl}[4-(iminopyrrolidinylmethyl)phenyl]carboxamide;

N-{2-[N-(5-ethynyl(2-pyridyl))carbamoyl]4-chloro-6-methoxyphenyl}[4-(iminopiperidylmethyl)phenyl]carboxamide;

ethyl 1-{[4-(N-{4-chloro-6-methoxy-2-[N-(5-ethynyl(2-pyridyl))carbamoyl]phenyl}carbamoyl)phenyl]iminomethyl}-piperidine-4-carboxylate;

1-{[4-(N-{4-chloro-6-methoxy-2-[N-(5-ethynyl(2-pyridyl))carbamoyl]phenyl}carbamoyl)phenyl]iminomethyl}-piperidine-4-carboxylic acid;

{4-[(N-ethylmethylamino)iminomethyl]phenyl}-N-{4-chloro-6-methoxy-2-[N-(5-ethynyl(2-pyridyl))carbamoyl]phenyl}-carboxamide;

{4-[(N-methylpropylamino)iminomethyl]phenyl}-N-{4-chloro-6-methoxy-2-[N-(5-ethynyl(2-pyridyl))carbamoyl]phenyl}-carboxamide;

4-[Azetidinylazetidinylidenemethy]phenyl)-N-{4-chloro-6-methoxy-2-[N-(5-ethynyl(2-pyridyl))carbamoyl]phenyl}-carboxamide;

1-{[4-(N-{4-chloro-6-methoxy-2-[N-(5-ethynyl(2-pyridyl))carbamoyl]phenyl}carbamoyl)phenyl]iminomethyl}-piperidine-4-carboxamide;

{4-[(dimethylamino)iminomethyl]-2-fluorophenyl-N-{4-chloro-6-methoxy-2-[N-(5-ethynyl(2-pyridyl))carbamoyl]phenyl}-carboxamide;

N-{4-chloro-6-methoxy-2-[N-(5-ethynyl(2-pyridyl))carbamoyl]phenyl}[4-(1-methyl(2-imidazolin-2-yl))-2-fluorophenyl]-carboxamide;

N-{2-[N-(5-ethynyl(2-pyridyl))carbamoyl]-4-chloro-6-methoxyphenyl}[4-(iminopyrrolidinylmethyl)-2-fluorophenyl]carboxamide;

N-{4-chloro-6-methoxy--2-[N-(5-ethynyl(2-pyridyl))carbamoyl]phenyl}[4-(1-methyl(2-imidazolin-2-yl))2-fluorophenyl]-carboxamide;

ethyl 1-{[4-(N-{4-chloro-6-methoxy-2-[N-(5-ethynyl(2-pyridyl))carbamoyl]phenyl}carbamoyl)-2-fluorophenyl]iminomethyl}-piperidine-4-carboxylate;

1-{[4-(N-{4-chloro-6-methoxy-2-[N-(5-ethynyl(2-pyridyl))carbamoyl]phenyl}carbamoyl)-2-fluorophenyl]iminomethyl}-piperidine4-carboxylic acid;

{4-[azetidinyliminomethyl]-2-fluorophenyl}-N-{4-chloro-6-methoxy-2-[N-(5-ethynyl(2-pyridyl))carbamoyl]phenyl}-carboxamide;

{4-[Azetidinylazetidinylidenemethy]-2-fluorophenyl}-N-{4-chloro-6-methoxy-2-[N-(5-ethynyl(2-pyridyl))carbamoyl]phenyl}-carboxamide;

{4-[(N-ethylmethylamino)iminomethyl]-2-fluorophenyl}-N-(4chloro-6-methoxy-2-[N-(5-ethynyl(2-pyridyl))carbamoyl]phenyl}-carboxamide;

{4-[(N-methylpropylamino)iminomethyl]-2-fluorophenyl}-N-{4-chloro-6-methoxy-2-[N-(5-ethynyl(2-pyridyl))carbamoyl]phenyl}-carboxamide;

[4-({[2-(dimethylamino)ethyl]methylamino}iminomethyl)-2-fluorophenyl]-N-{4-chloro-6-methoxy-2-[N-(5-ethynyl(2-pyridyl))carbamoyl]phenyl}carboxamide;

1-{[4-(N-{4-chloro-6methoxy-2-[N-(5-ethynyl(2-pyridyl))carbamoyl]-2-fluorophenyl}carbamoyl)phenyl]iminomethyl}-piperidine-4-carboxamide;

{4-[(N-methyl(furanylmethyl)amino)iminomethyl]-2-fluorophenyl}-N-{4-chloro-6-methoxy-2-[N-(5-ethynyl(2-pyridyl))carbamoyl]phenyl}-carboxamide;

{4-[(dimethylamino)iminomethyl]phenyl}-N-{2-[N-(5-ethynyl(2pyridyl))carbamoyl]phenyl}-carboxamide;

N-{2-[N-(5-ethynyl(2-pyridyl))carbamoyl]phenyl}[4-(1-methyl(2imidazolin-2-yl))phenyl]-carboxamide;

N-{2-[N-(5-ethynyl(2-pyridyl))carbamoyl]}[4-(iminopyrrolidinylmethyl)phenyl]carboxamide;

N-{2-[N-(5-ethynyl(2-pyridyl))carbamoyl]}[4-(iminopiperidylmethyl)phenyl]carboxamide;

ethyl 1-{[4-(N-{2-[N-(5-ethynyl(2-pyridyl))carbamoyl]phenyl}carbamoyl)phenyl]iminomethyl}-piperidine-4-carboxylate;

N-{4-chloro-2-[N-(5-ethynyl(2-pyridyl))carbamoyl]phenyl}[4-(1-propyl(2-imidazolin-2-yl))phenyl]-carboxamide; and N-{4-chloro-2-[N-(5-ethynyl(2-pyridyl))carbamoyl]phenyl}[4-(1-(2-hydroxy)ethyl(2-imidazolin-2-yl))phenyl]-carboxamide.

* * * * *

UNITED STATES PATENT AND TRADEMARK OFFICE
CERTIFICATE OF CORRECTION

PATENT NO.         : 7,312,235 B2                          Page 1 of 1
APPLICATION NO. : 10/115135
DATED              : December 25, 2007
INVENTOR(S)        : Bing-Yan Zhu et al.

It is certified that error appears in the above-identified patent and that said Letters Patent is hereby corrected as shown below:

TITLE PAGE:

Item (60) Related U.S. Application Data, please replace

"Provisional application No. 60/279,696, filed on Mar. 30, 2001"

with

-- Provisional application No. 60/279,697 filed on Mar. 30, 2001 --.

IN THE SPECIFICATION:

In Column 1, Line 5-8, please replace

"This application claims the benefit of priority under 35 U.S.C. 119(e) to U.S. Provisional Application No. 60/279,696 filed on Mar. 30, 2001 which is herein incorporated in its entirety by reference."

with

-- This application claims the benefit of priority under 35 U.S.C. 119(e) to U.S. Provisional Application No. 60/279,697 filed on Mar. 30, 2001 which is herein incorporated in its entirety by reference. --.

Signed and Sealed this

Ninth Day of November, 2010

David J. Kappos
*Director of the United States Patent and Trademark Office*